(12) United States Patent
Barton et al.

(10) Patent No.: US 11,649,238 B2
(45) Date of Patent: May 16, 2023

(54) SUBSTITUTED PYRAZOLO[1,5-A]PYRIMIDINES AS PI4K INHIBITORS

(71) Applicant: GLAXOSMITHKLINE INTELLECTUAL PROPERTY DEVELOPMENT LIMITED, Middlesex (GB)

(72) Inventors: Nicholas Paul Barton, Stevenage (GB); Sophie Marie Bertrand, Stevenage (GB); Kenneth David Down, Hertfordshire (GB); Matthew Gray, Stevenage (GB)

(73) Assignee: GLAXOSMITHKLINE INTELLECTUAL PROPERTY DEVELOPMENT LIMITED, Brentford (GB)

( * ) Notice: Subject to any disclaimer, the term of this patent is extended or adjusted under 35 U.S.C. 154(b) by 76 days.

(21) Appl. No.: 16/961,704

(22) PCT Filed: Jan. 15, 2019

(86) PCT No.: PCT/EP2019/050983
§ 371 (c)(1),
(2) Date: Jul. 13, 2020

(87) PCT Pub. No.: WO2019/141694
PCT Pub. Date: Jul. 25, 2019

(65) Prior Publication Data
US 2021/0387988 A1    Dec. 16, 2021

(30) Foreign Application Priority Data

Jan. 17, 2018 (GB) .................................... 1800734
Oct. 29, 2018 (GB) .................................... 1817616

(51) Int. Cl.
*A61K 31/519* (2006.01)
*C07D 487/04* (2006.01)

(52) U.S. Cl.
CPC .................. *C07D 487/04* (2013.01)

(58) Field of Classification Search
CPC ........................... A61K 31/519; C07D 487/04
USPC ...................................... 514/259.3; 544/281
See application file for complete search history.

(56) References Cited

U.S. PATENT DOCUMENTS

| | | | |
|---|---|---|---|
| 8,633,198 B1 | 1/2014 | Niazi et al. | |
| 2007/0072880 A1 | 3/2007 | Guzi et al. | |
| 2011/0166147 A1 | 7/2011 | Macleod et al. | |

FOREIGN PATENT DOCUMENTS

| | | |
|---|---|---|
| CL | 200301786 | 7/2004 |
| CL | 201501752 | 6/2016 |
| CL | 201902796 | 12/2019 |
| CL | 202000127 | 4/2020 |
| CL | 202001882 | 10/2020 |
| CL | 202101083 | 9/2021 |
| CL | 202101079 | 10/2021 |
| JP | 2015-511952 A | 4/2015 |
| JP | 2017-503830 A | 2/2017 |
| WO | 2001/23387 A2 | 4/2001 |
| WO | 2004/022561 A1 | 3/2004 |
| WO | 2004/081013 A1 | 9/2004 |
| WO | 2013/034738 A1 | 3/2013 |
| WO | 2013128028 A1 | 9/2013 |
| WO | 2014/096423 A1 | 6/2014 |
| WO | 2015/110491 A2 | 7/2015 |
| WO | 2015110491 A2 | 7/2015 |
| WO | 2015/193167 A1 | 12/2015 |
| WO | 2015/193168 A1 | 12/2015 |
| WO | 2015/193169 A1 | 12/2015 |
| WO | 2016/206999 A1 | 12/2016 |
| WO | 2017/055305 A1 | 4/2017 |

(Continued)

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*

*Primary Examiner* — Douglas M Willis
(74) *Attorney, Agent, or Firm* — Shan Liu; Nicole Ginanni

(57) ABSTRACT

The invention relates to compounds of formula (I) which are inhibitors of kinase activity, pharmaceutical formulations containing the compounds and their uses in treating and preventing viral infections and disorders caused or exacerbated by the viral infection

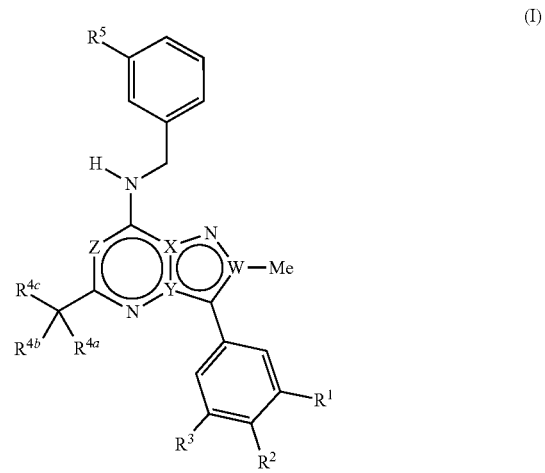

wherein $R^1$, $R^2$, $R^3$, $R^{4a}$, $R^{4b}$, $R^{4c}$, $R^5$, W, X, Y and Z are defined herein.

46 Claims, No Drawings

(56) References Cited

FOREIGN PATENT DOCUMENTS

| WO | 2018134265 A1 | 7/2018 | |
|---|---|---|---|
| WO | 2018177970 A1 | 10/2018 | |
| WO | 2019142126 A1 | 7/2019 | |
| WO | WO-2019141694 A1 * | 7/2019 | ............. A61P 31/16 |
| WO | 2020090585 A1 | 5/2020 | |
| WO | 2020092208 A1 | 5/2020 | |

* cited by examiner

SUBSTITUTED PYRAZOLO[1,5-A]PYRIMIDINES AS PI4K INHIBITORS

CROSS-REFERENCE TO RELATED APPLICATIONS

This application is filed pursuant to 35 U.S.C. § 371 as a United States National Phase Application of International Application No. PCT/EP2019/050983 filed Jan. 15, 2019 which claims priority from GB 1800734.4 and GB 1817616.4 filed Jan. 17, 2018 and Oct. 29, 2018, respectively.

FIELD OF INVENTION

The invention relates to compounds which are inhibitors of kinase activity, pharmaceutical formulations containing the compounds and their uses in treating and preventing viral infections and disorders caused or exacerbated by the viral infection.

BACKGROUND OF THE INVENTION

The genus Enterovirus of the family Picornaviridae of positive sense single stranded RNA viruses includes a number of human pathogens that can cause very serious illnesses. Examples include polio virus, coxsakie B virus (aseptic meningitis, myocarditis, pancreatitis and non-specific febrile illness), enterovirus-A71 (aseptic meningitis, encephalitis and poliomyelitis-like paralysis), enterovirus-D68 (acute flaccid myelitis) and parechovirus (myocarditis and encephalitis). Enteroviral infections (coxsackievirus A24 variant and enterovirus type 70) are responsible for most cases of acute hemorrhagic conjunctivitis (AHC) and there have been numerous AHC epidemics and three pandemics since 1969 (Yin-Murphy et al., British Journal of Ophthalmology, 1986, 70, 869; Nilsson et al., Journal of Virology, 2008 82, 3061). However, most people experiencing an enteroviral infection suffer much less serious illness. The common cold is one of the most frequently occurring human illnesses and is most often associated with another species of enterovirus, the human rhinovirus (HRV) which causes of 30-50% colds.

The optimal temperature for HRV replication is 33-35° C., favouring upper respiratory tract infection (URTI) and an illness that is most often mild and resolved without medical intervention. However, UTRI can have complications and HRV was detected in the middle ear of ~40% of children under 7 years of age suffering from otitis media with effusion, including chronic cases (Papadopoulus et al., Paediatric Allergy and Immunology, 2006: 17: 514), in sputum in 26% of 291 patients suffering from acute bronchitis (Park et al. Plos One, 2016, 11, e0165553), in maxillary aspirates and brushings from 15 of 34 patients suffering from acute sinusitis, (Pitksranta et al., Journal of Clinical Microbiology, 1997, 35, 1791 and Clinical Infectious Diseases, 2001 33, 909) and in 29% of patients undergoing functional endoscopic sinus surgery for chronic rhinosinusitis (Abshirini et al., Jundishapur Journal of Microbiology, 2015, 8, e20068).

The temperature of large and medium sized airways of the lung should also permit HRV replication (McFadden E R Jr, et al., J. Appl. Physiol., 1985, 58, 564) and in certain patient groups infection can cause very serious illness. In children under 5 years of age, rhinovirus infection frequently leads to hospitalisation (4.8 cases/1000 children: Miller et al., Journal of Infectious Diseases, 2007; 195, 773), a severity of illness similar to that from respiratory syncytial virus (RSV) infection (McMillan et al., Pediatric Infectious Disease Journal, 1993, 12, 321) and often leads to bronchiolitis and pneumonia (Kellner et al., Acta Paediatrica Scandinavica, 1989, 78, 390; McMillan et al., Pediatric Infectious Disease Journal, 1993, 12, 321; EI-Sahly et al., Clinical infectious Diseases, 2000, 31, 96; Jartti and Korppi, Pediatric Allergy and Immunology, 2011, 22, 350). In a study by Asner et al. (Influenza and Other espiratory Viruses, 2014, 8, 436) the majority of the HRV/enterovirus infected children had underlying immunosupression or cardiorespiratory co-morbidities and it is well established that the consequences of HRV infection can be particularly serious for patients with these conditions (Anzueto et al., Chest, 2003, 123, 1664; Rotbart, Antivir. Res. 2002, 53, 83). For example, 7 of 22 myelosuppressed transplant recipients with a rhinovirus infection went on to develop fatal pneumonia (Ghosh et al., Clinical infectious Diseases, 1999, 29, 528).

Enterovirus infections are also commonly associated with eruptive skin rashes (hand foot and mouth disease, eczema coxsackium and other atypical exanthems: Hubisch et al., Pediatric Infectious Disease Journal, 2014, 33, e92; Korman et al., Journal of the American Academy of Dermatology, 2017, 76, 538; Drago et al., Future Microbiology, 2017 12, 171).

HRV is the virus most commonly associated with exacerbations of asthma (approximately 25% exacerbations in adults and 50% in children, Nicholson et al., BMJ, 1993, 307, 982; Johnston et al., BMJ., 199, 310, 1225) and chronic obstructive pulmonary disease (COPD: 20-26% Seemungal et al., Am. J. Respir. Crit. Care Med., 2001, 164, 1618; Papi et al., Am. J. Respir. Crit. Care Med., 2006, 173, 1114), and in both cases experimental rhinoviral challenge has been shown to exacerbate disease (Zambrano et al., J Allergy Clin Immunol., 2003, 111, 1008; Mallia et al., Am. J. Respir. Crit. Care Med., 2011, 183, 734). Rhinoviral infections are also frequently associated with exacerbations of bronchiectasis (16 to 25%: Kapur et al. Arch Dis Child 2014, 99, 749; Gao et al Chest 2015, 147, 1635) and cystic fibrosis (CF) (Etherington, J. Cystic Fibrosis 2014, 13, 49; Flight et al. Thorax, 2014, 69, 247). In COPD, CF and bronchectasis exacerbations are more severe when associated with viral infection (Papi et al. Am. J. Respir. Crit. Care Med., 2006, 173, 1114; Etherington, J. Cystic Fibrosis, 2014, 13, 49; Kapur et al., Arch Dis Child, 2014, 99, 749) and in each case exacerbations contribute to disease progression and reduced survival (Liou et al., Am J Epidemiol., 2001, 153, 345; Soler-Cataluna et al., Thorax, 2005, 60, 925; Roberts et al., Intern Med J., 2012 42, 129). The majority of rhinovirus induced exacerbations of COPD are subsequently followed by a secondary bacterial infection (Mallia et al., Am. J. Respir. Crit. Care Med., 2012, 186, 1117; George et al., Eur Respir J., 2014; 8). In addition, infection with HRV is one of the factors that can direct the infant immune system towards an asthmatic phenotype (D. J. Jackson et al., Am. J. Respir. Crit. Care Med., 2008, 178, 667).

The socioeconomic impact of HRV is enormous and treatment often includes the inappropriate use of antibiotics. It has been estimated that the common cold accounts for at least twenty-five million absences from work, and nearly as many school absences, annually in the United States (Rotbart, Antivir. Res., 2002 53, 83). Direct and indirect costs from the common cold and related complications in asthmatics alone have been estimated as high as forty billion dollars annually in the United States (A. M. Fendrick et al., Arch. Intern. Med., 2003, 163, 487.

There are three species of HRV (A, B, and C) comprising more than 150 genotypes. HRV-A and —C are most commonly detected and the latter appears to be the more pathogenic group in the paediatric asthma patient population at least (Piralla et al., Journal of Clinical Virology, 2009, 45, 311; Bizzintino et al., Eur. Respir. J., 2011, 37, 1037). HRVs can also be devided into 3 broad groups based on the cellular receptor through which cell entry is mediated. The major group of HRVs (approximately 90% of serotype HRV-A and B) enter host cells through interaction with the human intracellular adhesion molecule (ICAM-1). The remaining ~10% HRV-A and B viruses comprise the minor group and utilize the low-density lipoprotein receptor for cell entry. The more recently discovered HRV-C species binds to human cadherin-related family member 3 (CDHR3) to facilitate entry. HRVs enter the cell by triggering receptor-mediated endocytosis, with uncoating occurring in the endosomes. The differences between the serotypes not only prevent the body from developing cross-immunity, they have greatly impeded the development of vaccines and other virus-specific methods of prevention and treatment.

The naked HRV RNA genome (~8 kb) is surrounded by a capsid composed of sixty copies each of four structural proteins, denoted VP1-VP4, in an icosahedral configuration producing a virus particle of ~30 nm diameter. HRV replication requires viral RNA-dependent RNA polymerase, as well as multiple virus and host-cell derived accessory proteins. The HRV genome is translated as a single polyprotein, which is first cleaved following translation by virus-encoded proteases into three proteins, which are themselves cleaved to produce at least eleven proteins. Viral genome replication can begin in as little as one hour following infection, and the release of nearly one million fully assembled virus particles at cell death can occur in as little as four hours following cell entry.

Currently, there are no medications approved for use in humans that cure the underlying HRV infection. A few attempts to attack HRVs directly have shown some promise. 4-[2-[1-(6-methyl-3-pyridazinyl)-4-piperidinyl]-ethoxy]benzoate, otherwise known as "pirodavir," is able to function as a capsid-binding inhibitor, but problems with solubility, endogenous cleavage, and cost have undermined its utility against HRV. Pleconaril (PICOVIR) was shown to be effective at inhibiting HRV replication, but has been rejected by the U.S. FDA, citing significant safety concerns. Rupintrivir, a viral 3C protease inhibitor was efficacious in experimental HRV challenge studies in humans but was ineffective against naturally occuring HRV infections (Bauer et al., Current Opinion in Virology, 2017, 24, 1). Certain imidazopyrazines have been suggested as being effective antiviral agents against HRV and other viruses; their mode of action is uncertain, though it is suggested that it is not through their effect on cyclin-dependent kinases (U.S. Pub. App. No. 2011/0166147 by Macleod et al.).

In light of the above, there remains a need for new therapeutics against HRVs and enteroviruses.

Notwithstanding other differences, positive-strand RNA viruses depend on a single fundamental step of RNA-dependent RNA synthesis for viral genome replication. This step is essential for the viral life cycle and these viruses are known to further depend on many host proteins to start and maintain RNA-dependent RNA polymerase activity. Without the interaction of host factors, the viruses would be unable to replicate/survive. Therefore, a possible therapeutic intervention for inhibiting viral infections of this class is to block the virus-host interaction, especially as it concerns viral genome replication. If host factors essential for the virus, but not essential for the host, can be manipulated, then significant inhibition of viral propagation could be achieved. Additionally, host factors with redundancies could represent promising targets for intervention. This would be particularly true if large classes of viruses evolved an ability to interact with only one of a series of redundant host factors. One set of host proteins that are thought to be potential targets for inhibiting viral replication are phosphatidylinositol-4-kinases.

Phosphatidylinositol-4-kinases (PI4K) are involved in several cellular activities, including membrane fusion, vesicular transport and cell signaling, through catalysing the phosphorylation of phosphatidylinositol to form phosphatidylinositol-4 phosphate (PI4P). There are several known isoforms of PI4K which differ across several properties, including sequence, size, tissue, cellular localization and function.

One type of PI4K, phosphatidylinositol (type III)-4-kinase, beta polypeptide (PI4KIIIβ) (also known in the literature as phosphatidylinositol 4-kinase (III) β, PtdIns 4-kinase (III) β, PI4 KB, Pi4kcb, and PI4K92) is thought to be important for controlling local populations of PI4P primarily in the golgi network where it is required to maintain structural integrity of the organelle. The enzyme has also been detected in the nucleus. PI4 KIIIβ has been implicated by recent studies to be involved in the genomic replication of several RNA viruses, including HRV, enteroviruses 68 and 71, poliovirus, coxsackie virus, hepatitis C virus, bovine kobuvirus, aichi virus, rubella and others (See, e.g., van der Schaar et al., Antimicrobial Agents and Chemotherapy, 57, 4971; Roulin et al., Cell Host & Microbe, 2014, 16, 677; Mello et al., Antimicrobial Agents and Chemotherapy 2014, 58, 1546; Jun Sasaki et al., EMBO J. 2011, 31, 754; Hsu et al., CELL 2010, 141, 799; Borawski, J. Virology 2009, 83, 10058; Altan-Bonnet et al., TIBS 2012, 37, 293). In addition PI4 KB catalytic activity has been shown to be essential for spike protein mediated cell entry of SARS coronavirus, the virus responsible for severe acute respiratory syndrome (Yang et al., J. Biol. Chem., 2012, 287, 8457). SARS was an epidemic originating in southern China that involved 8,448 cases and 774 deaths in 37 countries between November 2002 and July 2003. The macro-economic impact of the outbreak has been estimated to be between $30 and 100 billion (Smith, *Social Science & Medicine*, 2006, 63, 3113). The consensus is that inhibition of PI4 KB could substantially reduce viral replication in many RNA viruses, and in particular, positive-strand RNA viruses, implicating PI4 KB as a potential target in the development of broad spectrum antiviral agents. In addition, PI4 kinases have roles in bacterial entry and replication, and PI4 KB has been implicated in *Legionella pneumophila* infection through the role of PI4P in anchoring bacterial proteins to the intracellular legionella containing replicative vacuole (Clayton et al. Pu Progress in Lipid Research 2013, 52 294). A PI4 KB inhibitor may thus be effective at counteracting acute lung injury or acute respiratory distress syndrome associated with *Legionella* infection and possibly as a treatment for other intracellular bacterial infections.

E. P. Keaney et al. (*Bioorg. Med. Chem. Lett.*, 24 (2014) 3714-3718) describes 2-alkyloxazole derivatives as PI4KIIIβ inhibitors for possible treatment of Hepatitis C viral infections.

I. Medrova et al. (*J. Med. Chem.*, 2017, 60(1), 100-118) describes a number of imidazo[1,2-b]pyridazine derivatives as PI4KIIIβ inhibitors for possible treatment of viral infections.

J. B. Shotwell, in a set of presentation slides entitled "Chemical Optimization of Novel Inhibitor Classes for PI4KIIIβ: A Critical Host Factor for Enterovirus Replication" submitted to "The 27th International Conference on Antiviral Research" (held in Raleigh, N.C., USA) and presented on 12 May 2014 described a number compounds active at the PI4 KB receptor. The slides were predominantly directed to compounds for oral administration and include a slide entitled "Existing Chemotyopes were optimized for IN Delivery" showing the effect on the lung of intranasal administration of compound GSK3180404A and compound GSK3159043A in a rat model. The slide shows substantial accumulation of compound in lung tissue in respect of both compounds. The following slide entitled "Nasal Epithelian Findings Observed following IN dose" contains a series of histological images showing ulceration in the rat nasal cavity and bronchial epithelial hyperplasia in the rat lung from intranasal administration of GSK3159043.

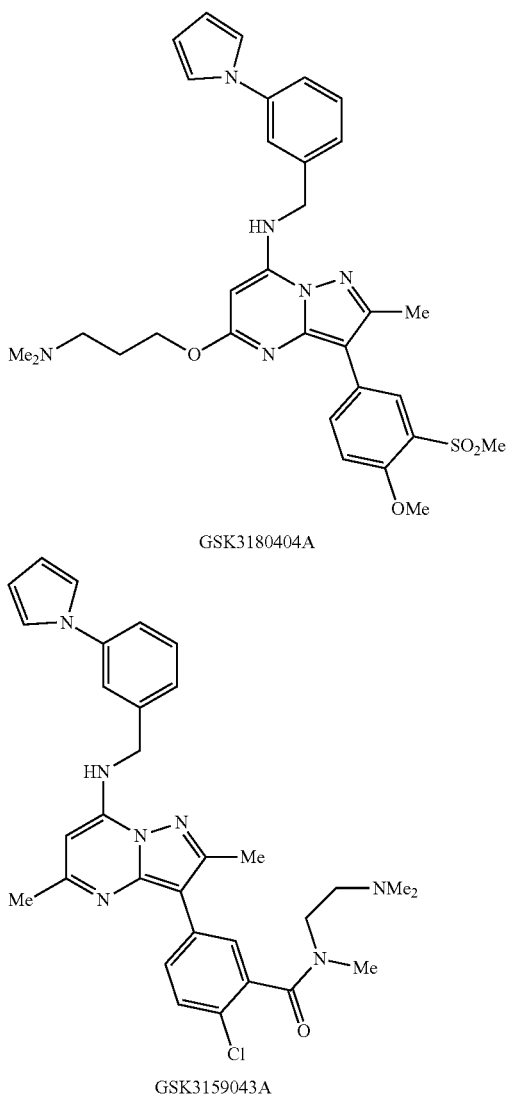

GSK3180404A

GSK3159043A

There exists a need for compounds which are potent PI4KIIIβ inhibitors. There is also a need for compounds which may also be useful as selective PI4KIIIβ inhibitors.

In particular, there is a need for compounds which are are potent PI4KIIIβ inhibitors and which do not substantially accumulate in body tissue, e.g. lung tissue, particularly when administered by the inhaled or intranasal routes. Such compounds may be useful in treating or preventing viral infections and disorders caused or exacerbated by the viral infection, particularly HRV infection.

BRIEF SUMMARY OF THE INVENTION

The invention is directed to compounds of formula (I) or pharmaceutically acceptable salts thereof,

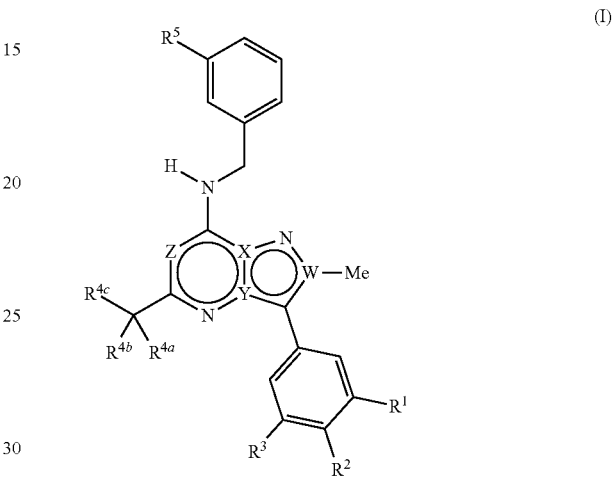

(I)

wherein $R^1$, $R^2$, $R^3$, $R^{4a}$, $R^{4b}$, $R^{4c}$, $R^5$, W, X, Y and Z are defined herein.

The compounds of formula (I) have been shown to be selective inhibitors of PI4KIIIβ and may be useful in treating or preventing viral infections and disorders caused or exacerbated by viral infections. Disorders that are particularly caused or exacerbated by viral infections include COPD, asthma, cystic fibrosis, bronchiectasis and congestive heart failure. In addition disorders that are caused or exacerbated by rhinoviral infections include bronchiolitis, otitis media, sinusitis and acute bronchitis. Also, rhinoviral infections may cause a secondary bacterial infection in children, the elderly and immunosuppressed. Such a secondary bacterial infection may cause pneumonia.

Accordingly, the invention is further directed to methods of treatment or prevention of viral infections and disorders caused or exacerbated by the viral infection, which method comprises administering to a patient in need thereof a therapeutically effective amount of a compound of formula (I) or a pharmaceutically acceptable salt thereof.

The invention is further directed to pharmaceutical formulations comprising a therapeutically effective amount of a compound of formula (I) or a pharmaceutically acceptable salt thereof and one or more pharmaceutically acceptable excipients.

The invention is further directed to compounds of formula (I) or pharmaceutically acceptable salts thereof for use in therapy.

The invention is further directed to the use of compounds of formula (I) or pharmaceutically acceptable salts thereof in the manufacture of a medicament for the treatment or prevention of viral infections and disorders caused or exacerbated by the viral infection.

DETAILED DESCRIPTION OF THE INVENTION

According to a first aspect, the invention provides a compound of general Formula (I) or a pharmaceutically acceptable salt thereof,

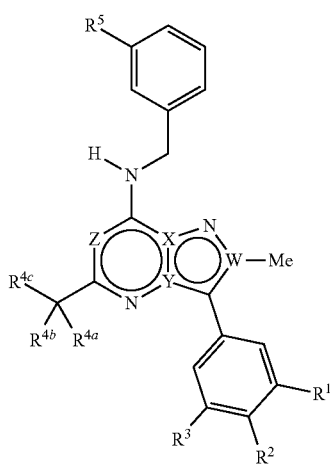

(I)

wherein
W is C, X is C, Y is N and Z is C;
W is C, X is N, Y is C and Z is C;
W is C, X is N, Y is C and Z is N;
W is N, X is C, Y is C and Z is N; or
W is N, X is C, Y is C and Z is C;
$R^1$ is $C_{1-4}$alkoxy, —C(=O)N($R^{1a}R^{1b}$), —S(=O)$_2$—N($R^{1a}R^{1b}$), —S(=O)$_2$—$R^{1c}$ or —S(=O)—$R^{1c}$, wherein
  $R^{1a}$ is $C_{1-3}$alkyl, halo$C_{1-3}$alkyl, hydroxy$C_{1-3}$alkyl, $C_{1-3}$alkoxy$C_{1-3}$alkyl, tetrahydropyranyl or tetrahydrofuranyl; $R^{1b}$ is H or $C_{1-3}$alkyl, or $R^{1a}$ and $R^{1b}$, together with the nitrogen to which they are attached, form a 4- to 7-membered ring, which ring contains ring-carbon atoms and optionally one ring-oxygen atom, wherein the ring is a) optionally substituted by one or two groups selected from $C_{1-3}$alkyl, halo, $C_{1-3}$alkoxy, hydroxy, hydroxy$C_{1-3}$alkyl and oxo, which may be the same or different or b) is ortho- or spiro-fused to an unsubstituted 4-6 membered cycloalkane ring or an unsubstituted 4-6 membered saturated heterocyclic ring; and
  $R^{1c}$ is $C_{1-3}$alkyl, $C_{1-3}$alkoxy, hydroxy, hydroxy$C_{1-3}$alkyl or $C_{1-3}$alkoxy$C_{1-3}$alkyl;
$R^2$ is H, $C_{1-3}$alkyl, halo or —O—$R^{2a}$, wherein $R^{2a}$ is H or an unsubstituted linear $C_{1-3}$alkyl chain, wherein one or two chain carbon atoms are optionally replaced by oxygen atoms;
$R^3$ is H or halo;
and wherein either
i) $R^{4a}$ is H, $C_{1-3}$alkyl or halo $R^{4b}$ is $C_{1-3}$alkyl, cyclopropyl or hydroxy$C_{1-2}$alkyl; or $R^{4a}$ and $R^{4b}$ together with the carbon to which they are attached form an unsubstituted 3-6 membered saturated ring containing ring-carbon atoms and optionally a ring-oxygen atom, wherein the ring is optionally substituted by one $C_{1-3}$alkyl group or one hydroxy$C_{1-2}$alkyl group; and $R^{4c}$ is OH, hydroxymethyl or hydroxyethyl;
ii) $R^{4a}$ H, $C_{1-3}$alkyl, halo or OH; $R^{4b}$ is H, $C_{1-3}$alkyl or halo $R^{4c}$ is an unsubstituted ring selected from the list consisting of oxetanyl, tetrahydrofuranyl and tetrahydropyranyl; or
iii) $R^{4a}$ is H, and $R^{4b}$ and $R^{4c}$ together with the carbon to which they are attached form an unsubstituted ring selected from the list consisting of oxetane, tetrahydrofuran or tetrahydropyran; and
$R^5$ is
  a) imidazol-2-yl optionally substituted by a $C_{1-3}$alkyl group at the 1-position and optionally substituted by a methyl group at the 5-position; or
  b) pyrazol-1-yl optionally substituted by a $C_{1-3}$alkyl group at the 5-position and optionally substituted by a methyl group at the 4-position.

In an embodiment W is C, X is N, Z is C and Y is C.
In a further embodiment $R^{4c}$ is OH.
In an embodiment $R^2$ is H, $C_{1-3}$alkyl, chloro or —O—$R^{2a}$, wherein $R^{2a}$ is H or an unsubstituted linear $C_{1-3}$alkyl chain, wherein one or two chain carbon atoms are optionally replaced by oxygen atoms; and $R^3$ is H or fluoro; In another embodiment i) $R^{4a}$ is H, $C_{1-3}$alkyl or fluoro; $R^{4b}$ is $C_{1-3}$alkyl, cyclopropyl or hydroxy$C_{1-2}$alkyl; or $R^{4a}$ and $R^{4b}$ together with the carbon to which they are attached form an unsubstituted 3-6 membered saturated ring containing ring-carbon atoms and optionally a ring-oxygen atom, wherein the ring is optionally substituted by one $C_{1-3}$alkyl group or one hydroxy$C_{1-2}$alkyl group; and $R^{4c}$ is OH, hydroxymethyl or hydroxyethyl;
ii) $R^{4a}$ H, $C_{1-3}$alkyl, fluoro or OH; $R^{4b}$ is H, $C_{1-3}$alkyl or fluoro; $R^{4c}$ is an unsubstituted ring selected from the list consisting of oxetanyl, tetrahydrofuranyl and tetrahydropyranyl; or
iii) $R^{4a}$ is H, and $R^{4b}$ and $R^{4c}$ together with the carbon to which they are attached form an unsubstituted ring selected from the list consisting of oxetane, tetrahydrofuran or tetrahydropyran;

In an embodiment, the present invention provides compounds of Formula (Ia) or pharmaceutically acceptable salts thereof:

(Ia)

wherein
X is N or C, Y is N or C and Z is N or C; wherein X and Y cannot both be N or both be C; and wherein when Z is N, X is N and Y is C;

$R^1$ is $C_{1-4}$alkoxy, —C(=O)N($R^{1a}R^{1b}$), —S(=O)$_2$—N($R^{1a}R^{1b}$), —S(=O)$_2$—$R^{1c}$ or —S(=O)—$R^{1c}$, wherein $R^{1a}$ is $C_{1-3}$alkyl, halo$C_{1-3}$alkyl, hydroxy$C_{1-3}$alkyl or $C_{1-3}$alkoxy$C_{1-3}$alkyl; $R^{1b}$ is H or $C_{1-3}$alkyl, or $R^{1a}$ and $R^{1b}$, together with the nitrogen to which they are attached, form a 4- to 7-membered ring, which ring contains ring-carbon atoms and optionally one ring-oxygen atom, wherein the ring is a) optionally substituted by one or two groups selected from $C_{1-3}$alkyl, halo, $C_{1-3}$alkoxy, hydroxy and oxo, which may be the same or different or b) is ortho- or spiro-fused to an unsubstituted 4-6 membered cycloalkane ring or an unsubstituted 4-6 membered saturated heterocyclic ring; and $R^{1c}$ is $C_{1-3}$alkyl, $C_{1-3}$alkoxy, hydroxy, hydroxy$C_{1-3}$alkyl or $C_{1-3}$alkoxy$C_{1-3}$alkyl;

$R^2$ is H, $C_{1-3}$alkyl, chloro or —O—$R^{2a}$, wherein $R^{2a}$ is H or an unsubstituted linear $C_{1-3}$alkyl chain, wherein one or two chain carbon atoms are optionally replaced by oxygen atoms;

$R^3$ is H or fluoro;

$R^{4a}$ is H or methyl;

$R^{4b}$ is $C_{1-3}$alkyl or hydroxy$C_{1-2}$alkyl; and $R^5$ is a) imidazol-2-yl optionally substituted by a $C_{1-3}$alkyl group at the 1-position and optionally substituted by a methyl group at the 5-position; or b) pyrazol-1-yl optionally substituted by a $C_{1-3}$alkyl group at the 5-position and optionally substituted by a methyl group at the 4-position.

In an embodiment, X is N, Z is C and Y is C.

In an embodiment the compound is a compound of formula (Ib):

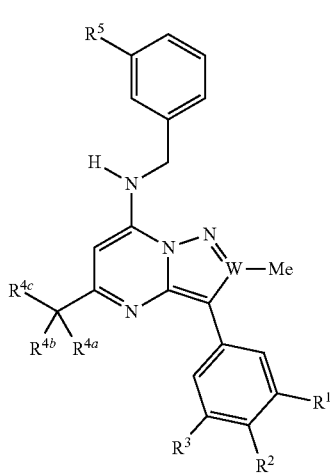

(Ib)

In another embodiment the compound is a compound of formula (Ic):

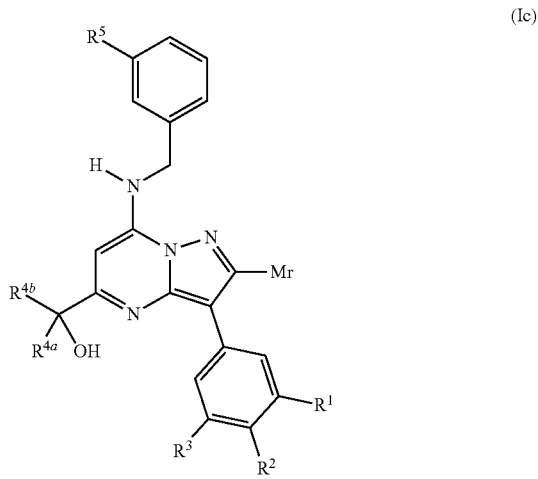

(Ic)

In an embodiment $R^1$ is —C(=O)N($R^{1a}R^{1b}$) or —S(=O)$_2$—$R^{1c}$. In a further embodiment $R^1$ is —C(=O)N($R^{1a}R^{1b}$).

In an embodiment $R^{1a}$ is hydroxy$C_{1-3}$alkyl or tetrahydropyranyl. In an embodiment $R^{1a}$ is hydroxy$C_{1-3}$alkyl. In a further embodiment $R^{1a}$ is 3-hydroxy-1-propyl, 2-hydroxy-1-ethyl, 3-hydroxy-2-propyl or 4-tetrahydropyranyl.

In an embodiment $R^{1b}$ is $C_{1-3}$alkyl. In a further embodiment $R^{1b}$ is methyl or ethyl.

In a further embodiment $R^{1a}$ is hydroxy$C_{1-3}$alkyl and $R^{1b}$ is $C_{1-3}$alkyl. In a further embodiment $R^{1a}$ is 3-hydroxy-1-propyl and $R^{1b}$ is $C_{1-3}$alkyl. In a further embodiment $R^{1a}$ is 3-hydroxy-2-propyl and $R^{1b}$ is $C_{1-3}$alkyl. In a further embodiment $R^{1a}$ is 3-hydroxy-1-propyl and $R^{1b}$ is methyl. In a further embodiment $R^{1a}$ is 3-hydroxy-2-propyl and $R^{1b}$ is methyl. In a further embodiment $R^{1a}$ is 2-hydroxy-1-ethyl and $R^{1b}$ is ethyl. In a further embodiment $R^{1a}$ is 3-hydroxy-2-propyl and $R^{1b}$ is methyl. In a further embodiment $R^{1a}$ is 4-tetrahydropyranyl and $R^{1b}$ is methyl.

In an embodiment $R^{1a}$ and $R^{1b}$, together with the nitrogen to which they are attached, form a 4- to 7-membered saturated ring, which ring contains ring-carbon atoms and optionally one ring-oxygen atom, wherein the ring is a) optionally substituted by one or two groups selected from $C_{1-3}$alkyl, halo, $C_{1-3}$alkoxy, hydroxy, hydroxy$C_{1-3}$alkyl and oxo, which may be the same or different or b) is ortho- or spiro-fused to an unsubstituted 4-6 membered cycloalkane ring or an unsubstituted 4-6 membered saturated heterocyclic ring.

In an embodiment $R^{1a}$ and $R^{1b}$, together with the nitrogen to which they are attached, form an optionally substituted pyrrolidine ring. In a further embodiment the pyrrolidine ring is substituted by $C_{1-3}$ alkyl, hydroxy or hydroxy$C_{1-3}$alkyl.

In an embodiment $R^{1c}$ is hydroxy$C_{1-3}$alkyl. In a further embodiment $R^{1c}$ is 2-hydroxy-1-ethyl.

In an embodiment $R^2$ is $C_{1-3}$alkyl, chloro or —O—$R^{2a}$. In a further embodiment $R^2$ is $C_{1-3}$alkyl, chloro or methoxy.

In an embodiment, $R^3$ is H or fluoro; In a further embodiment, $R^3$ is H.

In an embodiment $R^{4a}$ is methyl.

In an embodiment $R^{4b}$ is $C_{1-3}$alkyl. In a further embodiment, $R^{4b}$ is methyl or ethyl. In a further embodiment $R^{4b}$ is methyl.

In an embodiment, $R^{4a}$ is methyl and $R^{4b}$ is methyl.

In an embodiment, $R^{4a}$ is $C_{1-3}$alkyl, $R^{4b}$ is $C_{1-3}$alkyl and $R^{4c}$ is OH. In a further embodiment, $R^{4a}$ is methyl, $R^{4b}$ is methyl and $R^{4c}$ is OH.

In an embodiment $R^5$ is imidazol-2-yl optionally substituted by a $C_{1-3}$alkyl group at the 1-position and optionally substituted by a methyl group at the 5-position. In a further embodiment $R^5$ is 1-methyl-1H-imidazol-2-yl.

In an embodiment the compound is a compound according to Formula (I) and:
W is C, X is N, Z is C and Y is C;
$R^1$ is —C(=O)N($R^{1a}R^{1b}$) or —S(=O)$_2$—$R^{1c}$, wherein $R^{1a}$ is hydroxy$C_{1-3}$alkyl and $R^{1b}$ is $C_{1-3}$alkyl; or $R^{1a}$ and $R^{1b}$, together with the nitrogen to which they are attached, form an optionally substituted pyrrolidine ring; and wherein $R^{1c}$ is hydroxy$C_{1-3}$alkyl;
$R^2$ is $C_{1-3}$alkyl, chloro or —O—$R^{2a}$;
$R^3$ is H;
$R^{4a}$ is methyl;
$R^{4b}$ is $C_{1-3}$alkyl;
$R^{4c}$ is OH; and
$R^5$ is imidazol-2-yl optionally substituted by a $C_{1-3}$alkyl group at the 1-position and optionally substituted by a methyl group at the 5-position.

In an embodiment the compound is a compound according to Formula (I) and:
W is C, X is N, Z is C and Y is C;
$R^1$ is —C(=O)N($R^{1a}R^{1b}$) wherein $R^{1a}$ is hydroxy$C_{1-3}$alkyl and $R^{1b}$ is $C_{1-3}$alkyl; or $R^{1a}$ and $R^{1b}$, together with the nitrogen to which they are attached, form an optionally substituted pyrrolidine ring substituted by $C_{1-3}$ alkyl, hydroxy or hydroxy$C_{1-3}$alkyl;
$R^2$ is $C_{1-3}$alkyl, chloro or methoxy;
$R^3$ is H;
$R^{4a}$ is methyl;
$R^{4b}$ is methyl;
$R^{4c}$ is OH; and
$R^5$ is 1-methyl-1H-imidazol-2-yl.

In an embodiment, the compound of formula (I) is selected from the group consisting of:
2-chloro-N-ethyl-N-(2-hydroxyethyl)-5-(5-(1-hydroxyethyl)-2-methyl-7-((3-(1-methyl-1H-imidazol-2-yl)benzyl)amino)pyrazolo[1,5-a]pyrimidin-3-yl)benzamide (Compound 15);
5-(5-(2-Hydroxypropan-2-yl)-2-methyl-7-((3-(1-methyl-1H-imidazol-2-yl)benzyl)amino)pyrazolo[1,5-a]pyrimidin-3-yl)-N-(3-hydroxypropyl)-N,2-dimethylbenzamide (Compound 17);
N-ethyl-N-(2-hydroxyethyl)-5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methoxybenzamide (Compound 19);
(S)—N-(1-hydroxypropan-2-yl)-5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methoxy-N-methylbenzamide (Compound 20);
5-(5-(2-Hydroxypropan-2-yl)-2-methyl-7-((3-(1-methyl-1H-imidazol-2-yl)benzyl)amino)pyrazolo[1,5-a]pyrimidin-3-yl)-2-methoxy-N-methyl-N-(tetrahydro-2H-pyran-4-yl)benzamide (Compound 21);
(S)—N-(1-hydroxypropan-2-yl)-5-(5-(2-hydroxypropan-2-yl)-2-methyl-7-((3-(1-methyl-1H-imidazol-2-yl)benzyl)amino)pyrazolo[1,5-a]pyrimidin-3-yl)-N,2-dimethylbenzamide (Compound 22);
(R)-(2-(hydroxymethyl)pyrrolidin-1-yl)(5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methylphenyl)methanone (Compound 25);
(S)-(5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methylphenyl)(3-hydroxypyrrolidin-1-yl)methanone (Compound 29);
5-(5-(2-hydroxypropan-2-yl)-2-methyl-7-((3-(1-methyl-1H-imidazol-2-yl)benzyl)amino)pyrazolo[1,5-a]pyrimidin-3-yl)-N-(3-hydroxypropyl)-2-methoxy-N-methylbenzamide (Compound 32); and
(R)-(2-(hydroxymethyl)pyrrolidin-1-yl)(5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methoxyphenyl)methanone (Compound 36);
N-ethyl-N-(2-hydroxyethyl)-5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methylbenzamide (Compound 38);
N-(2-hydroxyethyl)-5-(5-(2-hydroxypropan-2-yl)-2-methyl-7-((3-(1-methyl-1H-imidazol-2-yl)benzyl)amino)pyrazolo[1,5-a]pyrimidin-3-yl)-N,2-dimethylbenzamide (Compound 43);
5-(5-(2-Hydroxypropan-2-yl)-2-methyl-7-((3-(1-methyl-1H-imidazol-2-yl)benzyl)amino)pyrazolo[1,5-a]pyrimidin-3-yl)-N,2-dimethyl-N-(tetrahydrofuran-3-yl)benzamide (Compound 59);
5-(5-(2-Hydroxypropan-2-yl)-2-methyl-7-((3-(1-methyl-1H-imidazol-2-yl)benzyl)amino)pyrazolo[1,5-a]pyrimidin-3-yl)-N-(2-hydroxypropyl)-N,2-dimethylbenzamide, isomer 1 (Compound 62);
5-(5-(2-Hydroxypropan-2-yl)-2-methyl-7-((3-(1-methyl-1H-imidazol-2-yl)benzyl)amino)pyrazolo[1,5-a]pyrimidin-3-yl)-N-(2-hydroxypropyl)-N,2-dimethylbenzamide, isomer 2 (Compound 63);
2-Chloro-N-(2-hydroxyethyl)-5-(5-(2-hydroxypropan-2-yl)-2-methyl-7-((3-(1-methyl-1H-imidazol-2-yl)benzyl)amino)pyrazolo[1,5-a]pyrimidin-3-yl)-N-methylbenzamide (Compound 37);
N—((S)-1-Hydroxypropan-2-yl)-5-(5-(1-hydroxypropyl)-2-methyl-7-((3-(1-methyl-1H-imidazol-2-yl)benzyl)amino)pyrazolo[1,5-a]pyrimidin-3-yl)-N,2-dimethylbenzamide, isomer 1 (Compound 80);
N—((S)-1-Hydroxypropan-2-yl)-5-(5-(1-hydroxypropyl)-2-methyl-7-((3-(1-methyl-1H-imidazol-2-yl)benzyl)amino)pyrazolo[1,5-a]pyrimidin-3-yl)-N,2-dimethylbenzamide, isomer 2 (Compound 81);
5-(5-(1-Hydroxybutan-2-yl)-2-methyl-7-((3-(1-methyl-1H-imidazol-2-yl)benzyl)amino)pyrazolo[1,5-a]pyrimidin-3-yl)-N-(3-hydroxypropyl)-N,2-dimethylbenzamide, isomer 1 (Compound 66); and
5-(5-(1-Hydroxybutan-2-yl)-2-methyl-7-((3-(1-methyl-1H-imidazol-2-yl)benzyl)amino)pyrazolo[1,5-a]pyrimidin-3-yl)-N-(3-hydroxypropyl)-N,2-dimethylbenzamide isomer 2 (Compound 67);
or a pharmaceutically acceptable salt of any of the above.

In an embodiment the compound of formula (I) is 5-(5-(2-Hydroxypropan-2-yl)-2-methyl-7-((3-(1-methyl-1H-imidazol-2-yl)benzyl)amino)pyrazolo[1,5-a]pyrimidin-3-yl)-N-(3-hydroxypropyl)-N,2-dimethylbenzamide (Compound 17)

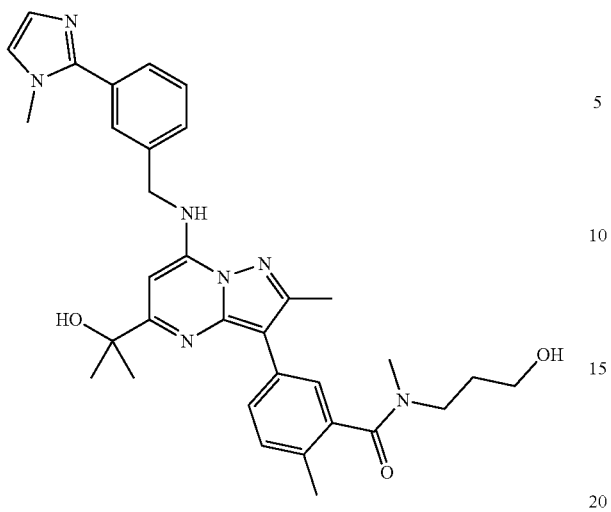

or a pharmaceutically acceptable salt thereof.

In an embodiment the compound of formula (I) is N-ethyl-N-(2-hydroxyethyl)-5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methoxybenzamide (Compound 19)

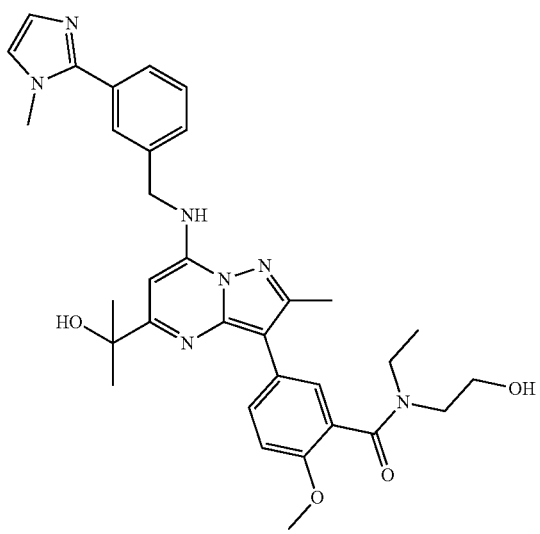 [SMILES: CCN(CCO)C(=O)c1cc(-c2c(C)nn3c(NCc4cccc(-c5nccn5C)c4)cc(C(C)(C)O)nc23)ccc1OC]

or a pharmaceutically acceptable salt thereof.

In an embodiment the compound of formula (I) is 5-(5-(2-Hydroxypropan-2-yl)-2-methyl-7-((3-(1-methyl-1H-imidazol-2-yl)benzyl)amino)pyrazolo[1,5-a]pyrimidin-3-yl)-2-methoxy-N-methyl-N-(tetrahydro-2H-pyran-4-yl)benzamide (Compound 21)

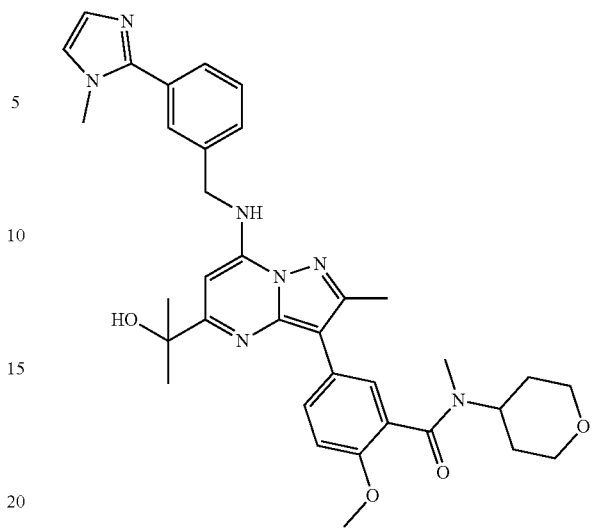

or a pharmaceutically acceptable salt thereof.

In an embodiment the compound of formula (I) is (S)—N-(1-hydroxypropan-2-yl)-5-(5-(2-hydroxypropan-2-yl)-2-methyl-7-((3-(1-methyl-1H-imidazol-2-yl)benzyl)amino)pyrazolo[1,5-a]pyrimidin-3-yl)-N,2-dimethylbenzamide (Compound 22)

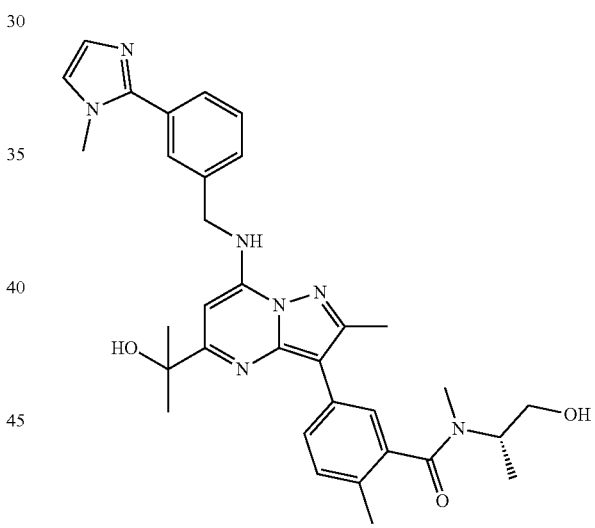

or a pharmaceutically acceptable salt thereof.

Terms and Definitions

Alkyl is a univalent radical derived by removal of a hydrogen atom from an acyclic alkane. For example, a $C_{1-4}$alkyl is alkyl comprising from 1 to 4 carbon atoms. Alkyl may be straight chain or branched chain. Examples of $C_{1-4}$alkyl are methyl, ethyl, n-propyl, n-butyl, iso-propyl, iso-butyl, sec-butyl and tert-butyl.

Alkoxy is a group of formula "—O—R" where R is alkyl (as defined hereinbefore). For example, $C_{1-4}$alkoxy is alkoxy consisting of 1 to 4 carbon atoms. Examples of $C_{1-4}$alkoxy are methoxy, ethoxy, n-propoxy, n-butoxy, iso-propoxy, iso-butoxy, sec-butoxy and tert-butoxy.

Halo refers to a halogen radical, i.e. fluoro, chloro, bromo or iodo.

Haloalkyl is alkyl (as defined hereinbefore) substituted by one or more halo (as defined hereinbefore), which halo may be the same or different. For example, haloC$_{1-3}$alkyl is haloalkyl consisting of 1 to 3 carbon atoms. Examples of haloC$_{1-3}$alkyl are monofluoromethyl, difluoromethyl, trifluoromethyl and 1-chloro-2-fluoroethyl.

Hydroxyalkyl is alkyl (as defined hereinbefore) substituted by one or more hydroxy substituents. For example, hydroxyC$_3$alkyl is of formula —(CH$_2$)$_3$OH (where the "-" indicates which atom is attached to the compound of Formula (I)).

Alkoxyalkyl is alkyl (as defined hereinbefore) substituted by one or more alkoxy substituents. For example, C$_3$alkoxyC$_2$alkyl is of formula —(CH$_2$)$_2$O(CH$_2$)$_2$CH$_3$ (where the "-" indicates which atom is attached to the compound of Formula (I)).

Oxo is a bivalent radical of formula =O.

A 4-6 membered saturated heterocyclic ring is monocyclic and consists of ring-carbon atoms and ring-heteroatoms selected from the group nitrogen, oxygen and sulfur. In an embodiment, the heterocyclic ring consists of 1 or 2 ring-heteroatoms. Examples are pyrrolidine, dioxolane, imidazolidine, pyrazolidine, piperidine, dioxane, morpholine, dithiane, thiomorpholine and piperazine.

A 4-6 membered cycloalkane ring does not contain any ring-heteroatoms and is saturated and monocyclic. Examples are cyclobutane, cyclopentane and cyclohexane.

An 'ortho-fused ring system' comprises two rings having only two atoms and one bond in common, for example

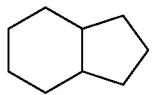

A 'spiro-fused ring system' comprises two rings joined at the same carbon, for example

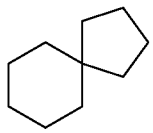

'Substituted' in reference to a group indicates that a hydrogen atom attached to a member atom within a group is replaced. It should be understood that the term 'substituted' includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

'Pharmaceutically acceptable' refers to those compounds, materials, formulations, and dosage forms which are, within the scope of sound medical judgment, suitable for use in contact with the tissues of human beings and animals without excessive toxicity, irritation, or other problem or complication, commensurate with a reasonable benefit/risk ratio.

Throughout the description and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The compounds of formula (I) and formula (Ia) and pharmaceutically acceptable salts thereof may exist in solid or liquid form. In the solid state, they may exist in crystalline or non-crystalline form, or as a mixture thereof. When in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, N,N-dimethylformamide (DMF), dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as 'hydrates'. Hydrates include stoichiometric hydrates as well as compositions containing variable amounts of water.

Compounds of formula (I) and formula (Ia) and pharmaceutically acceptable salts thereof that exist in crystalline form, including the various solvates thereof, may exhibit polymorphism (i.e. the capacity to occur in different crystalline structures). These different crystalline forms are typically known as 'polymorphs'. The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The invention also includes isotopically-labelled compounds, which are identical to the compounds of formula (I) and formula (Ia) and pharmaceutically acceptable salts thereof, but for the fact that one or more atoms are replaced by an atom having an atomic mass or mass number different from the atomic mass or mass number most commonly found in nature. Examples of isotopes that can be incorporated into the compounds of the invention include isotopes of hydrogen, carbon, nitrogen, oxygen and fluorine, such as $^3$H, $^{11}$C, $^{14}$C and $^{18}$F.

The compounds according to formula (I) and formula (Ia) may contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic modifications including racemic mixtures and racemates, enantiomerically-enriched mixtures, or as enantiomerically-pure individual stereoisomers.

Individual stereoisomers of a compound according to formula (I) and formula (Ia) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

It is to be understood that the references herein to a compound of formula (I) and formula (Ia) or a pharmaceutically acceptable salt thereof includes a compound of formula (I) and formula (Ia) respectively as a free base, or as a pharmaceutically acceptable salt thereof. Thus, in one embodiment, the invention is directed to a compound of formula (I). In another embodiment, the invention is directed to a pharmaceutically acceptable salt of a compound of formula (I).

Pharmaceutically acceptable salts include, amongst others, those described in Berge, J. Pharm. Sci., 1977, 66, 1-19, or those listed in P H Stahl and C G Wermuth, editors, *Handbook of Pharmaceutical Salts; Properties, Selection and Use*, Second Edition Stahl/Wermuth: Wiley—VCH/VHCA, 2011

Non-pharmaceutically acceptable salts may be used, for example as intermediates in the preparation of a compound of formula (I) or formula (Ia) or a pharmaceutically acceptable salt thereof. Alternatively non-pharmaceutically acceptable salts of formula (I) and formula (Ia) are included herein.

Suitable pharmaceutically acceptable salts can include acid addition salts.

Such acid addition salts can be formed by reaction of a compound of formula (I) or formula (Ia) (which, for example contains a basic amine or other basic functional group) with the appropriate acid, optionally in a suitable solvent such as an organic solvent, to give the salt which can be isolated by a variety of methods, including crystallisation and filtration.

Salts may be prepared in situ during the final isolation and purification of a compound of formula (I) or formula (Ia). If a basic compound of formula (I) or formula (Ia) is isolated as a salt, the corresponding free base form of that compound may be prepared by any suitable method known to the art, including treatment of the salt with an inorganic or organic base.

It will be understood that if a compound of formula (I) or formula (Ia) contains two or more basic moieties, the stoichiometry of salt formation may include 1, 2 or more equivalents of acid. Such salts would contain 1, 2 or more acid counterions, for example, a dihydrochloride salt. Stoichiometric and non-stoichiometric forms of a pharmaceutically acceptable salt of a compound of formula (I) or formula (Ia) are included within the scope of the invention, including sub-stoichiometric salts, for example where a counterion contains more than one acidic proton.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Compounds of formula (I) or formula (Ia) and their salts and pharmaceutically acceptable salts thereof including solvates (including hydrates), complexes, polymorphs, prodrugs, radiolabelled derivatives and stereoisomers of the compounds of formula (I) or formula (Ia) and their pharmaceutically acceptable salts, are referred to hereinafter as "compounds of the invention".

General Routes

Compounds of the invention may be prepared in a variety of ways. In the following reaction schemes and hereafter, unless otherwise stated $R^1$ to $R^5$, $R^{4a}$, $R^{4b}$, $R^{4c}$, $R^5$, W, X, Y and Z are as defined in the first aspect. Throughout the specification, general formulae are designated by Roman numerals (I), (II), (III), (IV) etc.

General Route to Formula (I)

Compounds for formula (Ix), i.e. compounds of formula (I) where $R^{4a}$ is H and $R^{4c}$ is OH, may be prepared according to reaction scheme 1 by treating (II) with a suitable Grignard reagent (such as methylmagnesium bromide) in a solvent (for example THF) followed by deprotection with a suitable acid (for example 4 M HCl in 1,4-dioxane) in a solvent (for example methanol).

Scheme 1

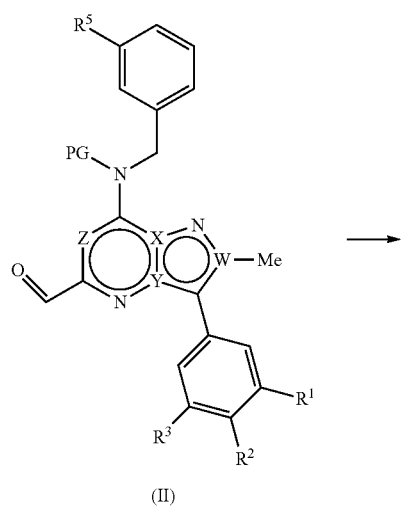

(II)

Compounds of formula (II) may be prepared according to reaction scheme 2 by treating compounds of formula (III) with a boronic ester (for example 2-((2-methoxy-5-(4,4,5,5-tetramethyl-1,3,2-dioxaborolan-2-yl)phenyl)sulfonyl)ethan-1-ol) in a solvent (for example 1,4-dioxane and water) in the presence of a catalyst [for example PdCl$_2$(dppf)] and a base (for example potassium fluoride).

Scheme 2

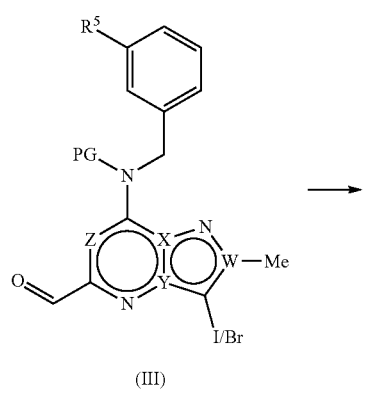

(III)

-continued

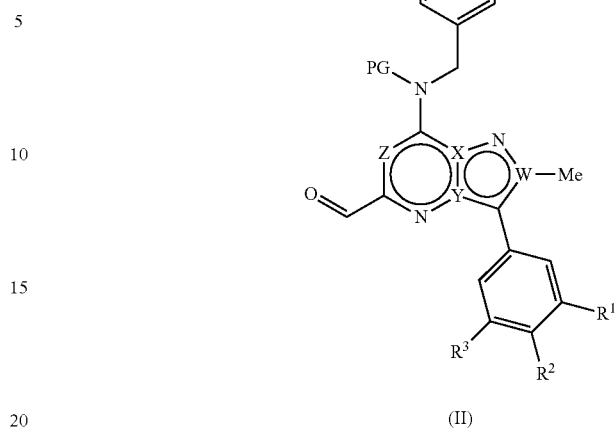

(II)

Compounds of formula (III) may be prepared according to reaction scheme 3 from compounds of formula (IV) by treatment of (IV) with a suitable oxidising agent (for example DMP) in a solvent (for example DCM).

Scheme 3

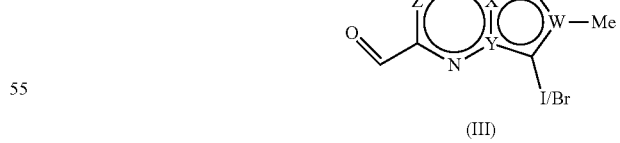

(IV)

(III)

Compounds of formula (IV) may be prepared according to reaction scheme 4 from compounds of formula (V). Firstly the amine is protected with an appropriate amine protecting group (for example tert-butylcarbamate via treatment with appropriate reagents for example di-tert-butyl dicarbonate, DIPEA and DMAP in DCM). Secondly the ester is reduced to the primary alcohol with a suitable reducing agent (for example sodium borohydride) in a solvent (for example ethanol).

Scheme 4

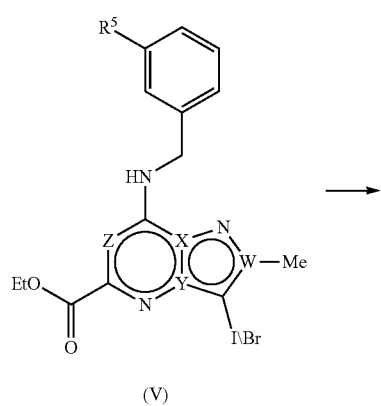

(V)

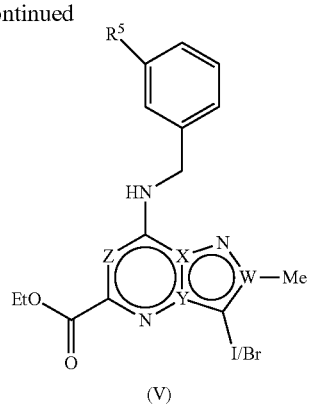

(V)

Compounds of formula (Ix'), i.e. compounds of formula (I) where $R^{4a}$ and $R^{4b}$ are $C_{1-3}$alkyl and $R^{4c}$ is OH, may be prepared according to reaction scheme 6 by treating (VII) with boronic ester (for example N-(3-hydroxypropyl)-2-methoxy-N-methyl-5-(4,4,5,5-tetramethyl-1,3,2-dioxaborolan-2-yl)benzamide) in the presence of a catalyst [for example $PdCl_2$(dppf)] in solvent (for example 1,4-dioxane and water) with base (for example sodium carbonate).

Scheme 6

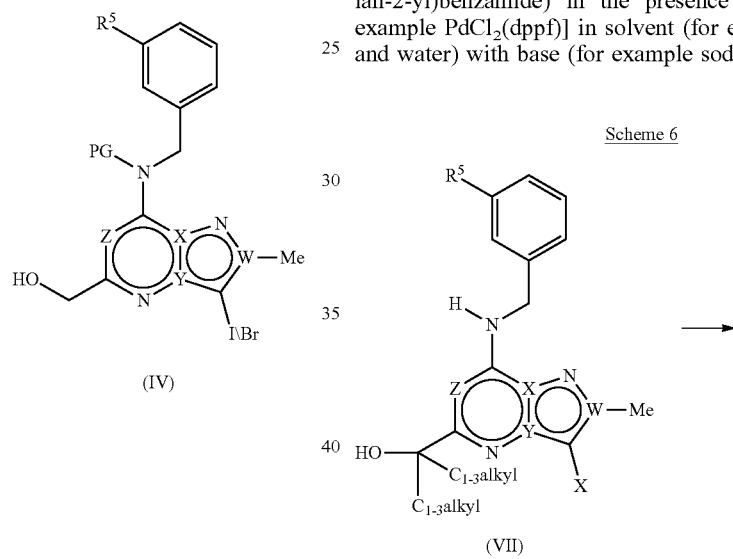

(IV)

Compounds of formula (V) may be prepared according to reaction scheme 5 from compounds of formula (VI) (where L is Cl or Br or a mixture of compounds of formula (VI) where L is Cl and Br) by treatment with an amine (for example (3-(1-methyl-1H-imidazol-2-yl)phenyl)methylamine) and a base (for example DIPEA) in a solvent (for example DMSO).

Scheme 5

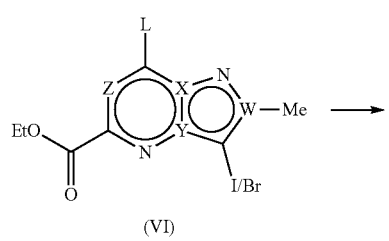

(VI)

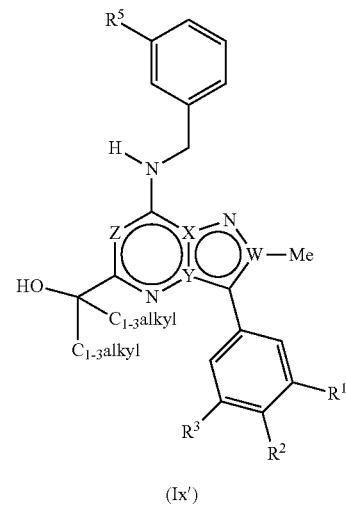

(Ix')

Compounds of formula (VII) may be prepared from compounds of formula (V) according to reaction scheme 7 by treating (V) with a Grignard reagent (for example methylmagnesium bromide) in a solvent (for example DCM). For the preparation of (V) see Scheme 5.

Scheme 7

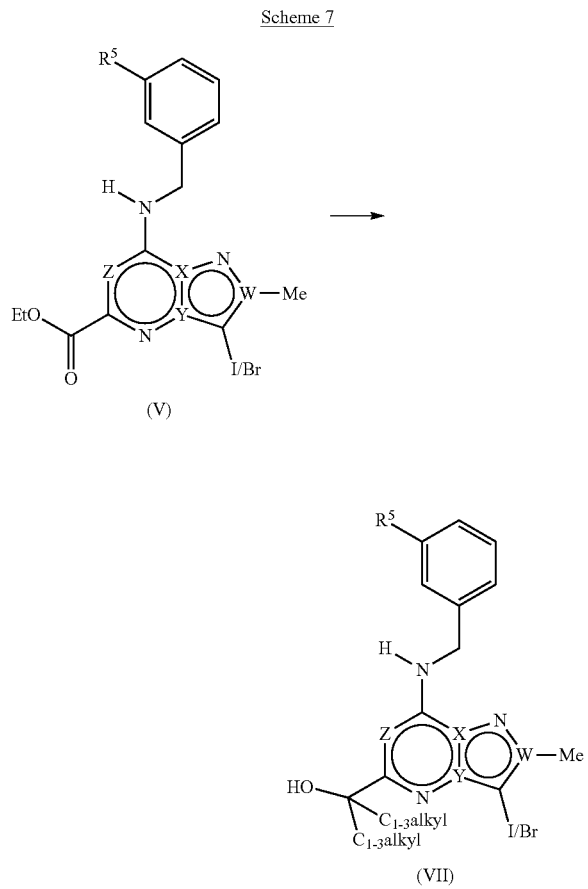

(V)

(VII)

Compounds of formula (VIa). i.e. compounds of formula (VI) (see scheme 5) where W is C, X is N, Y is C, Z is C and L is Cl, may be prepared according to reaction scheme 8. Firstly compounds of formula (VIII) may be obtained by condensation of esters (for example the sodium salt of diethyl oxalacetate) and compounds of formula (IX) using an acid (such as HCl) in a solvent (such as ethanol) with heat (for example 85° C.) to give compounds of formula (VIII). Secondly treatment of (VIII) with a chlorinating reagent (for example POCl₃) with heat (for example at 90° C.) gives compounds of formula (X). Treatment of compounds of formula (X) with an iodine or bromine source [for example N-iodosuccinimide (NIS) or N-bromosuccinimide (NBS)] in a solvent (for example DCM) gives compounds of formula (VIa).

Scheme 8

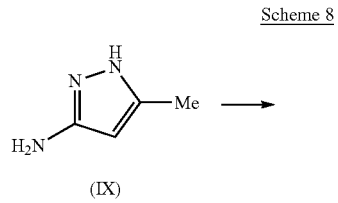

(IX)

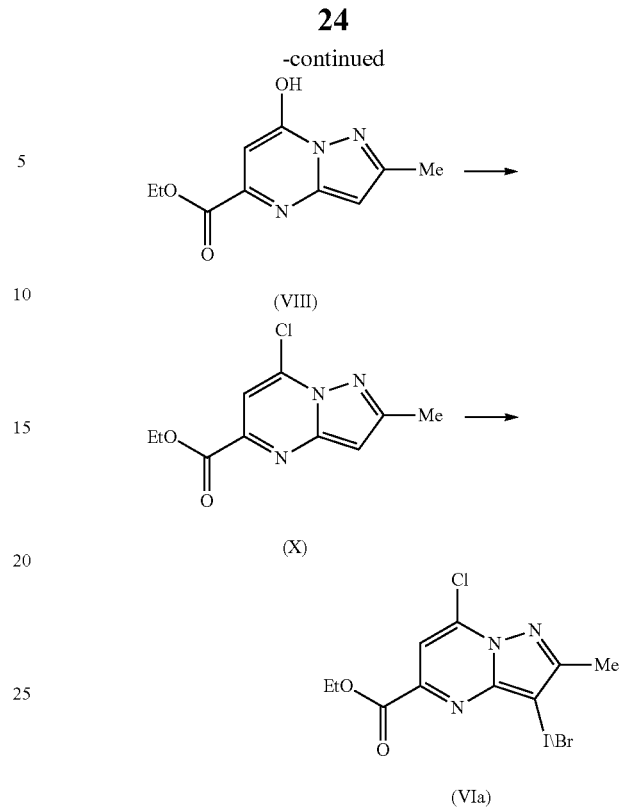

(VIII)

(X)

(VIa)

A mixture of compounds of formula (VIb), i.e. compounds of formula (VI) (see scheme 5) where W is C, X is C, Y is N, Z is C and L is Cl and Br, may be prepared according to reaction scheme 9 in a number of steps from compounds (XI). Firstly compounds of formula (XI) are treated with a brominating agent for example N-bromosuccinimide and sodium bicarbonate in a solvent (for example methanol) to give compounds of formula (XII). Secondly, treating compounds of formula (XII) with 1-chloropropan-2-one at elevated temperature (for example at 90° C.) gives a mixture of compounds of formula (XIII). Iodination or bromination of a mixture of compounds of formula (XIII) with, for example N-iodosuccinimide or N-bromosuccinimide, in a solvent (for example DMF) gives the mixture of compounds of formula (VIb).

Scheme 9

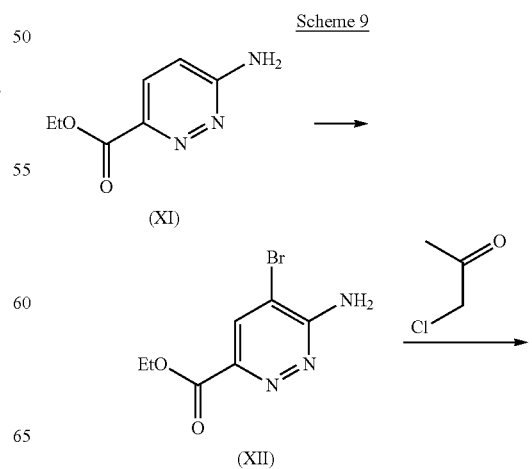

(XI)

(XII)

-continued

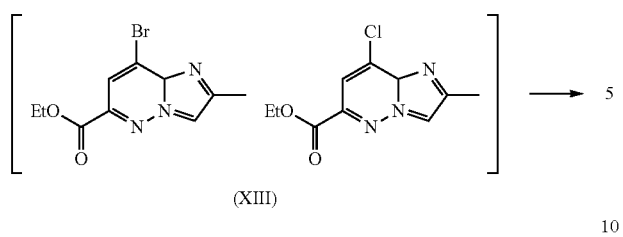

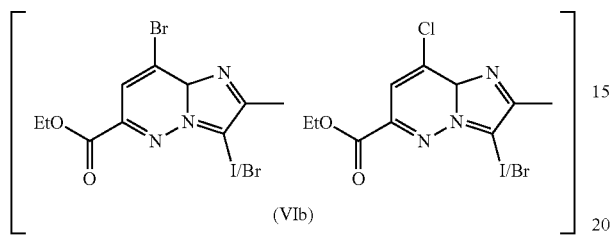

Compounds of formula (VIc), i.e. compounds of formula (VI) (see scheme 5) where W is C, X is N, Y is C, Z is N and L is Cl, may be prepared in a number of steps from compounds of formula (XIV) according to reaction scheme 10. Firstly, compounds of formula (XIV) may be reacted with methyl cyanoformate to give compounds of formula (XV). Secondly, compounds of formula (XV) may be cyclised using carbonyldiimidazole in a solvent (for example DMSO) or alternatively using diethyl carbonate in sodium ethoxide and ethanol to give compounds of formula (XVI). Compounds of formula (XVI) may then be chlorinated using for example POCl₃, with heat (for example at 90° C.) to give compounds of formula (XVII). Iodination (using for example N-iodosuccinimide) or bromination (using for example N-bromosuccinimide), in a solvent (for example DMF) gives the compounds of formula (VIc).

Scheme 10

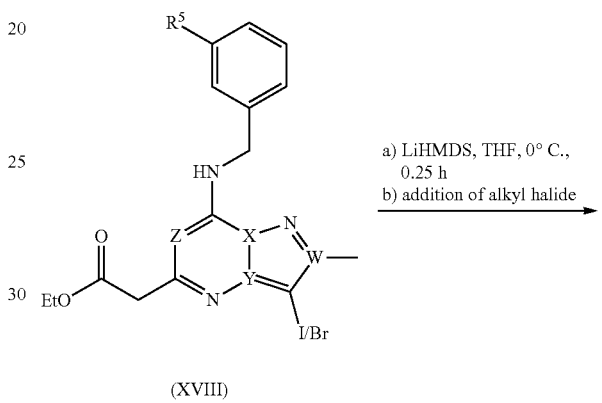

-continued

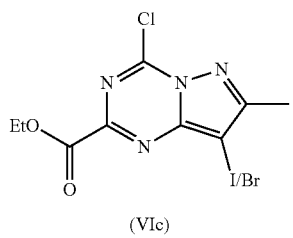

Compounds of formula (Ix″), i.e. compounds of formula (I) where $R^{4c}$ is hydroxymethyl, may be prepared according to reaction scheme 11 from compounds of formula (XVIII).

Scheme 11

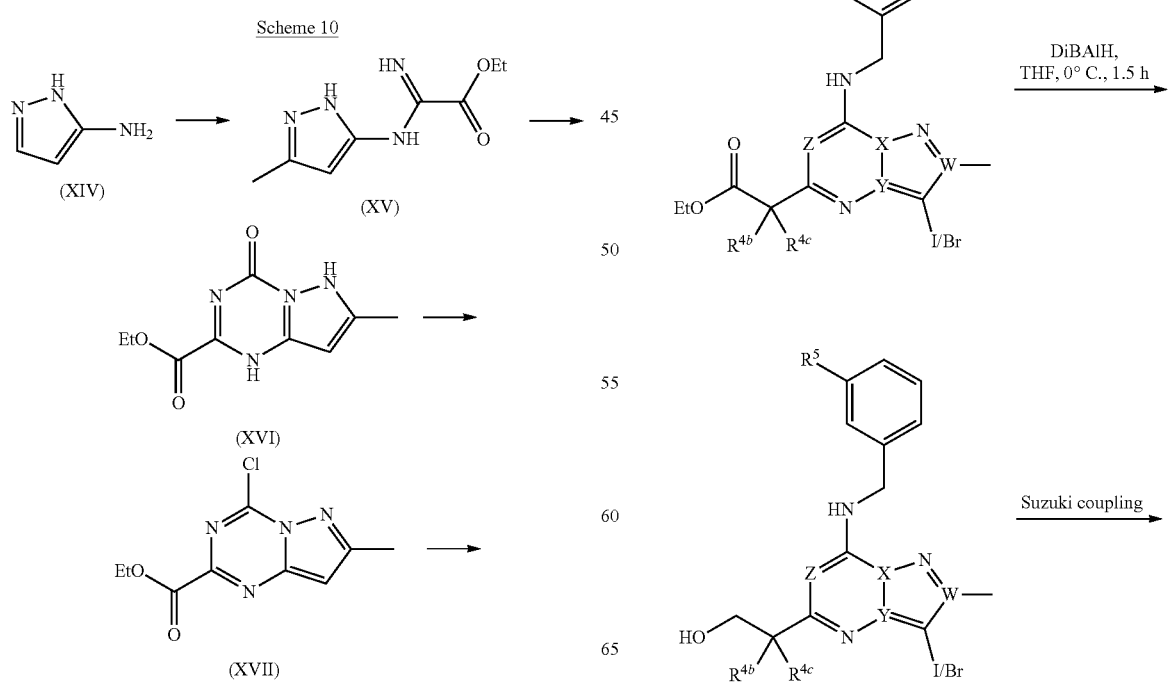

-continued
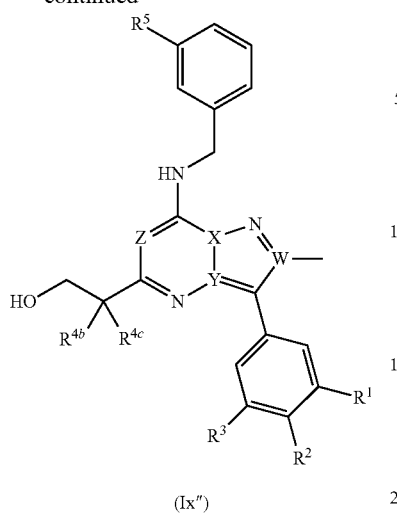
(IX″)
Compounds of formula (XVIIIa), i.e. compounds of formula (XVIII) where W is C, X is N, Y is C and Z is C, may be prepared according to reaction scheme 12.
Scheme 12
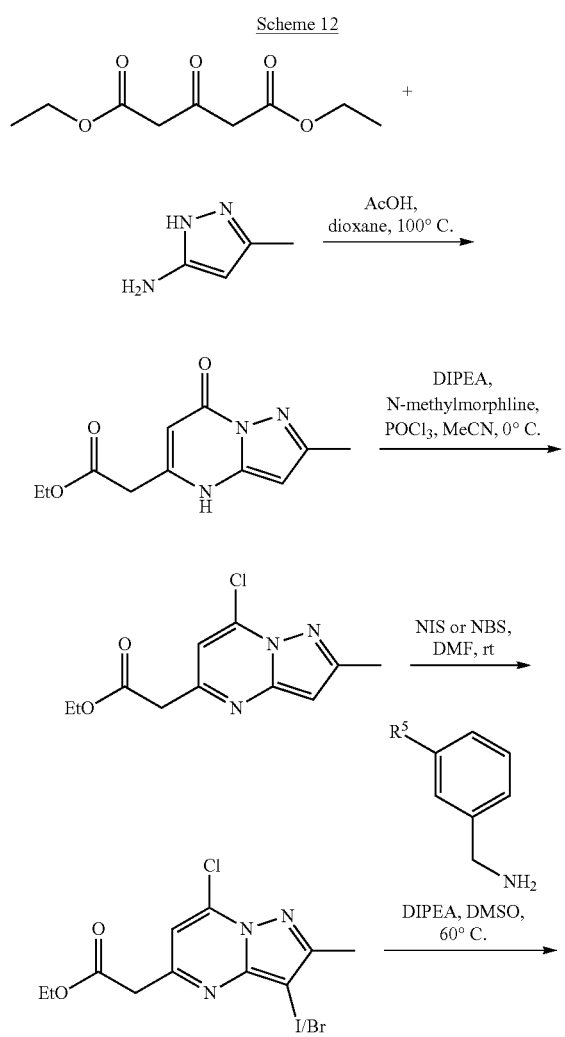
-continued
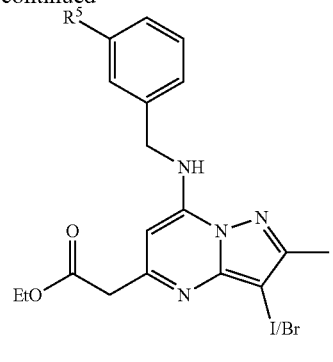
(XVIIIa)
Compounds of formula (XVIIIb), i.e. compounds of formula (XVIII) (from Scheme 11) where W is N, X is C and Y is C, may be prepared from compounds of formula (XIX) according to reaction scheme 13.
Scheme 13
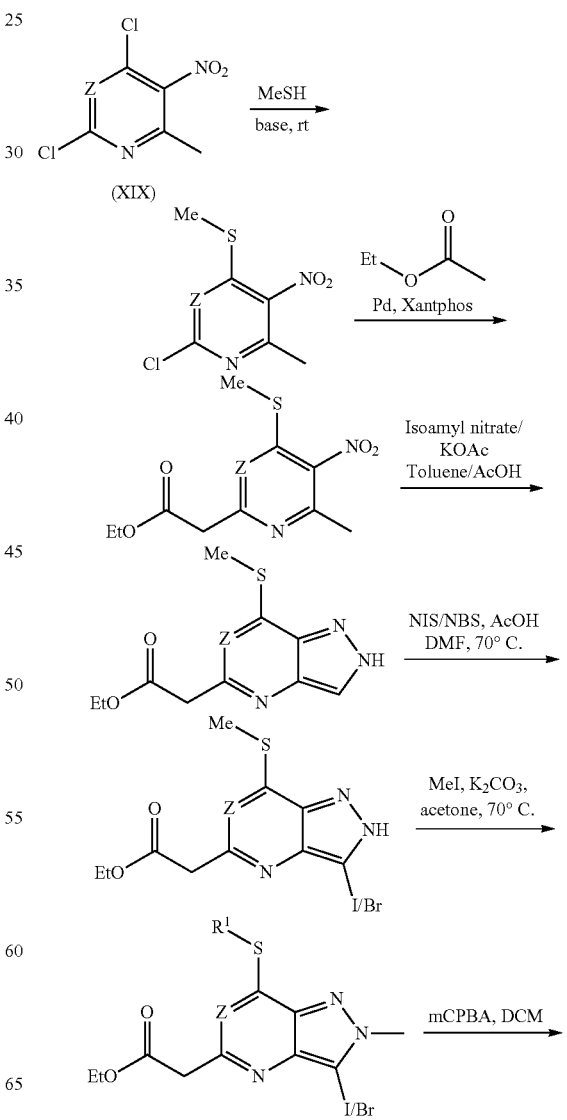

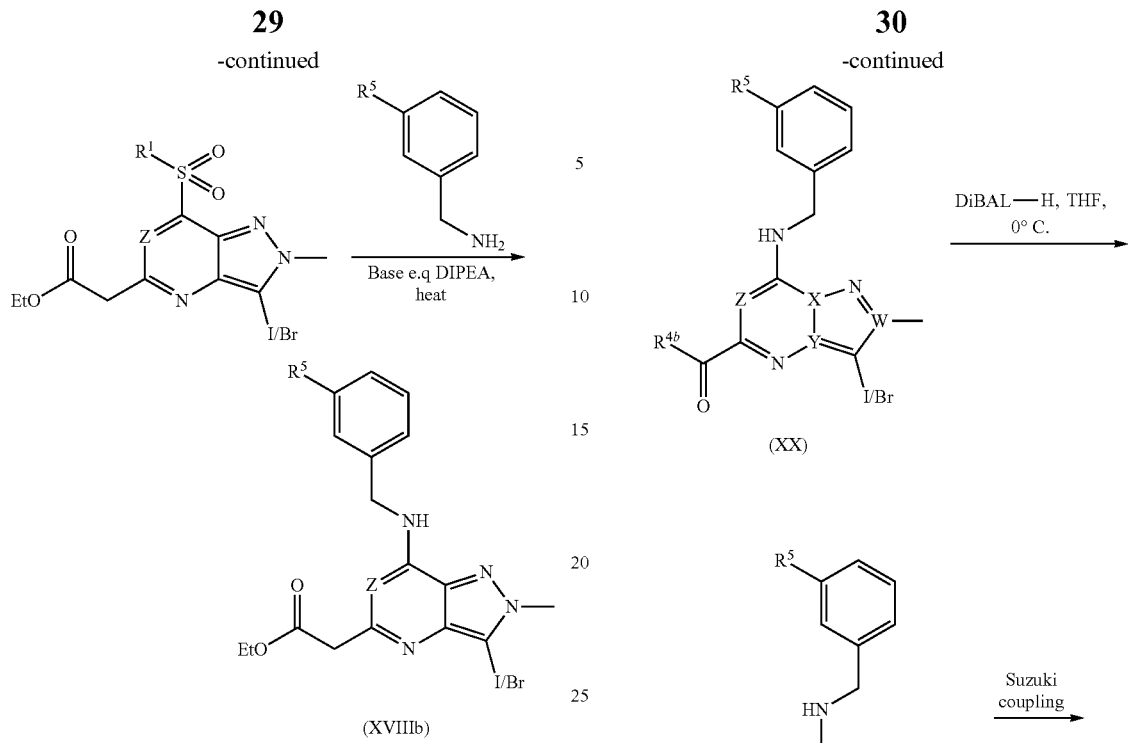

Alternatively compounds of formula (Ia) (see Scheme 1) may be prepared from compounds of formula (V) (see Scheme 4) according to reaction scheme 14. Compounds of formula (Ia) may be resolved into individual enantiomers using techniques familiar to the skilled chemist, for example chiral HPLC.

Scheme 14

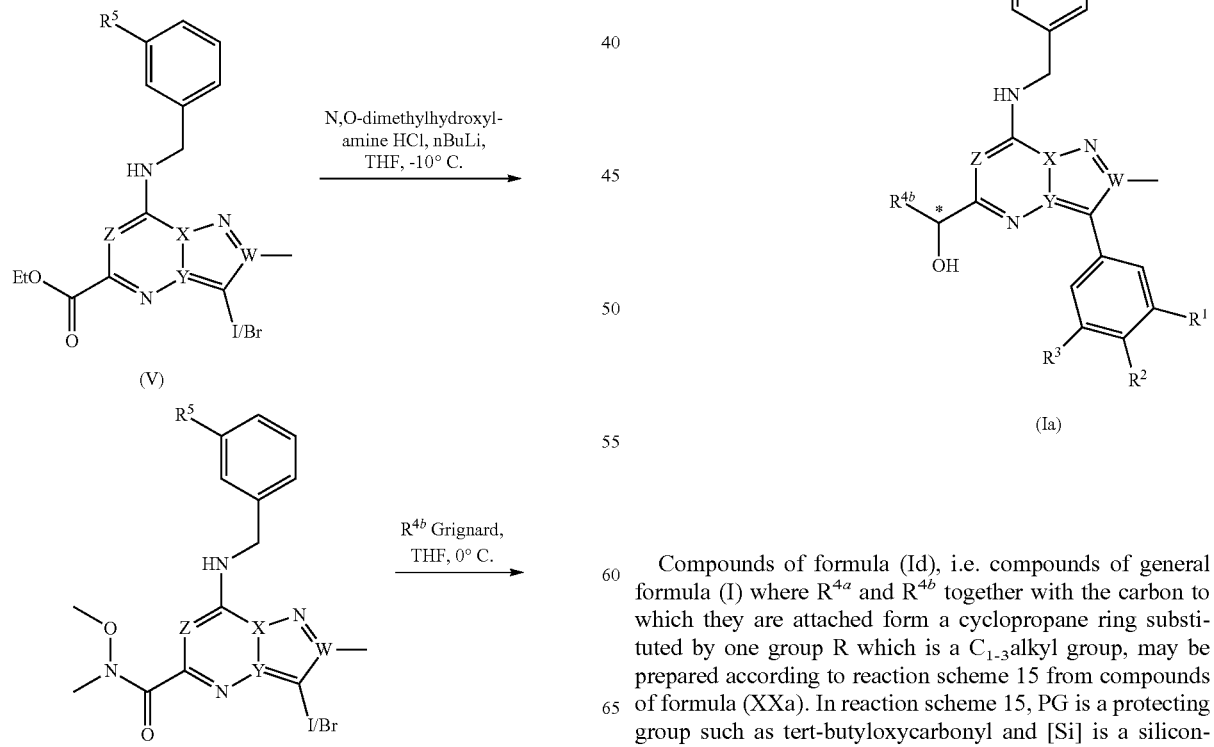

Compounds of formula (Id), i.e. compounds of general formula (I) where $R^{4a}$ and $R^{4b}$ together with the carbon to which they are attached form a cyclopropane ring substituted by one group R which is a $C_{1-3}$alkyl group, may be prepared according to reaction scheme 15 from compounds of formula (XXa). In reaction scheme 15, PG is a protecting group such as tert-butyloxycarbonyl and [Si] is a silicon-based alcohol protecting group such as TBDMS.

Scheme 15
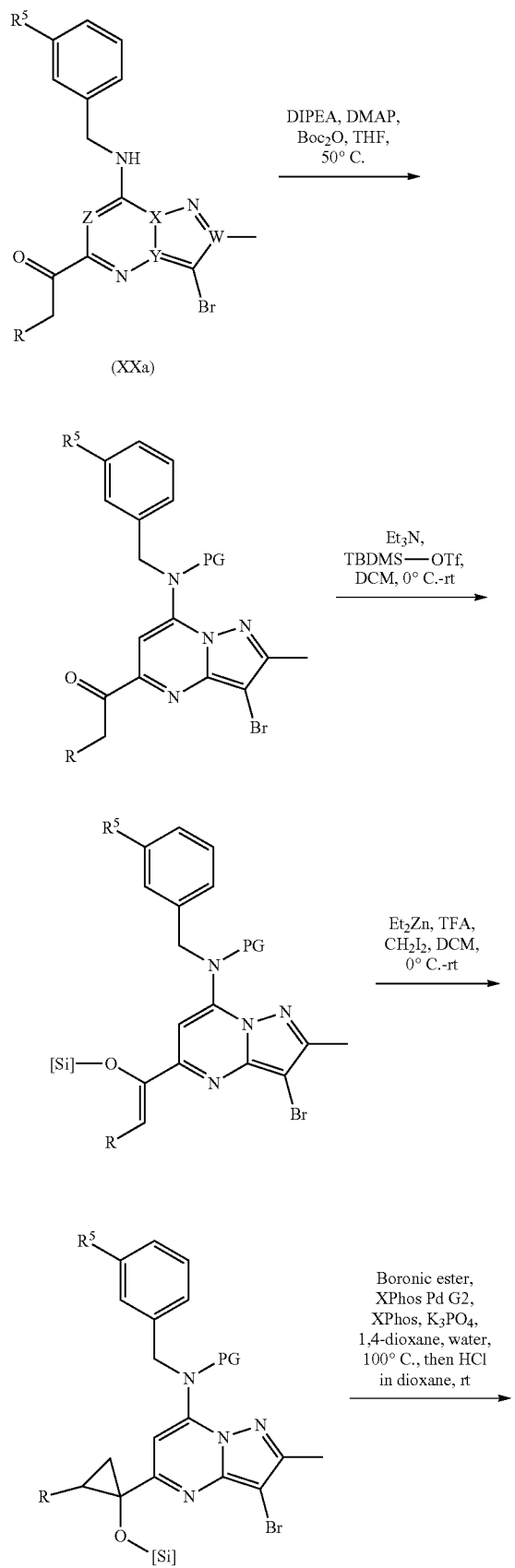
(XXa)
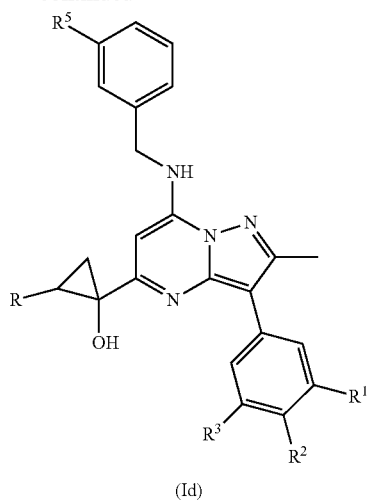
(Id)
Compounds of formula (Ie), i.e. compounds of formula (I) where $R^{4a}$ is H and $R^{4b}$ and $R^{4c}$ together with the carbon to which they are attached form an unsubstituted tetrahydropyran ring, may be prepared from compounds of formula (XXI) according to reaction scheme 15.
Scheme 15
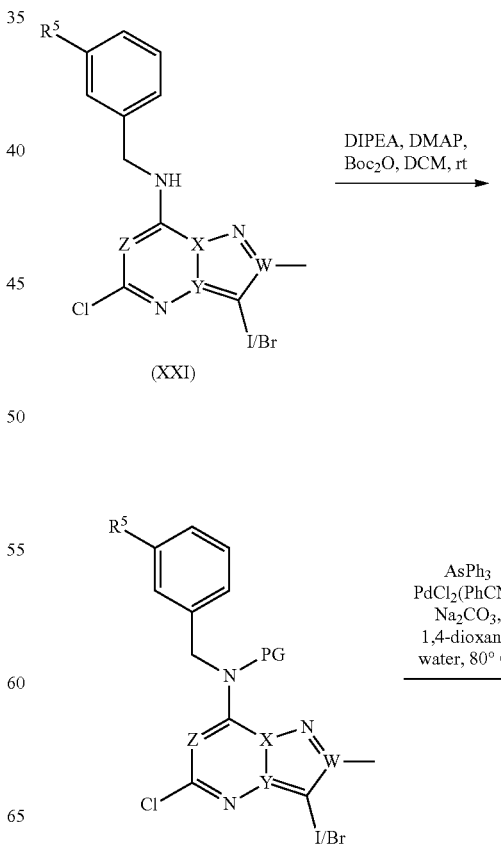
(XXI)

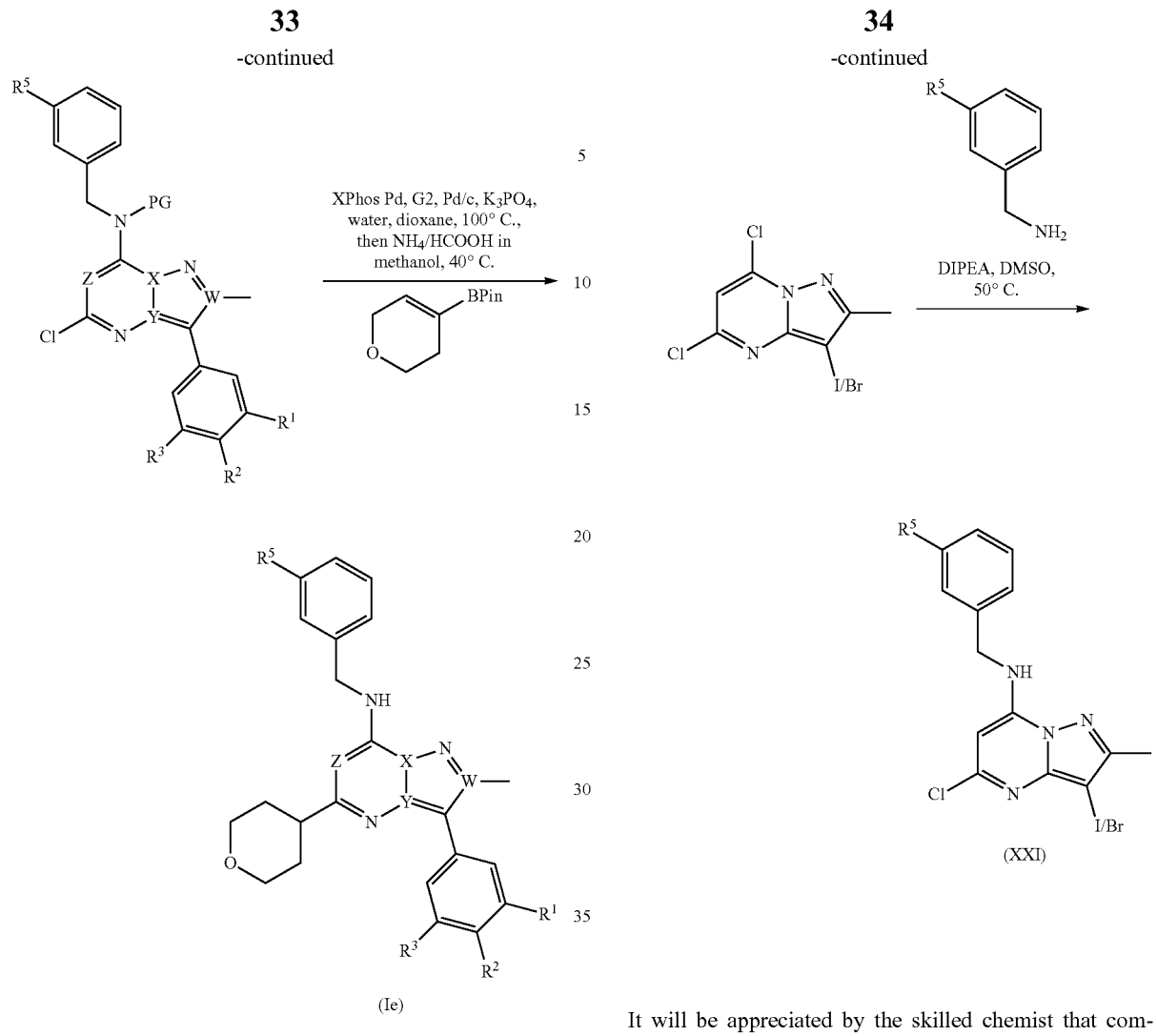

Compounds of formula (XXI) may be prepared from compounds of formula (XXII) according to reaction scheme (16).

It will be appreciated by the skilled chemist that compounds of formula (I) may also be prepared by elaboration at $R^1$ as the last step. In reaction scheme 17, compounds of formula (If) i.e. compounds of formula (I) where $R^1$ is —C(=O)N($R^{1a}R^{1b}$), may be prepared from compounds of formula (XXIII).

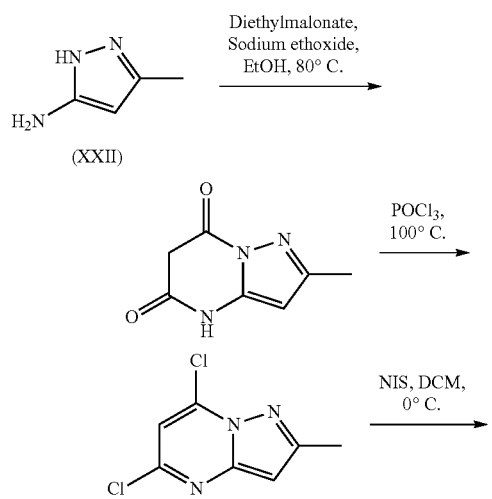

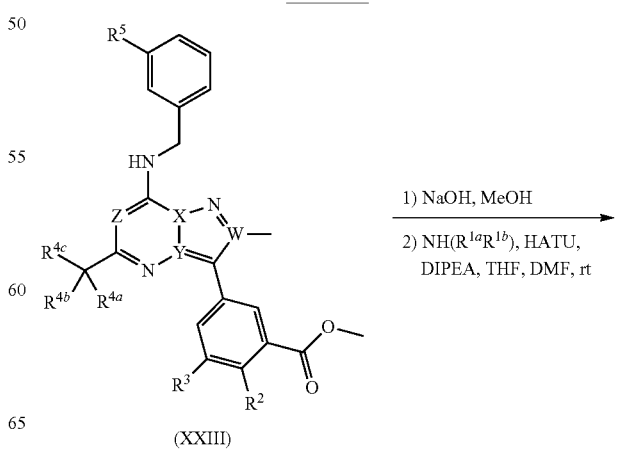

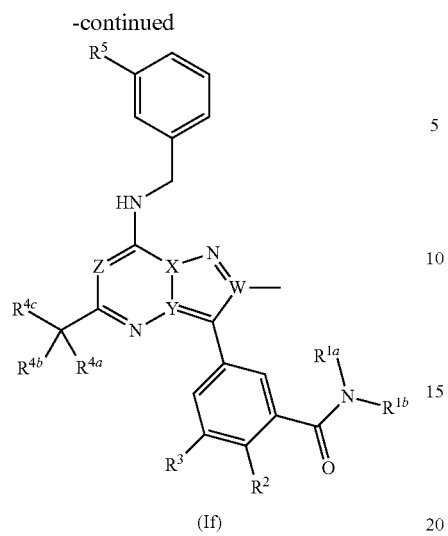

(If)

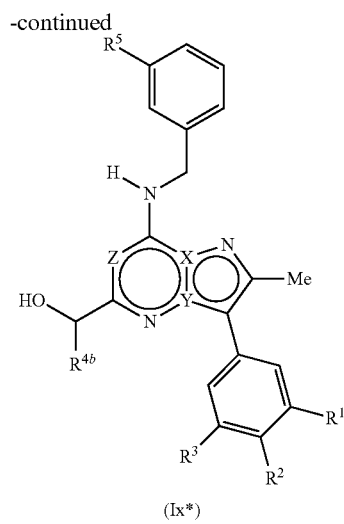

(Ix*)

It will be appreciated by the skilled chemist that compounds of formula (I) may be converted to other compounds of formula (I) by methods known in the art. In addition, intermediate compounds described in the reaction schemes above may be converted to other intermediates and then converted using the methods described to provide compounds of formula (I). It will also be appreciated that compounds of formula (I) may be prepared using a different sequence of the transformations described in the reaction schemes, including incorporation of protection/deprotection steps where appropriate.

General Route to Formula (Ia)

Compounds of formula (Ix*), i.e. compounds of formula (Ia) where $R^{4a}$ is H, may be prepared according to reaction scheme 1* by treating (IIa*) with a suitable Grignard reagent (such as methylmagnesium bromide) in a solvent (for example THF) followed by deprotection with a suitable acid (for example 4 M HCl in 1,4-dioxane) in a solvent (for example methanol).

Compounds of formula (IIa*) may be prepared according to reaction scheme 2a* by treating compounds of formula (IIIa*) with a boronic ester (for example 2-((2-methoxy-5-(4,4,5,5-tetramethyl-1,3,2-dioxaborolan-2-yl)phenyl)sulfonyl)ethan-1-ol) in a solvent (for example 1,4-dioxane and water) in the presence of a catalyst (for example PdCl$_2$(dppf)) and a base (for example potassium fluoride).

Scheme 2a*

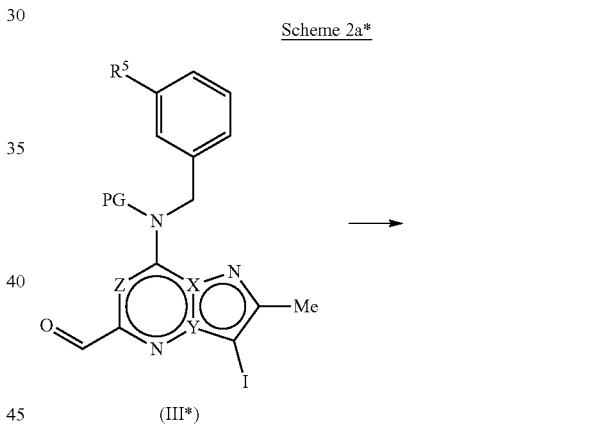

(III*)

Scheme 1*

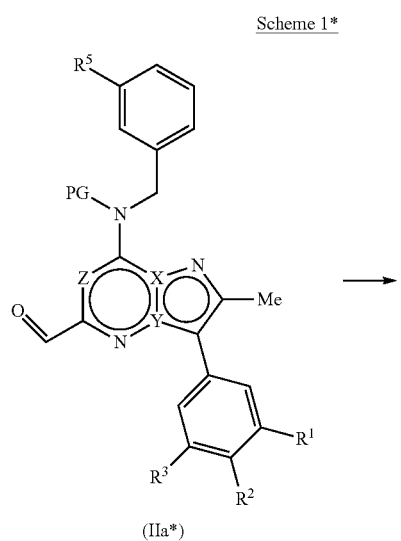

(IIa*)

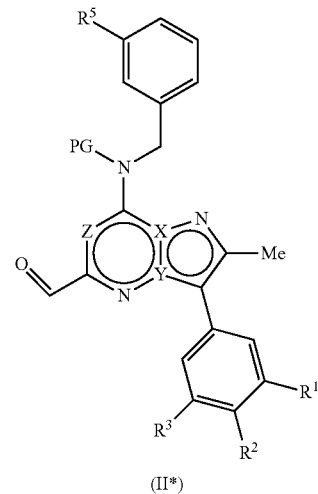

(II*)

Compounds of formula (III*) may be prepared according to reaction scheme 3* from compounds of formula (IV*) by treatment of (IV*) with a suitable oxidising agent (for example DMP) in a solvent (for example DCM).

Scheme 3*

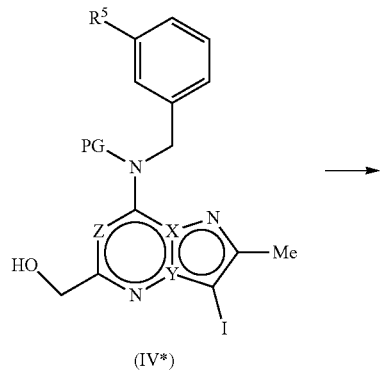

(IV*)

↓

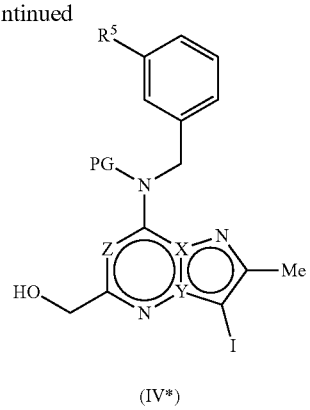

(IV*)

Compounds of formula (V*) may be prepared according to reaction scheme 5* from compounds of formula (VI*) (where L is Cl or Br or a mixture of compounds of formula (VI) where L is Cl and Br) by treatment with an amine (for example (3-(1-methyl-1H-imidazol-2-yl)phenyl)methylamine) and a base (for example DIPEA) in a solvent (for example DMSO).

Scheme 5*

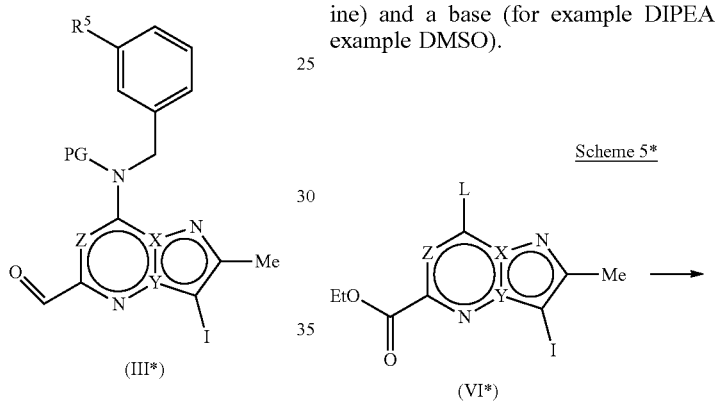

(III*)

(VI*)

Compounds of formula (IV*) may be prepared according to reaction scheme 4* from compounds of formula (V*). Firstly the amine is protected with an appropriate amine protecting group (for example tert-butylcarbamate via treatment with appropriate reagents for example di-tert-butyl dicarbonate, DIPEA and DMAP in DCM). Secondly the ester is reduced to the primary alcohol with a suitable reducing agent (for example sodium borohydride) in a solvent (for example ethanol).

Scheme 4*

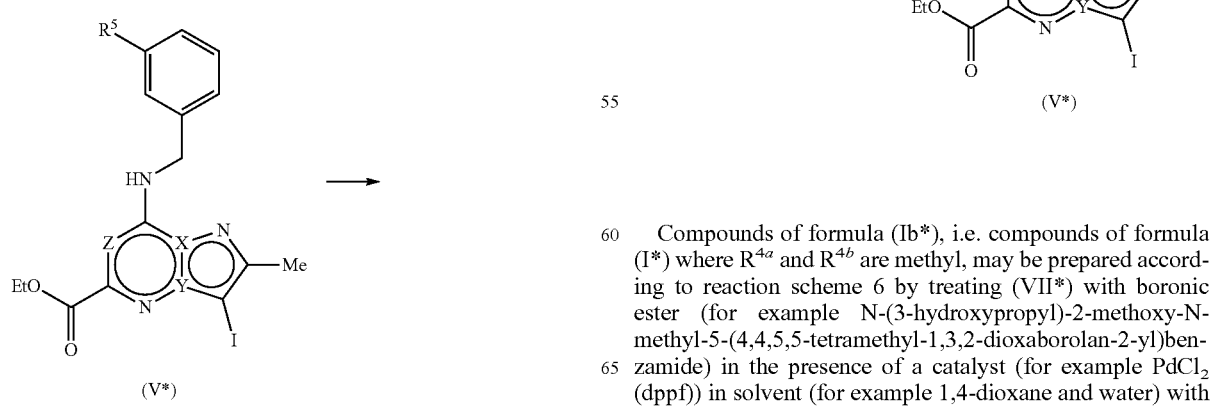

(V*)

(V*)

Compounds of formula (Ib*), i.e. compounds of formula (I*) where $R^{4a}$ and $R^{4b}$ are methyl, may be prepared according to reaction scheme 6 by treating (VII*) with boronic ester (for example N-(3-hydroxypropyl)-2-methoxy-N-methyl-5-(4,4,5,5-tetramethyl-1,3,2-dioxaborolan-2-yl)benzamide) in the presence of a catalyst (for example PdCl$_2$(dppf)) in solvent (for example 1,4-dioxane and water) with base (for example sodium carbonate).

Scheme 6*

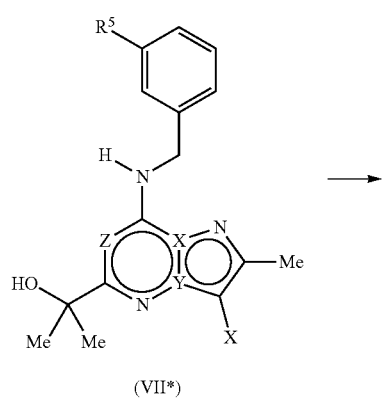

(VII*)

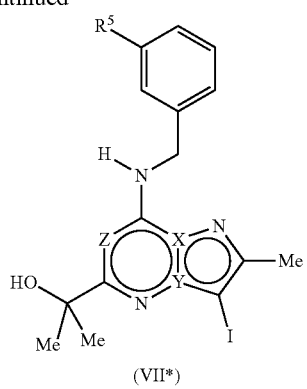

(VII*)

Compounds of formula (VIa*). i.e. compounds of formula (VI*) (see scheme 5*) where X is N, Y is C, Z is C and L is Cl, may be prepared according to reaction scheme 8*. Firstly compounds of formula (VIII*) may be obtained by condensation of esters (for example the sodium salt of diethyl oxalacetate) and compounds of formula (IX*) using an acid (such as HCl) in a solvent (such as ethanol) with heat (for example 85° C.) to give compounds of formula (VIII*). Secondly treatment of (VIII*) with a chlorinating reagent (for example $POCl_3$) with heat (for example at 90° C.) gives compounds of formula (X*). Treatment of compounds of formula (X*) with an iodine source (for example NIS) in a solvent (for example DCM) gives compounds of formula (VIa*).

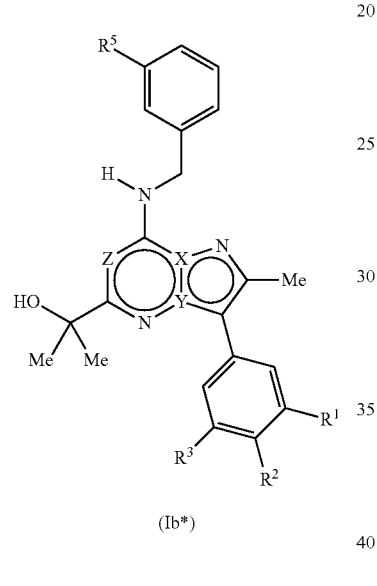

(Ib*)

Scheme 8*

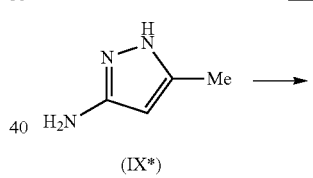

(IX*)

Compounds of formula (VII*) may be prepared from compounds of formula (V*) according to reaction scheme 7* by treating (V*) with a Grignard reagent (for example methylmagnesium bromide) in a solvent (for example DCM).

Scheme 7*

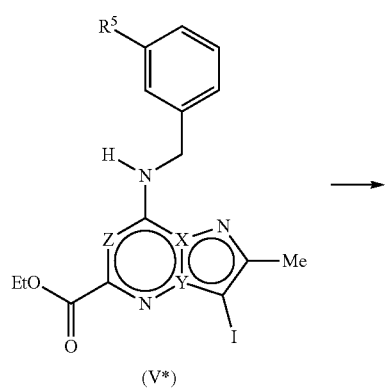

(V*)

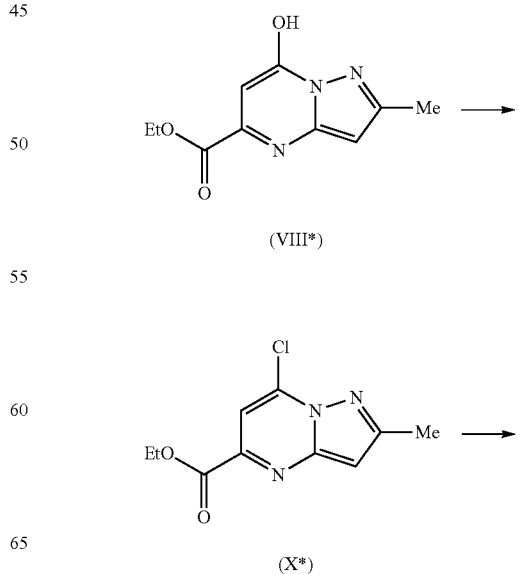

(VIII*)

(X*)

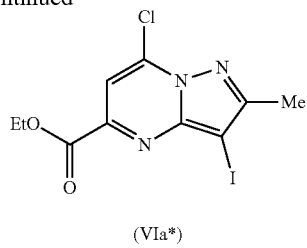

(VIa*)

A mixture of compounds of formula (VIb*), i.e. compounds of formula (VI*) (see scheme 5*) where X is C, Y is N, Z is C and L is Cl and Br, may be prepared according to reaction scheme 9 in a number of steps from compounds (XI*). Firstly compounds of formula (XI*) are treated with a brominating agent for example N-bromosuccinimide and sodium bicarbonate in a solvent (for example methanol) to give compounds of formula (XII*). Secondly, treating compounds of formula (XII*) with 1-chloropropan-2-one at elevated temperature (for example at 90° C.) gives a mixture of compounds of formula (XIII*). Iodination of a mixture of compounds of formula (XIII*) with, for example N-iodosuccinimide, in a solvent (for example DMF) gives the mixture of compounds of formula (VIb*).

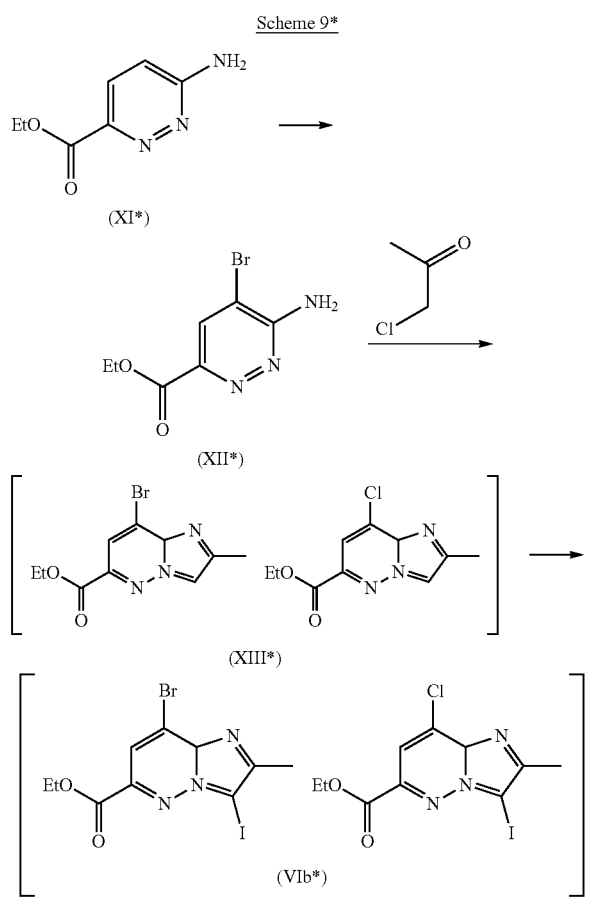

Compounds of formula (VIc*), i.e. compounds of formula (VI*) (see scheme 5*) where X is N, Y is C, Z is N and L is Cl, may be prepared in a number of steps from compounds of formula (XIV*) according to reaction scheme 10*.

Firstly, compounds of formula (XIV*) may be reacted with methyl cyanoformate to give compounds of formula (XV*). Secondly, compounds of formula (XV*) may be cyclised using carbonyldiimidazole in a solvent (for example DMSO) or alternatively using diethyl carbonate in sodium ethoxide and ethanol to give compounds of formula (XVI*). Compounds of formula (XVI*) may then be chlorinated using for example POCl$_3$, with heat (for example at 90° C.) to give compounds of formula (XVII*). Iodination using for example N-iodosuccinimide, in a solvent (for example DMF) gives the compounds of formula (VIc*).

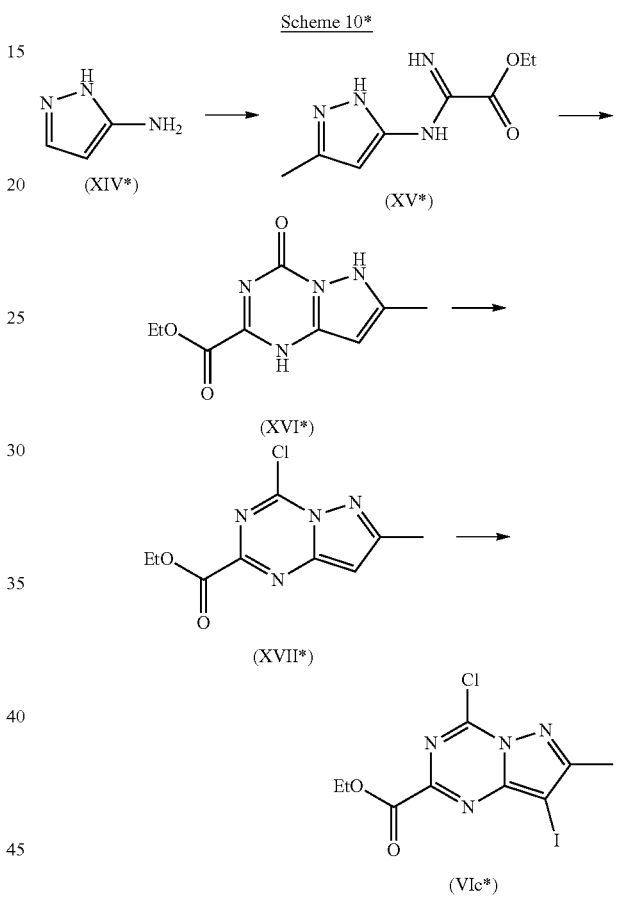

It will be appreciated by the skilled chemist that compounds of formula (Ia) may be converted to other compounds of formula (Ia) by methods known in the art. In addition, intermediate compounds described in the reaction schemes above may be converted to other intermediates and then converted using the methods described to provide compounds of formula (Ia). It will also be appreciated that compounds of formula (Ia) may be prepared using a different sequence of the the transformations described in the reaction schemes, including incorporation of protection/deprotection steps where appropriate.

Methods of Use

The compounds of the invention have been shown to be potent inhibitors of PI4KIIIβ. Further the compounds of the invention are selective inhibitors of PI4KIIIβ. Compounds of the invention may be useful in treating or preventing viral infections and disorders caused or exacerbated by viral infections. Disorders that are particularly caused or exacerbated by viral infections include COPD, asthma, cystic fibrosis, bronchiectasis, congestive heart failure, acute respiratory distress syndrome and acute lung injury. In addition disorders that are caused or exacerbated by rhinoviral infections include bronchiolitis, otitis media, sinusitis and acute bronchitis. Also, rhinoviral infections may cause a secondary bacterial infection in children, the elderly and immunosuppressed. Such a secondary bacterial infection may cause pneumonia.

As used herein, 'treat', 'treatment' or 'treating' in reference to a disorder means: (1) to ameliorate the disorder or one or more of the biological manifestations of the disorder; (2) to interfere with (a) one or more points in the biological cascade that leads to or is responsible for the disorder, or (b) one or more of the biological manifestations of the disorder; (3) to alleviate one or more of the symptoms or effects associated with the disorder; or (4) to slow the progression of the disorder or one or more of the biological manifestations of the disorder.

As used herein, 'patient' refers to a human (including adults and children) or other animal. In one embodiment, 'patient' refers to a human.

It is envisaged that the compounds of the invention may be administered topically, for example by inhalation or intranasally. Inhalation refers to administration into the patient's lungs whether inhaled through the mouth or through the nasal passages. In one embodiment, the compounds of formula (I) or pharmaceutically acceptable salts thereof may be administered topically. In another embodiment, the compounds of formula (I) or pharmaceutically acceptable salts thereof may be administered by inhalation. In a further embodiment, the compounds of formula (I) or pharmaceutically acceptable salts thereof may be administered intranasally. In a further embodiment, the compounds of formula (I) or pharmaceutically acceptable salts thereof may be administered intraoculaly. In a further embodiment, the compounds of formula (I) or pharmaceutically acceptable salts thereof may be administered aurally.

The compounds of the invention may be administered once per day or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages for inhaled administration range from 0.2 µg to 0.02 mg per kg of total body weight, for example from 0.5 µg to 0.01 mg per kg of total body weight. For example, daily dosages for inhaled administration may be from 20 µg to 2.0 mg per patient, such as 50 µg to 1.0 mg per patient.

Additionally, the compounds of the invention may be administered as prodrugs. As used herein, a 'prodrug' of a compound of the invention is a functional derivative which, upon administration to a patient, liberates the compound of the invention in vivo. Administration of a compound of the invention as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

While not wanting to be bound by any particular theory, it is thought that the compounds of the invention are able to inhibit the activity of the host cellular enzyme, PI4KIIIβ and thereby reduce the ability of the virus to replicate inside a host cell. Many viruses use PI4K to generate membranes enriched in phosphatidylinositol-4-phosphate (PI4P), which can be used as replication platforms. Viral replication machinery is assembled on these platforms as a supramolecular complex and the PI4P lipids help to enable viral RNA synthesis. Such intracellular lipid platforms create a more favorable environment for the virus to efficiently replicate itself. By disrupting the ability of the virus to utilitze PI4Ks, and PI4KIIIβ in particular, to create these lipid platforms and facilitate viral replication, viral infections can be treated and/or prevented.

Therefore according to a further aspect, the invention thus provides a method of treating a viral infection comprising administering a compound of formula (I), or a pharmaceutically acceptable salt thereof, to a patient in need thereof.

According to a further aspect, the invention provides a method of treating a disorder caused or exacerbated by a viral infection comprising administering a compound of formula (I), or a pharmaceutically acceptable salt thereof, to a patient in need thereof.

According to a further aspect, the invention provides a method of treating a secondary bacterial infection caused by a viral infection comprising administering a compound of formula (I), or a pharmaceutically acceptable salt thereof, to a patient in need thereof.

According to a further aspect, the invention provides a compound of formula (I), or a pharmaceutically acceptable salt thereof, for use in therapy.

According to a further aspect the invention provides a compound of formula (I), or a pharmaceutically acceptable salt thereof for use in the treatment of a viral infection.

According to a further aspect the invention provides a compound of formula (I), or a pharmaceutically acceptable salt thereof for use in the treatment of a disorder caused or exacerbated by a viral infection. In an embodiment, the disorder is COPD, cystic fibrosis, bronchiectasis, asthma or congestive heart failure. In a further embodiment, the disorder is COPD or asthma. In a still further embodiment, the disorder is COPD.

According to a further aspect the invention provides a compound of formula (I), or a pharmaceutically acceptable salt thereof for use in the treatment of a secondary bacterial infection caused by a bacterial infection.

According to a further aspect the invention provides the use of a compound of formula (I), or a pharmaceutically acceptable salt thereof, in the manufacture of a medicament for treating a viral infection.

According to a further aspect the invention provides the use of a compound of formula (I), or a pharmaceutically acceptable salt thereof, in the manufacture of a medicament for treating a disorder caused or exacerbated by a viral infection.

According to a further aspect the invention provides the use of a compound of formula (I), or a pharmaceutically acceptable salt thereof, in the manufacture of a medicament for treating a secondary bacterial infection caused by a viral infection.

In certain patients such as those with a compromised immune system or cardiopulmonary co-morbidities who have a heightened risk of severe illness following viral infection, it is envisaged that the compounds of the invention may be administered prophylactically so as to prevent infection taking hold and thereby avoiding exacerbations of the disorder, for example COPD, cystic fibrosis, bronchiectasis, asthma or congestive heart failure. It will be appreciated that 'prevention' is not an absolute term. In medicine, 'prevention' is understood to refer to the prophylactic administration of a drug to substantially diminish the likelihood or severity of a disorder or to delay the onset of such a disorder. Prophylactic administration may be particularly advisable when there is a heightened risk of infection, for example, in the case of HRV during the winter months.

According to a further aspect the invention provides a method of preventing a viral infection comprising administering a compound of formula (I), or a pharmaceutically acceptable salt thereof, to a patient in need thereof.

According to a further aspect the invention provides a method of preventing a disorder caused or exacerbated by a viral infection comprising administering a compound of formula (I), or a pharmaceutically acceptable salt thereof, to a patient in need thereof. In an embodiment, the disorder is COPD, cystic fibrosis, bronchiectasis, asthma or congestive heart failure. In a further embodiment, the disorder is COPD or asthma. In a still further embodiment, the disorder is COPD.

According to a further aspect the invention provides a compound of formula (I), or a pharmaceutically acceptable salt thereof for preventing a viral infection.

According to a further aspect the invention provides a compound of formula (I), or a pharmaceutically acceptable salt thereof for preventing a disorder caused or exacerbated by a viral infection. In an embodiment, the disorder is COPD, cystic fibrosis, bronchiectasis, asthma or congestive heart failure. In a further embodiment, the disorder is COPD or asthma. In a still further embodiment, the disorder is COPD.

According to a further aspect the invention provides the use of a compound of formula (I), or a pharmaceutically acceptable salt thereof, in the manufacture of a medicament for preventing a viral infection.

According to a further aspect the invention provides the use of a compound of formula (I), or a pharmaceutically acceptable salt thereof, in the manufacture of a medicament for preventing a disorder caused or exacerbated by a viral infection. In an embodiment, the disorder is COPD, cystic fibrosis, bronchiectasis, asthma or congestive heart failure. In a further embodiment, the disorder is COPD or asthma. In a still further embodiment, the disorder is COPD.

In addition the compounds of the invention may be prophylactically administered to healthy humans if they are to be exposed to a heightened risk of viral infection, for example during a SARS outbreak or in a nursing or care home environment when several residents have contracted an HRV infection. Therefore according to a further aspect the invention provides a method of preventing a viral infection comprising administering a compound of formula (I), or a pharmaceutically acceptable salt thereof, to a human in need thereof.

The following embodiments apply to each of the above aspects relating to medical use. In an embodiment the virus is a single stranded RNA virus. In a further embodiment the virus is a positive-sense, single-stranded RNA virus. In an embodiment the viral infection is human rhinovirus (HRV). In a further embodiment the viral infection is HRV wherein the disorder caused by the virus is the common cold. In a further embodiment the viral infection is HRV wherein the disorder caused by the virus is bronchiolitis, pneumonia, otitis media, sinusitis or acute bronchitis. In a further embodiment the secondary bacterial infection causes pneumonia. In a further embodiment, disorders exacerbated by the virus are COPD, cystic fibrosis, bronchiectasis, asthma or congestive heart failure. In a further embodiment the HRV is HRV-A. In a further embodiment the HRV is HRV-B. In a further embodiment the HRV is HRV-C. In a further embodiment, the compound of formula (I) is administered at the onset of nasal symptoms of HRV to prevent lung-HRV infection, thereby reducing the frequency and severity of asthma exacerbations. In a further embodiment, the compound of formula (I) is administered at the onset of nasal symptoms of HRV to prevent lung-HRV infection, thereby reducing the frequency and severity of COPD exacerbations. In a further embodiment, the compound of formula (I) is administered at the onset of nasal symptoms of HRV to prevent lung-HRV infection, thereby reducing the frequency and severity of cystic fibrosis exacerbations. In a further embodiment, the compound of formula (I) is administered at the onset of nasal symptoms of HRV to prevent lung-HRV infection, thereby reducing the frequency and severity of congestive heart failure exacerbations.

In an embodiment the viral infection is coronavirus wherein the disease or condition is severe acute respiratory syndrome (SARS).

Formulations

The compounds of the invention will normally, but not necessarily, be formulated into pharmaceutical formulations prior to administration to a patient. According to a further aspect the invention provides a pharmaceutical formulation comprising a compound of formula (I), or a pharmaceutically acceptable salt thereof, and a pharmaceutically acceptable excipient. According to a further aspect the invention provides a pharmaceutical formulation for treating a viral infection comprising a compound of formula (I) or a pharmaceutically acceptable salt thereof. According to a further aspect the invention provides a pharmaceutical formulation for treating a disorder caused or exacerbated by a viral infection comprising a compound of formula (I) or a pharmaceutically acceptable salt thereof. According to a further aspect the invention provides a pharmaceutical formulation for treating a secondary bacterial infection caused by a viral infection, comprising a compound of formula (I) or a pharmaceutically acceptable salt thereof. According to a further aspect the invention provides a pharmaceutical formulation for preventing a viral infection comprising a compound of formula (I) or a pharmaceutically acceptable salt thereof. According to a further aspect the invention provides a pharmaceutical formulation for preventing a disorder caused or exacerbated by a viral infection comprising a compound of formula (I) or a pharmaceutically acceptable salt thereof.

As used herein, 'pharmaceutically acceptable excipient' means a pharmaceutically acceptable material, composition or vehicle involved in giving form or consistency to the pharmaceutical formulation. Each excipient must be compatible with the other ingredients of the pharmaceutical formulation when commingled such that interactions which would substantially reduce the efficacy of the compound of the invention when administered to a patient and interactions which would result in pharmaceutical formulations that are not pharmaceutically acceptable are avoided. In addition, each excipient must of course be pharmaceutically acceptable e.g. of sufficiently high purity.

It is envisaged that the compounds of the invention may be administered topically, for example by inhalation, intranasally, transdermally, intraocularly or aurally.

According to a further aspect the invention is directed to a dosage form adapted for administration to a patient by inhalation, for example, as a dry powder, an aerosol, a suspension or a solution formulation.

Dry powder formulations for delivery to the lung by inhalation typically comprise a compound of the invention as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

The dry powder formulations for use in accordance with the present invention may be administered via inhalation devices. As an example, such devices can encompass capsules and cartridges of for example gelatin, or blisters of, for example, laminated aluminum foil. In various embodiments, each capsule, cartridge or blister may contain doses of formulation according to the teachings presented herein. Examples of inhalation devices may include those intended for unit dose or multi-dose delivery of formulation, including all of the devices set forth herein. As an example, in the case of multi-dose delivery, the formulation can be pre-metered (e.g., as in DISKUS, see GB2242134, U.S. Pat. Nos. 6,032,666, 5,860,419, 5,873,360, 5,590,645, 6,378,519 and 6,536,427 or Diskhaler, see GB 2178965, 2129691 and 2169265, U.S. Pat. Nos. 4,778,054, 4,811,731, 5,035,237) or metered in use (e.g. as in Turbuhaler, see EP 69715, or in the devices described in U.S. Pat. No. 6,321,747). An example of a unit-dose device is ROTAHALER (see GB 2064336). In one embodiment, the DISKUS inhalation device comprises an elongate strip formed from a base sheet having a plurality of recesses spaced along its length and a lid sheet peelably sealed thereto to define a plurality of containers, each container having therein an inhalable formulation containing the compound optionally with other excipients and additive taught herein. The peelable seal is an engineered seal, and in one embodiment the engineered seal is a hermetic seal. Preferably, the strip is sufficiently flexible to be wound into a roll. The lid sheet and base sheet will preferably have leading end portions which are not sealed to one another and at least one of the leading end portions is constructed to be attached to a winding means. Also, preferably the engineered seal between the base and lid sheets extends over their whole width. The lid sheet may preferably be peeled from the base sheet in a longitudinal direction from a first end of the base sheet.

A dry powder formulation may also be presented in an inhalation device which permits separate containment of two different components of the formulation, Thus, for example, these components are administrable simultaneously but are stored separately, e.g. in separate pharmaceutical formulations, for example as described in WO 03/061743 A1 WO 2007/012871 A1, WO2007/068896, as well as U.S. Pat. Nos. 8,113,199, 8,161,968, 8,511,304, 8,534,281, 8,746,242 and 9,333,310.

In one embodiment an inhalation device permitting separate containment of components is an inhaler device having two peelable blister strips, each strip containing pre-metered doses in blister pockets arranged along its length, e.g., multiple containers within each blister strip, e.g., ELLIPTA. Said device has an internal indexing mechanism which, each time the device is actuated, peels opens a pocket of each strip and positions the blisters so that each newly exposed dose of each strip is adjacent to the manifold which communicates with the mouthpiece of the device. When the patient inhales at the mouthpiece, each dose is simultaneously drawn out of its associated pocket into the manifold and entrained via the mouthpiece into the patient's respiratory tract. A further device that permits separate containment of different components is DUOHALER of Innovata. In addition, various structures of inhalation devices provide for the sequential or separate delivery of the pharmaceutical formulation(s) from the device, in addition to simultaneous delivery. Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 200 µg-10 mg of the compound of formula (I) or a pharmaceutically acceptable salt thereof.

Aerosols may be formed by suspending or dissolving a compound of the invention in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

According to a further aspect there is provided a pharmaceutical aerosol formulation comprising a compound of formula (I) or pharmaceutically acceptable salt thereof and a fluorocarbon or hydrogen-containing chlorofluorocarbon as propellant, optionally in combination with a surfactant and/or a cosolvent.

According to an embodiment, the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of a compound of the invention and a suitable powder base such as lactose or starch. Each capsule or cartridge may generally contain from 200 µg to 10 mg of the compound of the invention. Alternatively, the compound of the invention may be presented without excipients such as lactose.

The proportion of the compound of the invention in the local formulations according to the invention depends on the precise type of formulation to be prepared but will generally be within the range of from 0.01 to 10% by weight. Generally, for most types of preparations, the proportion used will be within the range of from 0.05 to 1%, for example from 0.1 to 0.5%.

Aerosol formulations are preferably arranged so that each metered dose or 'puff' of aerosol contains from 20 µg to 10 mg, preferably from 20 g to 5 mg, more preferably from about 20 µg to 0.5 mg of a compound of the invention. Administration may be once daily or several times daily, for example 2, 3, 4 or 8 times, giving for example 1, 2 or 3 doses each time. The overall daily dose with an aerosol will be within the range from 20 µg to 2.0 mg, for example from 50 µg to 1.0 mg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a compound of the invention in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the 'twin impinger' analytical process. As used herein reference to the 'twin impinger' assay means 'Determination of the deposition of the emitted dose in pressurised inhalations using apparatus A' as defined in British Pharmacopaeia 1988, pages A204-207, Appendix XVII C. Such techniques enable the 'respirable fraction' of the aerosol formulations to be calculated. One method used to calculate the 'respirable fraction' is by reference to 'fine particle fraction' which is the amount of active ingredient collected in the lower impingement chamber per actuation expressed as a percentage of the total amount of active ingredient delivered per actuation using the twin impinger method described above.

The term 'metered dose inhaler' or MDI means a unit comprising a can, a secured cap covering the can and a formulation metering valve situated in the cap. MDI system includes a suitable channelling device. Suitable channelling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO 96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO 96/32099). Preferably the canister is fitted with a cap assembly, wherein a drug-metering valve is situated in the cap, and said cap is crimped in place.

In one embodiment of the invention the metallic internal surface of the can is coated with a fluoropolymer, more preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. SPRAYMISER).

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing. Suspensions and solutions comprising a compound of the invention may also be administered to a patient via a nebuliser. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of the invention may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of formula (I) or pharmaceutically acceptable salt thereof. Preservatives may be added such as benzalkonium chloride or benzoic acid and salts thereof. Surfactant may be added particularly to improve the physical stability of suspensions. These include lecithin, disodium dioctylsulfosuccinate, oleic acid and sorbitan esters.

Formulations for administration to the nose may include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The compounds of the invention may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO 05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO 05/044354.

Pharmaceutical formulations adapted for intranasal administration wherein the carrier is a solid include a coarse powder having a particle size for example in the range 20 to 500 microns which is administered by rapid inhalation through the nasal passage from a container of the powder held close up to the nose. Suitable formulations wherein the carrier is a liquid, for administration as a nasal spray or as nasal drops, include aqueous or oil solutions of the compound of the invention.

Some of the disorders caused or exacerbated by viral infections my result in skin problems, for example skin rashes. Pharmaceutical formulations adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area. Over skin areas, occlusive dressings may advantageously be used. Continuous or prolonged delivery may be achieved by an adhesive reservoir system.

For intraocular or aural treatment formulations may be applied as a topical ointment or cream. When formulated in an ointment, the compound of formula (I) or a pharmaceutically acceptable salt thereof may be employed with either a paraffinic or a water-miscible ointment base. Alternatively, the compound of formula (I) or pharmaceutically acceptable salt thereof may be formulated in a cream with an oil-in-water cream base or a water-in-oil base.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Compounds or pharmaceutical formulations of the invention may be administered together with an anti-inflammatory agent such as a corticosteroid or a pharmaceutical formulation thereof, for the treatment of asthma exacerbated by viral infections, particularly HRV infections. For example, compounds of the invention may be formulated together with an anti-inflammatory agent, such as a corticosteroid, in a single formulation, such as a dry powder formulation for inhalation. Alternatively, a pharmaceutical formulation comprising a compound of the invention may be administered in conjunction with a pharmaceutical formulation comprising an anti-inflammatory agent, such as a corticosteroid, either simultaneously or sequentially. For example, a pharmaceutical formulation comprising a compound of the invention and a further pharmaceutical formulation comprising an anti-inflammatory agent, such as a corticosteroid, may each be held in device suitable for the simultaneous administration of both formulations via inhalation.

Suitable corticosteroids for administration together with compounds of the invention include fluticasone furoate, fluticasone propionate, beclomethasone diproprionate, budesonide, ciclesonide, mometasone furoate, triamcinolone, flunisolide and prednisolone. Suitable corticosteroids for administration together with compounds of the invention via inhalation include fluticasone furoate, fluticasone propionate, beclomethasone diproprionate, budesonide, ciclesonide, mometasone furoate, and flunisolide.

Therefore according to a further aspect, the invention provides a pharmaceutical formulation comprising a compound of formula (I) or a pharmaceutically acceptable salt thereof and one or more anti-inflammatory agents, such as a corticosteroid or an inhibitor of phosphatidylinositol-4,5-bisphosphate 3-kinase-delta (PI3Kδ).

According to a further aspect, the invention provides a method of treatment of asthma exacerbated by a viral infection, for example HRV, which method comprises administering to a subject in need thereof a therapeutically effective amount of a compound of formula (I) or a pharmaceutically acceptable salt thereof and one or more anti-inflammatory agents, such as a corticosteroid.

According to a further aspect, the invention provides a compound of formula (I) or a pharmaceutically acceptable salt thereof and one or more anti-inflammatory agents, such as a corticosteroid, for use in the treatment of asthma exacerbated by viral infection.

According to a further aspect, the invention provides the use of a compound of formula (I) or a pharmaceutically acceptable salt thereof and one or more anti-inflammatory agents, such as a corticosteroid, in the manufacture of a medicament for the treatment of asthma exacerbated by viral infection.

According to a further aspect, the invention provides a method of treatment of cystic fibrosis exacerbated by a viral infection, for example HRV, which method comprises administering to a subject in need thereof a therapeutically effective amount of a compound of formula (I) or a pharmaceutically acceptable salt thereof and one or more anti-inflammatory agents, such as a corticosteroid.

According to a further aspect, the invention provides a compound of formula (I) or a pharmaceutically acceptable salt thereof and one or more anti-inflammatory agents, such as a corticosteroid, for use in the treatment of cystic fibrosis exacerbated by viral infection.

According to a further aspect, the invention provides the use of a compound of formula (I) or a pharmaceutically acceptable salt thereof and one or more anti-inflammatory agents, such as a corticosteroid, in the manufacture of a medicament for the treatment of cystic fibrosis exacerbated by viral infection.

According to a further aspect, the invention provides a method of treatment of congestive heart failure exacerbated by a viral infection, for example HRV, which method comprises administering to a subject in need thereof a therapeutically effective amount of a compound of formula (I) or a pharmaceutically acceptable salt thereof and one or more anti-inflammatory agents, such as a corticosteroid.

According to a further aspect, the invention provides a compound of formula (I) or a pharmaceutically acceptable salt thereof and one or more anti-inflammatory agents, such as a corticosteroid, for use in the treatment of congestive heart failure exacerbated by viral infection.

According to a further aspect, the invention provides the use of a compound of formula (I) or a pharmaceutically acceptable salt thereof and one or more anti-inflammatory agents, such as a corticosteroid, in the manufacture of a medicament for the treatment of congestive heart failure exacerbated by viral infection.

The following embodiments apply to each of the above aspects relating to combinations with one or more anti-inflammatory agents.

In an embodiment the pharmaceutical formulation comprises one anti-inflammatory agent.

In one embodiment the anti-inflammatory agent is a corticosteroid.

In one embodiment the corticosteroid is fluticasone furoate.

In one embodiment the corticosteroid is fluticasone propionate.

In one embodiment the anti-inflammatory agent is an inhibitor of phosphatidylinositol-4,5-bisphosphate 3-kinase-delta (PI3Kδ), such as nemiralisib (see Sriskantharajah et al., Annals of the New York Academy of Sciences, (2013), 1280, 35; Cahn et al., Pulmonary Pharmacology and Therapeutics, (2017), 46, 69; and Stark et al., Current Opinion in Pharmacology, (2015), 23, 82).

Compounds or pharmaceutical formulations of the invention may be administered together with one or more bronchodilators, or pharmaceutical formulations thereof, for the treatment of COPD exacerbated by viral infection. For example, compounds of the invention may be formulated together with one or more bronchodilators in a single formulation, such as a dry powder formulation for inhalation. Alternatively, a pharmaceutical formulation comprising a compound of the invention may be administered in conjunction with a pharmaceutical formulation comprising one or more bronchodilators, either simultaneously or sequentially. In a further alternative, a formulation comprising a compound of the invention and a bronchodilator may be administered in conjunction with a pharmaceutical formulation comprising a further bronchodilator. For example, a pharmaceutical formulation comprising a compound of the invention and a further pharmaceutical formulation comprising one or more bronchodilators may each be held in device suitable for the simultaneous administration of both formulations via inhalation.

Suitable bronchodilators for administration together with compounds of the invention include $\beta_2$-adrenoreceptor agonists and anticholinergic agents. Examples of $\beta_2$-adrenoreceptor agonists, include, for example, vilanterol, salmeterol, salbutamol, formoterol, salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt of salbutamol or the fumarate salt of formoterol. Examples of anticholinergic agents include umeclidinium (for example as the bromide), ipratropium (for example, as the bromide), oxitropium (for example, as the bromide) and tiotropium (for example, as the bromide). In one embodiment, a compound of the invention may be administered together with a $\beta_2$-adrenoreceptor agonist, such as vilanterol, and an anticholinergic agent, such as, umeclidinium.

According to a further aspect the invention provides a pharmaceutical formulation comprising a compound of formula (I) or a pharmaceutically acceptable salt thereof and one or more bronchodilators.

According to a further aspect the invention provides a method of treatment of COPD exacerbated by a viral infection which method comprises administering to a subject in need thereof a therapeutically effective amount of a compound of formula (I) or a pharmaceutically acceptable salt thereof and one or more bronchodilators.

According to a further aspect, the invention provides a compound of formula (I) or a pharmaceutically acceptable salt thereof and one or more bronchodilators for use in the treatment of COPD exacerbated by viral infection.

According to a further aspect, the invention provides the use of a compound of formula (I) or a pharmaceutically acceptable salt thereof and one or more bronchodilators, in the manufacture of a medicament for the treatment of COPD exacerbated by a viral infection.

The following embodiments apply to each of the above aspects relating to combinations with one or more bronchodilators.

In an embodiment the one or more bronchodilators comprise one or more $\beta_2$-adrenoreceptor agonists.

In an embodiment the one or more bronchodilators comprise one or more anticholinergic agents.

In an embodiment the one or more bronchodilators comprise one or more $\beta_2$-adrenoreceptor agonists and one or more anticholinergic agents.

In an embodiment the one or more bronchodilators comprise a $\beta_2$-adrenoreceptor agonist and an anticholinergic agent.

In an embodiment the one or more bronchodilators comprise one bronchodilator which is a $\beta_2$-adrenoreceptor agonist.

In an embodiment the one or more bronchodilators comprise one bronchodilator which is an anticholinergic agent.

In an embodiment, the $\beta_2$-adrenoreceptor agonist is vilanterol.

In an embodiment, the anticholinergic agent is umeclidinium. In a further embodiment, the anticholinergic agent is umeclidinium bromide.

According to a further aspect the invention provides a pharmaceutical formulation comprising a) a compound of formula (I) or a pharmaceutically acceptable salt thereof, b) one or more bronchodilators, and c) one or more anti-inflammatory agent.

According to a further aspect the invention provides a method of treatment of COPD exacerbated by a viral infection which method comprises administering to a subject in need thereof a therapeutically effective amount of a) a compound of formula (I) or a pharmaceutically acceptable salt thereof, b) one or more bronchodilators, and c) one or more anti-inflammatory agent.

According to a further aspect, the invention provides a) a compound of formula (I) or a pharmaceutically acceptable salt thereof, b) one or more bronchodilators, and c) one or more anti-inflammatory agent for use in the treatment of COPD exacerbated by viral infection.

According to a further aspect, the invention provides the use of a) a compound of formula (I) or a pharmaceutically acceptable salt thereof, b) one or more bronchodilators, and c) one or more anti-inflammatory agent in the manufacture of a medicament for the treatment of COPD exacerbated by a viral infection.

The following embodiments apply to each of the above aspects relating to combinations with one or more bronchodilators and one or more anti-inflammatory agents.

In an embodiment the one or more bronchodilators comprise one or more $\beta_2$-adrenoreceptor agonists.

In an embodiment the one or more bronchodilators comprise one or more anticholinergic agents.

In an embodiment the one or more bronchodilators comprise one or more $\beta_2$-adrenoreceptor agonists and one or more anticholinergic agents.

In an embodiment the one or more bronchodilators comprise a $\beta_2$-adrenoreceptor agonist and an anticholinergic agent.

In an embodiment the one or more bronchodilators comprise one bronchodilator which is a $\beta_2$-adrenoreceptor agonist.

In an embodiment the one or more bronchodilators comprise one bronchodilator which is an anticholinergic agent.

In an embodiment, the $\beta_2$-adrenoreceptor agonist is vilanterol.

In an embodiment, the anticholinergic agent is umeclidinium. In a further embodiment, the anticholinergic agent is umeclidinium bromide.

In an embodiment the one or more anti-inflammatory agent is a corticosteroid.

In a further embodiment the corticosteroid is fluticasone furoate.

In a further embodiment the corticosteroid is fluticasone propionate.

In a further embodiment the one or more bronchodilators are vilanterol and umeclidinium.

In a further embodiment the one or more bronchodilators are both vilanterol and umeclidinium, and the one or more anti-inflammatory agents is fluticasone furoate.

In a further embodiment the one or more bronchodilators are both vilanterol and umeclidinium, and the one or more anti-inflammatory agents is fluticasone propionate.

The compounds of the invention may possess an improved profile over known PI4KIIIβ inhibitors, for example, compared to known PI4KIIIβ inhibitors certain compounds of the invention may have one or more of the following properties:

(i) more potent PI4KIIIβ inhibitory activity;
(ii) improved selectivity for PI4KIIIβ;
(iii) increased enzyme $T_{1/2}$;
(iv) improved cell potency;
(v) Improved lung retention
(vi) improved solubility; and/or
(vii) lower levels of compound accumulating in body tissue.

As stated above, when administered, lower levels of compounds of the present invention may accumulate in body tissue compared to known PI4KIIIβ inhibitors. In particular, compounds of the invention may have lower accumulation levels in the spleen. Previous studies have shown that accumulation of PI4KIIIβ inhibitors in the spleen may be disadvantageous e.g. may cause apoptosis.

Supporting Compounds

The following supporting compounds illustrate the invention, as guidance to the skilled artisan to prepare and use the compounds, formulations, and methods of the invention. While particular embodiments of the invention are described, the skilled artisan will appreciate that various changes and modifications can be made. References to preparations carried out in a similar manner to, or by the general method of, other preparations, may encompass variations in routine parameters such as time, temperature, workup conditions, changes in reagent amounts etc.

Reactions involving metal hydrides (including sodium hydride) and organo-metallic reagents are carried out under argon or nitrogen unless otherwise specified.

In the following Intermediates and Supporting Compounds, where the relative stereochemistry of the compound has been identified, this is indicated both in the name and structure of the compound.

In certain of the following Intermediates and Supporting compounds, starting materials are identified by reference to other Intermediate or Compound numbers. This does not signify that the actual material (or "batch") obtained from any particular Intermediate or Supporting Compound was necessarily used in a subsequent step exemplified herein.

Unless stated otherwise, starting materials were commercially available. All solvents and commercial reagents were of laboratory grade and were used as received.

Where the absolute stereochemistry is known and the compound is a single enantiomer, the bold or hashed wedges symbols (━/ ͟ ) are used as appropriate. Where the absolute stereochemistry is unknown but is known to be a single enantiomer, a star (*) is used.

The names of the intermediates and Supporting compounds have been obtained using the compound naming program within "ChemBioDraw Ultra v12" or "ACD Name Pro 6.02".

As used herein the symbols and conventions used in these processes, schemes and examples are consistent with those used in the contemporary scientific literature, for example, the Journal of the American Chemical Society.

Abbreviations

The following list provides definitions of certain abbreviations and symbols as used herein. It will be appreciated that the list is not exhaustive, but the meaning of those abbreviations and symbols not herein below defined will be readily apparent to those skilled in the art. In describing the invention, chemical elements are identified in accordance with the Periodic Table of the Elements.

Bu Butyl
m-CPBA Meta-Chloroperoxybenzoic acid
CV Column volume(s)
DCM Dichloromethane
DIBAL-H Diisobutylaluminium hydride
DIPEA N,N-Diisopropylethylamine
DMAP 4-Dimethylaminopyridine
DMP Dess-Martin periodinane
DMF N,N-Dimethylformamide
DMSO Dimethylsulfoxide
dppf 1,1'-Bis(diphenylphosphino)ferrocene
HATU 1-[Bis(dimethylamino)methylene]-1H-1,2,3-triazolo[4,5-b]pyridinium 3-oxide hexafluorophosphate
HCl Hydrochloric acid
IPA Iso-propanol
2-MeTHF 2-Methyltetrahydrofuran
NBS N-Bromosuccinimde
NIS N-Iodosuccinimde
rt Retention time
TFA Trifluoroacetic acid
THF Tetrahydrofuran
HPLC High performance liquid chromatography
MDAP Mass Directed Autopreparative HPLC
XPhos Dicyclohexyl(2',4',6'-triisopropyl-[1,1'-biphenyl]-3-yl)phosphane
XPhos Pd G2 Chloro(2-dicyclohexylphosphino-2',4',6'-triisopropyl-1,1'-biphenyl)[2-(2'-amino-1,1'-biphenyl)]palladium(II)

LCMS methods

Method A

Column: Acquity BEH $C_{18}$ (50 mm×2.1 mm, 1.7 μm). Mobile phase: A: 0.1% formic acid in water; B: 0.1% formic acid in acetonitrile. Time (min)/% B: 0/3, 0.4/3, 2.0/98, 3.4/98, 3.5/3, 4.0/3. Column temp: 35° C., Flow rate: 0.6 mL/min.

Method B

Column: XBridge BEH $C_{18}$ (50 mm×4.6 mm, 2.5 μM). Mobile phase: A: 5 mM ammonium bicarbonate; B: acetonitrile. Time (min)/% B: 0/5, 0.5/5, 1/15, 3.3/98, 5.2/98, 5.5/5, 6.0/5. Column temp: 35° C., Flow rate: 1.3 mL/min.

Method C

Column: Acquity BEH $C_{18}$ (50 mm×2.1 mm, 1.7 μm). Mobile phase: A: 0.1% formic acid in water; B: 0.1% formic acid in acetonitrile. Time (min)/% B: 0/3, 0.4/3, 2.5/98, 3.4/98, 3.5/3, 4.0/3. Column temp: 35° C., Flow rate: 0.6 mL/min.

Method D

Column: XBridge BEH $C_{18}$ (50 mm×4.6 mm, 2.5 μM). Mobile phase: A: 5 mM ammonium bicarbonate; B: acetonitrile. Time (min)/% B: 0/5, 1.5/15, 7/98, 9/98, 9.5/5, 10/5. Column temp: 35° C., Flow rate: 1.3 mL/min.
Method E
Column: Acquity BEH $C_{18}$ (50 mm×2.1 mm, 1.7 µm). Mobile phase: A: 0.05% formic acid in water; B: 0.05% formic acid in acetonitrile. Time (min)/% B: 0/3, 0.4/3, 3.2/98, 3.8/98, 4.2/3, 4.5/3. Column temp: 35° C., Flow rate: 0.6 mL/min.
Method F
Column: Acquity UPLC CSH $C_{18}$ column (50 mm×2.1 mm i.d. 1.7 µm) at 40° C. The solvents employed were: A=10 mM ammonium bicarbonate in water adjusted to pH 10 with ammonia solution. B=Acetonitrile. Time (min)/% B: 0/3, 0.05/3, 1.5/95, 1.9/95, 2.0/3. Flow rate: 1 mL/min. MS: Waters ZQ. Ionisation mode: Alternate-scan positive and negative electrospray Method G Column: Acquity BEH $C_{18}$ (50 mm×2.1 mm, 1.7 µm). Mobile phase: A: 0.1% formic acid in water; B: 0.1% formic acid in acetonitrile. Time (min)/% B: 0/3, 0.4/3, 3.2/98, 3.8/98, 4.2/3, 4.5/3. Column temp: 35° C., Flow rate: 0.6 mL/min.
Method H
Column: Acquity BEH $C_{18}$ (50 mm×2.1 mm, 1.7 µm). Mobile Phase: A: 5 mM Ammonium bicarbonate in water (pH 10); B: acetonitrile. Time (min)/% B: 0/3, 0.4/3, 2.5/98, 3.4/98, 3.5/3, 4.0/3. Column temp: 35° C., Flow Rate: 0.6 mL/min.
Method I
Column: Acquity BEH $C_{18}$ (100 mm×2.1 mm, 1.7 µm). Mobile phase: A: 0.05% TFA in water; B: acetonitrile. Time (min)/% B: 0/3, 0.4/3, 3.5/98, 4.5/98, 5.0/3, 5.5/3. Column temp: 35° C., Flow Rate: 0.45 mL/min.
Method J
Column: Acquity UPLC CSH $C_{18}$ (50 mm×2.1 mm, i.d. 1.7 µm) at 40° C. The solvents employed were: A=0.1% v/v solution of formic acid in water. B=0.1% v/v solution of formic acid in acetonitrile. Time (min)/% B: 0/3, 1.5/95, 1.9/95, 2.0/3. Flow rate: 1 mL/min. MS: Waters ZQ. Ionisation mode: Alternate-scan positive and negative electrospray
Method K
Column: XSelect CSH $C_{18}$ (150 mm×3.0 mm, 2.5 µm). Mobile phase: A: 0.05% TFA in water; B: 100% acetonitrile. Time (min)/% B: 0/3, 1/3, 8/98, 11/98, 11.1/3, 12/3. Column temp.: 35° C., Flow Rate: 0.7 mL/min.
Method L
Column: BEH $C_{18}$ (100 mm×2.1 mm, 1.7 µm). Mobile Phase: A: 0.1% TFA in water, B: 0.1% TFA in acetonitrile. Time (min)/% B: 0/3, 8.5/100, 9.0/100, 9.5/3, 10/3. Column temp.: 50° C., Flow Rate: 0.55 mL/min.
Method M
Column: CSH $C_{18}$ (100 mm×2.1 mm i.d. 1.7 µm). Mobile phase: A: 0.1% v/v solution of Formic Acid in Water; B: 0.1% v/v solution of Formic Acid in Acetonitrile. Time (min)/% B: 0/3, 8.5/99.9, 9/99.9, 9.5/3, 10/3. Column temp.: 50° C. Flow rate: 0.8 mL/min.
Mass Directed Automated Preparative HPLC (MDAP)
The methods for the Mass Directed Automated Preparative HPLC used for the purification of compounds are described below. Solvent elution gradients range between 0 to 99% of Solvent B in Solvent A and run over a time period of up to 25 min.
For all Methods (unless specified):
The DAD detection was 210 nm to 350 nm. MS Conditions: MS: aters ZQ
Ionisation mode: Alternate scan positive/negative Electrospray Scan Range: 100 to 1000 AMU. Scan Time: 0.2 s or 0.50 s. Inter scan Delay: 0.1 s or 0.2 s
Injection Volume: 1 mL or 3 mL
Method A
Column: Xselect CSH $C_{18}$ column (150 mm×30 mm i.d. 5 µm packing diameter) at ambient temp. The solvents employed were:
A=10 mM ammonium bicarbonate adjusted to pH 10 with ammonia in water.
B=acetonitrile.
Flow rate: 40 mL/min.
Method B
Column: Xselect CSH $C_{18}$ column (150 mm×30 mm i.d. 5 µm packing diameter) at ambient temp. The solvents employed were:
A=0.1% v/v solution of formic acid in water
B=0.1% v/v solution of formic acid in acetonitrile.
Flow rate: 40 mL/min.

Intermediate 1

2-Bromo-1-methyl-1H-imidazole

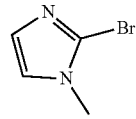

1-Methyl-1H-imidazole (20 g, 244 mmol) was dissolved in anhydrous THF (200 mL) under a nitrogen atmosphere. The solution was stirred at −78° C. and n-BuLi (167 mL, 268 mmol) was added dropwise slowly at −78° C. After 1 h, $CBr_4$ (97 g, 292 mmol) solution in anhydrous THF (200 mL) was added. The solution was stirred for 2 h at −78° C. and for 1 h at room temp. The reaction mixture was quenched with saturated aqueous ammonium chloride (300 mL), extracted with ethyl acetate (2×200 mL), dried over anhydrous sodium sulphate, filtered and evaporated under reduced pressure. The crude compound was purified by silica gel chromatography eluting with 60% ethyl acetate in pet. ether to afford the title compound. LCMS (method B): rt=1.89, $[M+H]^+$=161.

Intermediate 2

3-(1-Methyl-1H-imidazol-2-yl)benzonitrile

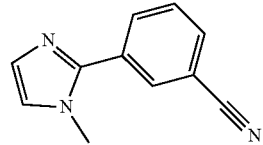

A mixture of (3-cyanophenyl)boronic acid (16 g, 109 mmol), 2-bromo-1-methyl-1H-imidazole (intermediate 1, 15.8 g, 98 mmol) and sodium carbonate (46.2 g, 436 mmol) in IPA (120 mL) and water (120 mL) was stirred and degassed with nitrogen for 20 min, and then $PdCl_2$(dppf)-DCM adduct (4.45 g, 5.44 mmol) was added and stirred at 130° C. for 18 h in a sealed tube. After cooling, the reaction mixture was diluted with ethyl acetate (300 mL), washed with water (300 mL), dried over anhydrous sodium sulphate, filtered and evaporated under reduced pressure. The crude compound was purified by silica gel chromatography eluting with 70% ethyl acetate in pet. ether to afford the title compound. LCMS (method C): rt=0.57, [M+H]⁺=184.

Intermediate 3

(3-(1-Methyl-1H-imidazol-2-yl)phenyl)methanamine

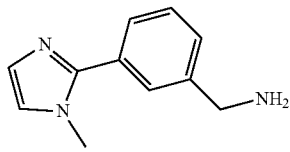

To a mixture of 3-(1-methyl-1H-imidazol-2-yl)benzonitrile (intermediate 2, 12 g, 65.5 mmol) in 7 M ammonia in methanol (150 mL) was added Raney nickel (5 g, 65.5 mmol) at 0° C. The reaction mixture was stirred under hydrogen pressure (60 psi) at room temp. for 24 h. The reaction mixture was filtered through a CELITE pad, washed with methanol (300 mL) and the filtrate was concentrated under reduced pressure. The reaction was repeated on the same scale. The two batches of crude material were combined and purified by neutral alumina chromatography to afford the title compound. LCMS (method D): rt=2.91, [M+H]⁺=188.

Intermediate 4

Ethyl 7-hydroxy-2-methylpyrazolo[1,5-a]pyrimidine-5-carboxylate

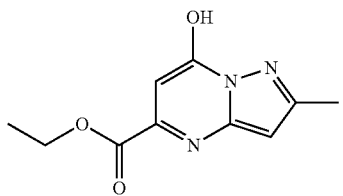 [SMILES: CCOC(=O)c1cc(O)n2nc(C)cc2n1]

To a solution of sodium (Z)-1,4-diethoxy-1,4-dioxobut-2-en-2-olate (21.64 g, 103 mmol) in ethanol (100 mL) was added 4 M HCl in 1,4 dioxane (28.3 mL) followed by 5-methyl-1H-pyrazol-3-amine (10 g, 103 mmol) at 0° C. The reaction was heated to 85° C. and stirred for 3 h. The reaction mixture was cooled to room temp. and concentrated. The residue was dissolved in 10% methanol in DCM (200 mL) and washed with saturated sodium bicarbonate solution (100 mL). The organic layer was washed with brine (50 mL), dried over anhydrous sodium sulphate, filtered and evaporated to dryness under reduced pressure. The residue was triturated with diethyl ether to give the title compound. LCMS (method A): rt=1.53, [M+H]⁺=222.

Intermediate 5

Ethyl 7-chloro-2-methylpyrazolo[1,5-a]pyrimidine-5-carboxylate

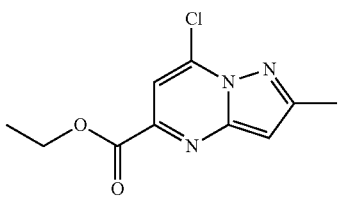

To ethyl 7-hydroxy-2-methylpyrazolo[1,5-a]pyrimidine-5-carboxylate (intermediate 4, 10 g, 45.2 mmol) was added phosphorous oxychloride (50 mL, 536 mmol) and the reaction was stirred for 24 h at 90° C. The reaction mixture was cooled to room temp. and concentrated under reduced pressure. The residue was dissolved in DCM (100 mL) and the pH was adjusted to neutral by using aqueous saturated sodium bicarbonate solution (60 mL). The organic layer was washed with water (100 mL), brine (100 mL), dried over sodium sulphate, filtered and concentrated. The residue was dissolved in 10% methanol in DCM (100 mL), and adsorbed on silica (14 g) then purified by silica chromatography (50 g), eluting with 10% ethyl acetate in pet. ether. Product fractions were combined and evaporated under reduced pressure to give the title compound. LCMS (method B): rt=3.13, [M+H]⁺=240.

Intermediate 6

Ethyl 7-chloro-3-iodo-2-methylpyrazolo[1,5-a]pyrimidine-5-carboxylate

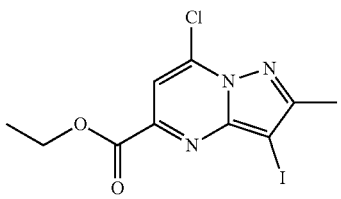 [SMILES: CCOC(=O)c1cc(Cl)n2nc(C)c(I)c2n1]

To a solution of ethyl 7-chloro-2-methylpyrazolo[1,5-a]pyrimidine-5-carboxylate (intermediate 5, 15 g, 62.6 mmol) in DCM (220 mL) was added acetic acid (25 mL) and NIS (14.79 g, 65.7 mmol). The reaction was stirred for 6 h at 28° C. The reaction mixture was diluted with DCM (150 mL), washed with saturated sodium thiosulphate (2×90 mL), brine (60 mL), dried over sodium sulphate, filtered and concentrated to give the title compound. LCMS (method A): rt=2.24, [M+H]⁺=366.

Intermediate 7

Ethyl 3-iodo-2-methyl-7-((3-(1-methyl-1H-imidazol-2-yl)benzyl)amino)pyrazolo[1,5-a]pyrimidine-5-carboxylate

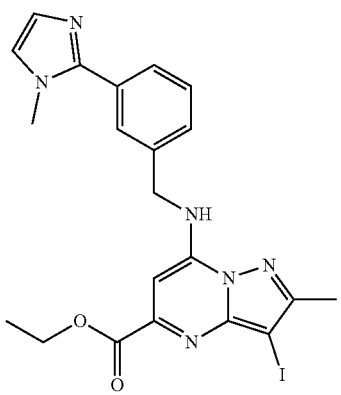 [SMILES: CCOC(=O)c1cc(NCc2cccc(-c3nccn3C)c2)n2nc(C)c(I)c2n1]

To a solution of DIPEA (14.33 mL, 82 mmol) in DMSO (50 mL) was added (3-(1-methyl-1H-imidazol-2-yl)phenyl)methanamine (intermediate 3, 5.38 g, 28.7 mmol) and ethyl 7-chloro-3-iodo-2-methylpyrazolo[1,5-a]pyrimidine-5-carboxylate (intermediate 6, 10 g, 27.4 mmol) and the reaction was stirred for 16 h. The reaction mixture was poured into ice cold water (200 mL) and a solid was filtered, washed with water (50 mL) and dried under vacuum to give the title compound. LCMS (method A): rt=1.79, [M+H]$^+$=517.

Intermediate 8

4-Bromo-1-methoxy-2-(methylsulfonyl)benzene

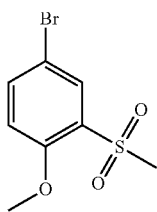

To a stirred solution of sodium sulfite (16.55 g, 131 mmol) and sodium bicarbonate (11.03 g, 131 mmol) in water (160 mL) was added 5-bromo-2-methoxybenzene-1-sulfonyl chloride (25 g, 88 mmol) in 1,4-dioxane (160 mL) at 70° C. The reaction mixture was stirred at 70° C. for 1 h. The reaction mixture was cooled to room temp. and the solvent was removed under reduced pressure to afford the crude intermediate as a white solid. The crude product was dissolved in DMF (300 mL) and methyl iodide (10.95 mL, 175 mmol) was added at room temp. and the mixture was stirred at room temp. for 2 h. The reaction mixture was poured into ice-cooled water, extracted with ethyl acetate (300 mL), dried over anhydrous sodium sulphate, filtered and dried under reduced pressure. The crude compound was washed with n-pentane (100 mL) to afford the title compound. LCMS (method A): rt=1.84, [M+H]$^+$=265.

Intermediate 9

2-(4-Methoxy-3-(methylsulfonyl)phenyl)-4,4,5,5-tetramethyl-1,3,2-dioxaborolane

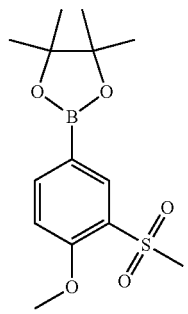

To a stirred solution of 4-bromo-1-methoxy-2-(methylsulfonyl)benzene (intermediate 8, 15 g, 56.6 mmol) and 4,4,4',4',5,5,5',5'-octamethyl-2,2'-bi(1,3,2-dioxaborolane) (21.55 g, 85 mmol) in 1,4-dioxane (150 mL) was added potassium acetate (8.33 g, 85 mmol) at room temp. The reaction mixture was degassed with argon for 15 min then PdCl$_2$(dppf)-DCM adduct (2.31 g, 2.83 mmol) was added to the reaction mixture at room temp. and again degassed for 15 min under argon atmosphere. The reaction mixture was stirred at 100° C. for 3 h. After cooling, the reaction mixture was filtered through a CELITE pad, washed with methanol (50 mL) and the filtrate was concentrated under reduced pressure. The crude product was purified by silica gel chromatography eluting with 20% ethyl acetate in hexane to afford the title compound. LCMS (method E): rt=2.16, [M+H]$^+$=313.

Intermediate 10

Ethyl 3-(4-methoxy-3-(methylsulfonyl)phenyl)-2-methyl-7-((3-(1-methyl-1H-imidazol-2-yl)benzyl)amino)pyrazolo[1,5-a]pyrimidine-5-carboxylate

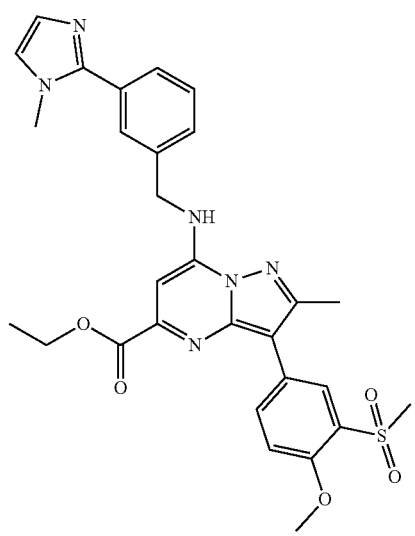 [SMILES: CCOC(=O)c1cc(NCc2cccc(-c3nccn3C)c2)n2nc(C)c(-c3ccc(OC)c(S(C)(=O)=O)c3)c2n1]

2-(4-Methoxy-3-(methylsulfonyl)phenyl)-4,4,5,5-tetramethyl-1,3,2-dioxaborolane (intermediate 9, 680 mg, 2.179 mmol), ethyl 3-iodo-2-methyl-7-((3-(1-methyl-1H-imidazol-2-yl)benzyl)amino)pyrazolo[1,5-a]pyrimidine-5-carboxylate (intermediate 7, 750 mg, 1.453 mmol), chloro(2-dicyclohexylphosphino-2',4',6'-triisopropyl-1,1'-biphenyl)[2-(2'-amino-1,1'-biphenyl)]palladium(II) (57.1 mg, 0.073 mmol) and potassium fluoride (253 mg, 4.36 mmol) were dissolved in 1,4-dioxane (10 mL) and water (5 mL) in a microwave vial, and the vial sealed and degassed with nitrogen. The reaction was stirred at 80° C. for 16 h. Further chloro(2-dicyclohexylphosphino-2',4',6'-triisopropyl-1,1'-biphenyl)[2-(2'-amino-1,1'-biphenyl)]palladium(II) (57.1 mg, 0.073 mmol), potassium fluoride (253 mg, 4.36 mmol) and 2-(4-methoxy-3-(methylsulfonyl)phenyl)-4,4,5,5-tetramethyl-1,3,2-dioxaborolane (intermediate 9, 680 mg, 2.179 mmol) were added and the reaction stirred for a further 8 h at 80° C. Further chloro(2-dicyclohexylphosphino-2',4',6'-triisopropyl-1,1'-biphenyl)[2-(2'-amino-1,1'-biphenyl)]palladium(II) (57.1 mg, 0.073 mmol), potassium fluoride (253 mg, 4.36 mmol) and 2-(4-methoxy-3-(methylsulfonyl)phenyl)-4,4,5,5-tetramethyl-1,3,2-dioxaborolane (intermediate 9, 680 mg, 2.179 mmol) were added and the reaction stirred for a further 16 h at 80° C. The reaction was cooled to room temp., filtered through CELITE (washing with 3×20 mL ethyl acetate) and the solvent removed in vacuo. The reaction mixture was partitioned between ethyl acetate (50 mL) and water (20 mL) and the organic phase separated, dried through a hydrophobic filter, and the solvent removed in vacuo. Purification by silica chromatography (120 g) eluting with 0-100% ethyl acetate in cyclohexane over 20 CV gave title compound. LCMS (method F): rt=1.04, [M+H]$^+$=515.

Intermediate 11

(3-(4-Methoxy-3-(methylsulfonyl)phenyl)-2-methyl-7-((3-(1-methyl-1H-imidazol-2-yl)benzyl)amino)pyrazolo[1,5-a]pyrimidin-5-yl)methanol

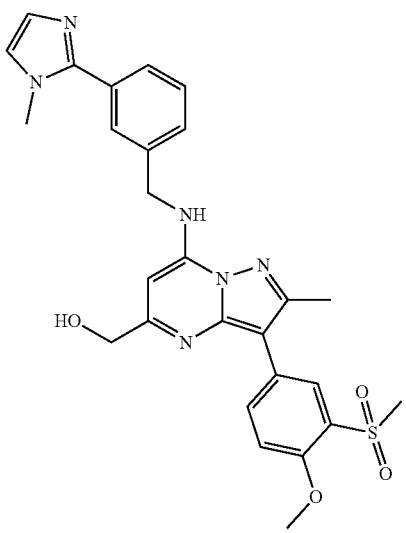 [SMILES: COc1ccc(-c2c(C)nn3c(NCc4cccc(-c5nccn5C)c4)cc(CO)nc23)cc1S(C)(=O)=O]

Ethyl 3-(4-methoxy-3-(methylsulfonyl)phenyl)-2-methyl-7-((3-(1-methyl-1H-imidazol-2-yl)benzyl)amino)pyrazolo[1,5-a]pyrimidine-5-carboxylate (intermediate 10, 180 mg, 0.313 mmol) was dissolved in THF (5 mL) under an atmosphere of nitrogen at 0° C., and lithium aluminum hydride (1 M in THF) (0.626 mL, 0.626 mmol) was added then the reaction was stirred for a further 3 h. The reaction was quenched by the addition of 2 M sodium hydroxide (5 mL) and stirred for a further 1 h. The organic phase was extracted with ethyl acetate (3×10 mL), the organic phase dried through a hydrophobic filter and the solvent removed in vacuo to afford title compound. LCMS (method F): rt=0.89, [M+H]$^+$=533.

Intermediate 12

3-(4-Methoxy-3-(methylsulfonyl)phenyl)-2-methyl-7-((3-(1-methyl-1H-imidazol-2-yl)benzyl)amino)pyrazolo[1,5-a]pyrimidine-5-carbaldehyde

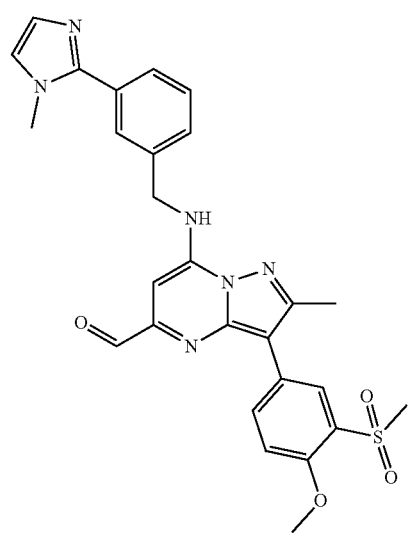 [SMILES: COc1ccc(-c2c(C)nn3c(NCc4cccc(-c5nccn5C)c4)cc(C=O)nc23)cc1S(C)(=O)=O]

(3-(4-Methoxy-3-(methylsulfonyl)phenyl)-2-methyl-7-((3-(1-methyl-1H-imidazol-2-yl)benzyl)amino)pyrazolo[1,5-a]pyrimidin-5-yl)methanol (intermediate 11, 112 mg, 0.21 mmol) was dissolved in DCM (2.5 mL), manganese dioxide (32 mg, 0.368 mmol) was added and the reaction stirred at room temp. for 4 h. Further manganese dioxide (183 mg, 2.103 mmol) was added and the reaction stirred at room temp. for a further 16 h. The reaction mixture was filtered through a CELITE cartridge, washing with DCM (3×5 mL) and the solvent was removed in vacuo to give the title compound. LCMS (method F): rt=1.0, [M+H]$^+$=531.

Intermediate 13

Ethyl 7-((tert-butoxycarbonyl)(3-(1-methyl-1H-imidazol-2-yl)benzyl)amino)-3-iodo-2-methylpyrazolo[1,5-a]pyrimidine-5-carboxylate

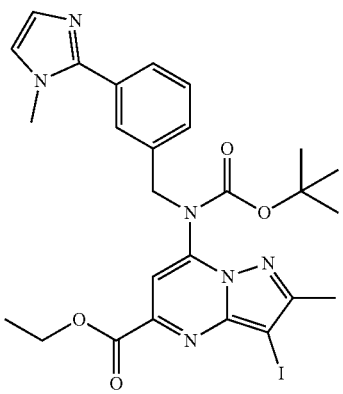 [SMILES: CCOC(=O)c1cc(N(Cc2cccc(-c3nccn3C)c2)C(=O)OC(C)(C)C)n2nc(C)c(I)c2n1]

To a solution of ethyl 2-methyl-7-((3-(1-methyl-1H-imidazol-2-yl)benzyl)amino)pyrazolo[1,5-a]pyrimidine-5-carboxylate (intermediate 7, 3.8 g, 9.73 mmol) in DCM (25 mL) was added DIPEA (5.1 mL, 29.2 mmol), DMAP (1.189 g, 9.73 mmol) and Boc-anhydride (3.39 mL, 14.6 mmol) and the reaction was stirred for 16 h at room temp. The reaction mixture was diluted with DCM (50 mL), washed with water (25 mL), dried over sodium sulphate, filtered and concentrated. The residue was dissolved in DCM (30 mL), absorbed on silica gel (5 g) and purified by silica gel chromatography (15 g) eluting with ethyl acetate in pet. ether to give the title compound. LCMS (method G): rt=2.14, [M+H]$^+$=617.

Intermediate 14 tert-Butyl (5-(hydroxymethyl)-3-iodo-2-methylpyrazolo[1,5-a]pyrimidin-7-yl)(3-(1-methyl-1H-imidazol-2-yl)benzyl)carbamate

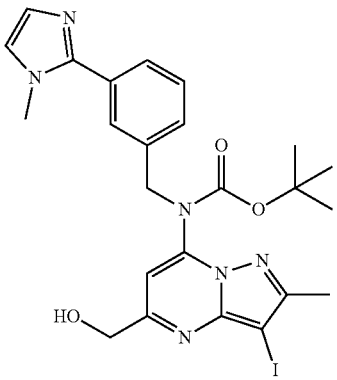

To a solution of ethyl 7-((tert-butoxycarbonyl)(3-(1-methyl-1H-imidazol-2-yl)benzyl)amino)-3-iodo-2-methylpyrazolo[1,5-a]pyrimidine-5-carboxylate (intermediate 13, 500 mg, 0.811 mmol) in ethanol (10 mL) was added sodium borohydride (92 mg, 2.433 mmol) and the reaction was stirred for 3 h at 10° C. The reaction mixture was quenched with 1 M HCl (5 mL), the pH was adjusted to 6, then concentrated. The residue was dissolved in ethyl acetate (25 mL), washed with water (20 mL), dried over sodium sulphate, filtered and concentrated to give the title compound. LCMS (method H): rt=2.01, [M+H]$^+$=573.

Intermediate 15 tert-Butyl (5-formyl-3-iodo-2-methylpyrazolo[1,5-a]pyrimidin-7-yl)(3-(1-methyl-1H-imidazol-2-yl)benzyl)carbamate

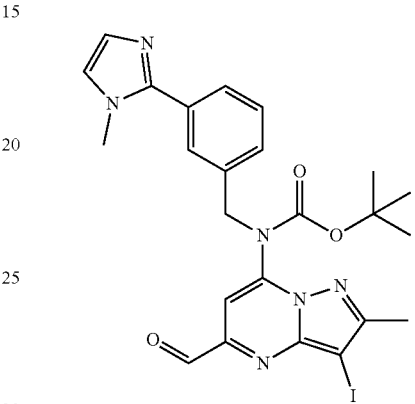

DMP (1752 mg, 4.13 mmol) was added in one portion to a stirred solution of tert-butyl (5-(hydroxymethyl)-3-iodo-2-methylpyrazolo[1,5-a]pyrimidin-7-yl)(3-(1-methyl-1H-imidazol-2-yl)benzyl)carbamate (intermediate 14, 1306 mg, 2.274 mmol) in DCM (7.5 mL). The reaction was left to stir for 18 h. Aqueous saturated sodium sulphite (10 mL) was added and the reaction was stirred for 2 h at room temp. The reaction mixture was partitioned between DCM (150 mL) and water (150 mL). The organic layer was separated and the aqueous extracted with further DCM (2×50 mL). The combined organic layers were washed with aqueous saturated sodium hydrogen carbonate (100 mL), water (100 mL), passed through a hydrophobic frit and then evaporated in vacuo. The residue was dissolved in the minimum amount of DCM and purified by silica gel chromatography (120 g), eluting with 0-50% ethyl acetate: ethanol (3:1, v/v) in cyclohexane to give the title compound. LCMS (method F): rt=1.27, [M+H]$^+$=573.

Intermediate 16

1-Methoxy-2-(methylsulfonyl)benzene

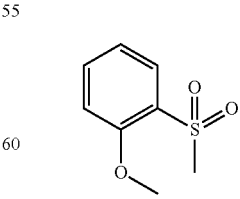

To a stirred solution of (2-methoxyphenyl)(methyl)sulfane (50 g, 324 mmol) in DCM (1 L) at 0° C. under nitrogen atmosphere was added m-CPBA (140 g, 810 mmol). The reaction mixture was allowed to stir at room temp. for 2 h.

The reaction mixture was diluted with DCM (300 mL), washed with saturated aqueous sodium carbonate (2×500 mL). The aqueous layer was extracted with DCM (200 mL). The combined organics were dried over anhydrous sodium sulphate, filtered and evaporated under reduced pressure to afford the title compound. LCMS (method I): rt=2.28, [M+H]$^+$=187.

Intermediate 17

2-((2-Methoxyphenyl)sulfonyl)ethanol

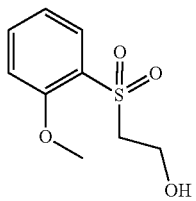

To a stirred solution of 1-methoxy-2-(methylsulfonyl)benzene (intermediate 16, 25 g, 123 mmol) in THF (250 mL) at −78° C. under nitrogen atmosphere was added n-butyllithium (115 mL, 184 mmol) dropwise and the reaction mixture was stirred at −78° C. for 30 min then cooled to 0° C. Paraformaldehyde (73.6 g, 2450 mmol) was added portionwise then the reaction mixture was stirred at 0° C. for 2 h. The reaction mixture was quenched with ammonium chloride solution (120 mL), extracted with ethyl acetate (2×200 mL). The combined organics were washed with brine (150 mL) and dried over anhydrous sodium sulphate, filtered and evaporated under reduced pressure. The crude compound was preabsorbed onto silica gel (4 g) and purified by silica gel chromatography (10 g column, 80% ethyl acetate in hexane) to afford the title compound. LCMS (method C): rt=1.16, [M+H]$^+$=217.

Intermediate 18

2-((5-Bromo-2-methoxyphenyl)sulfonyl)ethanol

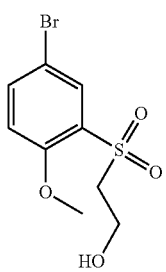

To a stirred solution of 2-((2-methoxyphenyl)sulfonyl)ethanol (intermediate 17, 10 g, 46.2 mmol) in DMF (100 mL) under nitrogen atmosphere at room temp. was added recrystallised NBS (16.46 g, 92 mmol). The reaction mixture was warmed to 50° C. for 18 h. The reaction mixture was cooled to room temp. and diluted with ethyl acetate (300 mL) and washed with ice cold water (2×500 mL). The organic layer was separated, and the aqueous layer was again extracted with ethyl acetate (300 mL). The combined organic layers were washed with brine (300 mL) and dried over sodium sulphate, filtered and concentrated under reduced pressure. The crude compound was preabsorbed onto silica gel (10 g) and purified by silica gel chromatography (90 g column, 40% ethyl acetate in hexane) to afford the title compound. LCMS (method C): rt=1.85, [M+H]$^+$=295.

Intermediate 19

2-((2-Methoxy-5-(4,4,5,5-tetramethyl-1,3,2-dioxaborolan-2-yl)phenyl)sulfonyl)ethanol

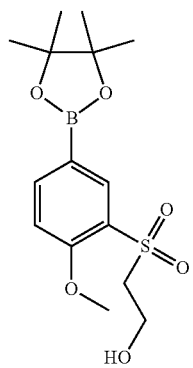 [SMILES: COc1ccc(B2OC(C)(C)C(C)(C)O2)cc1S(=O)(=O)CCO]

To a stirred solution of 2-((5-bromo-2-methoxyphenyl)sulfonyl)ethanol (intermediate 18, 10 g, 33.9 mmol) in 1,4-dioxane (150 mL) were added 4,4,4',4',5,5,5',5'-octamethyl-2,2'-bi(1,3,2-dioxaborolane) (17.2 g, 67.8 mmol) and potassium acetate (9.98 g, 102 mmol) at room temp., then the reaction mixture was degassed with nitrogen for 15 min. PdCl$_2$(dppf)-DCM adduct (2.77 g, 3.39 mmol) was added and the reaction mixture heated at 100° C. for 3 h in a sealed tube. The reaction mixture was filtered on a CELITE pad and the CELITE was washed with ethyl acetate (2×100 mL). The combined organics were concentrated under reduced pressure. The reaction was repeated on the same scale. The two batches of crude product were blended and dissolved in DCM (100 mL). The mixture was treated with charcoal (5 g) and refluxed for 10 min then filtered on a CELITE pad. The CELITE was washed with DCM (2×100 mL). The combined organics were concentrated under reduced pressure. The crude product was purified by silica gel chromatography (ethyl acetate in pet. ether) to afford the title compound. LCMS (method C): rt=2.17, [M+H]$^+$=343.

Intermediate 20 tert-Butyl (5-formyl-3-(3-((2-hydroxyethyl)sulfonyl)-4-methoxyphenyl)-2-methylpyrazolo[1,5-a]pyrimidin-7-yl)(3-(1-methyl-1H-imidazol-2-yl)benzyl)carbamate

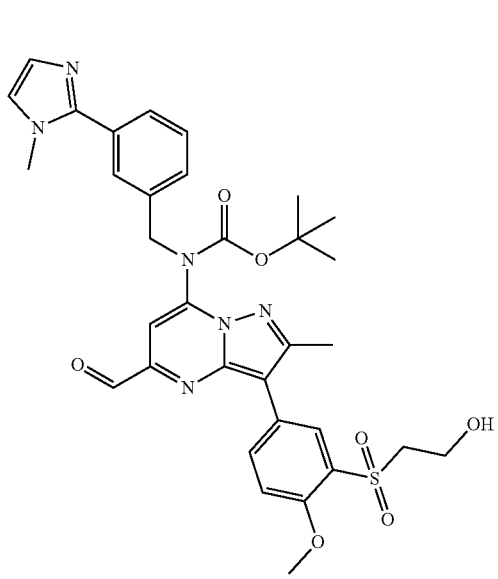 [SMILES: COc1ccc(-c2c(C)nn3c(N(Cc4cccc(-c5nccn5C)c4)C(=O)OC(C)(C)C)cc(C=O)nc23)cc1S(=O)(=O)CCO]

A microwave vial was charged with tert-butyl (5-formyl-3-iodo-2-methylpyrazolo[1,5-a]pyrimidin-7-yl)(3-(1-methyl-1H-imidazol-2-yl)benzyl)carbamate (intermediate 15, 487 mg, 0.851 mmol), 2-((2-methoxy-5-(4,4,5,5-tetramethyl-1,3,2-dioxaborolan-2-yl)phenyl)sulfonyl)ethan-1-ol (intermediate 19, 415 mg, 1.03 mmol), PdCl$_2$(dppf) (64 mg, 0.087 mmol) and potassium fluoride (151 mg, 2.6 mmol) in 1,4-dioxane (2 mL) and water (1 mL). The reaction vessel was sealed and heated in a microwave reactor at 100° C. for a total of 1.5 h. The reaction mixture was passed over CELITE, washed with methanol (50 mL) and evaporated in vacuo. The residue was dissolved in DCM (30 mL) and partitioned with water (15 mL). The organic layer was separated and the aqueous extracted with further DCM (2×20 mL). The combined organic layers were passed through a hydrophobic frit and evaporated in vacuo. The residue was purified by silica chromatography (80 g), eluting with 50-100% ethyl acetate:ethanol (3:1, v/v containing 1% triethylamine) in cyclohexane over 20 CV to give the title compound. LCMS (method F): rt=1.06, [M+H]$^+$=661.

Intermediate 21

2-(3-Iodo-2-methyl-7-((3-(1-methyl-1H-imidazol-2-yl)benzyl)amino)pyrazolo[1,5-a]pyrimidin-5-yl)propan-2-ol

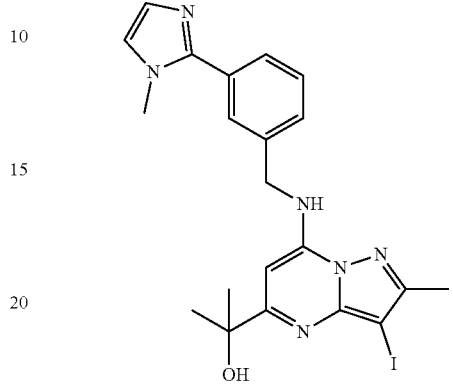

Ethyl 3-iodo-2-methyl-7-((3-(1-methyl-1H-imidazol-2-yl)benzyl)amino)pyrazolo[1,5-a]pyrimidine-5-carboxylate (intermediate 7, 275 mg, 0.533 mmol) was stirred in THF (5 mL) at 0° C. under nitrogen. Methylmagnesium bromide (1 M in dibutyl ether) (1.75 mL, 1.75 mmol) was added over 2 min and the mixture allowed to warm to room temp. then left for 4.5 h. The reaction mixture was quenched with water (2 mL) then partitioned with DCM (50 mL) and water (50 mL). The organic phase was collected and the aqueous washed with DCM (50 mL) and then ethyl acetate (50 mL). The combined organic layers were passed through a hydrophobic frit and evaporated to dryness. The residue was loaded in DCM (2 mL) onto a silica gel column (40 g) and eluted with 10-60% ethyl acetate:ethanol (3:1, v/v containing 1% triethylamine) in cyclohexane to give the title compound. LCMS (method J): rt=0.7, [M+H]$^+$=503.

Intermediate 22

5-Bromo-2-chloro-N-(3-hydroxypropyl)-N-methylbenzamide

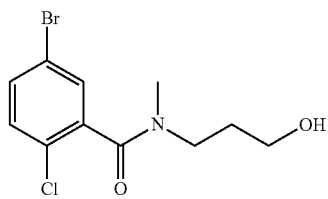 [SMILES: CN(CCCO)C(=O)c1cc(Br)ccc1Cl]

To a stirred solution of 5-bromo-2-chlorobenzoic acid (12.5 g, 53.1 mmol) in THF (100 mL) was added 3-(methylamino)propan-1-ol (5.21 g, 58.4 mmol), DIPEA (27.8 mL, 159 mmol) and HATU (22.2 g, 58.4 mmol) and the reaction mixture was stirred at room temp. for 18 h. The reaction mixture was diluted with water (100 mL) and extracted with ethyl acetate (200 mL). The organic layer was dried with anhydrous sodium sulphate and concentrated under reduced pressure. The crude product was dissolved in DCM (50 mL), pre-absorbed onto silica gel (50 g) and purified by silica gel Intermediate 23

2-Chloro-N-(3-hydroxypropyl)-N-methyl-5-(4,4,5,5-tetramethyl-1,3,2-dioxaborolan-2-yl)benzamide

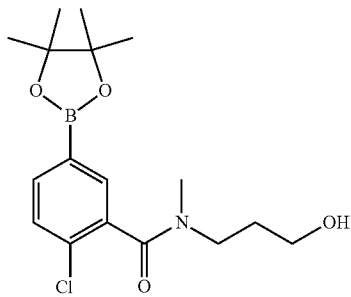 [SMILES: CN(CCCO)C(=O)c1cc(B2OC(C)(C)C(C)(C)O2)ccc1Cl]

To a stirred solution of 5-bromo-2-chloro-N-(3-hydroxypropyl)-N-methylbenzamide (intermediate 22, 10 g, 32.6 mmol) in 1,4-dioxane (100 mL) was added 4,4,4',4',5,5,5',5'-octamethyl-2,2'-bi(1,3,2-dioxaborolane) (9.69 g, 38.2 mmol), potassium acetate (9.60 g, 98 mmol) and the reaction was degassed with argon for 30 min. PdCl$_2$(dppf)-DCM adduct (0.266 g, 0.326 mmol) was added and the mixture was degassed for 20 min. The reaction mixture was heated to 100° C. for 18 h. The reaction mixture was cooled to room temp. and filtered through a CELITE pad and washed with 10% methanol in DCM then concentrated under reduced pressure. The crude product was dissolved in DCM (50 mL), pre-absorbed onto florisil (50 g) and purified by silica gel chromatography (250 g, 0-100% ethyl acetate in pet. ether) to afford the title compound. LCMS (method L): rt=2.45, [M+H]$^+$=354.

Intermediate 24

(S)-(5-Bromo-2-methoxyphenyl)(3-hydroxypyrrolidin-1-yl)methanone

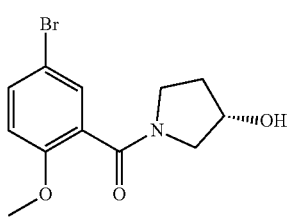 [SMILES: COc1ccc(Br)cc1C(=O)N1CC[C@H](O)C1]

DIPEA (1.134 mL, 6.49 mmol) was added to a solution of 5-bromo-2-methoxybenzoic acid (500 mg, 2.164 mmol) and HATU (987 mg, 2.6 mmol) in 2-MeTHF (10 mL) and the reaction was left to stir at room temp. for 30 min under nitrogen. (S)-pyrrolidin-3-ol (226 mg, 2.6 mmol) was then added and the reaction was left to stir at room temp. overnight with the addition of DMF (5 mL). The reaction mixture was concentrated under reduced pressure, diluted with saturated aqueous sodium hydrogen carbonate solution (50 mL) and 5% lithium chloride solution (50 mL), and extracted with ethyl acetate (2×100 mL). The combined organic layers were passed through a hydrophobic frit, concentrated under reduced pressure and further dried under a stream of nitrogen overnight. The residue was loaded in DCM and purified by silica chromatography (80 g) eluting with ethyl acetate:ethanol (3:1, v/v, containing 1% triethylamine) in ethyl acetate (0%, 2 CV; 0-100%, 12 CV) to give the title compound. LCMS (method F): rt=0.73, [M+H]$^+$=300.

Intermediate 25

(S)-(3-Hydroxypyrrolidin-1-yl)(2-methoxy-5-(4,4,5,5-tetramethyl-1,3,2-dioxaborolan-2-yl)phenyl)methanone

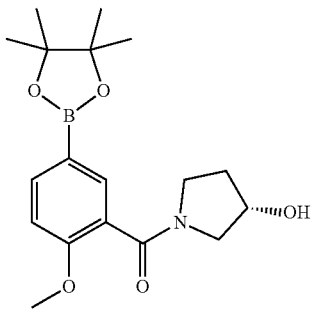 [SMILES: COc1ccc(B2OC(C)(C)C(C)(C)O2)cc1C(=O)N1CC[C@H](O)C1]

(S)-(5-Bromo-2-methoxyphenyl)(3-hydroxypyrrolidin-1-yl)methanone (intermediate 24, 750 mg, 2.249 mmol), 4,4,4',4',5,5,5',5'-octamethyl-2,2'-bi(1,3,2-dioxaborolane) (628 mg, 2.474 mmol), potassium acetate (662 mg, 6.75 mmol), PdCl$_2$(dppf) (165 mg, 0.225 mmol), and 1,4-dioxane (6 mL) were combined and placed under nitrogen by evacuation-refill. The mixture was heated in a microwave reactor at 100° C. for 1 h. The solvent was removed from the reaction mixture under reduced pressure. The residue was suspended in ethyl acetate (50 mL) and water (30 mL) and filtered through CELITE, rinsing with further ethyl acetate (50 mL). The solution was diluted with brine (20 mL) and the aqueous layer was washed with further ethyl acetate (100 mL), the combined organic layers were passed through a hydrophobic frit and the solvent removed under reduced pressure to give the title compound. LCMS (method J): rt=0.85, [M+H]$^+$=348.

Intermediate 26 tert-Butyl (5-(1-hydroxyethyl)-3-iodo-2-methylpyrazolo[1,5-a]pyrimidin-7-yl)(3-(1-methyl-1H-imidazol-2-yl)benzyl)carbamate

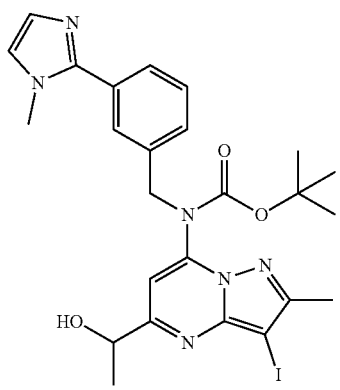 [SMILES: Cc1nn2c(N(Cc3cccc(-c4nccn4C)c3)C(=O)OC(C)(C)C)cc(C(C)O)nc2c1I]

tert-Butyl (5-formyl-3-iodo-2-methylpyrazolo[1,5-a]pyrimidin-7-yl)(3-(1-methyl-1H-imidazol-2-yl)benzyl)carbamate (intermediate 15, 465 mg, 0.812 mmol) was dissolved in THF (10 mL) and cooled to −78° C. Methylmagnesium bromide (1 M in dibutyl ether) (0.85 mL, 0.85 mmol) was added dropwise over 2 min. After 1 h 45 min methylmagnesium bromide (1 M in dibutyl ether) (0.203 mL, 0.203 mmol) was added and the mixture stirred at −78° C. for a further 3 h. Saturated aqueous ammonium chloride (5 mL) and water (10 mL) were added and the mixture was stirred for 10 min while warming to room temp. DCM (20 mL) was added and the mixture transferred and the organic layer was collected. The aqueous was further washed with DCM (2×20 mL) and the combined organic layers were passed through a hydrophobic frit and evaporated to dryness. The residue was wet-loaded in DCM (1.5 mL) onto a silica gel column and eluted with 50-60% ethyl acetate in cyclohexane over 30 CV and then 60-85% ethyl acetate in cyclohexane over 10 CV. The fractions containing product were combined and evaporated to dryness then triturated with diethyl ether to give the title compound. LCMS (method F): rt=1.2, $[M+H]^+$=589.

Intermediate 27

5-Bromo-N-(3-hydroxypropyl)-2-methoxy-N-methylbenzamide

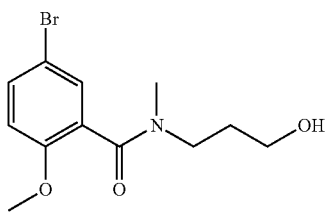 [SMILES: COc1ccc(Br)cc1C(=O)N(C)CCCO]

HATU (458.3 mg, 1.205 mmol) and DIPEA (0.655 mL, 3.75 mmol) were added to a stirred solution of 5-bromo-2-methoxybenzoic acid (288.9 mg, 1.250 mmol) in THF (10 mL) at room temp. After 10 min 3-(methylamino)propan-1-ol (0.146 mL, 1.500 mmol) was added. After 2 h the solvent was removed in vacuo and the resulting residue diluted with ethyl acetate (10 mL) and water (10 mL). The separated aqueous phase was further extracted with ethyl acetate (2×10 mL). The combined organic layers were passed through a hydrophobic frit and the solvent was removed in vacuo to give the title compound. LCMS (method F): rt=0.78, $[M+H]^+$=303.

Intermediate 28

N-(3-Hydroxypropyl)-2-methoxy-N-methyl-5-(4,4,5,5-tetramethyl-1,3,2-dioxaborolan-2-yl)benzamide

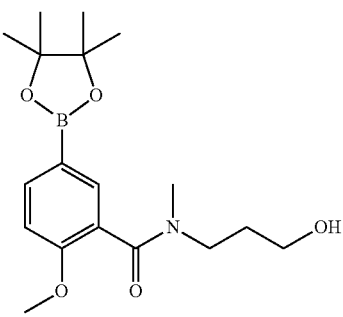 [SMILES: COc1ccc(B2OC(C)(C)C(C)(C)O2)cc1C(=O)N(C)CCCO]

4,4,4',4',5,5,5',5'-Octamethyl-2,2'-bi(1,3,2-dioxaborolane) (1.114 g, 4.39 mmol), potassium acetate (1.077 g, 10.97 mmol), PdCl$_2$(dppf).DCM adduct (0.299 g, 0.366 mmol) and 1,4-dioxane (7 mL) were combined and placed under nitrogen (cycled between vacuum/nitrogen 3 times). A solution of 5-bromo-N-(3-hydroxypropyl)-2-methoxy-N-methylbenzamide (intermediate 27, 1.7 g, 3.66 mmol) in 1,4-dioxane (7 mL) was added and the mixture cycled between vacuum/nitrogen 3 times. The reaction was then heated at 100° C. in a microwave reactor for 90 min. After cooling, the mixture was filtered through CELITE, washed with DCM (50 mL) and the solvent removed in vacuo. The resulting residue was dissolved in ethyl acetate (60 mL), water (60 mL) and brine (20 mL). The separated aqueous layer was re-extracted with ethyl acetate (2×30 mL). The combined organic layers were passed through a hydrophobic frit and the solvent removed in vacuo. The crude product was purified by silica gel column chromatography eluting with 50-100% ethyl acetate in cyclohexane to give the title compound. LCMS (method F): rt=0.89, $[M+H]^+$=350.

Intermediate 29

5-Bromo-N-ethyl-N-(2-hydroxyethyl)-2-methoxybenzamide

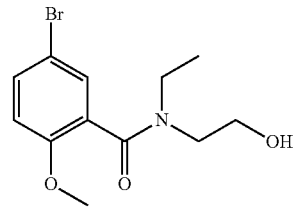 [SMILES: CCN(CCO)C(=O)c1cc(Br)ccc1OC]

DIPEA (1.2 mL, 6.87 mmol) and HATU (980 mg, 2.58 mmol) were added to a stirred solution of 5-bromo-2-methoxybenzoic acid (500 mg, 2.164 mmol) in 2-MeTHF (10 mL). After 15 min 2-(ethylamino)ethan-1-ol (0.25 mL, 2.56 mmol) was added and the reaction left to stir overnight. The mixture was partitioned between ethyl acetate (50 mL) and saturated aqueous sodium bicarbonate (50 mL). The aqueous phase was further extracted with ethyl acetate (50 mL). The combined organic phase was washed with saturated aqueous sodium bicarbonate (50 mL) and the solvent removed under reduced pressure. The residue was purified by silica gel chromatography eluting with 0-100% ethyl acetate:ethanol (3:1, containing 1% triethylamine) in cyclohexane to give the title compound. LCMS (method F): rt=0.8, [M+H]$^+$=302.

Intermediate 30

N-Ethyl-N-(2-hydroxyethyl)-2-methoxy-5-(4,4,5,5-tetramethyl-1,3,2-dioxaborolan-2-yl)benzamide

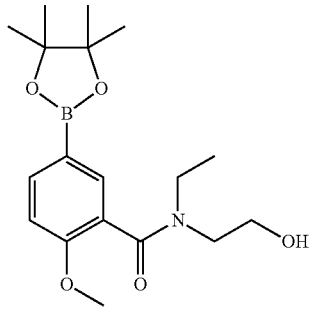 [SMILES: CCN(CCO)C(=O)c1cc(B2OC(C)(C)C(C)(C)O2)ccc1OC]

5-Bromo-N-ethyl-N-(2-hydroxyethyl)-2-methoxybenzamide (intermediate 29, 1.2 g, 3.97 mmol), 4,4,4',4',5,5,5',5'-octamethyl-2,2'-bi(1,3,2-dioxaborolane) (1.18 g, 4.65 mmol), PdCl$_2$(dppf) (0.301 g, 0.411 mmol), potassium acetate (1.17 g, 11.92 mmol) and 1,4-dioxane (8 mL) were combined and placed under nitrogen by evacuation and refill. The mixture was heated at 100° C. in a microwave reactor for 1.5 h. After cooling, the reaction mixture was filtered through CELITE, washed with methanol (250 mL) and the solvent removed under reduced pressure. The residue was re-dissolved in DCM (30 mL) and partitioned with water (30 mL). The aqueous layer was re-extracted with DCM (3×30 mL) and the combined organic extracts passed through a hydrophobic frit and evaporated to dryness to give the title compound. LCMS (method F): rt 0.92, [M+H]$^+$=350.

Intermediate 31

5-Bromo-2-chloro-N-ethyl-N-(2-hydroxyethyl)benzamide

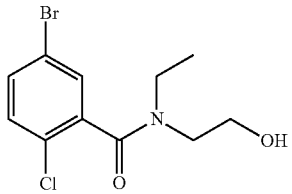 [SMILES: CCN(CCO)C(=O)c1cc(Br)ccc1Cl]

DIPEA (1.1 mL, 6.30 mmol) and HATU (1.05 g, 2.76 mmol) were added to a stirred solution of 5-bromo-2-chlorobenzoic acid (509 mg, 2.162 mmol) in 2-MeTHF (10 mL) and the reaction was left to stir at room temp. for 15 min. 2-(Ethylamino)ethan-1-ol (0.25 mL, 2.56 mmol) was added and the reaction stirred over the weekend. The mixture was partitioned between ethyl acetate (50 mL) and saturated aqueous sodium bicarbonate (50 mL). The aqueous phase was further washed with ethyl acetate (50 mL) and the combined organic phases washed with saturated aqueous sodium bicarbonate (50 mL) and the solvent removed under reduced pressure. The crude was purified by silica gel column chromatography eluting with 20-100% ethyl acetate in cyclohexane. The fractions containing product were combined and evaporated to dryness. The residue was further purified by reverse phase column chromatography eluting with 20-60% acetonitrile (containing 0.01% ammonia) in 10 mM ammonium bicarbonate in water adjusted to pH 10 with ammonia solution to give the title compound. LCMS (method E): rt=0.85, [M+H]$^+$=306.

Intermediate 32

2-Chloro-N-ethyl-N-(2-hydroxyethyl)-5-(4,4,5,5-tetramethyl-1,3,2-dioxaborolan-2-yl)benzamide

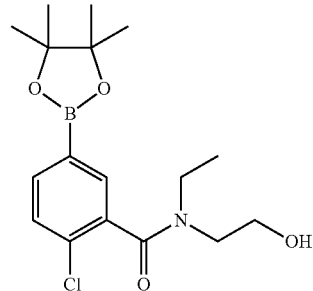 [SMILES: CCN(CCO)C(=O)c1cc(B2OC(C)(C)C(C)(C)O2)ccc1Cl]

4,4,4',4',5,5,5',5'-Octamethyl-2,2'-bi(1,3,2-dioxaborolane) (462 mg, 1.819 mmol), 5-bromo-2-chloro-N-ethyl-N-(2-hydroxyethyl)benzamide (intermediate 31, 453 mg, 1.478 mmol), PdCl$_2$(dppf) (111 mg, 0.152 mmol) and potassium acetate (445 mg, 4.53 mmol) were combined in 1,4-dioxane (4 mL). The mixture was degassed and heated at 100° C. in a microwave reactor for 1 h, three times. After cooling, the mixture was filtered through CELITE, washed with methanol (100 mL) and the solvent removed in vacuo. The residue was partitioned between DCM (20 mL) and water (10 mL). The separated aqueous layer was further washed with DCM (2×10 mL). The combined organic layers were passed through a hydrophobic frit and the solvent removed in vacuo to give the title compound. LCMS (method D): rt=1.05, [M+H]$^+$=354.

Intermediate 33

5-Bromo-2-methoxy-N-methyl-N-(tetrahydro-2H-pyran-4-yl)benzamide

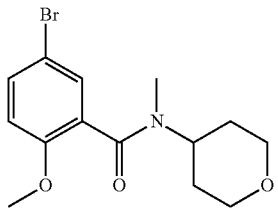 [SMILES: COc1ccc(Br)cc1C(=O)N(C)C1CCOCC1]

HATU (1.391 g, 3.66 mmol) and DIPEA (1.72 mL, 9.85 mmol) were added to a stirred suspension of 5-bromo-2-methoxybenzoic acid (0.752 g, 3.25 mmol) in THF (10 mL) and stirred for 20 min. N-Methyltetrahydro-2H-pyran-4-amine (0.382 g, 3.32 mmol) was added and the reaction mixture left to stir for 18 h. The solvent was removed in vacuo. The reaction mixture was partitioned between DCM (50 mL) and water (50 mL), the aqueous phase was extracted further with DCM (2×20 mL) and the organic phase was filtered through a hydrophobic frit and the solvent removed in vacuo. The residue was dissolved in the minimum amount of DCM and purified by silica gel chromatography (120 g) eluting with 0-100% ethyl acetate:ethanol (3:1, v/v) in cyclohexane to give the title compound. LCMS (method F): rt=0.89, [M+H]$^+$=328.

Intermediate 34

2-Methoxy-N-methyl-N-(tetrahydro-2H-pyran-4-yl)-5-(4,4,5,5-tetramethyl-1,3,2-dioxaborolan-2-yl)benzamide

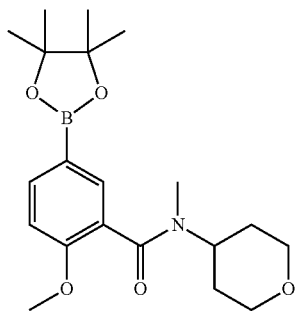 [SMILES: COc1ccc(B2OC(C)(C)C(C)(C)O2)cc1C(=O)N(C)C1CCOCC1]

5-Bromo-2-methoxy-N-methyl-N-(tetrahydro-2H-pyran-4-yl)benzamide (intermediate 33, 746 mg, 2.273 mmol), 4,4,4',4',5,5,5',5'-octamethyl-2,2'-bi(1,3,2-dioxaborolane) (692 mg, 2.73 mmol), PdCl$_2$(dppf).DCM (194 mg, 0.238 mmol), potassium acetate (664 mg, 6.77 mmol) and 1,4-dioxane (10 mL) were combined and heated in a microwave reactor at 100° C. for 1 h. The reaction mixture was filtered through CELITE and the solvent removed in vacuo. The residue was partitioned between water (25 mL) and DCM (25 mL), the aqueous phase was extracted further with DCM (2×15 mL) and the organic phase was filtered through a hydrophobic frit, then evaporated to dryness to give the title compound. LCMS (method F): rt=1.01, [M+H]$^+$=376.

Intermediate 35

5-Bromo-N-(3-hydroxypropyl)-N,2-dimethylbenzamide

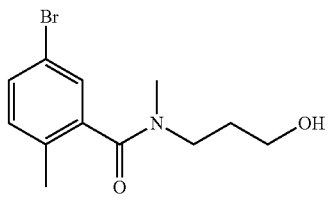 [SMILES: Cc1ccc(Br)cc1C(=O)N(C)CCCO]

5-Bromo-2-methylbenzoic acid (504 mg, 2.344 mmol), HATU (1053 mg, 2.77 mmol) and DIPEA (0.5 mL, 2.86 mmol) in DMF (4 mL) were stirred at room temp. for 30 min after which 3-(methylamino)propan-1-ol (0.275 mL, 2.83 mmol) was added. After 3 h the mixture was partitioned between ethyl acetate (20 mL) and water (15 mL). The separated aqueous layer was further extracted with ethyl acetate (15 mL). The combined organic layers were washed with 5% aqueous lithium chloride solution (2×10 mL), water (10 mL) and brine (10 mL). The organic layer was passed through a hydrophobic frit and the solvent removed in vacuo. The crude was purified by silica gel column chromatography eluting with 50-100% ethyl acetate in cyclohexane to give the title compound. LCMS (method F): rt=0.80, [M+H]$^+$=286.

Intermediate 36

N-(3-Hydroxypropyl)-N,2-dimethyl-5-(4,4,5,5-tetramethyl-1,3,2-dioxaborolan-2-yl)benzamide

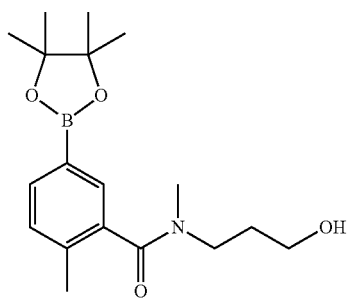 [SMILES: Cc1ccc(B2OC(C)(C)C(C)(C)O2)cc1C(=O)N(C)CCCO]

Potassium acetate (636 mg, 6.48 mmol), 5-bromo-N-(3-hydroxypropyl)-N,2-dimethylbenzamide (intermediate 35, 685 mg, 2.154 mmol), 4,4,4',4',5,5,5',5'-octamethyl-2,2'-bi(1,3,2-dioxaborolane) (663 mg, 2.61 mmol) and PdCl$_2$ (dppf) (131 mg, 0.179 mmol) were combined in 1,4-dioxane (5 mL). The mixture was placed under nitrogen by cycling between vacuum and nitrogen five times and heated in a microwave reactor at 100° C. for 1 h. After cooling, the solvent was removed in vacuo and the residue partitioned between DCM (30 mL) and water (20 mL). The separated aqueous layer was further washed with DCM (2×20 mL) and the combined organic layers passed through a hydrophobic frit and the solvent removed in vacuo to give the title compound. LCMS (method J): rt=0.97, [M+H]$^+$=334.

Intermediate 37

(S)-(5-bromo-2-chlorophenyl)(3-hydroxypyrrolidin-1-yl)methanone

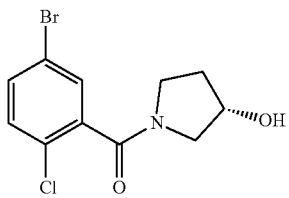 [SMILES: O=C(c1cc(Br)ccc1Cl)N1CC[C@H](O)C1]

Prepared in a similar manner to intermediate 33, using 5-bromo-2-chlorobenzoic acid (480 mg, 2.039 mmol) and (S)-pyrrolidin-3-ol (178 mg, 2.039 mmol) to give the title compound. LCMS (method F): rt=0.73, [M+H]$^+$=303.

Intermediate 38

(S)-(2-Chloro-5-(4,4,5,5-tetramethyl-1,3,2-dioxaborolan-2-yl)phenyl)(3-hydroxypyrrolidin-1-yl)methanone

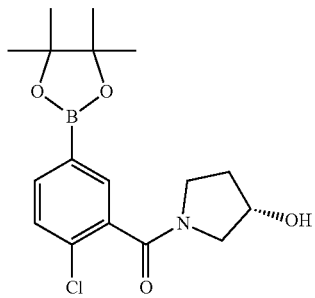 [SMILES: CC1(C)OB(c2ccc(Cl)c(C(=O)N3CC[C@H](O)C3)c2)OC1(C)C]

Prepared in a similar manner to intermediate 32, using (S)-(5-bromo-2-chlorophenyl)(3-hydroxypyrrolidin-1-yl)methanone (intermediate 37), to give the title compound. LCMS (method F): rt=0.72, [M+H]$^+$=352.

Intermediate 39

(S)-5-Bromo-N-(1-hydroxypropan-2-yl)-2-methoxy-N-methylbenzamide

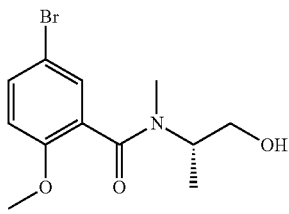 [SMILES: COc1ccc(Br)cc1C(=O)N(C)[C@@H](C)CO]

Prepared in a similar manner to intermediate 35, using 5-bromo-2-methoxybenzoic acid (0.747 g, 3.23 mmol) and (S)-2-(methylamino)propan-1-ol (0.321 g, 3.6 mmol) to give the title compound. LCMS (method F): rt=0.77, [M+H]$^+$=302.

Intermediate 40

(S)—N-(1-Hydroxypropan-2-yl)-2-methoxy-N-methyl-5-(4,4,5,5-tetramethyl-1,3,2-dioxaborolan-2-yl)benzamide

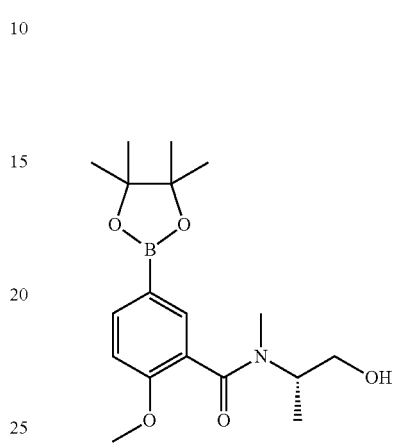

Prepared in a similar manner to intermediate 32, using (S)-5-bromo-N-(1-hydroxypropan-2-yl)-2-methoxy-N-methylbenzamide (intermediate 39) to give the title compound. LCMS (method F): rt=0.89, [M+H]$^+$=350.

Intermediate 41

Ethyl 3-bromo-7-chloro-2-methylpyrazolo[1,5-a]pyrimidine-5-carboxylate

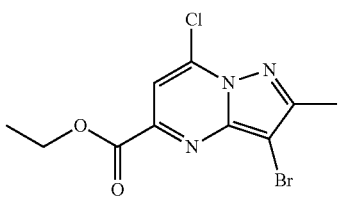 [SMILES: CCOC(=O)c1cc(Cl)n2nc(C)c(Br)c2n1]

Prepared in a similar manner to intermediate 6, using NBS, to give the title compound. LCMS (method J): rt=1.11, [M+H]$^+$=320.

Intermediate 42

Ethyl 3-bromo-2-methyl-7-((3-(1-methyl-1H-imidazol-2-yl)benzyl)amino)pyrazolo[1,5-a]pyrimidine-5-carboxylate

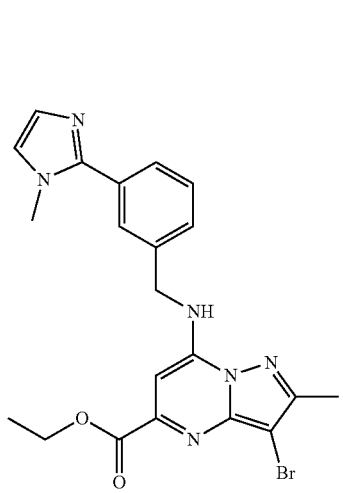 [SMILES: CCOC(=O)c1cc(NCc2cccc(-c3nccn3C)c2)n2nc(C)c(Br)c2n1]

Ethyl 3-bromo-7-chloro-2-methylpyrazolo[1,5-a]pyrimidine-5-carboxylate (intermediate 41, 685 mg, 2.15 mmol), (3-(1-methyl-1H-imidazol-2-yl)phenyl)methanamine (intermediate 3, 443 mg, 2.365 mmol) and DIPEA (0.751 mL, 4.3 mmol) were stirred in DMSO (5 mL) at 80° C. under nitrogen for 3.5 h. After cooling, the mixture was poured onto ice cold water and the precipitate collected by filtration. The cake was then dissolved in DCM, dried under reduced pressure and triturated with diethyl ether to give the title compound. LCMS (method F): rt=1.06, [M+H]$^+$=469.

Alternative Preparation of Intermediate 42

Ethyl 3-bromo-7-chloro-2-methylpyrazolo[1,5-a]pyrimidine-5-carboxylate (intermediate 41, 50 g, 157 mmol), (3-(1-methyl-1H-imidazol-2-yl)phenyl)methanamine (intermediate 3, 35.3 g, 188 mmol) and DIPEA (54.8 mL, 314 mmol) were stirred in DMSO (500 mL) at 80° C. for 3 h. After cooling, the reaction mixture was poured into ice cold water and the precipitate collected by filtration. The solid obtained was triturated with diethyl ether (500 mL), filtered and dried to afford the title compound. LCMS (method C): rt=1.44, [M+H]$^+$=469.

Intermediate 43

2-(3-Bromo-2-methyl-7-((3-(1-methyl-1H-imidazol-2-yl)benzyl)amino)pyrazolo[1,5-a]pyrimidin-5-yl)propan-2-ol

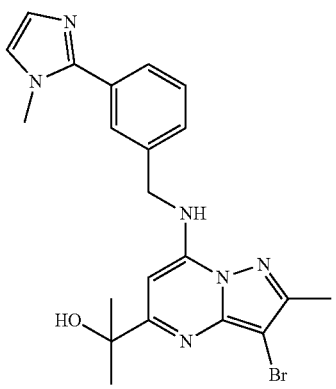 [SMILES: Cc1nn2c(NCc3cccc(-c4nccn4C)c3)cc(C(C)(C)O)nc2c1Br]

Ethyl 3-bromo-2-methyl-7-((3-(1-methyl-1H-imidazol-2-yl)benzyl)amino)pyrazolo[1,5-a]pyrimidine-5-carboxylate (intermediate 42, 1.76 g, 3.75 mmol) was stirred in THF (35 mL) at 0° C. under nitrogen. Methylmagnesium chloride (3 M in THF) (5.6 mL, 16.8 mmol) was added over 10 min and the mixture stirred at 0° C. for 30 min. The mixture was warmed to room temp. and stirred overnight. The reaction mixture was quenched with aqueous saturated ammonium chloride (5 mL), then partitioned with DCM (100 mL) and aqueous saturated ammonium chloride (100 mL). The organic phase was collected and the aqueous washed with DCM (2×25 mL). The combined organic layers were passed through a hydrophobic frit and evaporated to dryness. The residue was stirred in THF (35 mL) under nitrogen at 0° C. Methylmagnesium chloride (3 M in THF) (3.75 mL, 11.25 mmol) was added over 10 min and the mixture stirred at 0° C. for 40 min after which it was stirred at room temp. for 20 min. The reaction mixture was quenched with aqueous saturated ammonium chloride (5 mL) then partitioned with DCM (100 mL) and aqueous saturated ammonium chloride (100 mL). The organic phase was collected and the aqueous washed with DCM (2×25 mL). The combined organic layers were passed through a hydrophobic frit, concentrated under reduced pressure and dried for 4 days on the high-vac line to give the title compound. LCMS (method J): rt=0.65, [M+H]$^+$=455.

Alternative Preparation of Intermediate 43

Ethyl 3-bromo-2-methyl-7-((3-(1-methyl-1H-imidazol-2-yl)benzyl)amino)pyrazolo[1,5-a]pyrimidine-5-carboxylate (intermediate 42, 81 g, 173 mmol) was stirred in DCM (300 mL) and THF (100 mL) at 5° C. under nitrogen. Methylmagnesium chloride (3 M in THF) (230 mL, 690 mmol) was added dropwise over 45 min maintaining the internal temperature below 15° C. and stirred for an additional 10 min. The mixture was quenched with saturated aqueous ammonium chloride (400 mL) and partitioned between DCM (2 L) and water (2 L). The organic phase was dried over magnesium sulphate and concentrated under reduced pressure. The resulting residue was dissolved in DCM (500 mL) and THF (250 mL) and cooled to 0° C. under nitrogen. Methylmagnesium chloride (3 M in THF) (173 mL, 518 mmol) was added dropwise over 1 h, maintaining the internal temperature below 10° C. After addition, the mixture was stirred at 5° C. for 10 min. The mixture was quenched with saturated aqueous ammonium chloride (400 mL) and partitioned between DCM (2 L) and water (2 L). The organic phase was dried over magnesium sulphate and concentrated under reduced pressure to give the title compound. LCMS (method J): rt=0.60, [M+H]$^+$=455.

Intermediate 44

(S)-5-Bromo-N-(1-hydroxypropan-2-yl)-N,2-dimethylbenzamide

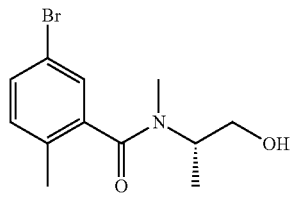 [SMILES: Cc1ccc(Br)cc1C(=O)N(C)[C@@H](C)CO]

Prepared in a similar manner to intermediate 33, using 5-bromo-2-methylbenzoic acid (800 mg, 3.72 mmol) and (S)-2-(methylamino)propan-1-ol (332 mg, 3.72 mmol) to give the title compound. LCMS (method F): rt=0.82, [M+H]$^+$=286.

Intermediate 45

(S)—N-(1-Hydroxypropan-2-yl)-N,2-dimethyl-5-(4,4,5,5-tetramethyl-1,3,2-dioxaborolan-2-yl)benzamide

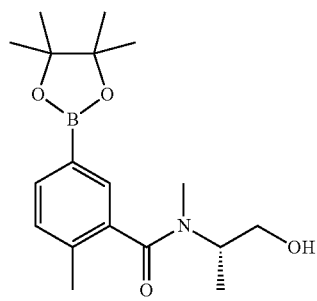

Prepared in a similar manner to intermediate 32, using (S)-5-bromo-N-(1-hydroxypropan-2-yl)-N,2-dimethylbenzamide (intermediate 44) to give the title compound. LCMS (method F): rt=0.92, [M+H]$^+$=334.

Intermediate 46

5-Bromo-2-methoxy-N,N-dimethylbenzamide

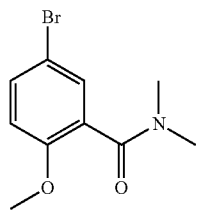

Prepared in a similar manner to intermediate 33, using 5-bromo-2-methoxybenzoic acid (483 mg, 2.091 mmol) and dimethylamine (2 M in THF) (1.254 mL, 2.509 mmol) to give the title compound. LCMS (method F): rt=0.85, [M+H]$^+$=258.

Intermediate 47

2-Methoxy-N,N-dimethyl-5-(4,4,5,5-tetramethyl-1,3,2-dioxaborolan-2-yl)benzamide

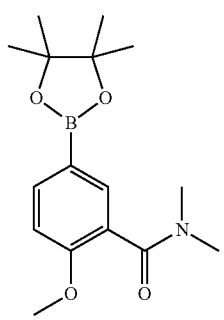

Prepared in a similar manner to intermediate 32, using 5-bromo-2-methoxy-N,N-dimethylbenzamide (intermediate 46) to give the title compound. LCMS (method F): rt=1.01, [M+H]$^+$=306.

Intermediate 48

(R)-(5-Bromo-2-chlorophenyl)(2-(hydroxymethyl)pyrrolidin-1-yl)methanone

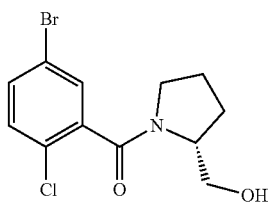 [SMILES: O=C(c1cc(Br)ccc1Cl)N1CCC[C@@H]1CO]

Prepared in a similar manner to intermediate 33, using 5-bromo-2-chlorobenzoic acid (503 mg, 2.136 mmol) and (R)-pyrrolidin-2-ylmethanol to give the title compound. LCMS (method F): rt=0.89, [M+H]$^+$=320.

Intermediate 49

(R)-(2-Chloro-5-(4,4,5,5-tetramethyl-1,3,2-dioxaborolan-2-yl)phenyl)(2-(hydroxymethyl)pyrrolidin-1-yl)methanone

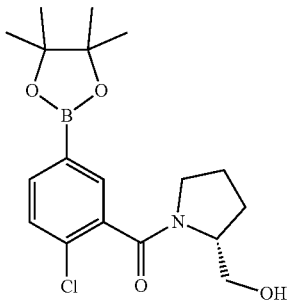 [SMILES: CC1(C)OB(c2ccc(Cl)c(C(=O)N3CCC[C@@H]3CO)c2)OC1(C)C]

Prepared in a similar manner to intermediate 32, using (R)-(5-Bromo-2-chlorophenyl)(2-(hydroxymethyl)pyrrolidin-1-yl)methanone (intermediate 48) to give the title compound. LCMS (method F): rt=0.94, [M+H]$^+$=366.

Intermediate 50

(R)-(5-Bromo-2-methylphenyl)(2-(hydroxymethyl)pyrrolidin-1-yl)methanone

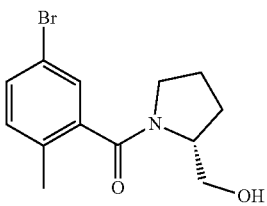 [SMILES: Cc1ccc(Br)cc1C(=O)N1CCC[C@@H]1CO]

5-Bromo-2-methylbenzoic acid (534 mg, 2.483 mmol), HATU (1074 mg, 2.82 mmol) and DIPEA (0.520 mL, 2.98 mmol) in DMF (1 mL) and THF (5 mL) were stirred at room temp. for 30 min when (R)-pyrrolidin-2-ylmethanol (0.3 mL, 3.04 mmol) was added in one portion. The reaction was stirred for 18 h. The solvent was removed in vacuo. The residue was dissolved in ethyl acetate (40 mL) and partitioned with water (20 mL). The organic layer was separated and washed with 5% aqueous lithium chloride solution (2×10 mL), water (10 mL) and brine (10 mL). The organic layer was then passed through a hydrophobic frit and the solvent removed in vacuo. The residue was dissolved in a minimal amount of DCM and loaded onto a silica column (80 g) and eluted over 12 CV with 0-100% ethyl acetate: ethanol (3:1, v/v, containing 1% triethylamine) in cyclohexane to give the title compound. LCMS (method F): rt=0.87, [M+H]$^+$=298.

Intermediate 51

(R)-(2-(Hydroxymethyl)pyrrolidin-1-yl)(2-methyl-5-(4,4,5,5-tetramethyl-1,3,2-dioxaborolan-2-yl)phenyl)methanone

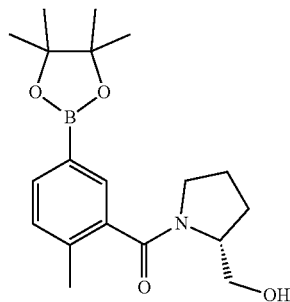 [SMILES: Cc1ccc(B2OC(C)(C)C(C)(C)O2)cc1C(=O)N1CCC[C@@H]1CO]

Prepared in a similar manner to intermediate 36, using (R)-(5-bromo-2-methylphenyl)(2-(hydroxymethyl)pyrrolidin-1-yl)methanone (intermediate 50) to give the title compound. LCMS (method F): rt=1.02, [M+H]$^+$=346.

Intermediate 52

5-Bromo-N-(2-hydroxyethyl)-2-methoxy-N-methylbenzamide

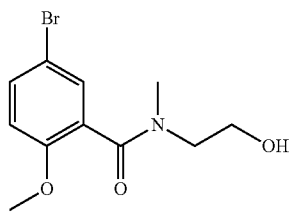 [SMILES: COc1ccc(Br)cc1C(=O)N(C)CCO]

Prepared in a similar manner to intermediate 33, using 5-bromo-2-methoxybenzoic acid (400 mg, 1.731 mmol) and 2-(methylamino)ethan-1-ol (0.167 mL, 2.078 mmol) to give the title compound. LCMS (method F): rt=0.72, [M+H]$^+$=288.

Intermediate 53

N-(2-Hydroxyethyl)-2-methoxy-N-methyl-5-(4,4,5,5-tetramethyl-1,3,2-dioxaborolan-2-yl)benzamide

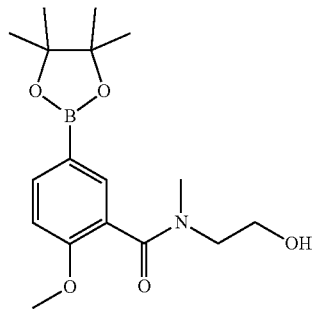 [SMILES: COc1ccc(B2OC(C)(C)C(C)(C)O2)cc1C(=O)N(C)CCO]

Prepared in a similar manner to intermediate 32 using 5-bromo-N-(2-hydroxyethyl)-2-methoxy-N-methylbenzamide (intermediate 52) to give the title compound. LCMS (method F): rt=0.85, [M+H]$^+$=336.

Intermediate 54

(5-Bromo-2-methoxyphenyl)(3-hydroxy-3-methylpyrrolidin-1-yl)methanone

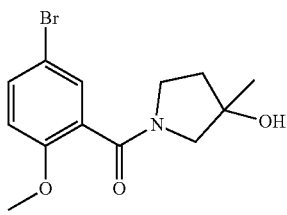 [SMILES: COc1ccc(Br)cc1C(=O)N1CCC(C)(O)C1]

Prepared in a similar manner to intermediate 33 using 5-bromo-2-methoxybenzoic acid (503 mg, 2.177 mmol) and 3-methylpyrrolidin-3-ol (244 mg, 2.412 mmol) to give the title compound.
LCMS (method F): rt=0.76, [M+H]$^+$=314.

Intermediate 55

(3-Hydroxy-3-methylpyrrolidin-1-yl)(2-methoxy-5-(4,4,5,5-tetramethyl-1,3,2-dioxaborolan-2-yl)phenyl)methanone

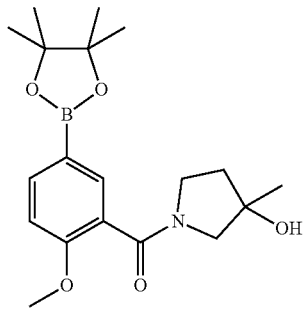 [SMILES: COc1ccc(B2OC(C)(C)C(C)(C)O2)cc1C(=O)N1CCC(C)(O)C1]

Prepared in a similar manner to intermediate 32 using (5-bromo-2-methoxyphenyl)(3-hydroxy-3-methylpyrrolidin-1-yl)methanone (intermediate 54) to give the title compound. LCMS (method F): rt=0.91, [M+H]$^+$=362.

Intermediate 56

(5-Bromo-2-methoxyphenyl)(1,4-oxazepan-4-yl)methanone

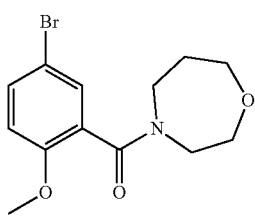 [SMILES: COc1ccc(Br)cc1C(=O)N1CCCOCC1]

Prepared in a similar manner to intermediate 33, using 5-bromo-2-methoxybenzoic acid (528 mg, 2.285 mmol) and 1,4-oxazepane (272 mg, 2.69 mmol) to give the title compound. LCMS (method F): rt=0.87, [M+H]$^+$=316.

Intermediate 57

(2-Methoxy-5-(4,4,5,5-tetramethyl-1,3,2-dioxaborolan-2-yl)phenyl)(1,4-oxazepan-4-yl)methanone

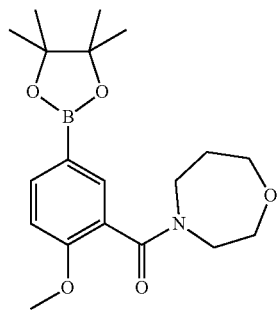 [SMILES: COc1ccc(B2OC(C)(C)C(C)(C)O2)cc1C(=O)N1CCCOCC1]

Prepared in a similar manner to intermediate 32, using (5-bromo-2-methoxyphenyl)(1,4-oxazepan-4-yl)methanone (intermediate 56) to give the title compound. LCMS (method F): rt=1.0, [M+H]$^+$=362.

Intermediate 58

(S)-(5-Bromo-2-methylphenyl)(3-hydroxypyrrolidin-1-yl)methanone

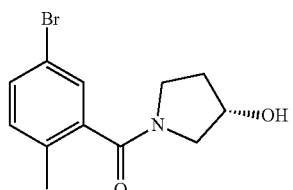

Prepared in a similar manner to intermediate 29, using 5-bromo-2-methylbenzoic acid (493 mg, 2.293 mmol) and (S)-pyrrolidin-3-ol (0.23 mL, 2.77 mmol) to give the title compound. LCMS (method F): rt=0.75, [M+H]$^+$=284.

Intermediate 59

(S)-(3-Hydroxypyrrolidin-1-yl)(2-methyl-5-(4,4,5,5-tetramethyl-1,3,2-dioxaborolan-2-yl)phenyl)methanone

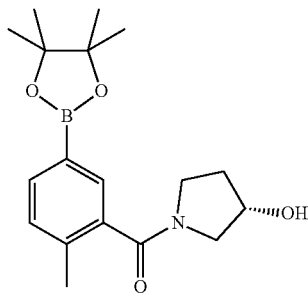 [SMILES: Cc1ccc(B2OC(C)(C)C(C)(C)O2)cc1C(=O)N1CC[C@H](O)C1]

Prepared in a similar manner to intermediate 32, using (S)-(5-bromo-2-methylphenyl)(3-hydroxypyrrolidin-1-yl)methanone (intermediate 58) to give the title compound. LCMS (method F): rt=0.87, [M+H]$^+$=332.

Intermediate 60

(S)-(5-Bromo-2-methoxyphenyl)(3-methylmorpholino)methanone

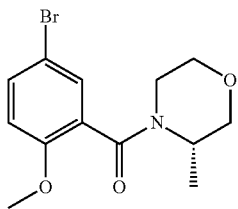 [SMILES: COc1ccc(Br)cc1C(=O)N1CCOC[C@@H]1C]

Prepared in a similar manner to intermediate 50, using 5-bromo-2-methoxybenzoic acid (505 mg, 2.186 mmol) and (S)-3-methylmorpholine (251 mg, 2.481 mmol) to give the title compound. LCMS (method F): rt=0.92, [M+H]$^+$=314.

Intermediate 61

(S)-(2-Methoxy-5-(4,4,5,5-tetramethyl-1,3,2-dioxaborolan-2-yl)phenyl)(3-methylmorpholino)methanone

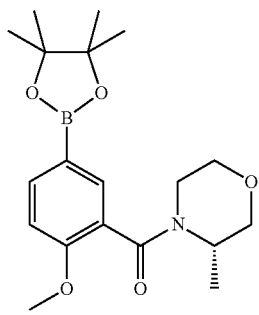 [SMILES: COc1ccc(B2OC(C)(C)C(C)(C)O2)cc1C(=O)N1CCOC[C@@H]1C]

Prepared in a similar manner to intermediate 32, using (S)-(5-bromo-2-methoxyphenyl)(3-methylmorpholino)methanone (intermediate 60) to give the title compound. LCMS (method F): rt=1.04, [M+H]$^+$=362.

Intermediate 62

(5-Bromo-2-methylphenyl)(3-hydroxy-3-methylpyrrolidin-1-yl)methanone

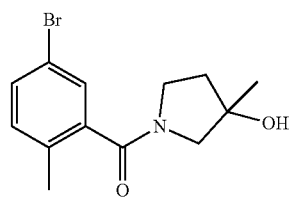 [SMILES: Cc1ccc(Br)cc1C(=O)N1CCC(C)(O)C1]

Prepared in a similar manner to intermediate 33, using 5-bromo-2-methylbenzoic acid (394 mg, 1.832 mmol) and 3-methylpyrrolidin-3-ol (222 mg, 2.199 mmol) to give the title compound. LCMS (method F): rt=0.81, [M+H]$^+$=298.

Intermediate 63

(3-Hydroxy-3-methylpyrrolidin-1-yl)(2-methyl-5-(4,4,5,5-tetramethyl-1,3,2-dioxaborolan-2-yl)phenyl)methanone

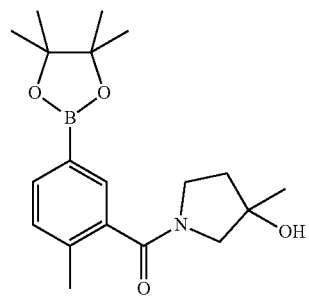 [SMILES: Cc1ccc(B2OC(C)(C)C(C)(C)O2)cc1C(=O)N1CCC(C)(O)C1]

Prepared in a similar manner to intermediate 32, using (5-bromo-2-methylphenyl)(3-hydroxy-3-methylpyrrolidin-1-yl)methanone (intermediate 62) to give the title compound. LCMS (method F): rt=0.91, [M+H]$^+$=346.

Intermediate 64

Ethyl 7-((3-(1H-pyrazol-1-yl)benzyl)amino)-3-bromo-2-methylpyrazolo[1,5-a]pyrimidine-5-carboxylate

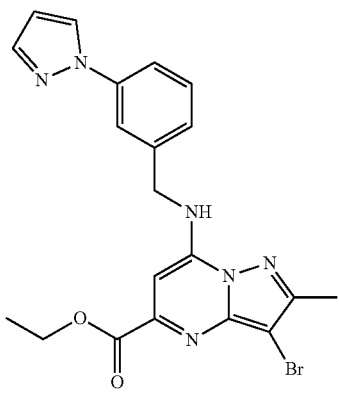 [SMILES: CCOC(=O)c1cc(NCc2cccc(-n3cccn3)c2)n2nc(C)c(Br)c2n1]

Prepared in a similar manner to intermediate 42, using (3-(1H-pyrazol-1-yl)phenyl)methanamine (available from Sigma-Aldrich Inc.) to give the title compound. LCMS (method F): rt=1.21, [M+H]$^+$=455.

Intermediate 65

Ethyl 7-((3-(1H-pyrazol-1-yl)benzyl)amino)-3-bromo-2-methylpyrazolo[1,5-a]pyrimidine-5-carboxylate

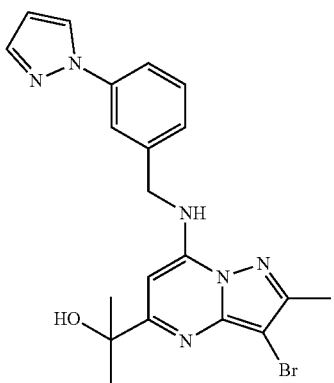 [SMILES: Cc1nn2c(NCc3cccc(-n4cccn4)c3)cc(C(C)(C)O)nc2c1Br]

Prepared in a similar manner to intermediate 43, using ethyl 7-((3-(1H-pyrazol-1-yl)benzyl)amino)-3-bromo-2-methylpyrazolo[1,5-a]pyrimidine-5-carboxylate (intermediate 64) to give the title compound. LCMS (method F): rt=1.20, [M+H]$^+$=441.

Intermediate 66

(R)-(5-Bromo-2-methoxyphenyl)(2-(hydroxymethyl)pyrrolidin-1-yl)methanone

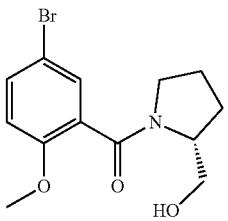 [SMILES: COc1ccc(Br)cc1C(=O)N1CCC[C@@H]1CO]

Prepared in a similar manner to intermediate 35, using 5-bromo-2-methoxybenzoic acid and (R)-pyrrolidin-2-yl-methanol to give the title compound. LCMS (method F): rt=0.83, [M+H]$^+$=314.

Intermediate 67

(R)-(2-(Hydroxymethyl)pyrrolidin-1-yl)(2-methoxy-5-(4,4,5,5-tetramethyl-1,3,2-dioxaborolan-2-yl)phenyl)methanone

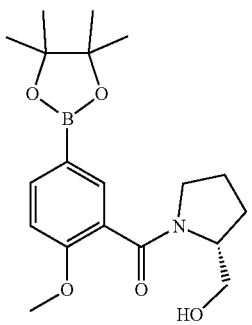 [SMILES: COc1ccc(B2OC(C)(C)C(C)(C)O2)cc1C(=O)N1CCC[C@@H]1CO]

Prepared in a similar manner to intermediate 36, using (R)-(5-bromo-2-methoxyphenyl)(2-(hydroxymethyl)pyrrolidin-1-yl)methanone (intermediate 66) to give the title compound. LCMS (method F): rt=1.02, [M+H]$^+$=362.

Intermediate 68

5-Bromo-2-chloro-N-(2-hydroxyethyl)-N-methyl-benzamide

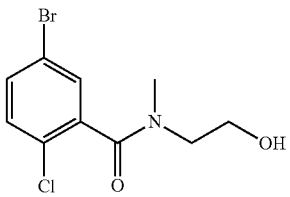

Prepared in a similar manner to intermediate 29, using 5-bromo-2-chlorobenzoic acid and 2-(methylamino)ethan-1-ol in THF, to give the title compound. LCMS (method F): rt=0.77, [M+H]⁺=294.

Intermediate 69

2-Chloro-N-(2-hydroxyethyl)-N-methyl-5-(4,4,5,5-tetramethyl-1,3,2-dioxaborolan-2-yl)benzamide

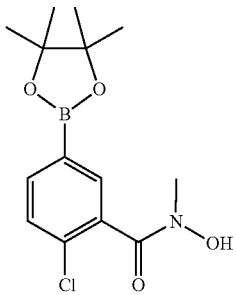 [SMILES: CN(O)C(=O)c1cc(B2OC(C)(C)C(C)(C)O2)ccc1Cl]

Prepared in a similar manner to intermediate 36, using Intermediate 68, to give the title compound. LCMS (method F): rt=0.75, [M+H]⁺=340.

Intermediate 70

5-Bromo-N-(2-hydroxyethyl)-N,2-dimethylbenzamide

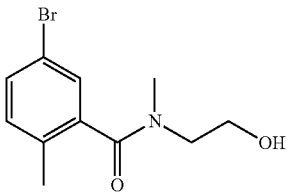

Prepared in a similar manner to Intermediate 29, using 5-bromo-2-methylbenzoic acid and 2-(methylamino)ethan-1-ol, to give the title compound. LCMS (method F): rt=0.76, [M+H]⁺=274.

Intermediate 71

N-(2-Hydroxyethyl)-N,2-dimethyl-5-(4,4,5,5-tetramethyl-1,3,2-dioxaborolan-2-yl)benzamide

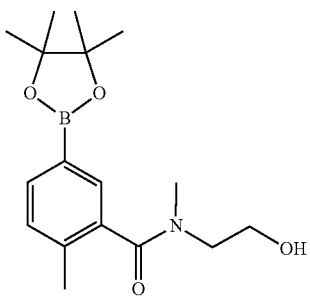 [SMILES: Cc1ccc(B2OC(C)(C)C(C)(C)O2)cc1C(=O)N(C)CCO]

Prepared in a similar manner to intermediate 36, using Intermediate 70, to give the title compound. LCMS (method F): rt=0.85, [M+H]⁺=320.

Intermediate 72

5-Bromo-N-(2-hydroxyethyl)-N,2-dimethylbenzamide

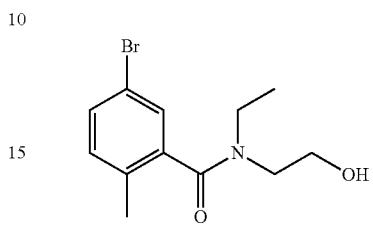

Prepared in a similar manner to intermediate 29, using 5-bromo-2-methylbenzoic acid and 2-(ethylamino)ethan-1-ol, in THF, to give the title compound. LCMS (method F): rt=0.84, [M+H]+=286.

Intermediate 73

N-Ethyl-N-(2-hydroxyethyl)-2-methyl-5-(4,4,5,5-tetramethyl1,3,2-dioxaborolan-2-yl)benzamide

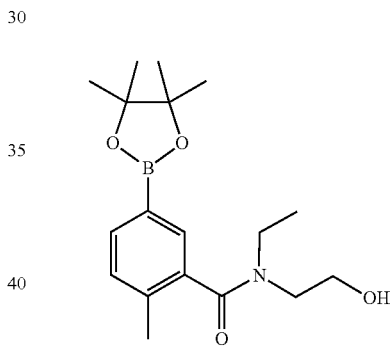

Prepared in a similar manner to intermediate 36, using Intermediate 72, to give the title compound. LCMS (method F): rt=0.95, [M+H]⁺=334.

Intermediate 74

Ethyl 2-(2-methyl-7-oxo-4,7-dihydropyrazolo[1,5-a]pyrimidin-5-yl)acetate

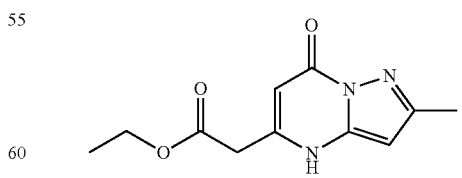

To a stirred solution of 5-methyl-1H-pyrazol-3-amine (25 g, 257 mmol) in 1,4-dioxane (150 mL), was added diethyl 3-oxopentanedioate (56.8 mL, 309 mmol), followed by acetic acid (7.37 mL, 129 mmol) at room temp. The reaction mixture was stirred at 100° C. for 6 h. The mixture was

Intermediate 75

Ethyl 2-(7-chloro-2-methylpyrazolo[1,5-a]pyrimi-din-5-yl)acetate

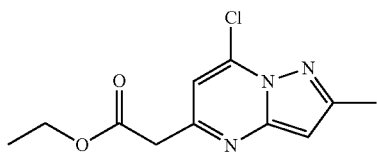 [SMILES: CCOC(=O)Cc1cc(Cl)n2nc(C)cc2n1]

To a stirred solution of ethyl 2-(2-methyl-7-oxo-4,7-dihydropyrazolo[1,5-a]pyrimidin-5-yl)acetate (Intermediate 74, 22.5 g, 96 mmol) in acetonitrile (250 mL), were added DIPEA (33.4 mL, 191 mmol), N-methylmorpholine (0.105 mL, 0.956 mmol) and POCl$_3$ (17.83 mL, 191 mmol) at 0° C. The reaction mixture was stirred at room temp. for 24 h. After completion of the reaction, the mixture was concentrated, and then poured onto ice/water. The mixture was neutralized with sodium bicarbonate and extracted with ethyl acetate (2×300 mL). The combined organic layers were washed with brine, dried over sodium sulfate, filtered and concentrated under reduced pressure. The residue was purified by silica chromatography (0-20% ethyl acetate in hexanes) to give the title compound. LCMS (method H): rt=2.05, [M+H]$^+$=254.

Intermediate 76

Ethyl 2-(7-chloro-3-iodo-2-methylpyrazolo[1,5-a]pyrimidin-5-yl)acetate

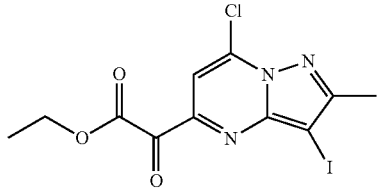 [SMILES: CCOC(=O)C(=O)c1cc(Cl)n2nc(C)c(I)c2n1]

To a stirred solution of ethyl 2-(7-chloro-2-methylpyrazolo[1,5-a]pyrimidin-5-yl)acetate (Intermediate 75, 8 g, 31.5 mmol) in DMF (160 mL) was added N-iodosuccinimide (7.09 g, 31.5 mmol) at 0° C. The resulting reaction mixture was stirred at room temp. for 1 h. The reaction mixture was poured onto ice-cooled water and the precipitated solid was collected by filtration. The residue was purified by silica chromatography (0-10% ethyl acetate in hexanes) to give the title compound. LCMS (method H): rt=2.43, [M+H]$^+$=380.

Intermediate 77

Ethyl 2-(3-iodo-2-methyl-7-((3-(1-methyl-1H-imidazol-2-yl)benzyl)amino)pyrazolo[1,5-a]pyrimidin-5-yl)acetate

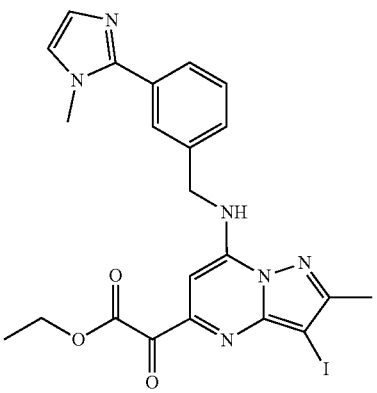 [SMILES: CCOC(=O)C(=O)c1cc(NCc2cccc(-c3nccn3C)c2)n2nc(C)c(I)c2n1]

A mixture of ethyl 2-(7-chloro-3-iodo-2-methylpyrazolo[1,5-a]pyrimidin-5-yl)acetate (Intermediate 76, 6 g, 15.81 mmol), (3-(1-methyl-1H-imidazol-2-yl)phenyl)methanamine (intermediate 3, 3.55 g, 18.97 mmol) and DIPEA (5.52 mL, 31.6 mmol) in DMSO (50 mL) was stirred and heated at 60° C. for 2 h. After cooling, the reaction mixture was poured onto ice-cooled water (300 mL) and the precipitated solid was collected by filtration, then dried under reduced pressure to give the title compound. LCMS (method H): rt=1.74, [M+H]$^+$=531.

Intermediate 78

Methyl 2-methoxy-5-(4,4,5,5-tetramethyl-1,3,2-dioxaborolan-2-yl)benzoate

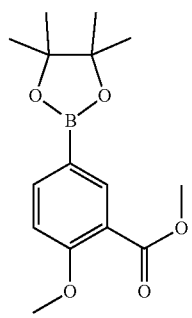

A solution/suspension of methyl 5-iodo-2-methoxybenzoate (20 g, 68.5 mmol), bis(pinacolato)diboron (17.39 g, 68.5 mmol), potassium acetate (20.16 g, 205 mmol) and bis(triphenylphosphine)palladium(II) chloride (3.85 g, 5.48 mmol) in 1,4-dioxane (200 mL) was heated to 100° C. under nitrogen. The reaction mixture was stirred at 100° C. for 20 h and then allowed to cool. The reaction mixture was filtered through a pad of CELITE. The pad was washed with ethyl acetate (250 mL). To the filtrate was added 1 M hydrochloric acid (250 mL). The organic phase was washed with brine (100 mL) and then dried over magnesium sulphate. The solvent was removed in vacuo. This was dissolved in DCM and applied to a silica cartridge (750 g) and eluted with a gradient of 0-50% ethyl acetate in cyclohexane over 9 CV. The required fractions were combined and evaporated in vacuo to give the title compound. LCMS (method J): rt=1.16, [M+H]$^+$=293.

Intermediate 79 and Intermediate 80

Ethyl 2-(3-iodo-2-methyl-7-((3-(1-methyl-1H-imidazol-2-yl)benzyl)amino)pyrazolo[1,5-a]pyrimidin-5-yl)propanoate and ethyl 2-(3-iodo-2-methyl-7-((3-(1-methyl-1H-imidazol-2-yl)benzyl)amino)pyrazolo[1,5-a]pyrimidin-5-yl)-2-methylpropanoate

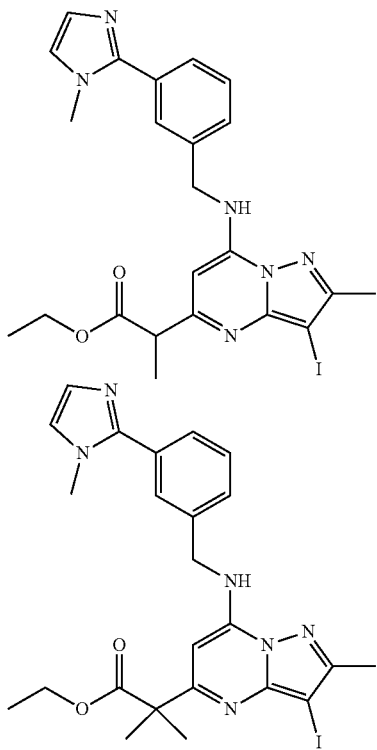

In a dried vial, ethyl 2-(3-iodo-2-methyl-7-((3-(1-methyl-1H-imidazol-2-yl)benzyl)amino)pyrazolo[1,5-a]pyrimidin-5-yl)acetate (Intermediate 77, 400 mg, 0.754 mmol) was stirred in THF (4.0 mL) under nitrogen at 0° C. methyl iodide (0.05 mL, 0.8 mmol) was added and the mixture stirred at 0° C. for 1 min after which LiHMDS (1 M in THF) (1.6 mL, 1.6 mmol) was added. The reaction was stirred at 0° C. for 5 min, then allowed to warm to room temperature. After 15 minutes the reaction mixture was diluted with sat. aq. NH$_4$Cl (2 mL) and stirred for 5 min. The mixture was transferred to a separating funnel with DCM (20 mL) and water (20 mL). The phases were partitioned and the organic layer collected. The aqueous was further washed with DCM (2×10 mL) and the combined organic layers were washed with brine (20 mL), filtered through a hydrophobic frit and evaporated to dryness. The crude was wet loaded from DCM (1 mL) onto a 28 g KP—NH column and eluted with 10-50% with ethyl acetate:ethanol (3:1, containing 1% triethylamine) in cyclohexane. The sample was further purified by reverse phase chromatography eluting with 40-90% acetonitrile in pH10 buffered ammonium carbonate water. The fractions containing each product were combined separately, concentrated under reduced pressure and dried in a vacuum oven over the weekend to afford the desired title compounds. Intermediate 79: LCMS (method F): rt=1.16, [M+H]$^+$=545. Intermediate 80: LCMS (method F): rt=1.27, [M+H]$^+$=559.

Intermediate 81

2-(3-Iodo-2-methyl-7-((3-(1-methyl-1H-imidazol-2-yl)benzyl)amino)pyrazolo[1,5-a]pyrimidin-5-yl)propan-1-ol

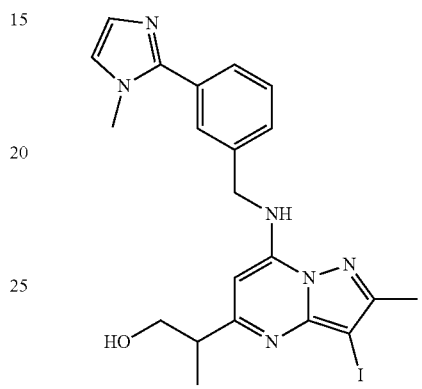

Ethyl 2-(3-iodo-2-methyl-7-((3-(1-methyl-1H-imidazol-2-yl)benzyl)amino)pyrazolo[1,5-a]pyrimidin-5-yl)propanoate (intermediate 79, 87 mg, 0.160 mmol) was stirred in THF (1.5 mL) at 0° C. under nitrogen. DIBAL-H (1 M in THF) (0.5 mL, 0.5 mmol) was added dropwise and the mixture stirred for 45 min. The mixture was quenched with aqueous 1 M Rochelle's salt and stirred vigorously for 30 min. The mixture was separated with DCM (10 mL) and water (10 mL). The separated aqueous phase was washed further with DCM (2×10 mL) and the combined organics passed through a hydrophobic frit and concentrated under reduced pressure to give the title compound. LCMS (method F): rt=0.99, [M+H]$^+$=503.

Intermediate 82

2-(3-Iodo-2-methyl-7-((3-(1-methyl-1H-imidazol-2-yl)benzyl)amino)pyrazolo[1,5-a]pyrimidin-5-yl)-2-methylpropan-1-ol

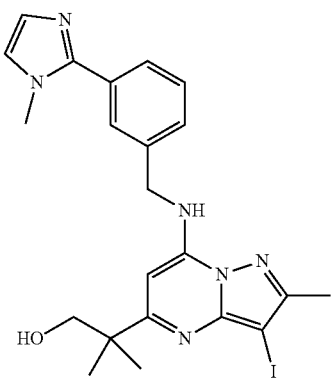 [SMILES: Cc1nn2c(NCc3cccc(-c4nccn4C)c3)cc(C(C)(C)CO)nc2c1I]

Prepared in a similar manner to Intermediate 81, using ethyl 2-(3-iodo-2-methyl-7-((3-(1-methyl-1H-imidazol-2-yl)benzyl)amino)pyrazolo[1,5-a]pyrimidin-5-yl)-2-methyl-propanoate (intermediate 80) to give the title compound. LCMS (method F): rt=1.12, [M+H]$^+$=517.

Intermediate 83

(5-Bromo-2-methoxyphenyl)(2-(hydroxymethyl)pyrrolidin-1-yl)methanone

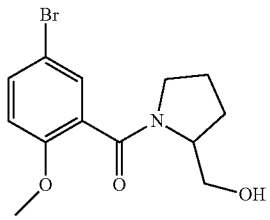 [SMILES: COc1ccc(Br)cc1C(=O)N1CCCC1CO]

Prepared in a similar manner to intermediate 29, using 5-bromo-2-methoxybenzoic acid and pyrrolidin-2-ylmethanol in THF, to give the title compound. LCMS (method F): rt=0.84, [M+H]$^+$=314.

Intermediate 84

(2-(Hydroxymethyl)pyrrolidin-1-yl)(2-methoxy-5-(4,4,5,5-tetramethyl-1,3,2-dioxaborolan-2-yl)phenyl)methanone

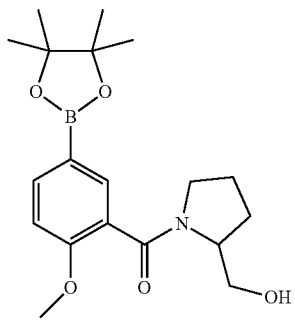 [SMILES: COc1ccc(B2OC(C)(C)C(C)(C)O2)cc1C(=O)N1CCCC1CO]

Prepared in a similar manner to intermediate 36, using intermediate 83, to give the title compound. LCMS (method F): rt=0.96, [M+H]$^+$=362.

Intermediate 85

(R)-5-Bromo-N-(1-hydroxypropan-2-yl)-N,2-dimethylbenzamide

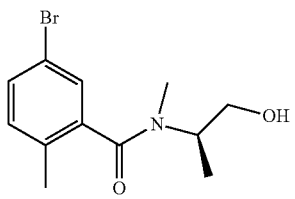 [SMILES: Cc1ccc(Br)cc1C(=O)N(C)[C@H](C)CO]

Prepared in a similar manner to intermediate 29, using 5-bromo-2-methoxybenzoic acid and (R)-2-(methylamino)propan-1-ol in THF, to give the title compound. LCMS (method F): rt=0.82, [M+H]$^+$=286.

Intermediate 86

(R)—N-(1-Hydroxypropan-2-yl)-N,2-dimethyl-5-(4,4,5,5-tetramethyl-1,3,2-dioxaborolan-2-yl)benzamide

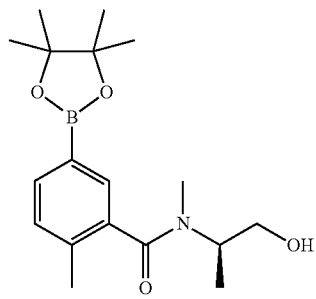 [SMILES: Cc1ccc(B2OC(C)(C)C(C)(C)O2)cc1C(=O)N(C)[C@H](C)CO]

Prepared in a similar manner to intermediate 36, using intermediate 85, to give the title compound. LCMS (method F): rt=0.91, [M+H]$^+$=334.

Intermediate 87

5-Bromo-N-(1-hydroxypropan-2-yl)-N,2-dimethyl-benzamide

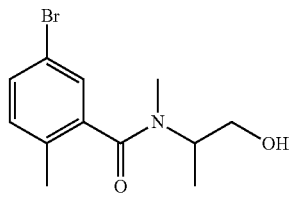

Prepared in a similar manner to intermediate 29, using 5-bromo-2-methylbenzoic acid and 2-(methylamino)propan-1-ol in THE to give the title compound. LCMS (method F): rt=0.82, [M+H]$^+$=286.

Intermediate 88

N-(1-Hydroxypropan-2-yl)-N,2-dimethyl-5-(4,4,5,5-tetramethyl-1,3,2-dioxaborolan-2-yl)benzamide

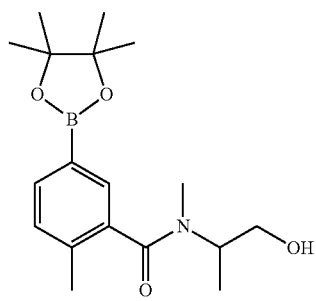 [SMILES: Cc1ccc(B2OC(C)(C)C(C)(C)O2)cc1C(=O)N(C)C(C)CO]

Prepared in a similar manner to intermediate 36, using 5-bromo-N-(1-hydroxypropan-2-yl)-N,2-dimethylbenzamide (intermediate 87) to give the title compound. LCMS (method F): rt=0.91, [M+H]⁺=334.

Intermediate 89

(5-Bromo-2-methylphenyl)(3-hydroxypyrrolidin-1-yl)methanone

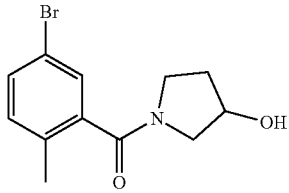 [SMILES: Cc1ccc(Br)cc1C(=O)N1CCC(O)C1]

Prepared in a similar manner to intermediate 29, using 5-bromo-2-methylbenzoic acid and pyrrolidin-3-ol in THF to give the title compound. LCMS (method F): rt=0.75, [M+H]⁺=284.

Intermediate 90

(3-Hydroxypyrrolidin1-yl)(2-methyl-5-(4,4,5,5-tetramethyl1,3,2-dioxaborolan-2-yl)phenyl)methanone

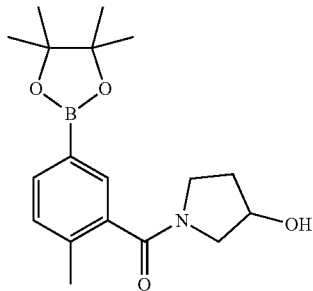 [SMILES: Cc1ccc(B2OC(C)(C)C(C)(C)O2)cc1C(=O)N1CCC(O)C1]

Prepared in a similar manner to intermediate 36, using (5-bromo-2-methylphenyl)(3-hydroxypyrrolidin-1-yl)methanone (Intermediate 89) to give the title compound. LCMS (method F): rt=0.84, [M+H]⁺=332.

Intermediate 91

5-Bromo-N-(1-hydroxypropan-2-yl)-2-methoxy-N-methylbenzamide

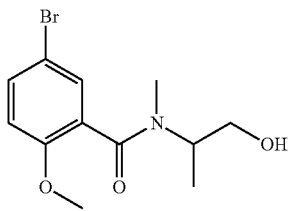 [SMILES: COc1ccc(Br)cc1C(=O)N(C)C(C)CO]

Prepared in a similar manner to intermediate 29, using 5-bromo-2-methoxybenzoic acid and 2-(methylamino)propan-1-ol in THF to give the title compound. LCMS (method F): rt=0.76, [M+H]⁺=302.

Intermediate 92

N-(1-Hydroxypropan2-yl)-2-methoxy-N-methyl-5-(4,4,5,5-tetramethyl-1,3,2-dioxaborolan-2-yl)benzamide

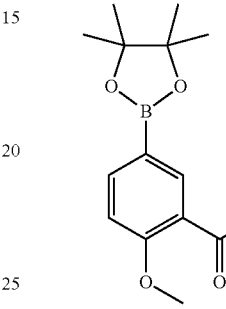

Prepared in a similar manner to intermediate 36, using 5-Bromo-N-(1-hydroxypropan-2-yl)-2-methoxy-N-methylbenzamide (intermediate 91) to give the title compound. LCMS (method F): rt=0.89, [M+H]⁺=350.

Intermediate 93 and Intermediate 94 tert-Butyl (5-(1-hydroxyethyl)-3-iodo-2-methylpyrazolo[1,5-a]pyrimidin-7-yl)(3-(1-methyl-1H-imidazol-2-yl)benzyl)carbamate, Isomer 1 and Isomer 2

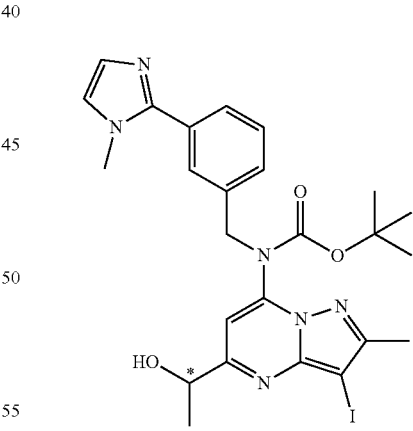

tert-Butyl (5-(1-hydroxyethyl)-3-iodo-2-methylpyrazolo[1,5-a]pyrimidin-7-yl)(3-(1-methyl-1H-imidazol-2-yl)benzyl)carbamate (intermediate 26, 60 mg, 0.123 mmol) was separated using a Chiralpak AD-H (30 mm×250 mm, 5 μm) and a solvent system of 30% ethanol (containing 0.2% isopropylamine)/heptane (containing 0.2% isopropylamine) at 30 mL/min to give the chiral title compounds. Isomer 1: LCMS (method F): rt=0.97, [M+H]⁺=489. Chiral HPLC: rt 10.73, 99.7%. Isomer 2: LCMS (method F): rt=0.97, [M+H]⁺=489. Chiral HPLC: rt 7.53, 100%.

Intermediate 95

5-Bromo-N,2-dimethyl-N-(tetrahydro-2H-pyran-4-yl)benzamide

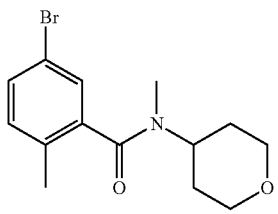

Prepared in a similar manner to intermediate 33, using 5-bromo-2-methylbenzoic acid and N-methyltetrahydro-2H-pyran-4-amine in THF to give the title compound. LCMS (method F): rt=0.96, [M+H]$^+$=312.

Intermediate 96

N,2-Dimethyl-N-(tetrahydro-2H-pyran-4-yl)-5-(4,4,5,5-tetramethyl-1,3,2-dioxaborolan-2-yl)benzamide

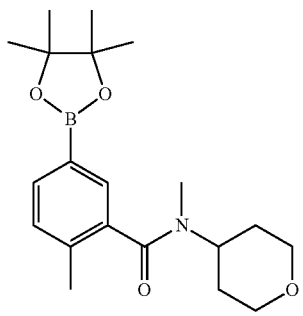 [SMILES: Cc1ccc(B2OC(C)(C)C(C)(C)O2)cc1C(=O)N(C)C1CCOCC1]

Prepared in a similar manner to intermediate 32, using 5-bromo-N,2-dimethyl-N-(tetrahydro-2H-pyran-4-yl)benzamide (Intermediate 95) to give the title compound. LCMS (method F): rt=1.06, [M+H]$^+$=360.

Intermediate 97

2-Methylpyrazolo[1,5-a]pyrimidine-5,7(4H,6H)-dione

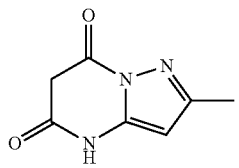

5-Methyl-1H-pyrazol-3-amine (50 g, 515 mmol) was dissolved in ethanol (500 mL) under nitrogen atmosphere. Sodium ethanolate (334 g, 1030 mmol) in ethanol was added followed by diethyl malonate (86 mL, 566 mmol). The reaction mixture was stirred at 80° C. for 4 h. The reaction mixture was allowed to cooled to room temp., and the precipitated solid was collected by filtration, washed with excess of ethanol (1000 mL) and dried to afford the title compound. LCMS (method B): rt=0.48, [M+H]$^+$=166.

Intermediate 98

5,7-Dichloro-2-methylpyrazolo[1,5-a]pyrimidine

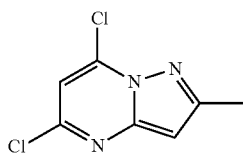

2-Methylpyrazolo[1,5-a]pyrimidine-5,7(4H,6H)-dione (intermediate 97, 35 g, 212 mmol) was added to phosphorus oxychloride (395 ml, 4239 mmol) and the mixture was heated at 100° C. for 24 h. The mixture was cooled to room temp. and excess phosphorus oxychloride was distilled under reduced pressure. The mixture was co-distilled with toluene (2×200 mL). The crude product was purified by silica gel column chromatography (20% ethyl acetate in pet. ether) to afford the title compound. LCMS (method B): rt=3.21, [M+H]$^+$=201.

Intermediate 99

5,7-Dichloro-3-iodo-2-methylpyrazolo[1,5-a]pyrimidine

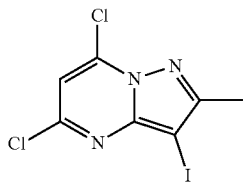

To a stirred solution of 5,7-dichloro-2-methylpyrazolo[1,5-a]pyrimidine (intermediate 98, 15 g, 74.2 mmol) in DCM (200 mL) at 0° C. was added acetic acid (29.8 mL, 520 mmol) followed by NIS (16.70 g, 74.2 mmol) portion wise. The resulting reaction mixture was stirred at 0° C. for 1 h. 10% Aqueous sodium sulphite solution (200 mL) was added and vigorously stirred at room temp. for 30 min. The DCM layer was separated and washed with saturated sodium thiosulphate (300 mL), brine (200 mL), followed by water (100 mL) and the organic layer was dried over anhydrous sodium sulphate and filtered. The filtrate was concentrated under reduced pressure to afford the title compound. LCMS (method E): rt=2.37, [M+H]$^+$=328.

Intermediate 100

5-Chloro-3-iodo-2-methyl-N-(3-(1-methyl-1H-imidazol-2-yl)benzyl)pyrazolo[1,5-a]pyrimidin-7-amine

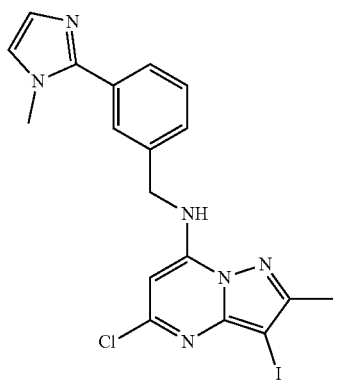 [SMILES: Cc1nn2c(NCc3cccc(-c4nccn4C)c3)cc(Cl)nc2c1I]

A mixture of (3-(1-methyl-1H-imidazol-2-yl)phenyl)methylamine (intermediate 3, 31 g, 122 mmol), 5,7-dichloro-3-iodo-2-methylpyrazolo[1,5-a]pyrimidine (Intermediate 99, 39.9 g, 122 mmol) and DIPEA (63.8 mL, 365 mmol) in DMSO (500 mL) was stirred and heated at 50° C. for 18 h. After cooling, the reaction mixture was poured onto ice-cooled water (1500 mL). The precipitated solid was collected by filtration, dried under reduced pressure to afford the title compound. LCMS (method C): rt=2.19, [M+H]$^+$=479.

Intermediate 101 tert-Butyl (5-chloro-3-iodo-2-methylpyrazolo[1,5-a]pyrimidin-7-yl)(3-(1-methyl-1H-imidazol-2-yl)benzyl)carbamate

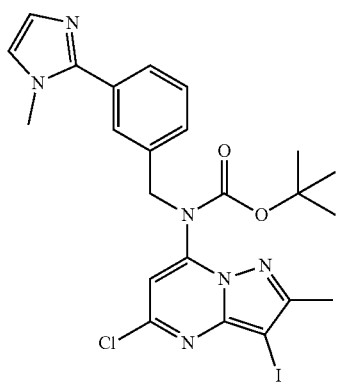 [SMILES: Cc1nn2c(N(Cc3cccc(-c4nccn4C)c3)C(=O)OC(C)(C)C)cc(Cl)nc2c1I]

To a stirred solution of 5-chloro-3-iodo-2-methyl-N-(3-(1-methyl-1H-imidazol-2-yl)benzyl)pyrazolo[1,5-a]pyrimidin-7-amine (intermediate 100, 50 g, 96 mmol) in DCM (1000 mL) was added DIPEA (25.03 mL, 143 mmol), DMAP (1.167 g, 9.55 mmol) and di-tert-butyl dicarbonate (33.3 mL, 143 mmol). The reaction was stirred at room temp. for 3 h. The reaction mixture was diluted with DCM (1000 mL), washed with water (1000 mL), dried over anhydrous sodium sulphate, filtered and concentrated under reduced pressure. The crude product was purified by silica gel chromatography (80% ethyl acetate in pet. ether) to afford the title compound. LCMS (method D): rt=6.33, [M+H]$^+$=579.

Intermediate 102 tert-Butyl (5-chloro-3-(3-((2-hydroxyethyl)sulfonyl)-4-methoxyphenyl)-2-methylpyrazolo[1,5-a]pyrimidin-7-yl)(3-(1-methyl-1H-imidazol-2-yl)benzyl)carbamate

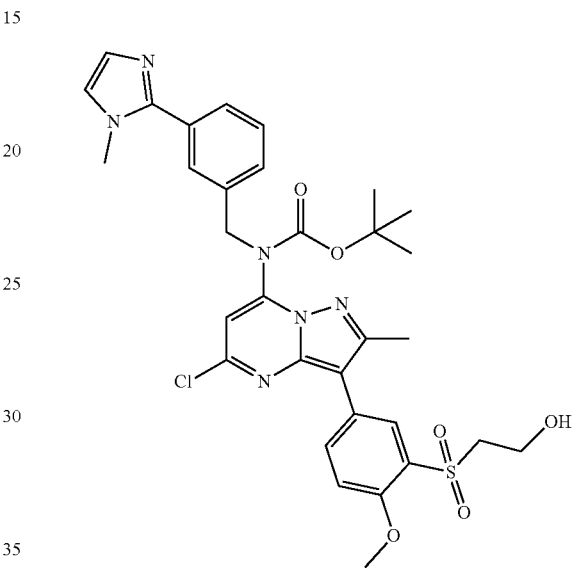

tert-Butyl (5-chloro-3-iodo-2-methylpyrazolo[1,5-a]pyrimidin-7-yl)(3-(1-methyl-1H-imidazol-2-yl)benzyl)carbamate (intermediate 101, 506 mg, 0.874 mmol), 2-((2-methoxy-5-(4,4,5,5-tetramethyl-1,3,2-dioxaborolan-2-yl)phenyl)sulfonyl)ethan-1-ol (intermediate 19, 268 mg, 0.783 mmol), triphenylarsine (13 mg, 0.042 mmol), PdCl$_2$(PhCN)$_2$ (18 mg, 0.047 mmol) and sodium carbonate (193 mg, 1.821 mmol) were combined in 1,4-dioxane (6 mL) and water (1.5 mL). The mixture was sparged with nitrogen for 1 min and the heated to 80° C. for 4 h. 2-((2-Methoxy-5-(4,4,5,5-tetramethyl1,3,2-dioxaborolan-2-yl)phenyl)sulfonyl)ethan-1-ol (intermediate 19, 113 mg, 0.330 mmol), triphenylarsine (13 mg, 0.042 mmol) and PdCl$_2$(PhCN)$_2$ (18 mg, 0.047 mmol) were added. The mixture was sparged with nitrogen for 1 min and then heated to 80° C. overnight. The mixture was allowed to cool and concentrated under reduced pressure. The residue was slurried in ethyl acetate (20 mL) and filtered through CELITE, washing with ethyl acetate (40 mL) and then DCM (40 mL). The combined filtrate was concentrated under reduced pressure to remove the DCM and then partitioned with water (40 mL). The organic phase was separated, passed through a hydrophobic frit and concentrated under reduced pressure. The residue was dissolved in DMSO: methanol (6 mL, 1:1) and purified by MDAP (method A). Fractions containing product were combined and concentrated under reduced pressure to give the title compound. LCMS (method F): rt=1.12, [M+H]$^+$=667.

Intermediate 103

Ethyl 2-(3-iodo-2-methyl-7-((3-(1-methyl-1H-imidazol-2-yl)benzyl)amino)pyrazolo[1,5-a]pyrimidin-5-yl)butanoate

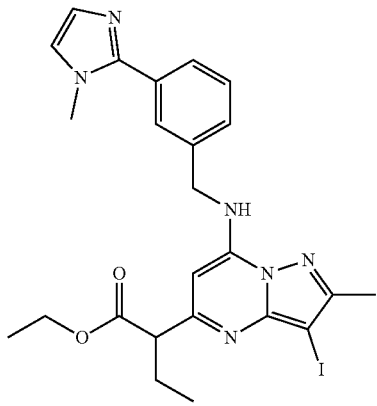 [SMILES: CCOC(=O)C(CC)c1cc(NCc2cccc(-c3nccn3C)c2)n2nc(C)c(I)c2n1]

Prepared in a similar manner to Intermediate 79, using iodoethane, to give the title compound. LCMS (method F): rt=1.24, [M+H]$^+$=559.

Intermediate 104

2-(3-Iodo-2-methyl-7-((3-(1-methyl-1H-imidazol-2-yl)benzyl)amino)pyrazolo[1,5-a]pyrimidin-5-yl)butan-1-ol

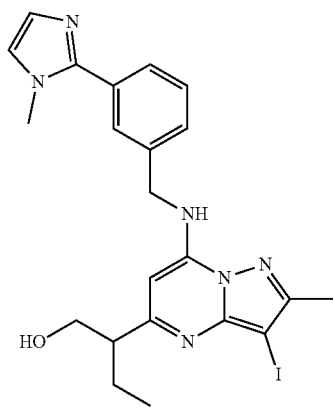 [SMILES: CCC(CO)c1cc(NCc2cccc(-c3nccn3C)c2)n2nc(C)c(I)c2n1]

Prepared in a similar manner to intermediate 81, using ethyl 2-(3-iodo-2-methyl-7-((3-(1-methyl-1H-imidazol-2-yl)benzyl)amino)pyrazolo[1,5-a]pyrimidin-5-yl)butanoate (intermediate 103), to give the title compound. LCMS (method F): rt=1.05, [M+H]$^+$=517.

Intermediate 105

3-(3-Bromo-2-methyl-7-((3-(1-methyl-1H-imidazol-2-yl)benzyl)amino)pyrazolo[1,5-a]pyrimidin-5-yl)pentan-3-ol Ethyl 3-bromo-2-methyl-7-((3-(1-methyl-1H-imidazol-2-yl)benzyl)amino)pyrazolo[1,5-a]pyrimidine-5-carboxylate (intermediate 42, 253 mg, 0.539 mmol) was stirred in THF (5 mL) at 0° C. under nitrogen. Ethylmagnesium bromide (1 M in THF) (2.4 mL, 2.4 mmol) was added over 5 min and the mixture stirred at 0° C. for 30 min then warmed to room temp. After 2 h, the reaction mixture was quenched with aqueous saturated ammonium chloride (2 mL) and partitioned with DCM (10 mL) and aqueous saturated ammonium chloride (10 mL). The organic phase was collected and the aqueous washed with DCM (2×5 mL). The combined organic layers were passed through a hydrophobic frit and evaporated to dryness. The residue was stirred in THF (5 mL) under nitrogen at 0° C. Ethylmagnesium bromide (1 M in THF) (1.6 mL, 1.6 mmol) was added over 5 min and the mixture stirred at 0° C. for 30 min. The mixture was quenched with aqueous saturated ammonium chloride (2 mL) and partitioned with DCM (10 mL) and aqueous saturated ammonium chloride (10 mL). The organic phase was collected and the aqueous washed with DCM (2×5 mL). The combined organic layers were passed through a hydrophobic frit and concentrated under reduced pressure. The residue was dissolved in methanol: DMSO (2 mL, 1:1) and purified by MDAP (method A). The fractions containing product were combined, evaporated to dryness and further dried in a vacuum oven overnight to give the title compound. LCMS (method J): rt=0.80, [M+H]$^+$=483.

Intermediate 106

3-Bromo-N-methoxy-N,2-dimethyl-7-((3-(1-methyl-1H-imidazol-2-yl)benzyl)amino)pyrazolo[1,5-a]pyrimidine-5-carboxamide

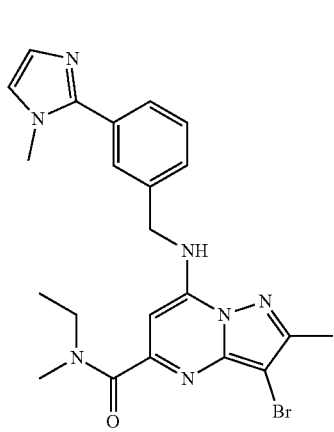 [SMILES: CCN(C)C(=O)c1cc(NCc2cccc(-c3nccn3C)c2)n2nc(C)c(Br)c2n1]

A suspension of N,O-dimethylhydroxylamine hydrochloride (1.62 g, 16.61 mmol) in THF (10 mL) was cooled to −10° C.). n-Butyllithium (2.5 M in hexanes) (13 mL, 32.5 mmol) was added dropwise over 40 min to maintain the reaction temperature below 5° C. The mixture was then stirred in the ice bath for 15 min. To this solution was added slowly ethyl 3-bromo-2-methyl-7-((3-(1-methyl-1H-imidazol-2-yl)benzyl)amino)pyrazolo[1,5-a]pyrimidine-5-carboxylate (intermediate 42, 1.5 g, 3.2 mmol) in THF (10 mL). The temperature of the mixture was maintained below 0° C. during the addition. Once the addition was complete, the mixture was stirred in the ice bath (at −8° C.) for 20 min and then allowed to warm to room temp. and stirred for 1 h. Sat. aq. ammonium chloride (20 mL) was added and the mixture stirred for 30 min. DCM (50 mL) was added. The solution was sonicated and transferred to a separating funnel. The solid remaining was suspended in a mixture of water (50 mL) and DCM (50 mL) and sonicated. The mixture was added to the separating funnel. The organic was separated and the aqueous extracted further with DCM (100 mL×2). The combined organics were passed through a hydrophobic frit and concentrated under reduced pressure. The residue was dissolved in DCM and purified by silica chromatography eluting with 30-100% ethyl acetate:ethanol (3:1, v/v, containing 1% triethylamine) in cyclohexane over 10 CV. The fractions containing product were combined and concentrated under reduced pressure to give the title compound. LCMS (method J): rt=0.63, [M+H]$^+$=484.

Intermediate 107

1-(3-Bromo-2-methyl-7-((3-(1-methyl-1H-imidazol-2-yl)benzyl)amino)pyrazolo[1,5-a]pyrimidin-5-yl)propan-1-one 3-Bromo-N-methoxy-N,2-dimethyl-7-((3-(1-methyl-1H-imidazol-2-yl)benzyl)amino)pyrazolo[1,5-a]pyrimidine-5-carboxamide (Intermediate 106, 530 mg, 1.094 mmol) was dissolved in THF (20 mL) and cooled to 0° C. Ethylmagnesium bromide (1 M in THF) (2.7 mL, 2.7 mmol) was added slowly. After 20 min the mixture was quenched with saturated aqueous ammonium chloride (5 mL) and stirred vigorously for 10 min. The slurry was partitioned between water (50 mL) and DCM (50 mL). The separated aqueous phase was washed with further DCM (2×50 mL) and the combined organics passed through a hydrophobic frit and concentrated under reduced pressure. The residue was purified by reverse phase chromatography (C$_{18}$, 60 g) eluting with 30-85% acetonitrile in 10 mM ammonium bicarbonate in water (adjusted to pH 10 with ammonia solution) over 25 CV. The fractions containing the desired product were combined and concentrated under reduced pressure. The residue was purified by reverse phase chromatography (C$_{18}$, 40 g) eluting with 20-50% acetonitrile in water (containing 0.1% formic acid). The fractions containing the product were combined and neutralised using sat. aq. sodium bicarbonate, then extracted with DCM (2×50 mL). The combined organics were passed through a hydrophobic frit and dried under reduced pressure to give the title compound. LCMS (method J): rt=0.84, [M+H]$^+$=453.

Intermediate 108 and 109

1-(3-Bromo-2-methyl-7-((3-(1-methyl-1H-imidazol-2-yl)benzyl)amino)pyrazolo[1,5-a]pyrimidin-5-yl)propan-1-ol, Isomer 1 and Isomer 2

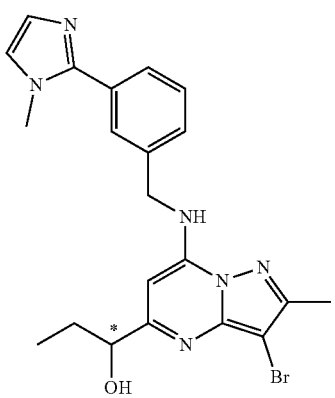 [SMILES: CCC(O)c1cc(NCc2cccc(-c3nccn3C)c2)n2nc(C)c(Br)c2n1]

1-(3-Bromo-2-methyl-7-((3-(1-methyl-1H-imidazol-2-yl)benzyl)amino)pyrazolo[1,5-a]pyrimidin-5-yl)propan-1-one (Intermediate 107, 164 mg, 0.362 mmol) was stirred in THF (3 mL) at 0° C. under nitrogen. DIBAL-H (1 M in THF) (0.75 mL, 0.75 mmol) was added dropwise and the mixture stirred for 90 min. The mixture was quenched with aqueous potassium sodium tartrate (1 M) and stirred vigorously for 1 h. The mixture was separated with DCM (20 mL) and water (20 mL). The separated aqueous phase was washed further with DCM (2×20 mL) and the combined organics were passed through a hydrophobic frit and concentrated under reduced pressure. The residue was purified by reverse phase chromatography ($C_{18}$, 30 g) eluting with 10-40% acetonitrile (containing 0.1% formic acid) in water (containing 0.1% formic acid) over 10 CV. The fractions containing the product were combined and basified using saturated aqueous sodium bicarbonate then extracted using DCM (2×50 mL). The combined organic layers were passed through a hydrophobic frit and concentrated under reduced pressure. The residue was purified using a Chiralpak AD-H column (30 mm×250 mm, 5 µm), eluting with 30% ethanol (containing 0.2% isopropylamine) in hexane (containing 0.2% isopropylamine) to give title compounds. Isomer 1: LCMS (method J): rt=0.61, [M+H]⁺=455. Chiral HPLC, rt 5.95, 100%. Isomer 2: LCMS (method J): rt=0.61, [M+H]⁺=455. Chiral HPLC, rt 9.02, 100%.

Intermediate 110

1-(3-Bromo-2-methyl-7-((3-(1-methyl-1H-imidazol-2-yl)benzyl)amino)pyrazolo[1,5-a]pyrimidin-5-yl)ethan-1-one

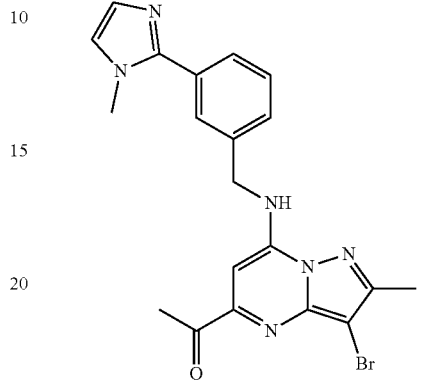

Prepared in a similar manner to Intermediate 107, using methylmagnesium bromide, to give the title compound. LCMS (method J): rt=0.73, [M+H]⁺=439.

Intermediate 111 and 112

1-(3-Bromo-2-methyl-7-((3-(1-methyl-1H-imidazol-2-yl)benzyl)amino)pyrazolo[1,5-a]pyrimidin-5-yl)ethan-1-ol, Isomer 1 and Isomer 2

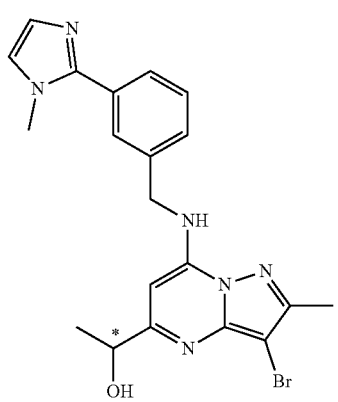 [SMILES: Cc1nn2c(NCc3cccc(-c4nccn4C)c3)cc(C(C)O)nc2c1Br]

Prepared in a similar manner to intermediate 108 and 109, to give the title compounds. Isomer 1: LCMS (method F): rt=0.95, [M+H]⁺=441. Chiral HPLC, rt 7.37, 100%. Isomer 2: LCMS (method F): rt=0.95, [M+H]⁺=441. Chiral HPLC, rt 11.07, 99.4%.

Intermediate 113 tert-Butyl (5-acetyl-3-bromo-2-methylpyrazolo[1,5-a]pyrimidin-7-yl)(3-(1-methyl-1H-imidazol-2-yl)benzyl)carbamate

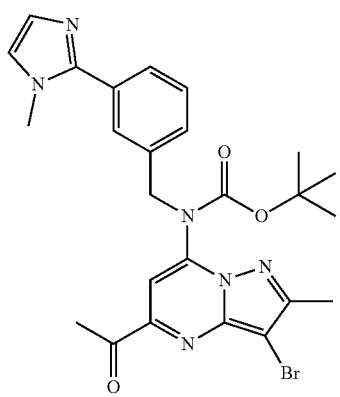 [SMILES: CC(=O)c1cc(N(Cc2cccc(-c3nccn3C)c2)C(=O)OC(C)(C)C)n2nc(C)c(Br)c2n1]

1-(3-Bromo-2-methyl-7-((3-(1-methyl-1H-imidazol-2-yl)benzyl)amino)pyrazolo[1,5-a]pyrimidin-5-yl)ethan-1-one (intermediate 110, 358 mg, 0.815 mmol) was suspended in THF (10 mL). DIPEA (0.21 mL, 1.202 mmol) and DMAP (10 mg, 0.082 mmol) were added followed by Boc-anhydride (0.28 mL, 1.206 mmol). The mixture was stirred and heated to 50° C. for 1.5 h. The reaction was cooled to ambient temp., diluted with water (25 mL) and ethyl acetate (25 mL). The organic phase was collected and the aqueous further washed with ethyl acetate (2×25 mL). The combined organics were passed through a hydrophobic frit and evaporated to dryness. The residue was dissolved in the minimum of DCM (1.5 mL) and wet loaded onto a 40 g silica gel column. The product was eluted with 0-50% ethanol:ethyl acetate (3:1, v/v, containing 1% triethylamine) in cyclohexane. Fractions containing product were combined and evaporated to dryness, then dried under high vacuum for 2 days to give the title compound. LCMS (method F): rt=1.35, [M+H]$^+$=539.

Intermediate 114 tert-Butyl (3-bromo-5-(1-((tert-butyldimethylsilyl)oxy)vinyl)-2-methylpyrazolo[1,5-a]pyrimidin-7-yl)(3-(1-methyl-1H-imidazol-2-yl)benzyl)carbamate

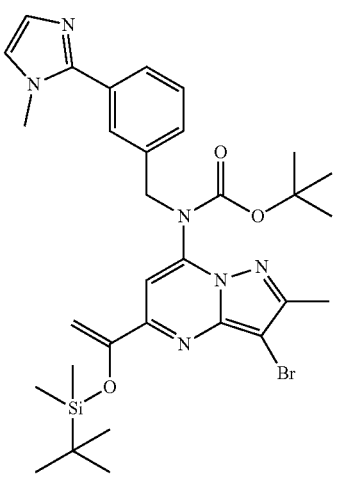 [SMILES: C=C(O[Si](C)(C)C(C)(C)C)c1cc(N(Cc2cccc(-c3nccn3C)c2)C(=O)OC(C)(C)C)n2nc(C)c(Br)c2n1]

tert-Butyl (5-acetyl-3-bromo-2-methylpyrazolo[1,5-a]pyrimidin-7-yl)(3-(1-methyl-1H-imidazol-2-yl)benzyl)carbamate (intermediate 113, 456 mg, 0.676 mmol) was stirred in DCM (5 mL) and triethylamine (0.32 mL, 2.296 mmol) at 0° C. under nitrogen. TBS-OTf (0.21 mL, 0.914 mmol) was added and the mixture allowed to warm to ambient temp. where it was stirred for 4 h. Additional triethylamine (0.3 mL, 2.152 mmol) then TBS-OTf (0.25 mL, 1.089 mmol) were added and the mixture was left overnight. The mixture was partitioned between DCM (20 mL) and water (20 mL). The separated aqueous phase was washed with DCM (2×10 mL) and the combined organics passed through a hydrophobic frit and concentrated under reduced pressure. The residue was purified by silica chromatography eluting with 0-50% ethyl acetate in cyclohexane. The residue was triturated with DCM and dried under high vacuum for 2 days to give the title compound. LCMS (method F): rt=1.70, [M+H]$^+$=653.

Intermediate 115 tert-Butyl (3-bromo-5-(1-((tert-butyldimethylsilyl)oxy)cyclopropyl)-2-methylpyrazolo[1,5-a]pyrimidin-7-yl)(3-(1-methyl-1H-imidazol-2-yl)benzyl)carbamate

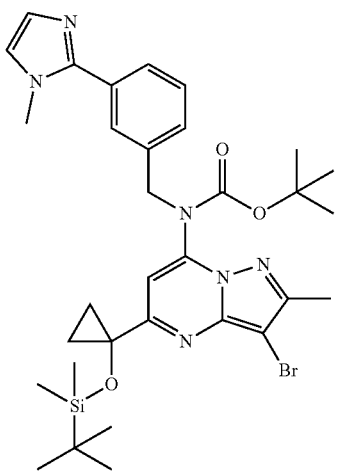 [SMILES: Cc1nn2c(N(Cc3cccc(-c4nccn4C)c3)C(=O)OC(C)(C)C)cc(C3(O[Si](C)(C)C(C)(C)C)CC3)nc2c1Br]

Diethylzinc (1 M in heptane) (0.795 mL, 0.795 mmol) was stirred in DCM (0.5 mL) at 0° C. under nitrogen. TFA (0.061 mL, 0.795 mmol) in DCM (0.5 mL) was added very slowly dropwise and the mixture stirred for 10 min. Diiodomethane (0.064 mL, 0.795 mmol) in DCM (0.5 mL) was added dropwise. After 5 minutes of stirring tert-butyl (3-bromo-5-(1-((tert-butyldimethylsilyl)oxy)vinyl)-2-methylpyrazolo[1,5-a]pyrimidin-7-yl)(3-(1-methyl-1H-imidazol-2-yl)benzyl)carbamate (Intermediate 114, 260 mg, 0.398 mmol) in DCM (2 mL) was added. After 1 h the mixture was allowed to warm to ambient temp. After 6 h sat. aq. ammonium chloride (1 mL) was added and the mixture stirred vigorously for 30 min. Sat. aq. sodium bicarbonate (2 mL) was added and the mixture stirred for a further 30 min. The mixture was partitioned between DCM (20 mL) and sat. aq. ammonium chloride (20 mL). The separated aqueous phase was washed with DCM (2×10 mL) and the combined organics passed through a hydrophobic frit and concentrated under reduced pressure. The crude material was combined with the crude material from a similar reaction performed on tert-butyl (3-bromo-5-(1-((tert-butyldimethylsilyl)oxy)vinyl)-2-methylpyrazolo[1,5-a]pyrimidin-7-yl)(3-(1-methyl-1H-imidazol-2-yl)benzyl)carbamate (intermediate 114, 51 mg, 0.078 mmol) and purified by MDAP (method A). The fractions containing product were combined, concentrated under reduced pressure and dried under high vacuum to give the title compound. LCMS (method F): rt=1.72, [M+H]$^+$=667.

Intermediate 116

Methyl 2-methyl-5-(4,4,5,5-tetramethyl-1,3,2-dioxaborolan-2-yl)benzoate

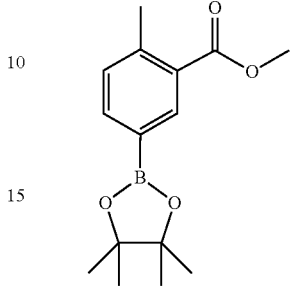

Methyl 5-bromo-2-methylbenzoate (50 g, 218 mmol), bis(pinacolato)diboron (55.4 g, 218 mmol), potassium acetate (64.3 g, 655 mmol) and bis(triphenylphosphine)palladium(II) chloride (12.26 g, 17.46 mmol) in 1,4-dioxane (500 mL) were heated to 100° C. under nitrogen for 2 h. After cooling, the mixture was filtered CELITE and washed with ethyl acetate (500 mL). 1 M aqueous hydrochloric acid (500 mL) was added to the filtrate and the phases partitioned. The organic phase was washed with 1 M aqueous hydrochloric acid (250 mL), brine (250 mL), dried over magnesium sulphate and the solvent removed in vacuo. The crude was subject to purification by silica gel column chromatography eluting with 0-50% ethyl acetate in cyclohexane to give the title compound. LCMS (method J): rt=1.34, [M+H]$^+$=277.

Intermediate 117

Methyl 5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methylbenzoate

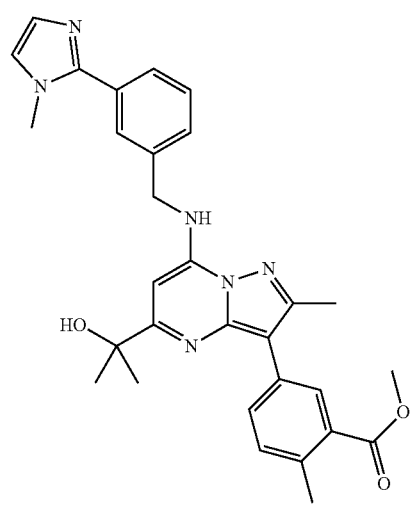 [SMILES: COC(=O)c1cc(-c2c(C)nn3c(NCc4cccc(-c5nccn5C)c4)cc(C(C)(C)O)nc23)ccc1C]

2-(3-Bromo-2-methyl-7-((3-(1-methyl-1H-imidazol-2-yl)benzyl)amino)pyrazolo[1,5-a]pyrimidin-5-yl)propan-2-ol (intermediate 43, 25.77 g, 56.6 mmol), methyl 2-methyl-5-

(4,4,5,5-tetramethyl-1,3,2-dioxaborolan-2-yl)benzoate (intermediate 116, 23.44 g, 85 mmol), potassium phosphate (18.02 g, 85 mmol), XPhos (2.70 g, 5.66 mmol) and XPhos Pd G2 (4.45 g, 5.66 mmol) were combined in 1,4-dioxane (300 mL) and water (100 mL). The mixture was cycled between vacuum and nitrogen three times and then stirred and heated to 100° C. for 2 h. After cooling, the mixture was partitioned between ethyl acetate (250 mL) and 2 M aqueous hydrochloric acid (250 mL). The separated organic phase was washed with 2 M aqueous hydrochloric acid (250 mL). The combined aqueous phases were basified with 1 M aqueous sodium hydroxide solution to ~pH 10 and extracted with ethyl acetate (2×250 mL). The organics were washed with brine (100 mL), dried over magnesium sulphate and concentrated under reduced pressure to give the title compound. LCMS (method J): rt=0.78, [M+H]⁺=525.

Intermediate 118

5-(5-(2-Hydroxypropan-2-yl)-2-methyl-7-((3-(1-methyl-1H-imidazol-2-yl)benzyl)amino)pyrazolo[1,5-a]pyrimidin-3-yl)-2-methylbenzoic acid

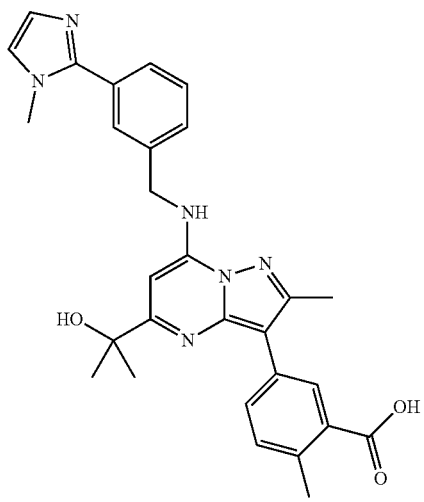 [SMILES: Cc1ccc(-c2c(C)nn3c(NCc4cccc(-c5nccn5C)c4)cc(C(C)(C)O)nc23)cc1C(=O)O]

Methyl 5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methylbenzoate (intermediate 117, 32.66 g, 62.3 mmol) was stirred in methanol (300 mL). 10 M aqueous sodium hydroxide (31.1 mL, 311 mmol) was added and the reaction mixture stirred at 50° C. for 6 h. After cooling, ethyl acetate (500 mL) and water (500 mL) were added and the phases partitioned. The organic phase was washed with 1 M aqueous sodium hydroxide (2×100 mL). The combined aqueous phases were neutralised to ~pH 5-6 using 2 M aqueous hydrochloric acid and extracted with ethyl acetate (4×500 mL). The combined organic layers were concentrated under reduced pressure to give the title compound. LCMS (method J): rt=0.65, [M+H]⁺=511.

Intermediate 119

Methyl 5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methoxybenzoate

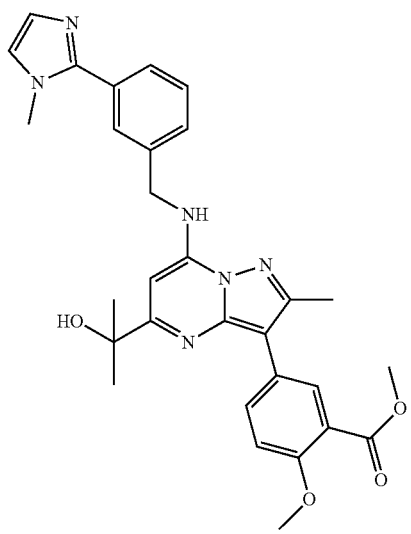 [SMILES: COC(=O)c1cc(-c2c(C)nn3c(NCc4cccc(-c5nccn5C)c4)cc(C(C)(C)O)nc23)ccc1OC]

2-(3-Bromo-2-methyl-7-((3-(1-methyl-1H-imidazol-2-yl)benzyl)amino)pyrazolo[1,5-a]pyrimidin-5-yl)propan-2-ol (intermediate 43, 10 g, 21.96 mmol), methyl 2-methoxy-5-(4,4,5,5-tetramethyl1,3,2-dioxaborolan-2-yl)benzoate (intermediate 78, 9.62 g, 32.9 mmol), potassium phosphate (6.99 g, 32.9 mmol), XPhos (1.047 g, 2.196 mmol) and XPhos Pd G2 (1.728 g, 2.196 mmol) in 1,4-dioxane (100 mL) and water (33.3 mL) was degassed (vacuum/nitrogen× 3). The reaction mixture was stirred under nitrogen at 100° C. for 2 h. The reaction mixture was allowed to cool and was separated between ethyl acetate (250 mL) and 2 M hydrochloric acid (200 mL). The organic phase was washed with 2 M hydrochloric acid (100 mL). The combined aqueous phases were basified with 1 M aqueous sodium hydroxide solution to pH ~10 and extracted with ethyl acetate (250 mL). The organic phase was washed with brine and dried over magnesium sulphate. The solvent was evaporated in vacuo to give the title compound. LCMS (method J): rt=0.63, [M+H]⁺=541.

Intermediate 120

5-(5-(2-Hydroxypropan-2-yl)-2-methyl-7-((3-(1-methyl-1H-imidazol-2-yl)benzyl)amino)pyrazolo[1,5-a]pyrimidin-3-yl)-2-methoxybenzoic acid

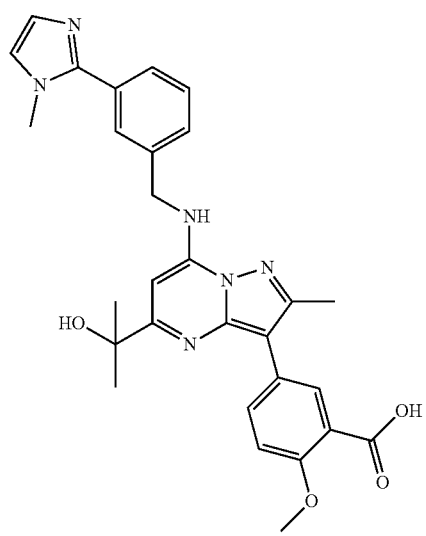 [SMILES: COc1ccc(-c2c(C)nn3c(NCc4cccc(-c5nccn5C)c4)cc(C(C)(C)O)nc23)cc1C(=O)O]

To a solution of methyl 5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methoxybenzoate (intermediate 119, 13.55 g, 25.06 mmol) in methanol (100 mL) was added 1 M sodium hydroxide aqueous solution (12.53 mL, 125 mmol) and the reaction mixture was stirred at 50° C. for 6 h. The reaction mixture was allowed to cool then diluted with ethyl acetate (200 mL) and water (200 mL) and then filtered. The phases were separated. The aqueous phase was neutralised to pH~5-6 using 2 M hydrochloric acid and then extracted using ethyl acetate (3 times). To the aqueous phase was added solid sodium chloride. This was extracted with ethyl acetate (2×150 mL). The combined ethyl acetate extractions were dried over magnesium sulphate. The solvent was evaporated in vacuo to give the title compound. LCMS (method J): rt=0.57, [M+H]$^+$=527.

Intermediate 121

Ethyl 2-(3-iodo-2-methyl-7-((3-(1-methyl-1H-imidazol-2-yl)benzyl)amino)pyrazolo[1,5-a]pyrimidin-5-yl)-2-(tetrahydro-2H-pyran-4-yl)acetate

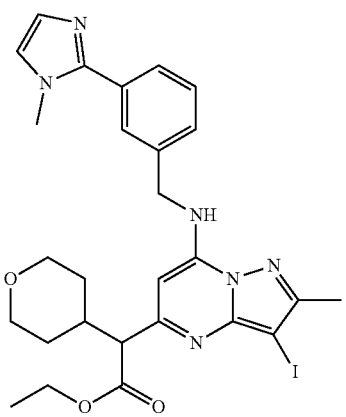 [SMILES: CCOC(=O)C(c1cc(NCc2cccc(-c3nccn3C)c2)n2nc(C)c(I)c2n1)C1CCOCC1]

In a dried vial ethyl 2-(3-iodo-2-methyl-7-((3-(1-methyl-1H-imidazol-2-yl)benzyl)amino)pyrazolo[1,5-a]pyrimidin-5-yl)acetate (intermediate 77, 255 mg, 0.481 mmol) was stirred in THF (2 mL) under nitrogen at 0° C. 4-Iodotetrahydro-2H-pyran (0.06 mL, 0.503 mmol) was added and the mixture stirred at 0° C. for 1 min after which LiHMDS (1 M in THF) (1 mL, 1 mmol) was added. The reaction was stirred at 0° C. for 10 min, then allowed to warm to room temperature and then heated to 40° C. for 2 days. The reaction mixture was diluted with sat. aq. ammonium chloride (3 mL) and stirred for 5 min. The slurry was transferred to a separating funnel with DCM (20 mL) and water (20 mL). The phases were partitioned and the organic layer collected. The aqueous was further washed with DCM (20 mL) and the combined organic layers washed with brine (20 mL), then filtered through a hydrophobic frit and evaporated to dryness. The residue was loaded from DCM (1 mL) onto a silica gel column (40 g) and eluted with 10-60% ethanol:ethyl acetate (3:1, v/v, containing 1% triethylamine) in cyclohexane. The fractions containing product were combined and evaporated to dryness to give the title compound. LCMS (method F): rt=1.14, [M+H]$^+$=615.

Intermediate 122

3-iodo-2-methyl-N-(3-(1-methyl-1H-imidazol-2-yl)benzyl)-5-((tetrahydro-2H-pyran-4-yl)methyl)pyrazolo[1,5-a]pyrimidin-7-amine

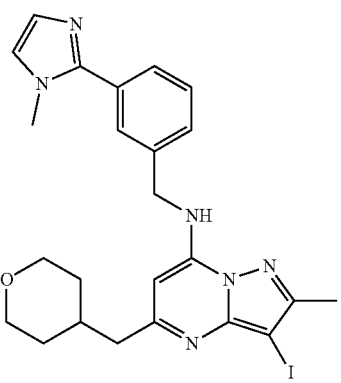 [SMILES: Cc1nn2c(NCc3cccc(-c4nccn4C)c3)cc(CC3CCOCC3)nc2c1I]

Ethyl 2-(3-iodo-2-methyl-7-((3-(1-methyl-1H-imidazol-2-yl)benzyl)amino)pyrazolo[1,5-a]pyrimidin-5-yl)-2-(tetrahydro-2H-pyran-4-yl)acetate (Intermediate 121, 158 mg, 0.188 mmol) was dissolved in THF (2 mL) and 2 M sodium hydroxide (aq.) (1 mL, 2 mmol) and heated to 110° C. in a sealed tube for 6 h. After cooling, DCM (20 mL) and water (20 mL) were added and the aqueous neutralised to pH 7 with 2 M aq. HCl. The phases were partitioned and the organic layer collected. The aqueous was further washed with DCM (2×10 mL) and the combined organic layers passed through a hydrophobic frit and evaporated to dryness to give the title compound. LCMS (method F): rt=1.07, [M+H]$^+$=543.

Intermediate 123

N-(3-hydroxypropyl)-N-methyl-3-(4,4,5,5-tetramethyl-1,3,2-dioxaborolan-2-yl)benzamide

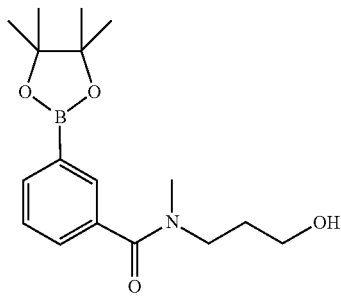 [SMILES: CN(CCCO)C(=O)c1cccc(B2OC(C)(C)C(C)(C)O2)c1]

3-(4,4,5,5-Tetramethyl-1,3,2-dioxaborolan-2-yl)benzoic acid (245 mg, 0.988 mmol) and HATU (413 mg, 1.086 mmol) and DIPEA (0.35 mL, 2.004 mmol) were stirred in THF (5 mL) under air at ambient temperature. After 10 minutes 3-(methylamino)propan-1-ol (0.12 mL, 1.234 mmol) was added and the mixture stirred overnight. The mixture was partitioned between aqueous saturated sodium bicarbonate (30 mL) and ethyl acetate (20 mL). The separated aqueous phase was washed with further ethyl acetate (2×20 mL) and the combined organics washed with brine (20 mL). The organic layer was passed through a hydrophobic frit and concentrated under reduced pressure. The crude was purified by silica gel column chomatography eluting with 40-100% ethyl acetate:ethanol (3:1 containing 1% triethylamine) in cyclohexane to afford the title compound. LCMS (method J): rt=0.93, [M+H]$^+$=320.

SUPPORTING COMPOUNDS

Compound 1

1-(3-(4-Methoxy-3-(methylsulfonyl)phenyl)-2-methyl-7-((3-(1-methyl-1H-imidazol-2-yl)benzyl)amino)pyrazolo[1,5-a]pyrimidin-5-yl)ethanol

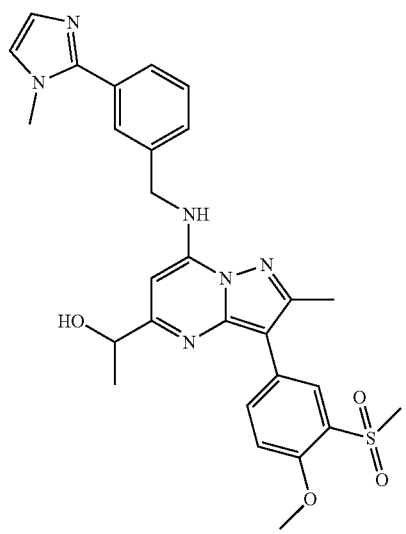 [SMILES: COc1ccc(-c2c(C)nn3c(NCc4cccc(-c5nccn5C)c4)cc(C(C)O)nc23)cc1S(C)(=O)=O]

3-(4-Methoxy-3-(methylsulfonyl)phenyl)-2-methyl-7-((3-(1-methyl-1H-imidazol-2-yl)benzyl)amino)pyrazolo[1,5-a]pyrimidine-5-carbaldehyde (intermediate 12, 30 mg, 0.057 mmol) was dissolved in THF (2.5 mL) and cooled to 0° C. Methylmagnesium bromide (3 M in diethyl ether) (0.1 mL, 0.3 mmol) was added dropwise and the reaction allowed to warm to room temp. and stirred for a further 3 h. Further methylmagnesium bromide (3 M in diethyl ether) (0.1 mL, 0.3 mmol) was added and the reaction stirred for a further 20 h. The reaction was quenched by the addition of 1 M HCl (10 mL), and then extracted with ethyl acetate (3×10 mL). The combined organic phases were dried through a hydrophobic frit and the solvent removed in vacuo. The residue was purified by MDAP (method A) to give the title compound. LCMS (method F): rt=0.94, [M+H]$^+$=547.

Compound 2

2-((5-(5-(1-Hydroxyethyl)-2-methyl-7-((3-(1-methyl-1H-imidazol-2-yl)benzyl)amino)pyrazolo[1,5-a]pyrimidin-3-yl)-2-methoxyphenyl)sulfonyl)ethan-1-ol

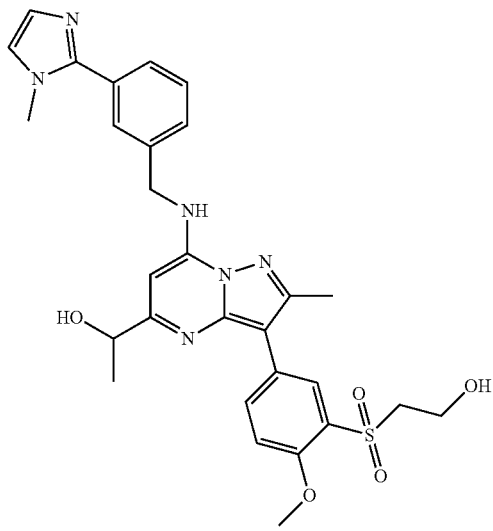 [SMILES: COc1ccc(-c2c(C)nn3c(NCc4cccc(-c5nccn5C)c4)cc(C(C)O)nc23)cc1S(=O)(=O)CCO]

tert-Butyl (5-formyl-3-(3-((2-hydroxyethyl)sulfonyl)-4-methoxyphenyl)-2-methylpyrazolo[1,5-a]pyrimidin-7-yl)(3-(1-methyl-1H-imidazol-2-yl)benzyl)carbamate (intermediate 20, 100 mg, 0.151 mmol) in THF (3 mL) was stirred at 0° C. under nitrogen when 3.4 M methylmagnesium bromide in 2-MeTHF (0.1 mL) was added in one portion. The reaction mixture was allowed to cool to room temp. and the reaction was stirred under nitrogen for 1 h. The reaction mixture was quenched with water (10 mL) and stirred under nitrogen for 5 min. The solvent was removed in vacuo. The crude material was dissolved in DCM (20 mL) and partitioned with water (15 mL). The organic layer was separated and the aqueous extracted with further DCM (2×20 mL). The combined organic layers were passed through a hydrophobic frit and the solvent was removed in vacuo. The crude material was dissolved in methanol (3 mL) and 4 M HCl in 1,4-dioxane (2 mL, 8 mmol) was added. The reaction was stirred under nitrogen for 5 h. The solvent was removed in vacuo. The crude material was dissolved in methanol:DMSO (2×1 mL, 1:1, v/v) and purified by MDAP (method A) to give the title compound. LCMS (method F): rt=0.86, [M+H]$^+$=577.

The following Compounds were made in a similar manner to the preparation of Compound 2 using the following grignard reagents:

1 M Ethylmagnesium bromide in THF,
0.5 M cyclopropylmagnesium bromide in THF,
1 M isopropylmagnesium bromide in THF.

| Compound Number | Structure | MDAP method | LCMS method | rt | [M + H]$^+$ |
|---|---|---|---|---|---|
| 3 | 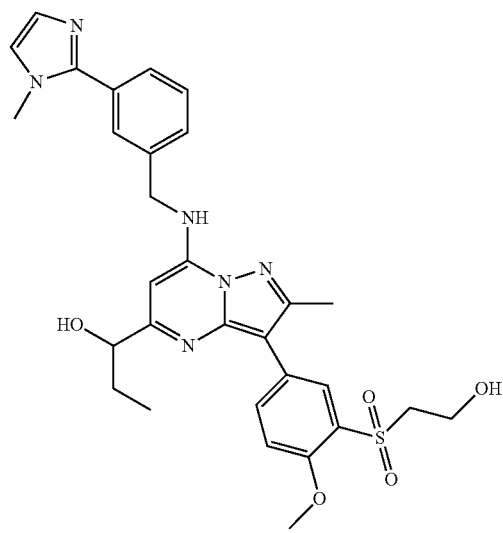 [SMILES: CCC(O)c1cc(NCc2cccc(-c3nccn3C)c2)n2nc(C)c(-c3ccc(OC)c(S(=O)(=O)CCO)c3)c2n1] | B | F | 0.91 | 591 |

| Compound Number | Structure | MDAP method | LCMS method | rt | [M + H]+ |
|---|---|---|---|---|---|
| 4 | 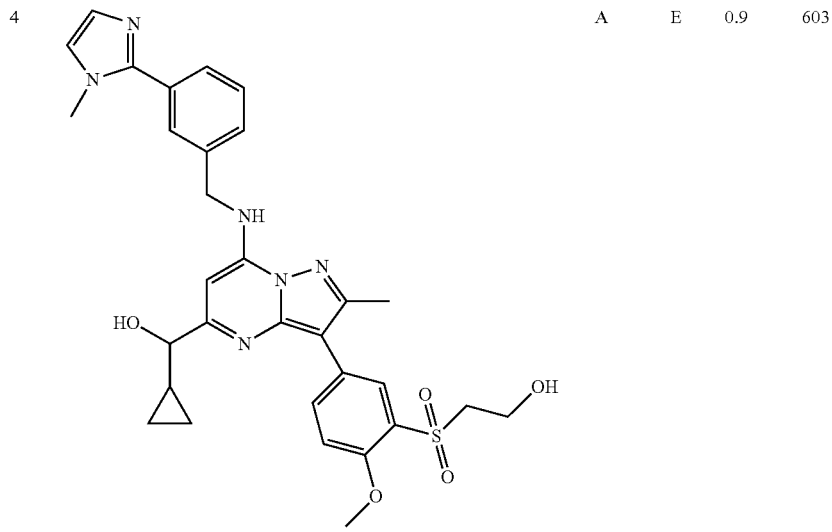 | A | E | 0.9 | 603 |
| 5 | 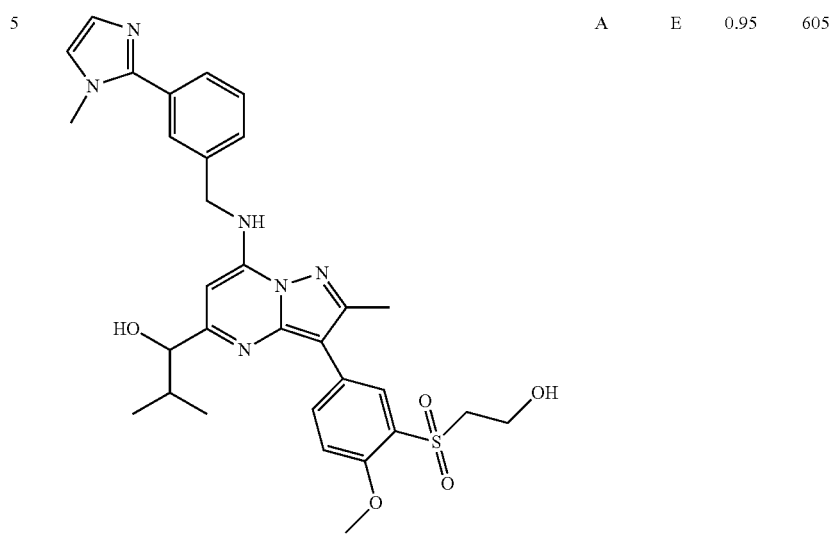 | A | E | 0.95 | 605 |

Compound 6

2-(3-(3-((2-Hydroxyethyl)sulfonyl)-4-methoxyphenyl)-2-methyl-7-((3-(1-methyl-1H-imidazol-2-yl)benzyl)amino)pyrazolo[1,5-a]pyrimidin-5-yl)propan-2-ol

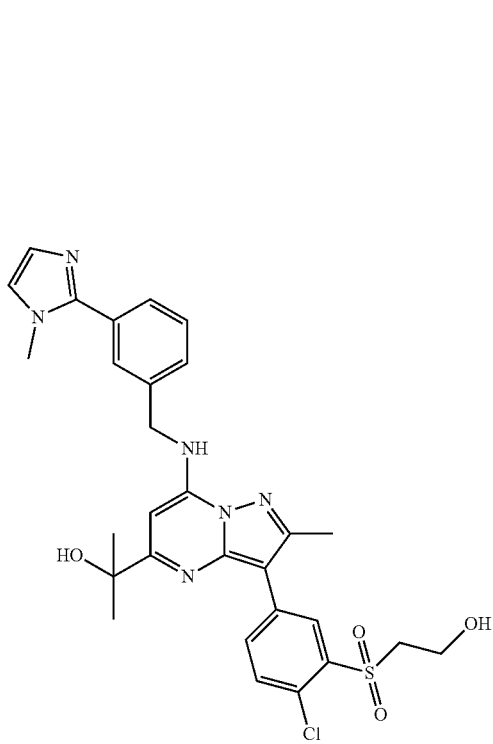 [SMILES: Cc1nn2c(NCc3cccc(-c4nccn4C)c3)cc(C(C)(C)O)nc2c1-c1ccc(Cl)c(S(=O)(=O)CCO)c1]

2-((2-Methoxy-5-(4,4,5,5-tetramethyl-1,3,2-dioxaborolan-2-yl)phenyl)sulfonyl)ethan-1-ol (intermediate 19, 121 mg, 0.354 mmol), sodium carbonate (87 mg, 0.821 mmol), PdCl$_2$(dppf) (19 mg, 0.026 mmol), water (1 mL) and 2-(3-iodo-2-methyl-7-((3-(1-methyl-1H-imidazol-2-yl)benzyl)amino)pyrazolo[1,5-a]pyrimidin-5-yl)propan-2-ol (intermediate 21, 136 mg, 0.271 mmol) in IPA (1 mL) were combined and heated at 120° C. in a microwave reactor for 1.5 h. The reaction mixture was filtered through CELITE (washing with DCM) and evaporated to dryness. The filtrate was then partitioned between water (20 mL) and DCM (20 mL). The organic phase was collected and the aqueous washed with DCM (2×10 mL). The combined organic layers were passed through a hydrophobic frit and evaporated to dryness. The residue was dissolved in DMSO:methanol (2 mL) and purified by MDAP (method A) to give the title compound. LCMS (method F): rt=0.91, [M+H]$^+$=591.

Compound 7

2-Chloro-5-(5-(2-hydroxypropan-2-yl)-2-methyl-7-((3-(1-methyl-1H-imidazol-2-yl)benzyl)amino)pyrazolo[1,5-a]pyrimidin-3-yl)-N-(3-hydroxypropyl)-N-methylbenzamide

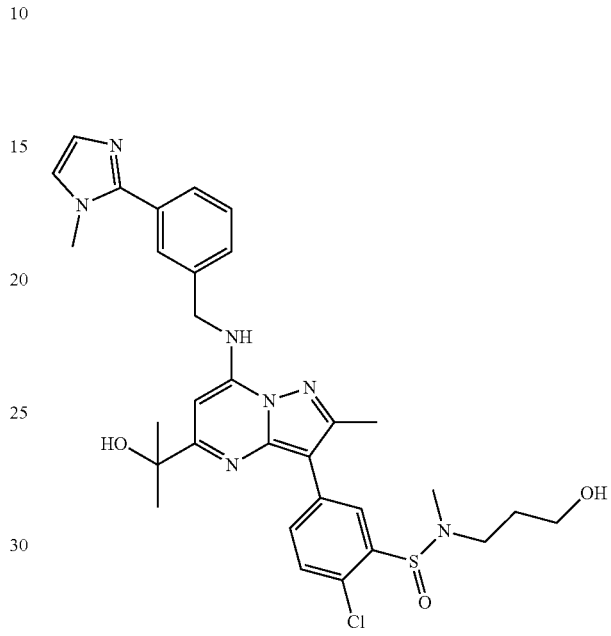

2-Chloro-N-(3-hydroxypropyl)-N-methyl-5-(4,4,5,5-tetramethyl-1,3,2-dioxaborolan-2-yl)benzamide (intermediate 23, 105 mg, 0.297 mmol), sodium carbonate (69.6 mg, 0.657 mmol), PdCl$_2$(dppf)-DCM (12.5 mg, 0.015 mmol), water (1 mL) and 2-(3-iodo-2-methyl-7-((3-(1-methyl-1H-imidazol-2-yl)benzyl)amino)pyrazolo[1,5-a]pyrimidin-5-yl)propan-2-ol (intermediate 21, 110 mg, 0.219 mmol) in IPA (1 mL) were combined and heated at 120° C. in a microwave reactor for 2 h. Further 2-chloro-N-(3-hydroxypropyl)-N-methyl-5-(4,4,5,5-tetramethyl-1,3,2-dioxaborolan-2-yl)benzamide (intermediate 23, 105 mg, 0.297 mmol) was added and the reaction heated at 120° C. in a microwave reactor for 2 h. The reaction mixture was filtered through CELITE using DCM (20 mL). The filtrate was washed with water (20 mL) and the aqueous was extracted with further DCM (2×20 mL). The combined organic layers were passed through a hydrophobic frit and the solvent removed under reduced pressure. The residue was dissolved in methanol:DMSO (0.6 mL, 1:1, v/v) and purified by MDAP (method A). The residue was loaded in DCM (2 mL) and passed through a silica cartridge (1 g) eluting with ethyl acetate:ethanol (3:1, v/v, containing 1% triethylamine). The residue was loaded in DCM (2 mL) and purified by silica chromatography (4 g), eluting with ethyl acetate:ethanol (3:1, v/v, containing 1% triethylamine) in cyclohexane (0%, 2 CV; 0-100%, 5 CV; 100%, 7 CV) to give the title compound. LCMS (method F): rt=0.98, [M+H]$^+$=602.

Compound 8

(S)-(5-(5-(2-Hydroxypropan-2-yl)-2-methyl-7-((3-(1-methyl-1H-imidazol-2-yl)benzyl)amino)pyrazolo[1,5-a]pyrimidin-3-yl)-2-methoxyphenyl)(3-hydroxypyrrolidin-1-yl)methanone

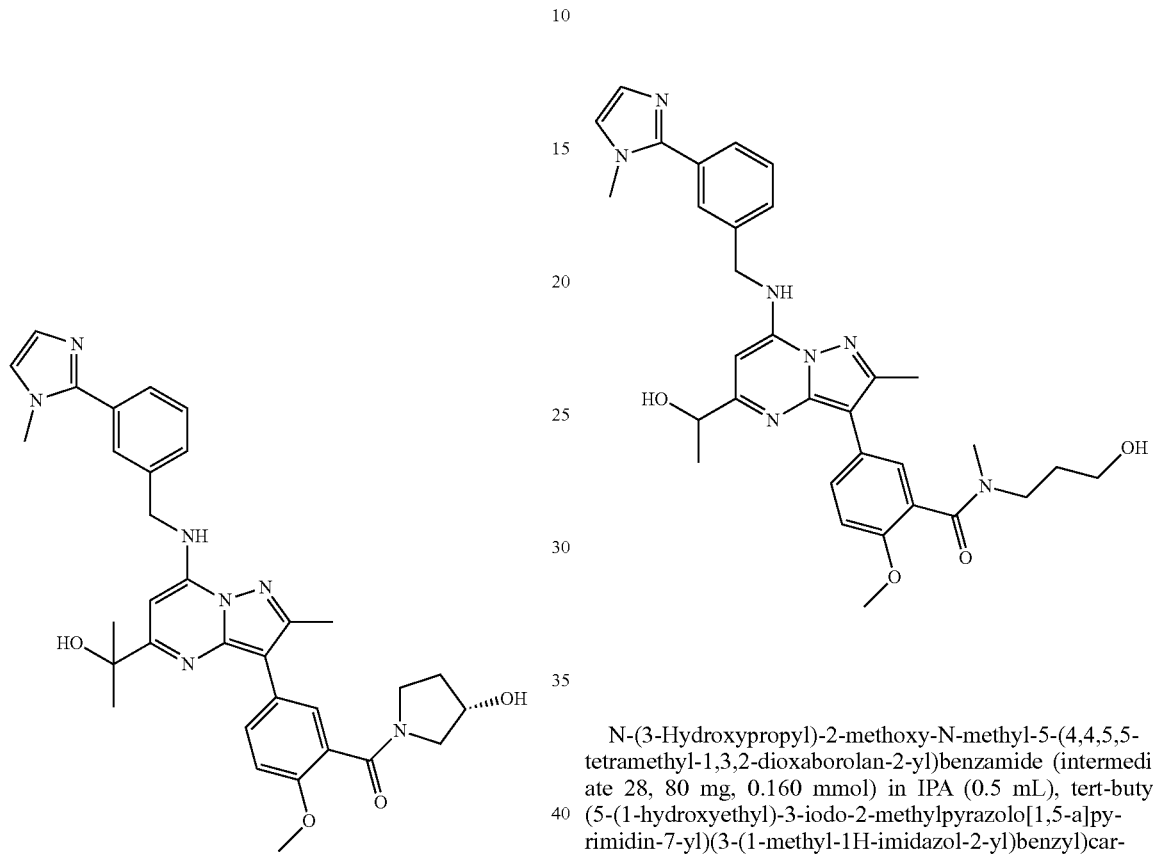

Prepared in a similar manner to Compound 7, using (S)-(3-hydroxypyrrolidin-1-yl)(2-methoxy-5-(4,4,5,5-tetramethyl-1,3,2-dioxaborolan-2-yl)phenyl)methanone (intermediate 25) to give the title compound. LCMS (method F): rt=0.88, [M+H]$^+$=596.

Compound 9

5-(5-(1-Hydroxyethyl)-2-methyl-7-((3-(1-methyl-1H-imidazol-2-yl)benzyl)amino)pyrazolo[1,5-a]pyrimidin-3-yl)-N-(3-hydroxypropyl)-2-methoxy-N-methylbenzamide N-(3-Hydroxypropyl)-2-methoxy-N-methyl-5-(4,4,5,5-tetramethyl-1,3,2-dioxaborolan-2-yl)benzamide (intermediate 28, 80 mg, 0.160 mmol) in IPA (0.5 mL), tert-butyl (5-(1-hydroxyethyl)-3-iodo-2-methylpyrazolo[1,5-a]pyrimidin-7-yl)(3-(1-methyl-1H-imidazol-2-yl)benzyl)carbamate (intermediate 26, 80 mg, 0.136 mmol), PdCl$_2$(dppf) (9 mg, 0.012 mmol), sodium carbonate (45 mg, 0.425 mmol) and water (0.5 mL) were combined and heated at 120° C. for 1.5 h in a microwave reactor. The reaction was diluted into DCM (10 mL) and water (10 mL) and the phases partitioned. The organic layer was collected and the aqueous was further washed with DCM (2×10 mL) and the combined organics were passed through a hydrophobic frit and then evaporated to dryness. The residue was dissolved in DMSO:methanol (1:1, v/v, 1 mL) and purified by MDAP (method A). The fractions containing product were combined and evaporated to dryness. The residue was purified by silica gel column chromatography eluting with 50-100% ethyl acetate:ethanol (3:1, v/v, containing 1% triethylamine) in cyclohexane to give the title compound. LCMS (method F): rt=0.87, [M+H]$^+$=584.

The following Compounds were prepared in a similar manner to the preparation of Compound 9, using the following boronic esters:

2-Chloro-N-(3-hydroxypropyl)-N-methyl-5-(4,4,5,5-tetramethyl-1,3,2-dioxaborolan-2-yl)benzamide (intermediate 23), N-ethyl-N-(2-hydroxyethyl)-2-methoxy-5-(4,4,5,5-tetramethyl-1,3,2-dioxaborolan-2-yl)benzamide (intermediate 30),

| Cmp Number | Structure | MDAP method | LCMS method | rt | [M + H]+ |
|---|---|---|---|---|---|
| 10 | 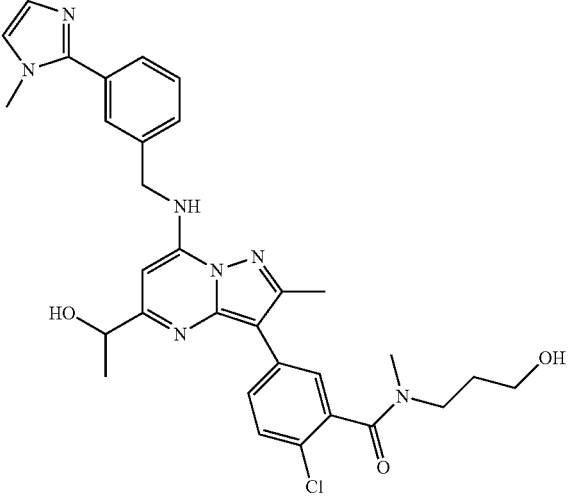 [SMILES: Cc1nn2c(NCc3cccc(-c4nccn4C)c3)cc(C(C)O)nc2c1-c1ccc(Cl)c(C(=O)N(C)CCCO)c1] | A | F | 0.93 | 588 |
| 11 | 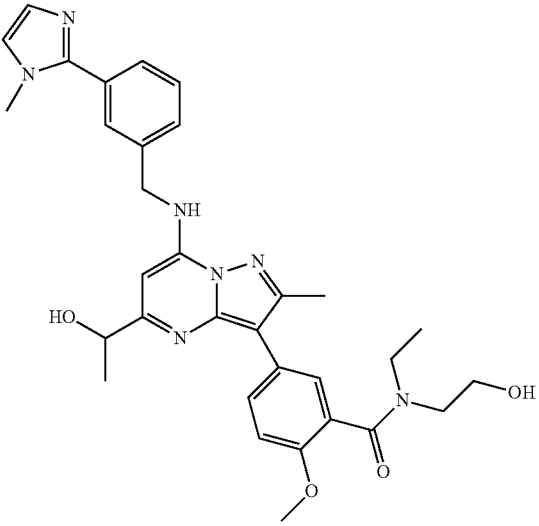 [SMILES: CCN(CCO)C(=O)c1cc(-c2c(C)nn3c(NCc4cccc(-c5nccn5C)c4)cc(C(C)O)nc23)ccc1OC] | B | F | 0.89 | 584 |

Compound 12

5-(5-(1-Hydroxyethyl)-2-methyl-7-((3-(1-methyl-1H-imidazol-2-yl)benzyl)amino)pyrazolo[1,5-a]pyrimidin-3-yl)-2-methoxy-N-methyl-N-(tetrahydro-2H-pyran-4-yl)benzamide

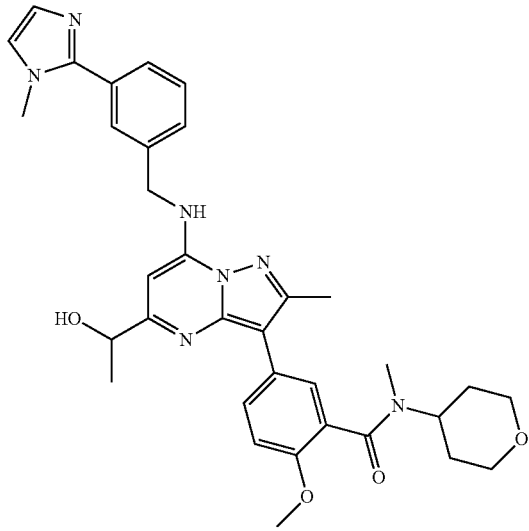 [SMILES: COc1ccc(-c2c(C)nn3c(NCc4cccc(-c5nccn5C)c4)cc(C(C)O)nc23)cc1C(=O)N(C)C1CCOCC1]

tert-Butyl (5-(1-hydroxyethyl)-3-iodo-2-methylpyrazolo[1,5-a]pyrimidin-7-yl)(3-(1-methyl-1H-imidazol-2-yl)benzyl)carbamate (intermediate 26, 70 mg, 0.119 mmol), 2-methoxy-N-methyl-N-(tetrahydro-2H-pyran-4-yl)-5-(4,4,5,5-tetramethyl-1,3,2-dioxaborolan-2-yl)benzamide (intermediate 34, 77 mg, 0.143 mmol), PdCl$_2$(dppf) (9 mg, 0.012 mmol), sodium carbonate (41 mg, 0.387 mmol), IPA (2 mL) and water (1 mL) were combined and heated in a microwave reactor at 120° C. for 1.5 h. The reaction mixture was filtered over CELITE, washed with methanol (100 mL) and the solvent removed in vacuo. The residue was dissolved in DCM (20 mL) and partitioned with water (10 mL). The organic layer was separated and the aqueous extracted with further DCM (2×10 mL). The combined organic layers were passed through a hydrophobic frit and the solvent removed in vacuo. The residue was dissolved in methanol (2 mL) and 4 M HCl in 1,4-dioxane (2 mL) was added. The reaction mixture was stirred under nitrogen at room temp. for 5 h. The solvent was removed in vacuo. The residue was dissolved in water (15 mL), neutralised with 2 M sodium hydroxide and partitioned with DCM (20 mL). The organic layer was separated and the aqueous extracted with further DCM (2×20 mL). The combined organic layers were passed through a hydrophobic frit and the solvent removed in vacuo. The sample was dissolved in methanol:DMSO (1 mL, 1:1, v/v) and purified by MDAP (method B). The solvent was removed in vacuo. The residue was triturated with ethyl acetate then diethyl ether to give the title compound. LCMS (method F): rt=0.94, [M+H]$^+$=610.

The following compounds were made in a similar manner to the preparation of Compound 12, varying the organic reaction solvent between IPA or 1,4-dioxane, and using the following boronic esters:

N-(3-Hydroxypropyl)-N,2-dimethyl-5-(4,4,5,5-tetramethyl-1,3,2-dioxaborolan-2-yl)benzamide (intermediate 36), (S)-(2-chloro-5-(4,4,5,5-tetramethyl-1,3,2-dioxaborolan-2-yl)phenyl)(3-hydroxypyrrolidin-1-yl)methanone (intermediate 38), 2-chloro-N-ethyl-N-(2-hydroxyethyl)-5-(4,4,5,5-tetramethyl-1,3,2-dioxaborolan-2-yl)benzamide (intermediate 32), (S)—N-(1-hydroxypropan-2-yl)-2-methoxy-N-methyl-5-(4,4,5,5-tetramethyl-1,3,2-dioxaborolan-2-yl)benzamide (intermediate 40),

| Cmp Number | Structure | MDAP method | LCMS method | rt | [M + H]$^+$ |
|---|---|---|---|---|---|
| 13 | 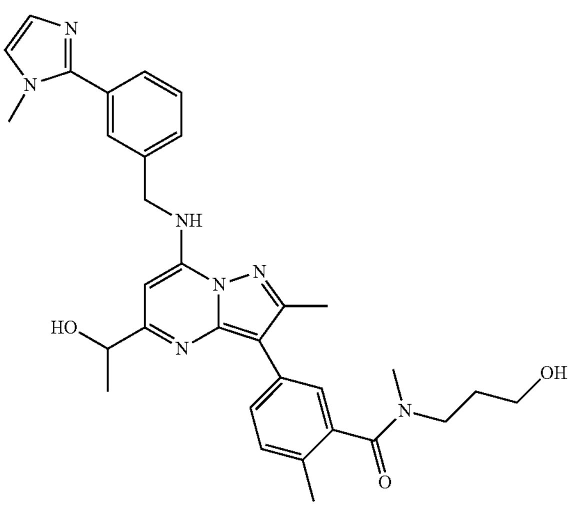 [SMILES: Cc1ccc(-c2c(C)nn3c(NCc4cccc(-c5nccn5C)c4)cc(C(C)O)nc23)cc1C(=O)N(C)CCCO] | A | F | 0.9 | 568 |

-continued

| Cmp Number | Structure | MDAP method | LCMS method | rt | [M + H]+ |
|---|---|---|---|---|---|
| 14 | 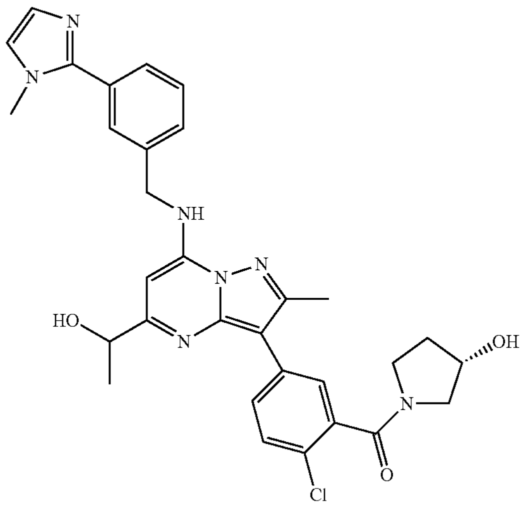 [SMILES: Cc1nn2c(NCc3cccc(-c4nccn4C)c3)cc(C(C)O)nc2c1-c1ccc(Cl)c(C(=O)N2CC[C@H](O)C2)c1] | A | F | 0.88 | 586 |
| 15 | 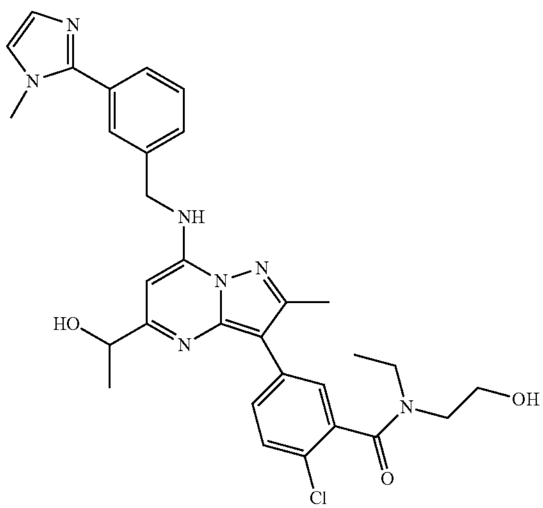 [SMILES: CCN(CCO)C(=O)c1cc(-c2c(C)nn3c(NCc4cccc(-c5nccn5C)c4)cc(C(C)O)nc23)ccc1Cl] | B | J | 0.61 | 588 |
| 16 | 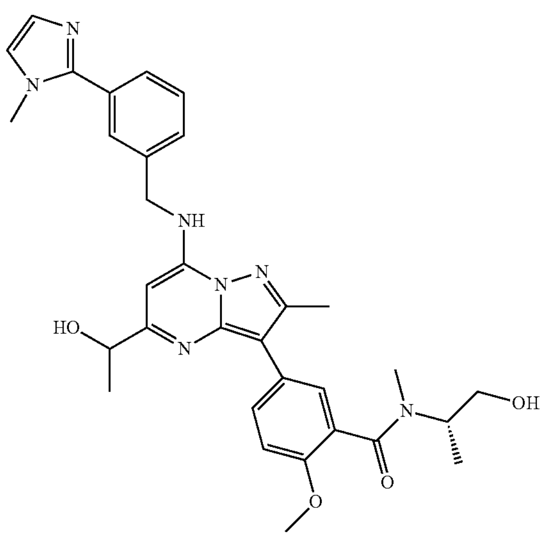 [SMILES: COc1ccc(-c2c(C)nn3c(NCc4cccc(-c5nccn5C)c4)cc(C(C)O)nc23)cc1C(=O)N(C)[C@@H](C)CO] | A | F | 0.88 | 584 |

Compound 17

5-(5-(2-Hydroxypropan-2-yl)-2-methyl-7-((3-(1-methyl-1H-imidazol-2-yl)benzyl)amino)pyrazolo[1,5-a]pyrimidin-3-yl)-N-(3-hydroxypropyl)-N,2-dimethylbenzamide

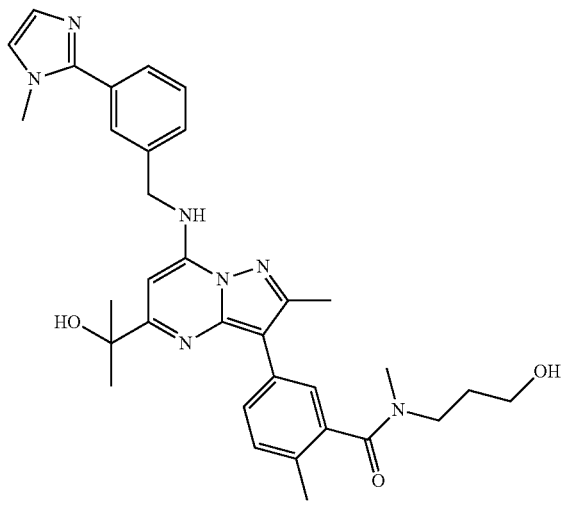 [SMILES: Cc1ccc(-c2c(C)nn3c(NCc4cccc(-c5nccn5C)c4)cc(C(C)(C)O)nc23)cc1C(=O)N(C)CCCO]

N-(3-Hydroxypropyl)-N,2-dimethyl-5-(4,4,5,5-tetramethyl-1,3,2-dioxaborolan-2-yl)benzamide (intermediate 36, 542 mg, 0.813 mmol), 2-(3-bromo-2-methyl-7-((3-(1-methyl-1H-imidazol-2-yl)benzyl)amino)pyrazolo[1,5-a]pyrimidin-5-yl)propan-2-ol (intermediate 43, 333 mg, 0.622 mmol), PdCl$_2$(dppf) (47 mg, 0.064 mmol), sodium carbonate (198 mg, 1.865 mmol), 1,4-dioxane (3 mL) and water (1 mL) were combined and heated at 120° C. for 1.5 h in a microwave reactor. N-(3-Hydroxypropyl)-N,2-dimethyl-5-(4,4,5,5-tetramethyl-1,3,2-dioxaborolan-2-yl)benzamide (intermediate 36, 262 mg, 0.393 mmol) and PdCl$_2$(dppf) (20 mg, 0.027 mmol) were added and the reaction mixture was heated at 120° C. for 1.5 h in a microwave reactor. The reaction was diluted into DCM (20 mL) and water (20 mL) and the phases partitioned. The organic layer was collected and the aqueous was further washed with DCM (2×20 mL) and the combined organics were passed through a hydrophobic frit then evaporated to dryness. The residue was dissolved in DMSO:methanol (4 mL) and purified by MDAP (method A). The fractions containing product were combined and evaporated to dryness. The residue was purified by silica gel column chromatography eluting with 20-100% ethyl acetate:ethanol (3:1, v/v, containing 1% triethylamine) in cyclohexane. The fractions containing product were combined, evaporated to dryness and dried further on a high-vacuum line over 3 days to give the title compound. LCMS (method F): rt=0.96, [M+H]$^+$=582.

The following Compounds were prepared in a similar manner to the preparation of Compound 17, using either 1,4-dioxane or IPA as reaction solvent, and the following boronic esters:

(S)-(2-Chloro-5-(4,4,5,5-tetramethyl-1,3,2-dioxaborolan-2-yl)phenyl)(3-hydroxypyrrolidin-1-yl)methanone (intermediate 38), N-ethyl-N-(2-hydroxyethyl)-2-methoxy-5-(4,4,5,5-tetramethyl-1,3,2-dioxaborolan-2-yl)benzamide (intermediate 30), (S)—N-(1-hydroxypropan-2-yl)-2-methoxy-N-methyl-5-(4,4,5,5-tetramethyl-1,3,2-dioxaborolan-2-yl)benzamide (intermediate 40), N-(tetrahydro-2H-pyran-4-yl)-5-(4,4,5,5-tetramethyl-1,3,2-dioxaborolan-2-yl)benzamide (intermediate 34), (S)—N-(1-hydroxypropan-2-yl)-N,2-dimethyl-5-(4,4,5,5-tetramethyl-1,3,2-dioxaborolan-2-yl)benzamide (intermediate 45), 2-methoxy-N,N-dimethyl-5-(4,4,5,5-tetramethyl-1,3,2-dioxaborolan-2-yl)benzamide (intermediate 47), (R)-(2-chloro-5-(4,4,5,5-tetramethyl-1,3,2-dioxaborolan-2-yl)phenyl)(2-(hydroxymethyl)pyrrolidin-1-yl)methanone (intermediate 49), (R)-(2-(hydroxymethyl)pyrrolidin-1-yl)(2-methyl-5-(4,4,5,5-tetramethyl-1,3,2-dioxaborolan-2-yl)phenyl)methanone (intermediate 51), N-(2-hydroxyethyl)-2-methoxy-N-methyl-5-(4,4,5,5-tetramethyl-1,3,2-dioxaborolan-2-yl)benzamide (intermediate 53), (3-hydroxy-3-methylpyrrolidin-1-yl)(2-methoxy-5-(4,4,5,5-tetramethyl-1,3,2-dioxaborolan-2-yl)phenyl)methanone (intermediate 55), (2-methoxy-5-(4,4,5,5-tetramethyl-1,3,2-dioxaborolan-2-yl)phenyl)(1,4-oxazepan-4-yl)methanone (intermediate 57), (S)-(3-hydroxypyrrolidin-1-yl)(2-methyl-5-(4,4,5,5-tetramethyl-1,3,2-dioxaborolan-2-yl)phenyl)methanone (intermediate 59), (S)-(2-methoxy-5-(4,4,5,5-tetramethyl-1,3,2-dioxaborolan-2-yl)phenyl)(3-methyl morpholino)methanone (intermediate 61), (3-hydroxy-3-methylpyrrolidin-1-yl)(2-methyl-5-(4,4,5,5-tetramethyl-1,3,2-dioxaborolan-2-yl)phenyl)methanone (intermediate 63), N-(3-hydroxypropyl)-2-methoxy-N-methyl-5-(4,4,5,5-tetramethyl-1,3,2-dioxaborolan-2-yl)benzamide (intermediate 28)

| Cmp Number | Structure | MDAP method | LCMS method | rt | [M + H]+ |
|---|---|---|---|---|---|
| 18 | 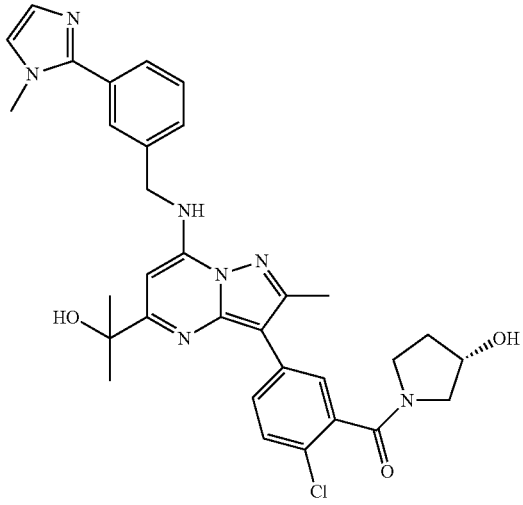 [SMILES: Cc1nn2c(NCc3cccc(-c4nccn4C)c3)cc(C(C)(C)O)nc2c1-c1ccc(Cl)c(C(=O)N2CC[C@H](O)C2)c1] | A | F | 0.96 | 600 |
| 19 | 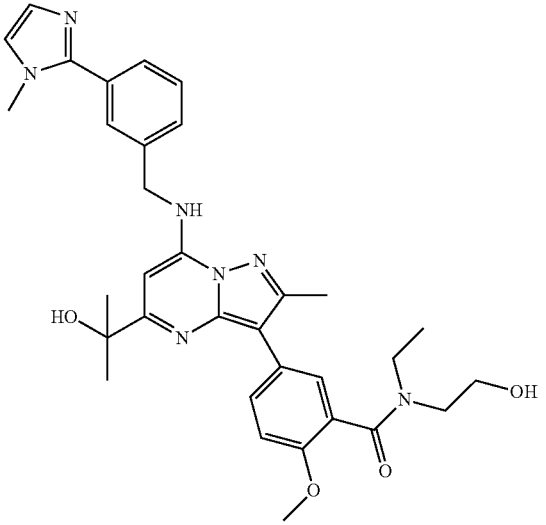 [SMILES: CCN(CCO)C(=O)c1cc(-c2c(C)nn3c(NCc4cccc(-c5nccn5C)c4)cc(C(C)(C)O)nc23)ccc1OC] | A | F | 0.95 | 598 |
| 20 | 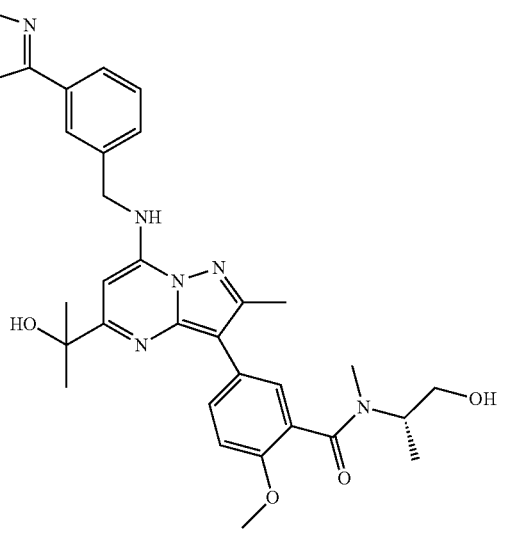 | A | F | 0.93 | 598 |

-continued

| Cmp Number | Structure | MDAP method | LCMS method | rt | [M + H]+ |
|---|---|---|---|---|---|
| 21 | 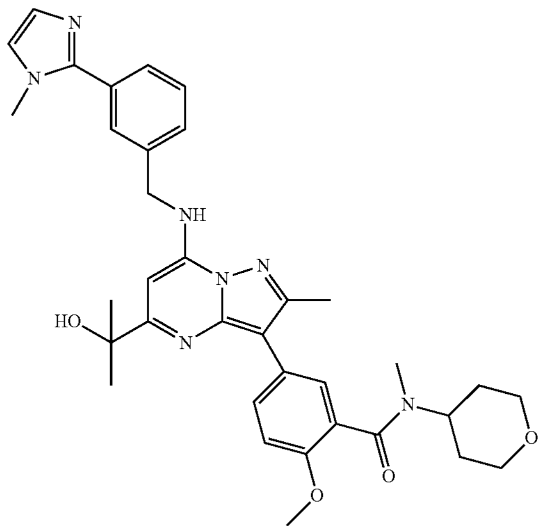 [SMILES: COc1ccc(-c2c(C)nn3c(NCc4cccc(-c5nccn5C)c4)cc(C(C)(C)O)nc23)cc1C(=O)N(C)C1CCOCC1] | A | F | 0.99 | 624 |
| 22 | 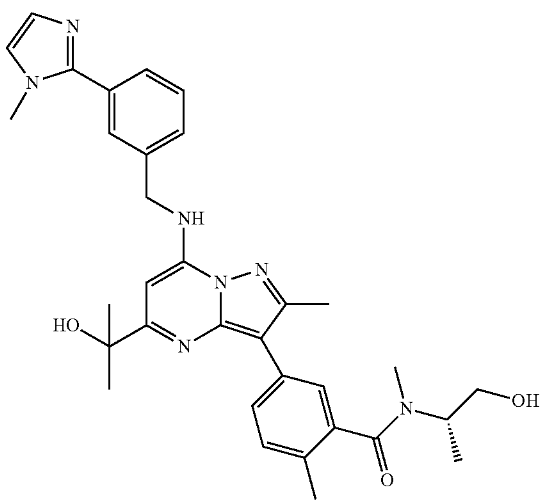 | A | F | 0.98 | 582 |
| 23 | 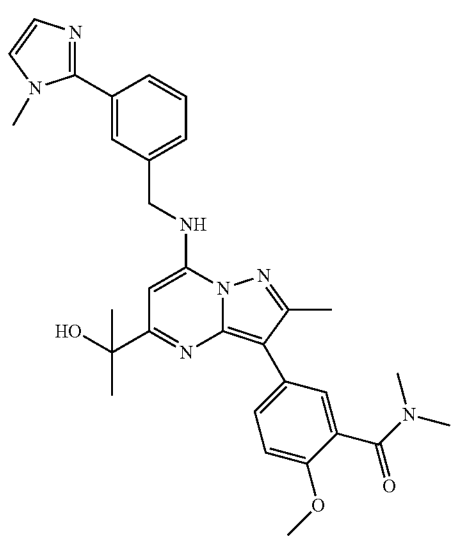 [SMILES: COc1ccc(-c2c(C)nn3c(NCc4cccc(-c5nccn5C)c4)cc(C(C)(C)O)nc23)cc1C(=O)N(C)C] | A | F | 1.0 | 554 |

-continued

| Cmp Number | Structure | MDAP method | LCMS method | rt | [M + H]+ |
|---|---|---|---|---|---|
| 24 | 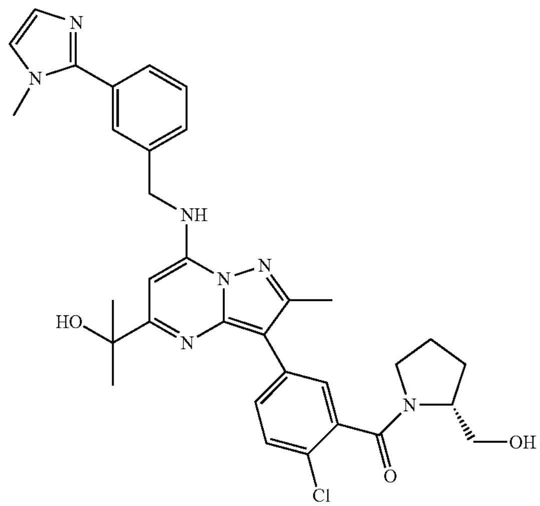 [SMILES: Cc1nn2c(NCc3cccc(-c4nccn4C)c3)cc(C(C)(C)O)nc2c1-c1ccc(Cl)c(C(=O)N2CCC[C@@H]2CO)c1] | A | F | 1.05 | 614 |
| 25 | 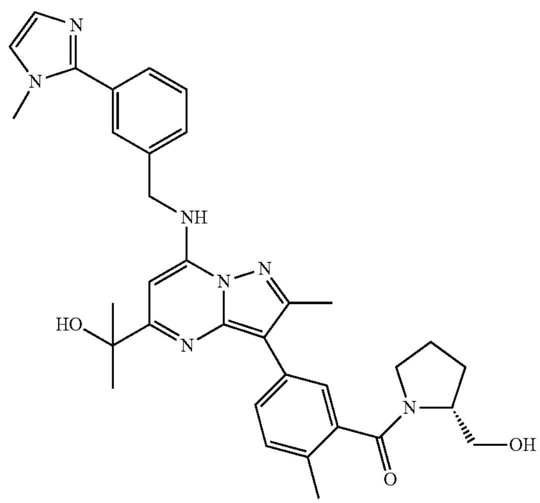 [SMILES: Cc1ccc(-c2c(C)nn3c(NCc4cccc(-c5nccn5C)c4)cc(C(C)(C)O)nc23)cc1C(=O)N1CCC[C@@H]1CO] | A | F | 1.01 | 594 |
| 26 | 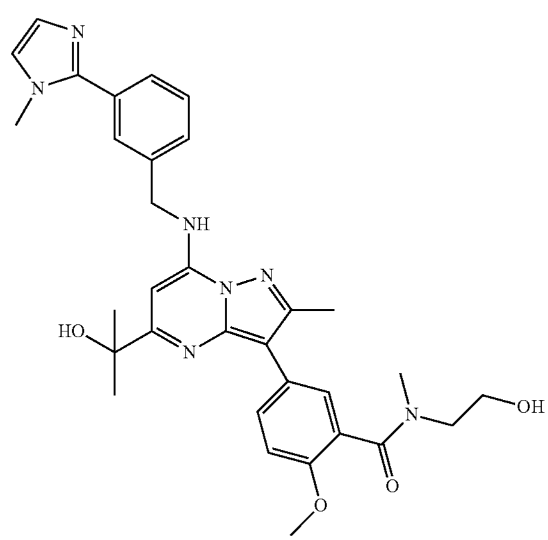 [SMILES: COc1ccc(-c2c(C)nn3c(NCc4cccc(-c5nccn5C)c4)cc(C(C)(C)O)nc23)cc1C(=O)N(C)CCO] | A, A | F | 0.9 | 584 |

-continued
| Cmp Number | Structure | MDAP method | LCMS method | rt | [M + H]+ |
|---|---|---|---|---|---|
| 27 | 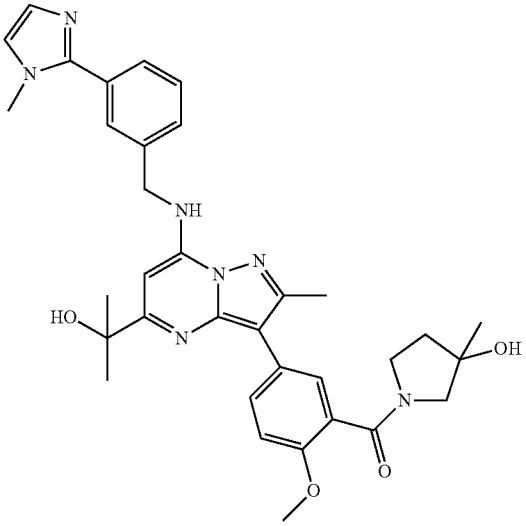 [SMILES: COc1ccc(-c2c(C)nn3c(NCc4cccc(-c5nccn5C)c4)cc(C(C)(C)O)nc23)cc1C(=O)N1CCC(C)(O)C1] | A | F | 0.92 | 610 |
| 28 | 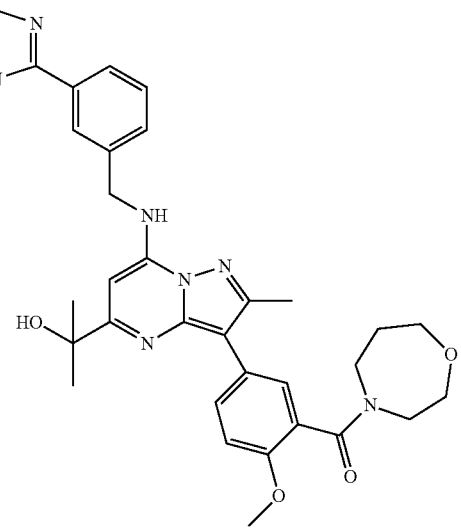 | A | F | 0.98 | 610 |
| 29 | 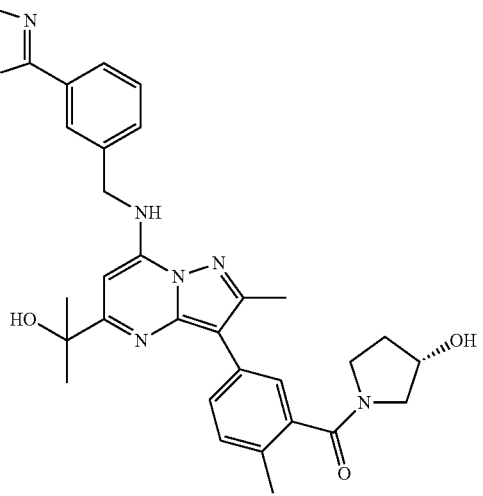 | A | F | 0.92 | 580 |

-continued
| Cmp Number | Structure | MDAP method | LCMS method | rt | [M + H]+ |
|---|---|---|---|---|---|
| 30 | 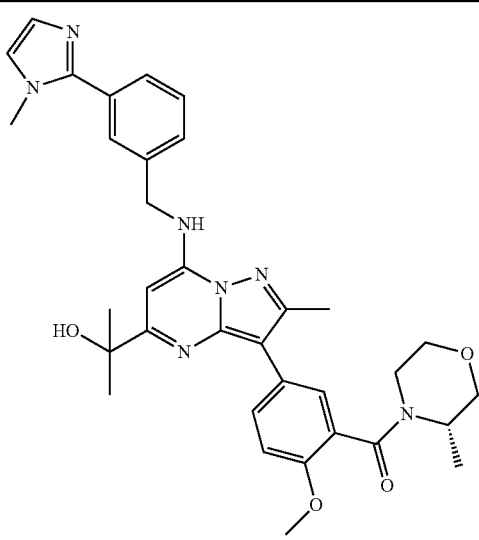 | A | F | 1.02 | 610 |
| 31 | 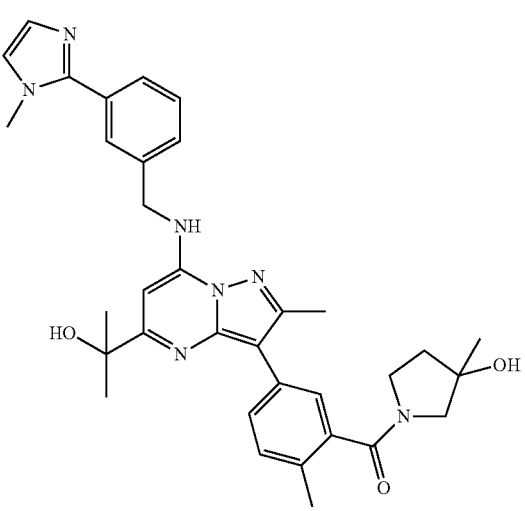 [SMILES: Cc1ccc(-c2c(C)nn3c(NCc4cccc(-c5nccn5C)c4)cc(C(C)(C)O)nc23)cc1C(=O)N1CCC(C)(O)C1] | A | F | 0.95 | 594 |
| 32 | 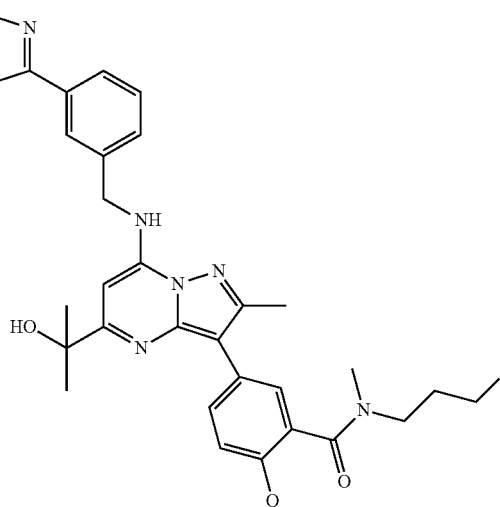 | A, A | F | 0.93 | 598 |

The following Compounds were prepared in a similar manner to the preparation of Compound 17, using intermediate 65, and either 1,4-dioxane or IPA as reaction solvent, and a temperature between 100° C. and 120° C., and the following boronic esters:

N-(3-Hydroxypropyl)-2-methoxy-N-methyl-5-(4,4,5,5-tetramethyl-1,3,2-dioxaborolan-2-yl)benzamide (intermediate 28), N-(3-hydroxypropyl)-N,2-dimethyl-5-(4,4,5,5-tetramethyl-1,3,2-dioxaborolan-2-yl)benzamide (intermediate 36), (R)-(2-(hydroxymethyl)pyrrolidin-1-yl)(2-methyl-5-(4,4,5,5-tetramethyl-1,3,2-dioxaborolan-2-yl)phenyl)methanone (intermediate 51).

| Cmp Number | Structure | MDAP method | LCMS method | rt | [M + H]⁺ |
|---|---|---|---|---|---|
| 33 | 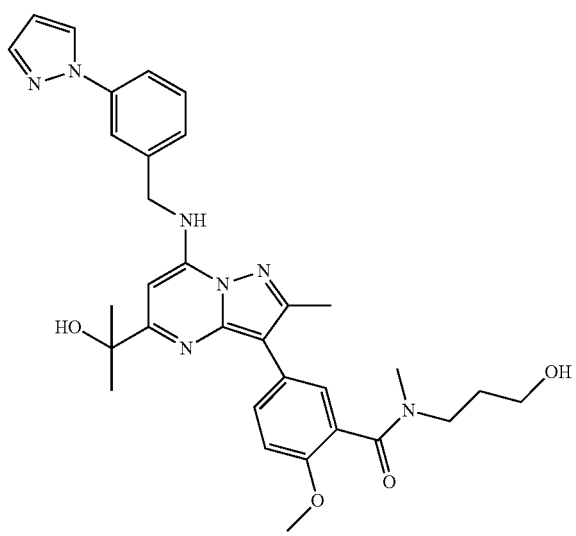 [SMILES: COc1ccc(-c2c(C)nn3c(NCc4cccc(-n5cccn5)c4)cc(C(C)(C)O)nc23)cc1C(=O)N(C)CCCO] | A | F | 1.03 | 584 |
| 34 | 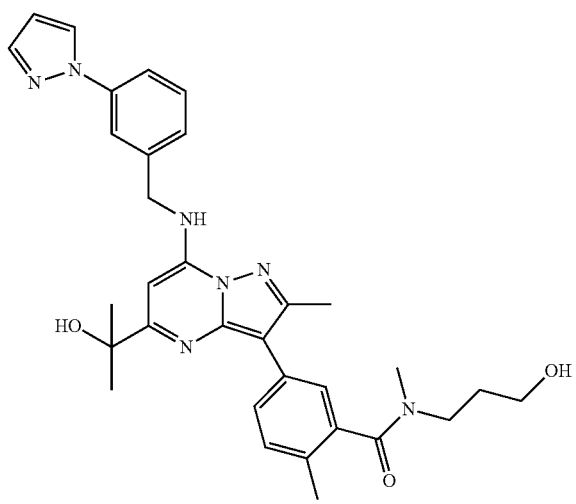 [SMILES: Cc1ccc(-c2c(C)nn3c(NCc4cccc(-n5cccn5)c4)cc(C(C)(C)O)nc23)cc1C(=O)N(C)CCCO] | A, B | F | 1.06 | 568 |

| Cmp Number | Structure | MDAP method | LCMS method | rt | [M + H]+ |
|---|---|---|---|---|---|
| 35 | 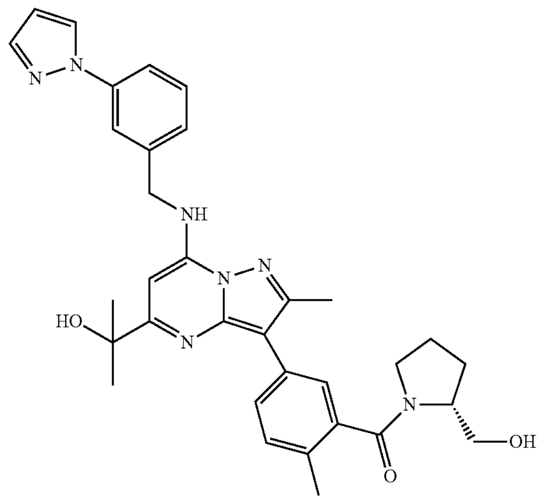 [SMILES: Cc1ccc(-c2c(C)nn3c(NCc4cccc(-n5cccn5)c4)cc(C(C)(C)O)nc23)cc1C(=O)N1CCC[C@@H]1CO] | A | F | 1.11 | 580 |
The following Compound was prepared in a similar manner to the preparation of Compound 17, using the following boronic ester:
(R)-(2-(hydroxymethyl)pyrrolidin-1-yl)(2-methoxy-5-(4,4,5,5-tetramethyl-1,3,2-dioxaborolan-2-yl)phenyl)methanone (Intermediate 67).
| Cmp Number | Structure | MDAP method | LCMS method | rt | [M + H]+ |
|---|---|---|---|---|---|
| 36 | 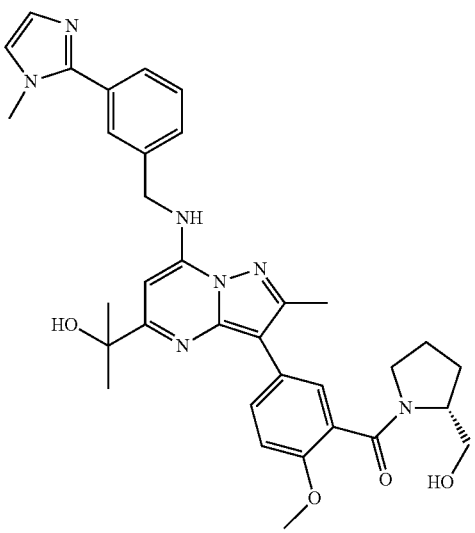 [SMILES: COc1ccc(-c2c(C)nn3c(NCc4cccc(-c5nccn5C)c4)cc(C(C)(C)O)nc23)cc1C(=O)N1CCC[C@@H]1CO] | A | F | 0.96 | 610 |

Alternative Preparation of Compound 17

5-(5-(2-Hydroxypropan-2-yl)-2-methyl-7-((3-(1-methyl-1H-imidazol-2-yl)benzyl)amino)pyrazolo[1,5-a]pyrimidin-3-yl)-N-(3-hydroxypropyl)-N,2-dimethylbenzamide

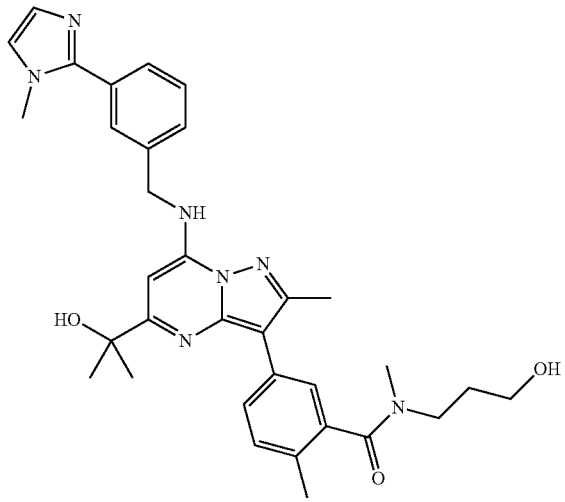 [SMILES: Cc1ccc(-c2c(C)nn3c(NCc4cccc(-c5nccn5C)c4)cc(C(C)(C)O)nc23)cc1C(=O)N(C)CCCO]

5-(5-(2-Hydroxypropan-2-yl)-2-methyl-7-((3-(1-methyl-1H-imidazol-2-yl)benzyl)amino)pyrazolo[1,5-a]pyrimidin-3-yl)-2-methylbenzoic acid (Intermediate 118, 12 g, 23.5 mmol), 3-(methylamino)propan-1-ol (2.81 mL, 29.4 mmol) and DIPEA (8.21 mL, 47.0 mmol) were stirred in THF (100 mL). HATU (11.17 g, 29.4 mmol) and DMF (10 mL) were added and the mixture stirred under nitrogen at room temperature for 3 h. The mixture was separated between ethyl acetate (400 mL) and saturated aqueous sodium bicarbonate (400 mL). The aqueous phase was extracted again with ethyl acetate (200 mL). The combined organic phases were washed with brine (200 mL), dried over magnesium sulphate and concentrated under reduced pressure. The residue was subjected to silica gel column chromatography eluting with 0-25% ethanol in ethyl acetate for 5 CV and 25% ethanol in ethyl acetate for 7 CV. Fractions containing product were combined, evaporated in vacuo and purified by the same chromatographic method until material was >97.5% by HPLC. The residue was triturated with diethyl ether and the solvent evaporated in vacuo. Ethyl acetate (40 mL) was added and the mixture stirred at room temperature for 5 days. The resultant white solid was collected by filtration, washed with ethyl acetate (25 mL) and dried in vacuo at 40° C. to give the title compound. LCMS (method M): rt=2.49, [M+H]$^+$=582. $\delta_H$ (400 MHz, d$_6$-DMSO) (mixture of rotamers) 8.53 (t, J=6.5 Hz, 1H), 7.73 (s, 1H), 7.71-7.67 (m, 0.75H), 7.65 (s, 0.75H), 7.61 (d, J=1.3 Hz, 0.5H), 7.59-7.54 (m, 1H), 7.48-7.42 (m, 2H), 7.33-7.27 (m, 1H), 7.22 (d, J=1.0 Hz, 1H), 6.94 (d, J=1.0 Hz, 1H), 6.45 (s, 1H), 5.18 (s, 1H), 4.70 (d, J=6.6 Hz, 2H), 4.47 (t, J=5.3 Hz, 0.5H), 4.34 (t, J=4.9 Hz, 0.5H), 3.70 (s, 3H), 3.56-3.46 (m, 2H), 3.28-3.20 (m, 2H), 3.00 (s, 1.5H), 2.82 (s, 1.5H), 2.58 (s, 3H), 2.21 (app. d, J=5.1 Hz, 3H), 1.79-1.70 (m, 1H), 1.66-1.57 (m, 1H), 1.39 (s, 6H) ppm. $\delta_C$ (151 MHz, d$_6$-DMSO) (mixture of rotamers) 170.3, 170.2, 169.0, 150.3, 150.2, 146.39, 146.36, 146.3, 145.4, 138.6, 137.0, 136.9, 130.8, 130.14, 130.05, 130.0, 128.6, 127.5, 127.4, 126.89, 126.86, 126.81, 124.84, 124.79, 123.4, 104.72, 104.67, 81.55, 81.53, 72.39, 72.38, 58.4, 58.0, 47.4, 44.4, 43.5, 36.3, 34.3, 31.8, 31.0, 30.1, 30.0, 18.2, 18.1, 14.7, 14.6 ppm. HRMS (ESI) calcd. for C$_{33}$H$_{39}$N$_7$O$_3$+H$^+$ 582.3193, found 582.3190 [M+H]$^+$.

Alternative Preparation of Compound 22

(S)—N-(1-Hydroxypropan-2-yl)-5-(5-(2-hydroxypropan-2-yl)-2-methyl-7-((3-(1-methyl-1H-imidazol-2-yl)benzyl)amino)pyrazolo[1,5-a]pyrimidin-3-yl)-N,2-dimethylbenzamide

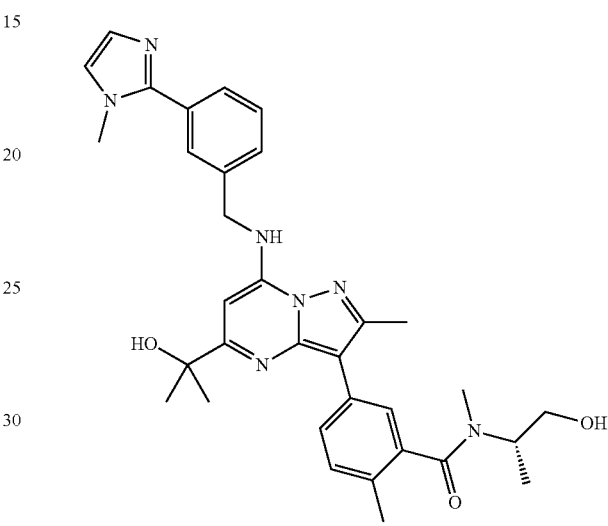

5-(5-(2-Hydroxypropan-2-yl)-2-methyl-7-((3-(1-methyl-1H-imidazol-2-yl)benzyl)amino)pyrazolo[1,5-a]pyrimidin-3-yl)-2-methylbenzoic acid (Intermediate 118, 7.55 g, 14.79 mmol), (S)-2-(methylamino)propan-1-ol (1.977 g, 22.18 mmol) and DIPEA (5.17 mL, 29.6 mmol) were stirred in THF (50 mL). DMF (2.5 mL) and HATU (7.03 g, 18.48 mmol) were added the mixture stirred under nitrogen at room temperature for 20 h. The mixture was partitioned between ethyl acetate (200 mL) and saturated aqueous sodium bicarbonate (200 mL). The aqueous phase was extracted using ethyl acetate (100 mL). The combined organic phases were washed with brine (100 mL), dried over magnesium sulphate and the solvent removed in vacuo. The residue was subject to KP—NH end-capped silica gel column chromatography eluting with 0-100% ethyl acetate in cyclohexane. The mixture was further purified by reverse phase column chromatography eluting with 5-50% acetonitrile (containing ammonia) in water (10 mM ammonium bicarbonate/ammonia). The residue obtained was triturated in methanol followed by diethyl ether (50 mL) in which the mixture was stirred rapidly for 30 minutes. The solvent was removed in vacuo and the residue was dissolved in ethyl acetate (70 mL) and stirred rapidly for 24 h. The solid was collected by filtration, washed with ethyl acetate dried in vacuo at 40° C. LCMS (method M): rt=2.56, [M+H]$^+$=582. $\delta_H$ (400 MHz, d$_6$-DMSO) (mixture of rotamers) 8.58-8.49 (m, 1H), 7.81 (d, J=8.1 Hz, 0.3H), 7.73 (s, 1H), 7.71-7.62 (m, 1H), 7.59-7.51 (m, 1.7H), 7.49-7.42 (m, 2H), 7.32-7.25 (m, 1H), 7.22 (s, 1H), 6.97-6.92 (m, 1H), 6.49-6.42 (m, 1H), 5.17 (s, 1H), 4.80 (t, J=5.3 Hz, 0.7H), 4.76 (t, J=5.5 Hz, 0.3H), 4.70 (d, J=6.2 Hz, 2H), 3.74-3.64 (m, 3.5H), 3.64-3.57 (m, 0.5H), 3.53-3.39 (m, 1.3H), 3.29-3.23 (m, 0.7H), 2.90-2.84 (m, 2H), 2.68 (s, 1H), 2.60-2.56 (m, 3H), 2.25-2.18 (m, 3H), 1.41-1.35 (m, 6H), 1.10 (d, J=7.0 Hz, 1H), 1.06-1.00 (m, 2H) ppm. $\delta_C$ (176 MHz, $d_6$-DMSO, 120° C.) 170.2, 168.3, 149.8, 146.1, 146.0, 145.0, 137.9, 137.2, 130.7, 130.2, 129.3, 128.0, 127.1, 126.6, 126.50, 126.47, 124.5, 122.6, 104.8, 81.2, 71.8, 62.0, 44.5, 33.5, 29.5, 17.5, 13.8 ppm. HRMS (ESI) calcd. for $C_{33}H_{39}N_7O_3+H^+$ 582.3193, found 582.3195 $[M+H]^+$.

Alternative Preparation of Compound 36

(R)-(2-(Hydroxymethyl)pyrrolidin-1-yl)(5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methoxyphenyl)methanone

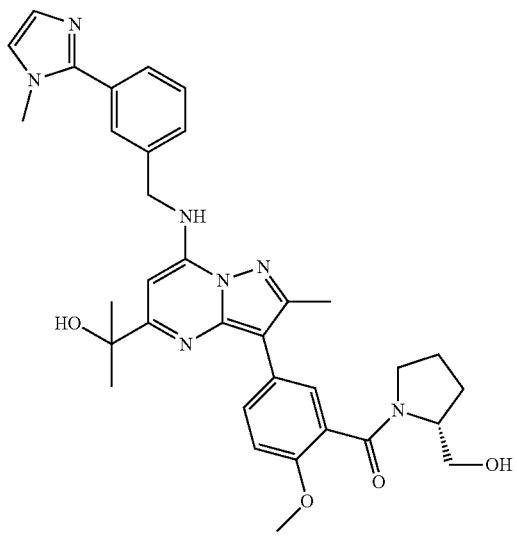 [SMILES: COc1ccc(-c2c(C)nn3c(NCc4cccc(-c5nccn5C)c4)cc(C(C)(C)O)nc23)cc1C(=O)N1CCC[C@@H]1CO]

To a solution/suspension of 5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methoxybenzoic acid (Intermediate 120, 3.0 g, 5.7 mmol), (R)-pyrrolidin-2-ylmethanol (0.576 g, 5.7 mmol) and DIPEA (1.990 mL, 11.39 mmol) in THF (100 mL) was added HATU (2.71 g, 7.12 mmol). The reaction mixture was stirred under nitrogen at room temperature for 20 h. The reaction mixture was partitioned between ethyl acetate (200 mL) and saturated sodium bicarbonate solution (200 mL). The organic phase was washed with brine (100 mL) and dried over magnesium sulphate. The solvent was removed in vacuo. The residue was dissolved in DCM and applied to a silica cartridge (120 g) and eluted with 0-25% ethanol in ethyl acetate for 5 CV and 25% ethanol in ethyl acetate for 6 CV. The required fractions were combined and evaporated in vacuo. The residue was dissolved in DMSO:methanol (1:1 v/v) and applied to a $C_{18}$ cartridge (120 g), pre-conditioned to 5% acetonitrile (containing ammonia) in water (10 mM ammonium bicarbonate containing ammonia). This was eluted with a gradient of 5-40% acetonitrile (containing ammonia) in water (10 mM ammonium bicarbonate containing ammonia). The gradient was held at 29% acetonitrile (containing ammonia) in water (10 mM ammonium bicarbonate containing ammonia) whilst the product eluted. The required fractions were combined and evaporated in vacuo. The residue was triturated with diethyl ether and the solvent evaporated. To the residue was added ethyl acetate (25 mL) and methanol (1 mL). The mixture was temperature cycled from room temp. to 45° C. and back 6 times and then left to stir at room temp. for 18 h. The resultant white solid was collected by filtration and washed with ethyl acetate (25 mL). The solid was dried in vacuo at 40° C. for 20 h to give the title compound. LCMS (method J): rt=0.59, $[M+H]^+$=610. $\delta_H$ (700 MHz, DMSO-$d_6$, 120° C.) 7.94 (br s, 1H), 7.75 (s, 1H), 7.75-7.72 (m, 1H), 7.65 (br s, 1H), 7.58 (br d, J=7.3 Hz, 1H), 7.50-7.47 (m, 1H), 7.47-7.42 (m, 1H), 7.16-7.14 (m, 1H), 7.16-7.13 (m, 1H), 6.95 (s, 1H), 6.44 (s, 1H), 4.74 (s, 2H), 4.18 (br s, 1H), 3.85 (s, 3H), 3.75-3.71 (m, 1H), 3.70 (s, 3H), 3.51-3.42 (m, 1H), 3.39-3.15 (m, 2H), 2.56 (s, 3H), 1.96-1.71 (m, 2H), 2.04-1.68 (m, 2H), 1.44 (s, 6H) ppm. $\delta_C$ NMR (176 MHz, DMSO-$d_6$, 120° C.) 168.11, 166.71, 152.36, 149.48, 146.05, 146.01, 144.77, 137.90, 130.71, 128.70, 127.90, 127.35, 127.05, 126.65, 126.56, 126.44, 126.43, 125.52, 122.51, 111.87, 104.61, 81.02, 71.72, 61.77, 58.17, 55.49, 47.62, 44.49, 33.51, 29.45, 26.86, 23.05, 13.61 ppm. HRMS (ESI) calcd. for $C_{34}H_{39}N_7O_4+H^+$ 610.3063, found 610.3141 $[M+H]^+$.

Alternative Preparation of Compound 21

5-(5-(2-Hydroxypropan-2-yl)-2-methyl-7-((3-(1-methyl-1H-imidazol-2-yl)benzyl)amino)pyrazolo[1,5-a]pyrimidin-3-yl)-2-methoxy-N-methyl-N-(tetrahydro-2H-pyran-4-yl)benzamide

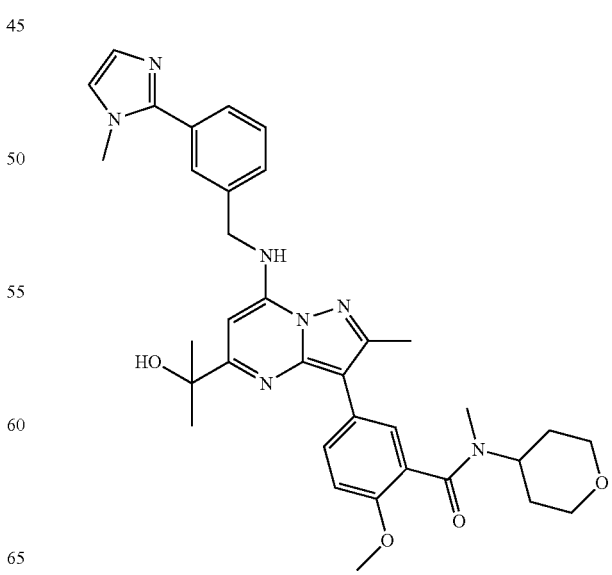

To a solution/suspension of 5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methoxybenzoic acid (Intermediate 120, 2.35 g, 4.46 mmol) and DIPEA (1.6 mL, 9.16 mmol) in THF (50 mL) was added HATU (2.35 g, 6.18 mmol). The mixture was stirred at room temperature for 10 min and N-methyltetrahydro-2H-pyran-4-amine (0.514 g, 4.46 mmol) was added. The mixture was stirred under nitrogen at room temp. for 16 h. The reaction mixture was partitioned between ethyl acetate (100 mL) and sat. aq. sodium bicarbonate solution (100 mL). The aqueous was extracted a second time with ethyl acetate (100 mL). The combined organic phases were washed with brine (100 mL) and passed through a hydrophobic frit. The solvent was removed under reduced pressure. The residue was purified by silica chromatography (340 g). The compound was dissolved in a minimum of DCM (+few drops of methanol), loaded onto the top of the column by injection, then eluted using 0-25% ethanol in ethyl acetate over 6 CV and then held at 25% ethanol in ethyl acetate for 6 CV. The fractions containing the desired product were combined and concentrated under reduced pressure. Approximately half the material was dissolved in DMSO:methanol (1:1 v/v) and applied to a $C_{18}$ cartridge (120 g), pre-conditioned to 5% acetonitrile (containing ammonia) in water (10 mM ammonium bicarbonate containing ammonia), then eluted with a gradient of 5-20% acetonitrile (containing ammonia) in water (10 mM ammonium bicarbonate containing ammonia) over 6 CV and then 20-60% acetonitrile (containing ammonia) in water (10 mM ammonium bicarbonate containing ammonia) over 6 CV. The gradient was held at 47.5% acetonitrile (containing ammonia) in water (10 mM ammonium bicarbonate containing ammonia) whilst the product eluted. The remainder of the material was purified in a similar manner, using a gradient of 25-55% acetonitrile (containing ammonia) in water (10 mM ammonium bicarbonate containing ammonia), bicarbonate/NH3). The gradient was held at 45% acetonitrile (containing ammonia) in water (10 mM ammonium bicarbonate containing ammonia) whilst the product eluted. The fractions containing pure products from both purifications were combined, concentrated under reduced pressure, then dried under vacuum for 24 h to give the title compound. LCMS (method J): rt=0.65, $[M+H]^+$=624. $\delta_H$ (600 MHz, $d_6$-DMSO) (mixture of rotamers) 8.54-8.49 (m, 1H), 7.77-7.72 (m, 2H), 7.63 (d, J=1.8 Hz, 0.5H), 7.59-7.54 (m, 1H), 7.53 (d, J=2.2 Hz, 0.5H), 7.47-7.43 (m, 2H), 7.22 (s, 1H), 7.18-7.13 (m, 1H), 6.94 (s, 1H), 6.43 (s, 1H), 5.17 (s, 1H), 4.69 (d, J=6.2 Hz, 2H), 4.64-4.58 (m, 0.5H), 3.98-3.91 (m, 1H), 3.90-3.85 (m, 0.5H), 3.82-3.75 (m, 3.5H), 3.70 (s, 3H), 3.57-3.50 (m, 0.5H), 3.43 (t, J=11.2 Hz, 1H), 3.12 (t, J=11.2 Hz, 0.5H), 3.00 (t, J=11.6 Hz, 0.5H), 2.88 (s, 1.5H), 2.69 (s, 1.5H), 2.56 (ap. d, J=15.8 Hz, 3H), 1.89-1.72 (m, 2H), 1.59-1.51 (m, 1.5H), 1.42 (d, J=11.4 Hz, 0.5H), 1.39-1.33 (m, 6H) ppm. $\delta_C$ (151 MHz, $d_6$-DMSO) (mixture of rotamers) 168.80, 168.77, 168.1, 167.9, 152.50, 152.47, 150.0, 149.9, 146.4, 146.34, 146.26, 145.18, 145.16, 138.6, 130.8, 129.2, 128.9, 128.6, 127.5, 126.89, 126.87, 126.80, 126.7, 126.6, 126.5, 125.9, 123.4, 111.6, 111.4, 104.7, 104.5, 81.4, 81.3, 72.4, 72.3, 66.5, 66.3, 66.2, 55.7, 55.4, 54.9, 54.8, 49.4, 44.4, 34.3, 30.5, 30.3, 30.09, 30.07, 30.0, 29.2, 26.6, 14.5, 14.4 ppm. HRMS (ESI) calcd. for $C_{35}H_{41}N_7O_4+H^+$ 624.3220, found 624.3294 $[M+H]^+$.

Compound 37

2-Chloro-N-(2-hydroxyethyl)-5-(5-(2-hydroxypropan-2-yl)-2-methyl-7-((3-(1-methyl-1H-imidazol-2-yl)benzyl)amino)pyrazolo[1,5-a]pyrimidin-3-yl)-N-methylbenzamide

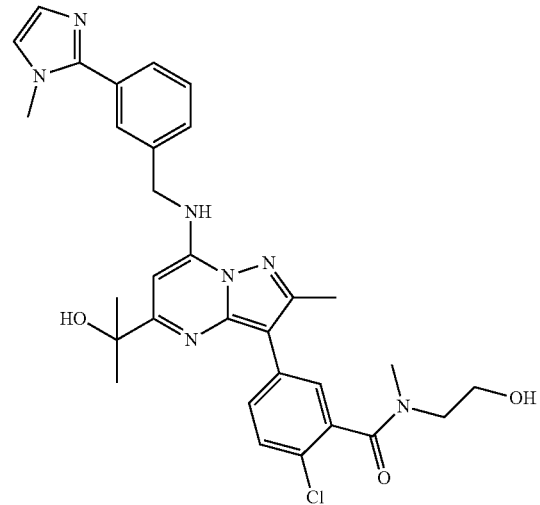 [SMILES: Cc1nn2c(NCc3cccc(-c4nccn4C)c3)cc(C(C)(C)O)nc2c1-c1ccc(Cl)c(C(=O)N(C)CCO)c1]

A microwave vial was charged with 2-(3-bromo-2-methyl-7-((3-(1-methyl-1H-imidazol-2-yl)benzyl)amino)pyrazolo[1,5-a]pyrimidin-5-yl)propan-2-ol (Intermediate 43, 305 mg, 0.636 mmol), XPhos (32 mg, 0.067 mmol), XPhos Pd G2 (53 mg, 0.067 mmol) and tripotassium phosphate (443 mg, 2.087 mmol). 2-Chloro-N-(2-hydroxyethyl)-N-methyl-5-(4,4,5,5-tetramethyl-1,3,2-dioxaborolan-2-yl)benzamide (Intermediate 69), 446 mg, 0.788 mmol) was dissolved in 1,4-dioxane (7.5 mL) and added to the microwave vial followed by water (2.5 mL). The vial was sealed and heated in a microwave at 100° C. for 1.5 h. The reaction mixture was diluted with water (25 mL) and partitioned with DCM (25 mL). The organic phase was collected and the aqueous phase was washed with DCM (4×25 mL). The organic phases were combined and the solvent was passed through a hydrophobic frit and then a second hydrophobic frit with a layer of Florisil (2 cm deep). The Florisil layer was washed with ethyl acetate:ethanol (3:1, containing 1% triethylamine) (25 mL). The filtrate was evaporated to dryness. The residue was dissolved in a minimum amount of DMSO:methanol (1:1, v/v) and purified by MDAP (method A). The relevant fractions were combined and the solvent was removed. The residue was purified by silica column chromatography eluting with 30-100 ethyl acetate:ethanol (3:1, containing 1% triethylamine) in cyclohexane. The relevant fractions were combined and the solvent was removed. The residue was triturated with a minimum amount of diethyl ether to give the title compound. LCMS (method F): rt=0.96, $[M+H]^+$=588.

The following Compounds were prepared in a similar manner to the preparation of Compound 37, using the following boronic esters:

N-Ethyl-N-(2-hydroxyethyl)-2-methyl-5-(4,4,5,5-tetramethyl1,3,2-dioxaborolan-2-yl)benzamide (Intermediate 73), (R)—N-(1-Hydroxypropan-2-yl)-N,2-dimethyl-5-(4,4,5,5-tetramethyl-1,3,2-dioxaborolan-2-yl)benzamide (intermediate 86), N-(1-Hydroxypropan-2-yl)-N,2-dimethyl-5-(4,4,5,5-tetramethyl-1,3,2-dioxaborolan-2-yl)benzamide (intermediate 88),
(3-Hydroxypyrrolidin1-yl)(2-methyl-5-(4,4,5,5-tetramethyl1,3,2-dioxaborolan-2-yl)phenyl)methanone (intermediate 90),
N-(1-Hydroxypropan2-yl)-2-methoxy-N-methyl-5-(4,4,5,5-tetramethyl-1,3,2-dioxaborolan-2-yl)benzamide (intermediate 92)
| Cmp Number | Structure | LCMS method | rt | [M + H]⁺ |
|---|---|---|---|---|
| 38 | 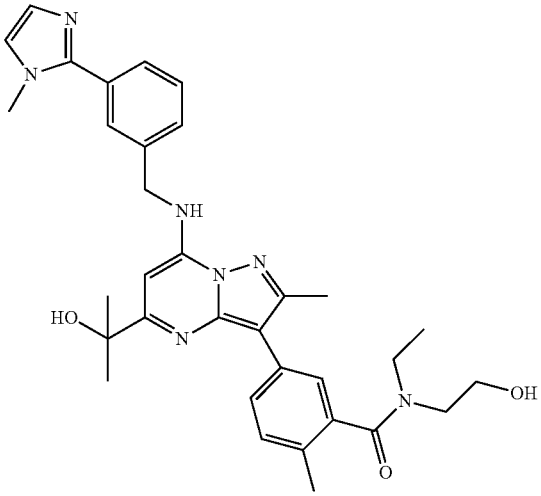 [SMILES: CCN(CCO)C(=O)c1cc(-c2c(C)nn3c(NCc4cccc(-c5nccn5C)c4)cc(C(C)(C)O)nc23)ccc1C] | F | 0.98 | 582 |
| 39 | 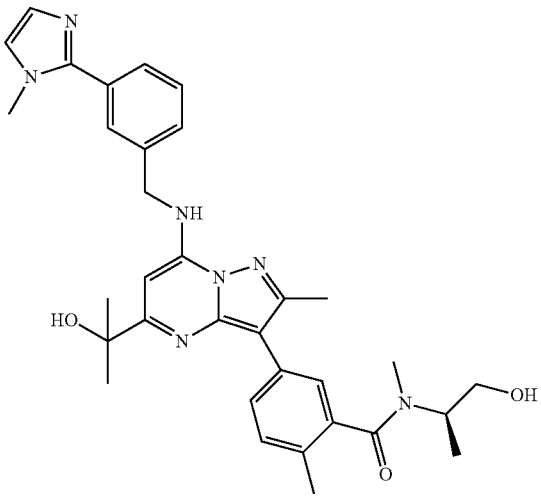 [SMILES: Cc1ccc(-c2c(C)nn3c(NCc4cccc(-c5nccn5C)c4)cc(C(C)(C)O)nc23)cc1C(=O)N(C)[C@H](C)CO] | F | 0.98 | 582 |

-continued

| Cmp Number | Structure | LCMS method | rt | [M + H]+ |
|---|---|---|---|---|
| 40 | 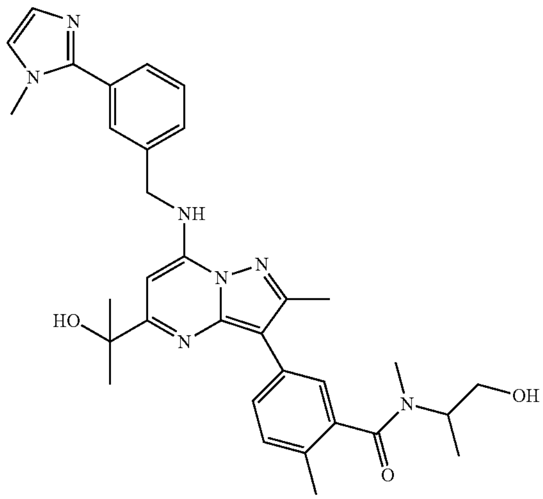 [SMILES: Cc1ccc(-c2c(C)nn3c(NCc4cccc(-c5nccn5C)c4)cc(C(C)(C)O)nc23)cc1C(=O)N(C)C(C)CO] | F | 0.99 | 582 |
| 41 | 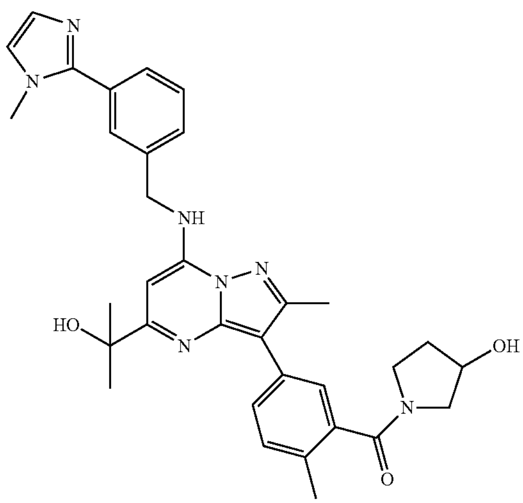 | F | 0.92 | 580 |
| 42 | 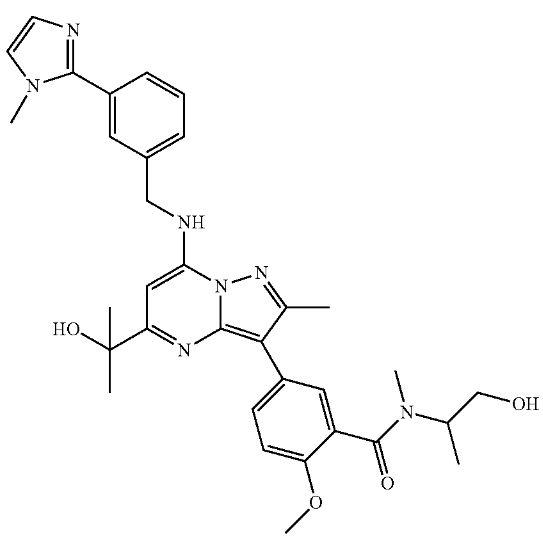 [SMILES: COc1ccc(-c2c(C)nn3c(NCc4cccc(-c5nccn5C)c4)cc(C(C)(C)O)nc23)cc1C(=O)N(C)C(C)CO] | F | 0.93 | 598 |

The following Compounds were prepared in a similar manner to the preparation of Compound 17, and either 1,4-dioxane or IPA as reaction solvent, and a temperature between 100° C. and 140° C., and the following boronic esters:

N-(2-Hydroxyethyl)-N,2-dimethyl-5-(4,4,5,5-tetramethyl-1,3,2-dioxaborolan-2-yl)benzamide (Intermediate 71), (2-(Hydroxymethyl)pyrrolidin-1-yl)(2-methoxy-5-(4,4,5,5-tetramethyl-1,3,2-dioxaborolan-2-yl)phenyl)methanone (intermediate 84), N,2-Dimethyl-N-(tetrahydro-2H-pyran-4-yl)-5-(4,4,5,5-tetramethyl-1,3,2-dioxaborolan-2-yl)benzamide (intermediate 96),

| Cmp Number | Structure | MDAP method | LCMS method | rt | [M + H]⁺ |
|---|---|---|---|---|---|
| 43 | 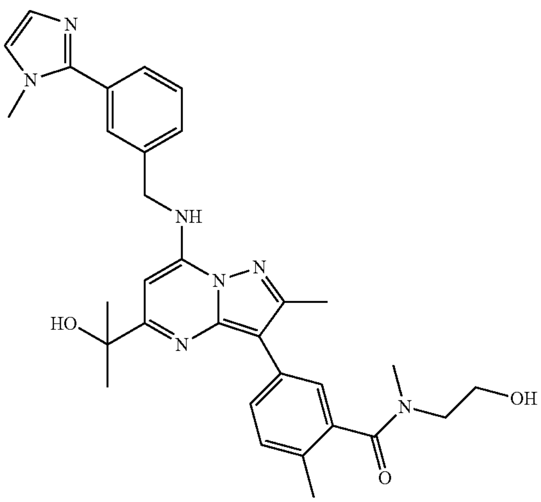 [SMILES: Cc1ccc(-c2c(C)nn3c(NCc4cccc(-c5nccn5C)c4)cc(C(C)(C)O)nc23)cc1C(=O)N(C)CCO] | A | F | 0.93 | 568 |
| 44 | 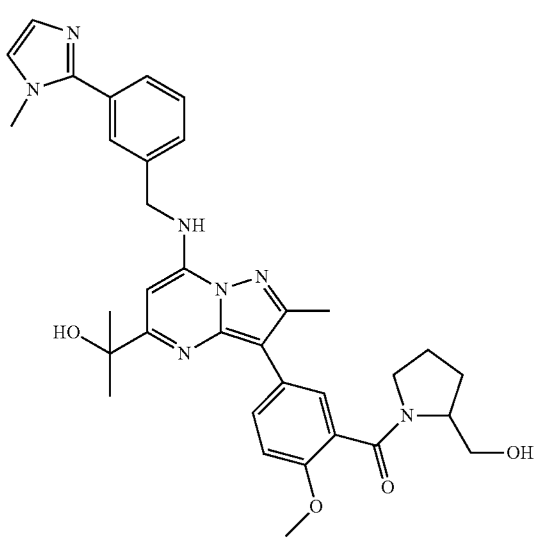 [SMILES: COc1ccc(-c2c(C)nn3c(NCc4cccc(-c5nccn5C)c4)cc(C(C)(C)O)nc23)cc1C(=O)N1CCCC1CO] | A | F | 0.97 | 610 |

| Cmp Number | Structure | MDAP method | LCMS method | rt | [M + H]⁺ |
|---|---|---|---|---|---|
| 45 | 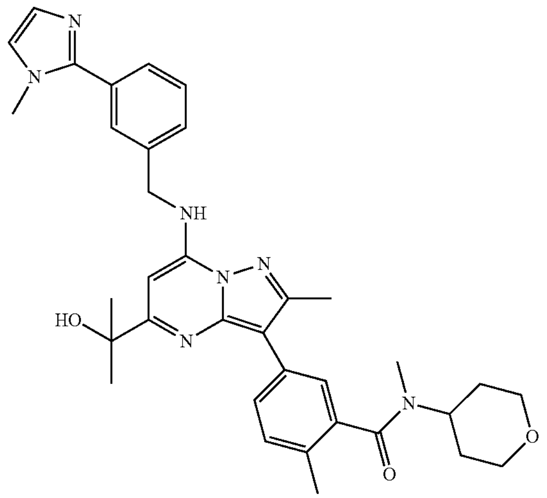 [SMILES: Cc1ccc(-c2c(C)nn3c(NCc4cccc(-c5nccn5C)c4)cc(C(C)(C)O)nc23)cc1C(=O)N(C)C1CCOCC1] | A, B | F | 1.04 | 608 |

The following Compounds were prepared in a similar manner to the preparation of Compound 17, using intermediate 65, and either 1,4-dioxane or IPA as reaction solvent, and a temperature between 100° C. and 140° C., and the following boronic esters:

N-(2-hydroxyethyl)-2-methoxy-N-methyl-5-(4,4,5,5-tetramethyl-1,3,2-dioxaborolan-2-yl)benzamide (Intermediate 53), N-(2-Hydroxyethyl)-N,2-dimethyl-5-(4,4,5,5-tetramethyl-1,3,2-dioxaborolan-2-yl)benzamide (Intermediate 71), 2-Chloro-N-(2-hydroxyethyl)-N-methyl-5-(4,4,5,5-tetramethyl-1,3,2-dioxaborolan-2-yl)benzamide (Intermediate 69), (R)-(2-(Hydroxymethyl)pyrrolidin-1-yl)(2-methoxy-5-(4,4,5,5-tetramethyl-1,3,2-dioxaborolan-2-yl)phenyl)methanone (Intermediate 67), (S)-(3-Hydroxypyrrolidin-1-yl)(2-methyl-5-(4,4,5,5-tetramethyl-1,3,2-dioxaborolan-2-yl)phenyl)methanone (Intermediate 59), (3-Hydroxy-3-methylpyrrolidin-1-yl)(2-methoxy-5-(4,4,5,5-tetramethyl-1,3,2-dioxaborolan-2-yl)phenyl)methanone (Intermediate 55), (S)-(3-Hydroxypyrrolidin-1-yl)(2-methoxy-5-(4,4,5,5-tetramethyl-1,3,2-dioxaborolan-2-yl)phenyl)methanone (Intermediate 25),

| Cmp Number | Structure | MDAP method | LCMS method | rt | [M + H]⁺ |
|---|---|---|---|---|---|
| 46 | 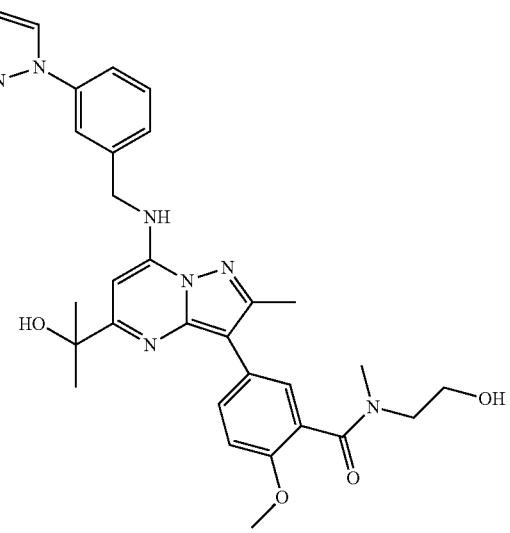 | A, B | F | 1.00 | 570 |

-continued

| Cmp Number | Structure | MDAP method | LCMS method | rt | [M + H]+ |
|---|---|---|---|---|---|
| 47 | 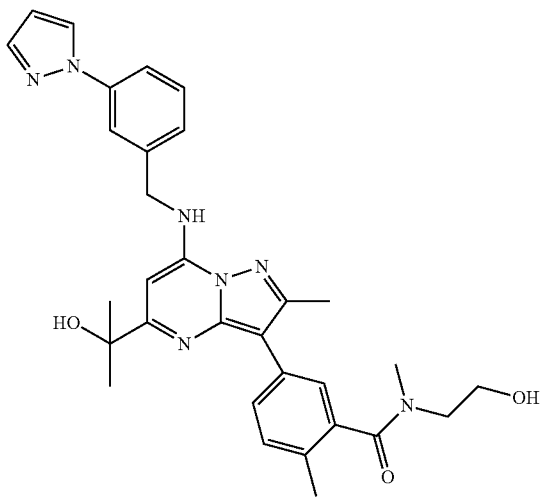 [SMILES: Cc1ccc(-c2c(C)nn3c(NCc4cccc(-n5cccn5)c4)cc(C(C)(C)O)nc23)cc1C(=O)N(C)CCO] | A, B | F | 1.04 | 554 |
| 48 | 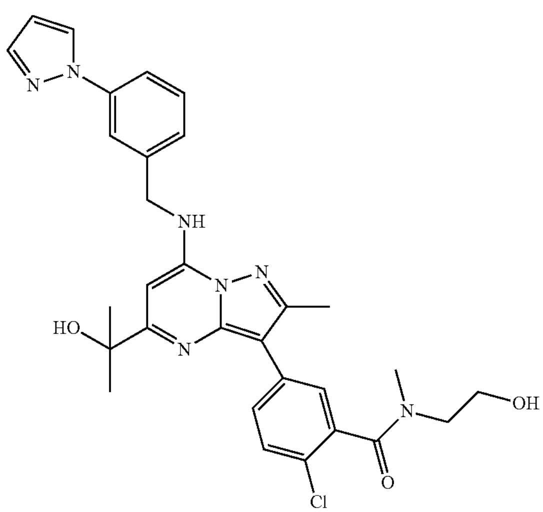 [SMILES: Cc1nn2c(NCc3cccc(-n4cccn4)c3)cc(C(C)(C)O)nc2c1-c1ccc(Cl)c(C(=O)N(C)CCO)c1] | A | F | 1.07 | 574 |
| 49 | 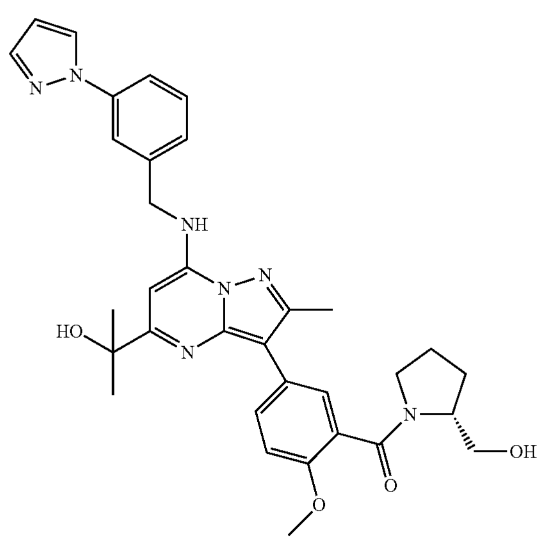 [SMILES: COc1ccc(-c2c(C)nn3c(NCc4cccc(-n5cccn5)c4)cc(C(C)(C)O)nc23)cc1C(=O)N1CCC[C@@H]1CO] | A, A | F | 1.08 | 596 |

-continued
| Cmp Number | Structure | MDAP method | LCMS method | rt | [M + H]+ |
|---|---|---|---|---|---|
| 50 | 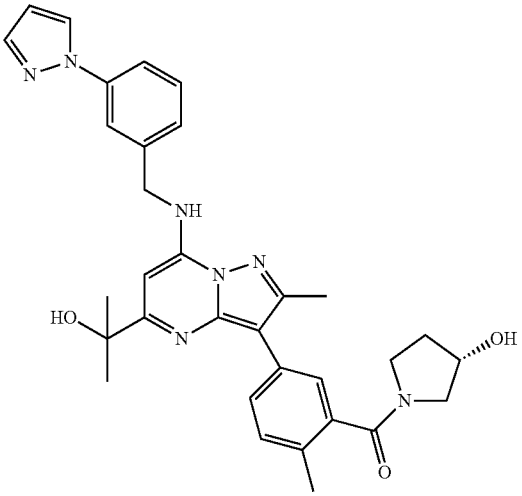 [SMILES: Cc1ccc(-c2c(C)nn3c(NCc4cccc(-n5cccn5)c4)cc(C(C)(C)O)nc23)cc1C(=O)N1CC[C@H](O)C1] | A, B | F | 1.02 | 566 |
| 51 | 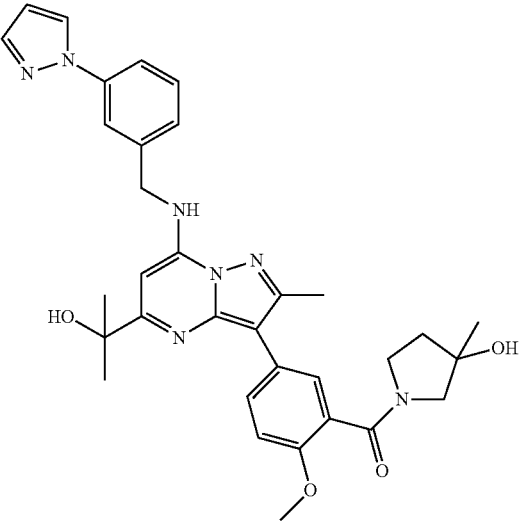 [SMILES: COc1ccc(-c2c(C)nn3c(NCc4cccc(-n5cccn5)c4)cc(C(C)(C)O)nc23)cc1C(=O)N1CCC(C)(O)C1] | A | F | 1.02 | 596 |
| 52 | 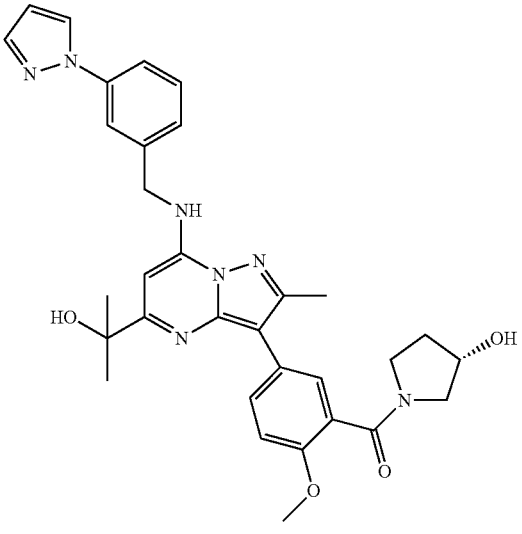 [SMILES: COc1ccc(-c2c(C)nn3c(NCc4cccc(-n5cccn5)c4)cc(C(C)(C)O)nc23)cc1C(=O)N1CC[C@H](O)C1] | B, B | J | 0.87 | 582 |

Compound 53

2-(3-(3-((2-Hydroxyethyl)sulfonyl)-4-methoxyphenyl)-2-methyl-7-((3-(1-methyl-1H-imidazol-2-yl)benzyl)amino)pyrazolo[1,5-a]pyrimidin-5-yl)propan-1-ol

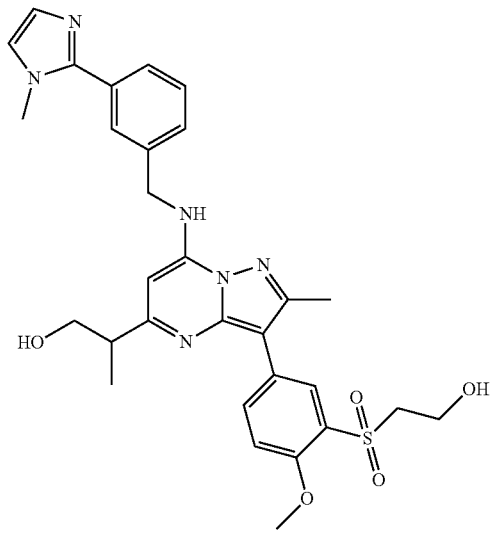 [SMILES: COc1ccc(-c2c(C)nn3c(NCc4cccc(-c5nccn5C)c4)cc(C(C)CO)nc23)cc1S(=O)(=O)CCO]

Prepared in a similar manner to compound 37 using 2-(3-iodo-2-methyl-7-((3-(1-methyl-1H-imidazol-2-yl)benzyl)amino)pyrazolo[1,5-a]pyrimidin-5-yl)propan-1-ol (intermediate 81) and 2-((2-methoxy-5-(4,4,5,5-tetramethyl-1,3,2-dioxaborolan-2-yl)phenyl)sulfonyl)ethanol (Intermediate 19) to give the title compound. LCMS (method J): rt=0.53, [M+H]$^+$=591.

Compound 54

5-(5-(1-Hydroxypropan-2-yl)-2-methyl-7-((3-(1-methyl-1H-imidazol-2-yl)benzyl)amino)pyrazolo[1,5-a]pyrimidin-3-yl)-N-(3-hydroxypropyl)-N,2-dimethylbenzamide

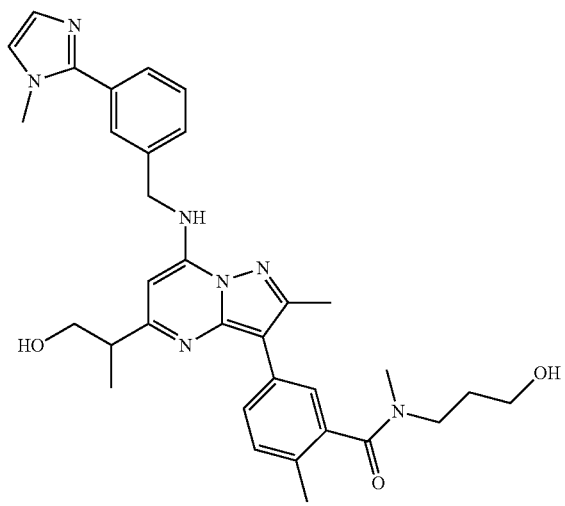 [SMILES: Cc1ccc(-c2c(C)nn3c(NCc4cccc(-c5nccn5C)c4)cc(C(C)CO)nc23)cc1C(=O)N(C)CCCO]

Prepared in a similar manner to Compound 17, using 2-(3-iodo-2-methyl-7-((3-(1-methyl-1H-imidazol-2-yl)benzyl)amino)pyrazolo[1,5-a]pyrimidin-5-yl)propan-1-ol (Intermediate 81) and N-(3-hydroxypropyl)-N,2-dimethyl-5-(4,4,5,5-tetramethyl-1,3,2-dioxaborolan-2-yl)benzamide (Intermediate 36) to give the title compound. LCMS (method F): rt=0.92, [M+H]$^+$=582.

Compound 55

5-(5-(1-Hydroxy-2-methylpropan-2-yl)-2-methyl-7-((3-(1-methyl-1H-imidazol-2-yl)benzyl)amino)pyrazolo[1,5-a]pyrimidin-3-yl)-N-(3-hydroxypropyl)-N,2-dimethylbenzamide Prepared in a similar manner to Compound 17 using 2-(3-Iodo-2-methyl-7-((3-(1-methyl-1H-imidazol-2-yl)benzyl)amino)pyrazolo[1,5-a]pyrimidin-5-yl)-2-methylpropan-1-ol (Intermediate 82) and N-(3-hydroxypropyl)-N,2-dimethyl-5-(4,4,5,5-tetramethyl-1,3,2-dioxaborolan-2-yl)benzamide (Intermediate 36) to give the title compound. LCMS (method F): rt=0.99, [M+H]$^+$=596.

Compound 56

2-(3-(3-((2-Hydroxyethyl)sulfonyl)-4-methoxyphenyl)-2-methyl-7-((3-(1-methyl-1H-imidazol-2-yl)benzyl)amino)pyrazolo[1,5-a]pyrimidin-5-yl)-2-methylpropan-1-ol

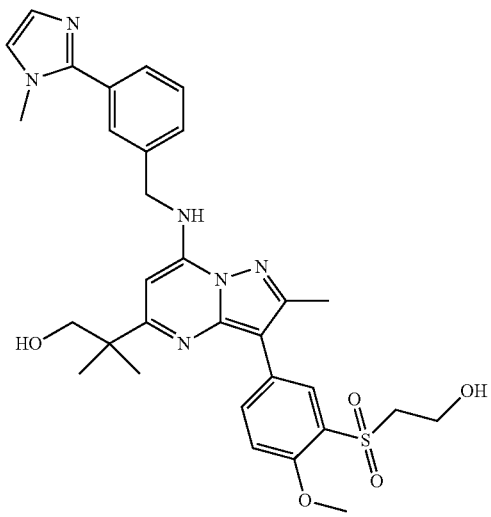 [SMILES: COc1ccc(-c2c(C)nn3c(NCc4cccc(-c5nccn5C)c4)cc(C(C)(C)CO)nc23)cc1S(=O)(=O)CCO]

Prepared in a similar manner to Compound 17 using 2-(3-Iodo-2-methyl-7-((3-(1-methyl-1H-imidazol-2-yl)benzyl)amino)pyrazolo[1,5-a]pyrimidin-5-yl)-2-methylpropan-1-ol (intermediate 82) and 2-((2-methoxy-5-(4,4,5,5-tetramethyl-1,3,2-dioxaborolan-2-yl)phenyl)sulfonyl)ethanol (Intermediate 19) to give the title compound. LCMS (method F): rt=0.95, [M+H]$^+$=605.

Compound 57

2-Chloro-5-(5-(1-hydroxyethyl)-2-methyl-7-((3-(1-methyl-1H-imidazol-2-yl)benzyl)amino)pyrazolo[1,5-a]pyrimidin-3-yl)-N-(3-hydroxypropyl)-N-methylbenzamide, Isomer 1

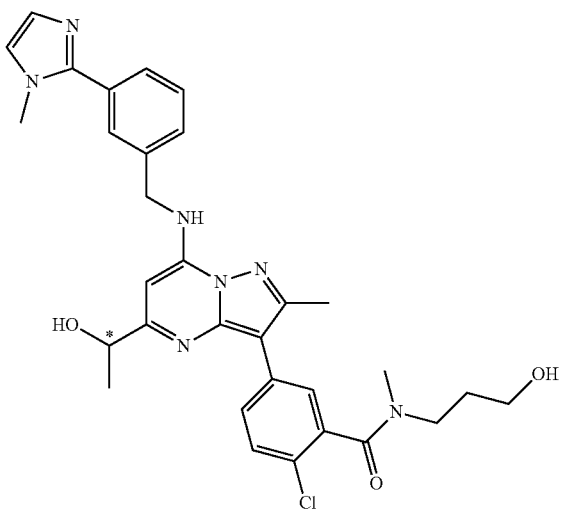 [SMILES: Cc1nn2c(NCc3cccc(-c4nccn4C)c3)cc(C(C)O)nc2c1-c1ccc(Cl)c(C(=O)N(C)CCCO)c1]

Prepared in a similar manner to Compound 37 using tert-butyl (5-(1-hydroxyethyl)-3-iodo-2-methylpyrazolo[1,5-a]pyrimidin-7-yl)(3-(1-methyl-1H-imidazol-2-yl)benzyl)carbamate, isomer 1 (Intermediate 93) and 2-chloro-N-(3-hydroxypropyl)-N-methyl-5-(4,4,5,5-tetramethyl-1,3,2-dioxaborolan-2-yl)benzamide (Intermediate 23) to give the title compound. LCMS (method F): rt=0.95, [M+H]$^+$=588.

Compound 58

2-Chloro-5-(5-(1-hydroxyethyl)-2-methyl-7-((3-(1-methyl-1H-imidazol-2-yl)benzyl)amino)pyrazolo[1,5-a]pyrimidin-3-yl)-N-(3-hydroxypropyl)-N-methylbenzamide, Isomer 2

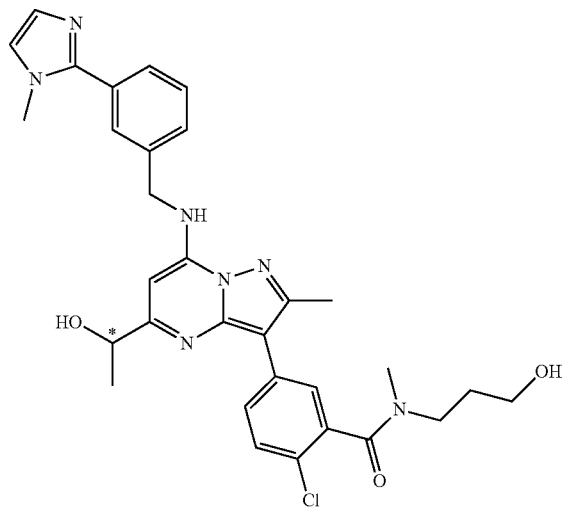 [SMILES: Cc1nn2c(NCc3cccc(-c4nccn4C)c3)cc(C(C)O)nc2c1-c1ccc(Cl)c(C(=O)N(C)CCCO)c1]

Prepared in a similar manner to compound 37 using tert-butyl (5-(1-hydroxyethyl)-3-iodo-2-methylpyrazolo[1,5-a]pyrimidin-7-yl)(3-(1-methyl-1H-imidazol-2-yl)benzyl)carbamate, isomer 2 (intermediate 94) and 2-chloro-N-(3-hydroxypropyl)-N-methyl-5-(4,4,5,5-tetramethyl-1,3,2-dioxaborolan-2-yl)benzamide (Intermediate 23) to give the title compound. LCMS (method F): rt=0.95, [M+H]$^+$=588.

Compound 59

5-(5-(2-Hydroxypropan-2-yl)-2-methyl-7-((3-(1-methyl-1H-imidazol-2-yl)benzyl)amino)pyrazolo[1,5-a]pyrimidin-3-yl)-N,2-dimethyl-N-(tetrahydrofuran-3-yl)benzamide

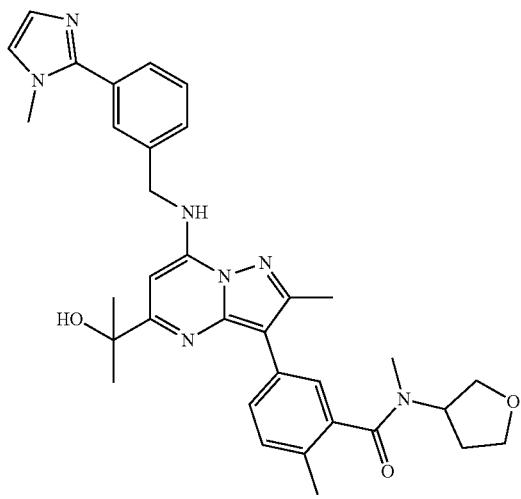 [SMILES: Cc1ccc(-c2c(C)nn3c(NCc4cccc(-c5nccn5C)c4)cc(C(C)(C)O)nc23)cc1C(=O)N(C)C1CCOC1]

A solution of 5-(5-(2-hydroxypropan-2-yl)-2-methyl-7-((3-(1-methyl-1H-imidazol-2-yl)benzyl)amino)pyrazolo[1,5-a]pyrimidin-3-yl)-2-methylbenzoic acid (Intermediate 118, 49 mg, 0.096 mmol), HATU (40.1 mg, 0.106 mmol) and DIPEA (0.034 mL, 0.192 mmol) in DMF (0.4 mL) was stirred for 20 min at room temp. N-Methyltetrahydrofuran-3-amine (0.013 mL, 0.115 mmol) was added to the reaction mixture and stirred for 1 h at room temp. then left overnight. The reaction mixture was diluted with methanol (0.6 mL) and purified by MDAP (method A). Appropriate fractions were combined, concentrated, triturated with diethyl ether, then dried under high vacuum to give the title compound. LCMS (method F): rt=1.04, $[M+H]^+$=594.

The following compounds were prepared in a similar manner to Compound 59, using the following amines:
3-Aminopropan-1-ol,
1-(methylamino)propan-2-ol

| Cmp Number | Structure | MDAP method | LCMS method | rt | $[M + H]^+$ |
|---|---|---|---|---|---|
| 60 | 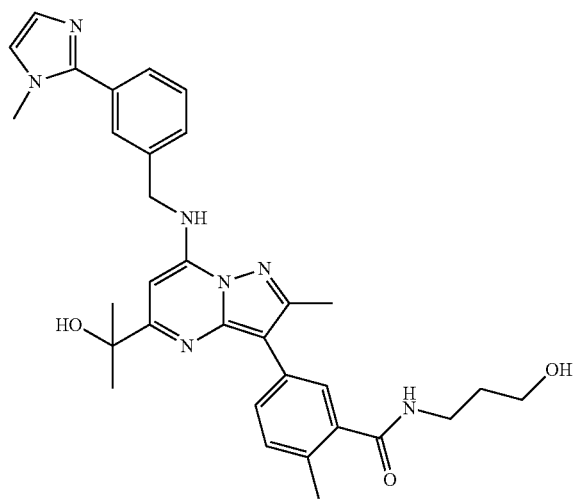 [SMILES: Cc1ccc(-c2c(C)nn3c(NCc4cccc(-c5nccn5C)c4)cc(C(C)(C)O)nc23)cc1C(=O)NCCCO] | A | F | 0.92 | 568 |

| Cmp Number | Structure | MDAP method | LCMS method | rt | [M + H]+ |
|---|---|---|---|---|---|
| 61 | 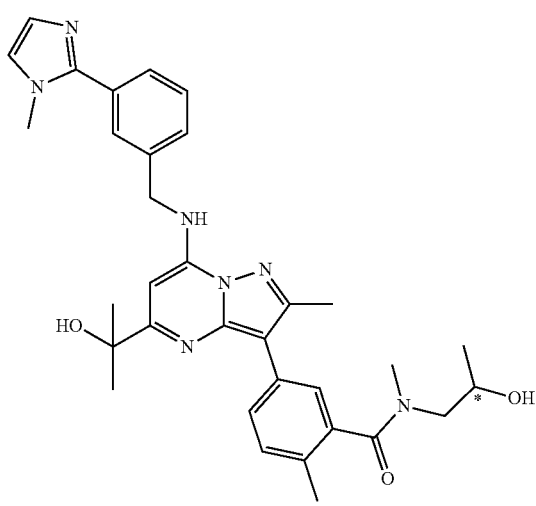 [SMILES: Cc1ccc(-c2c(C)nn3c(NCc4cccc(-c5nccn5C)c4)cc(C(C)(C)O)nc23)cc1C(=O)N(C)CC(C)O] | A | J | 0.6 | 582 |

Compound 62 and Compound 63

5-(5-(2-Hydroxypropan-2-yl)-2-methyl-7-((3-(1-methyl-1H-imidazol-2-yl)benzyl)amino)pyrazolo[1,5-a]pyrimidin-3-yl)-N-(2-hydroxypropyl)-N,2-dimethylbenzamide, Isomer 1 (Compound 62) and Isomer 2 (Compound 63)

Compound 61 was purified using a Chiralpak AS-H column (30 mm×250 mm, 5 μm), eluting with acetonitrile containing 0.2% isopropylamine to give the title compounds. Isomer 1: LCMS (method F): rt=0.98, [M+H]+=582. Chiral HPLC: rt 6.85, 100%. Isomer 2: LCMS (method F): rt=0.98, [M+H]+=582. Chiral HPLC: rt 8.36, 98.5%.

Compound 64

2-((2-Methoxy-5-(2-methyl-7-((3-(1-methyl-1H-imidazol-2-yl)benzyl)amino)-5-(tetrahydro-2H-pyran-4-yl)pyrazolo[1,5-a]pyrimidin-3-yl)phenyl)sulfonyl)ethan-1-ol

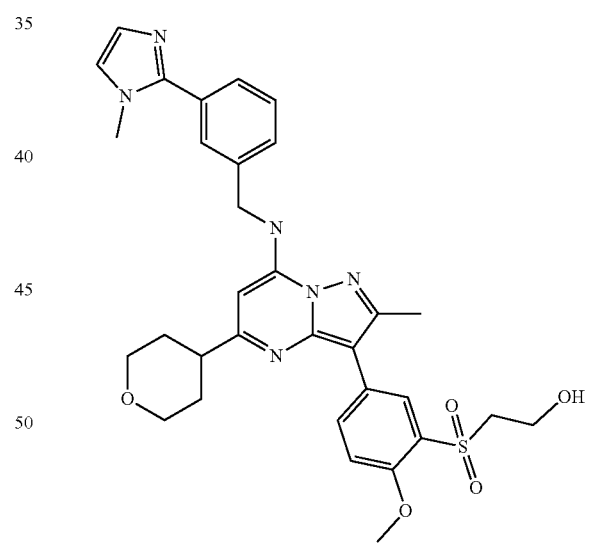

To a dried vial was added 2-(3,6-dihydro-2H-pyran-4-yl)-4,4,5,5-tetramethyl-1,3,2-dioxaborolane (18 mg, 0.086 mmol), Pd XPhos G2 (6 mg, 7.63 μmol), Pd/C (51 mg, 0.048 mmol), tripotassium phosphate (51 mg, 0.240 mmol) and tert-butyl (5-chloro-3-(3-((2-hydroxyethyl)sulfonyl)-4-methoxyphenyl)-2-methylpyrazolo[1,5-a]pyrimidin-7-yl)(3-(1-methyl-1H-imidazol-2-yl)benzyl)carbamate (Intermediate 102, 55 mg, 0.082 mmol). The vial was capped and purged with nitrogen. Water (0.2 mL) and 1,4-dioxane (0.8 mL) were added and the mixture heated to 100° C. for 45 min. The mixture was allowed to cool to room temp.

Ammonium formate (1.25 M in methanol) (0.659 mL, 0.824 mmol) was added and the mixture stirred overnight. The mixture was heated to 40° C. for 6 h. The vial was purged with nitrogen and the contents filtered through CELITE, washing with DCM (10 mL). The filtrate was partitioned with water (10 mL) and the separated aqueous phase washed with DCM (2×10 mL). The combined organic layers were passed through a hydrophobic frit and concentrated under reduced pressure. The residue was combined with the residue from a similar reaction performed on tert-butyl (5-chloro-3-(3-((2-hydroxyethyl)sulfonyl)-4-methoxyphenyl)-2-methylpyrazolo[1,5-a]pyrimidin-7-yl)(3-(1-methyl-1H-imidazol-2-yl)benzyl)carbamate (Intermediate 102, 20 mg, 0.03 mmol), dissolved in methanol (1.4 mL) and hydrochloric acid (3 M in CPME) (0.35 mL, 1.05 mmol) was added. The mixture was stirred overnight at room temp., then 40° C. for 7 h. The mixture was allowed to stand at room temp. over the weekend. Sat. aq. sodium bicarbonate (1 mL) was added and the mixture stirred for 5 min. DCM (2 mL) was added and the mixture partitioned. The separated aqueous phase was washed with DCM (2×1 mL) and the combined organics passed through a hydrophobic frit and concentrated under a stream of inert gas. The residue was dissolved in DMSO:methanol (0.5 mL, 1:1) and purified by MDAP (method A). The fractions containing product were combined, concentrated under reduced pressure and dried on the high vacuum line to give the title compound. LCMS (method F): rt=0.95, [M+H]⁺=617.

Compound 65

5-(5-(1-Hydroxybutan-2-yl)-2-methyl-7-((3-(1-methyl-1H-imidazol-2-yl)benzyl)amino)pyrazolo[1,5-a]pyrimidin-3-yl)-N-(3-hydroxypropyl)-N,2-dimethylbenzamide

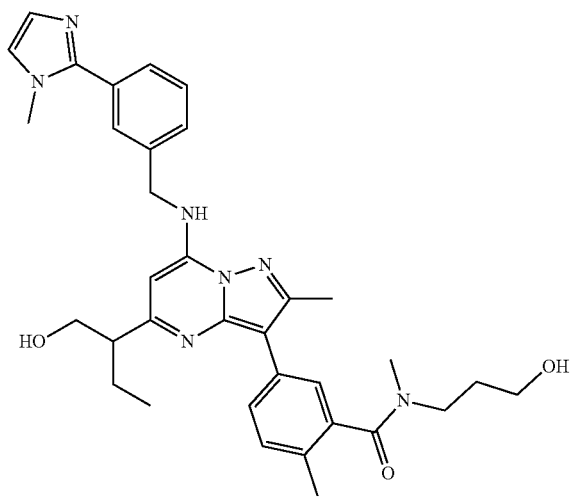 [SMILES: CCC(CO)c1cc(NCc2cccc(-c3nccn3C)c2)n2nc(C)c(-c3ccc(C)c(C(=O)N(C)CCCO)c3)c2n1]

Prepared in a similar manner to Compound 37, using 2-(3-iodo-2-methyl-7-((3-(1-methyl-1H-imidazol-2-yl)benzyl)amino)pyrazolo[1,5-a]pyrimidin-5-yl)butan-1-ol (Intermediate 104) and N-(3-hydroxypropyl)-N,2-dimethyl-5-(4,4,5,5-tetramethyl-1,3,2-dioxaborolan-2-yl)benzamide (Intermediate 36) to give the title compound. LCMS (method F): rt=0.97, [M+H]⁺=596.

Compounds 66 and 67

5-(5-(1-Hydroxybutan-2-yl)-2-methyl-7-((3-(1-methyl-1H-imidazol-2-yl)benzyl)amino)pyrazolo[1,5-a]pyrimidin-3-yl)-N-(3-hydroxypropyl)-N,2-dimethylbenzamide, Isomer 1 (Compound 66) and Isomer 2 (Compound 67)

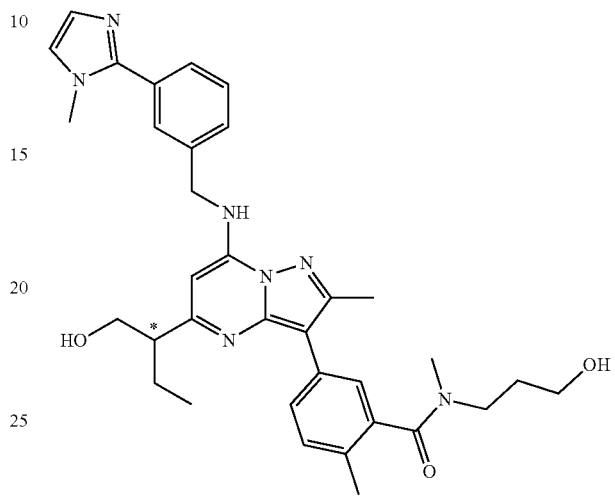

Compound 65 was purified using a Chiralpak AD-H column (30 mm×250 mm, 5 μm), eluting with 40% ethanol (containing 0.2% isopropylamine) in heptane (containing 0.2% isopropylamine) to give the title compounds. Isomer 1: LCMS (method J): rt=0.58, [M+H]⁺=596. Chiral HPLC: rt 9.41, 100%. Isomer 2: LCMS (method J): rt=0.58, [M+H]⁺=596. Chiral HPLC: rt 14.57, 99.5%.

Compound 68

5-(5-(3-Hydroxypentan-3-yl)-2-methyl-7-((3-(1-methyl-1H-imidazol-2-yl)benzyl)amino)pyrazolo[1,5-a]pyrimidin3-yl)-N-(3-hydroxypropyl)-N,2-dimethylbenzamide

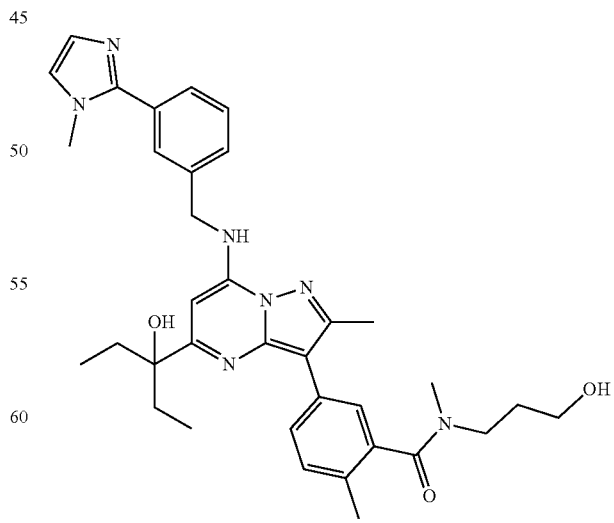

Prepared in a similar manner to Compound 37, using 3-(3-bromo-2-methyl-7-((3-(1-methyl-1H-imidazol-2-yl)

benzyl)amino)pyrazolo[1,5-a]pyrimidin-5-yl)pentan-3-ol (Intermediate 105) and N-(3-hydroxypropyl)-N,2-dimethyl-5-(4,4,5,5-tetramethyl-1,3,2-dioxaborolan-2-yl)benzamide (intermediate 36) to give the title compound. LCMS (method J): rt=0.71, [M+H]⁺=610.

Compound 69

N-(3-Hydroxypropyl)-5-(5-(1-hydroxypropyl)-2-methyl-7-((3-(1-methyl-1H-imidazol-2-yl)benzyl)amino)pyrazolo[1,5-a]pyrimidin-3-yl)-N,2-dimethyl-benzamide, Isomer 1

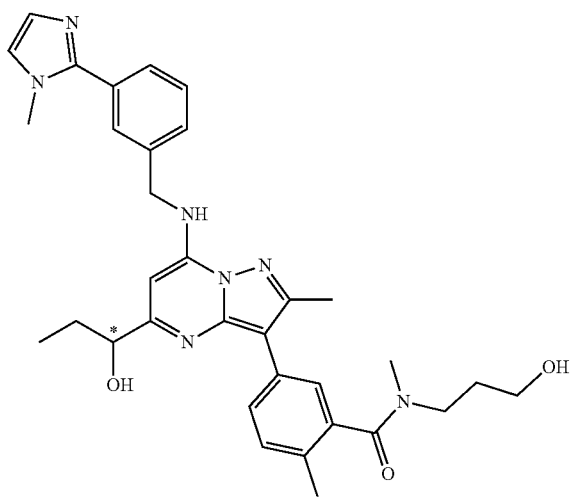 [SMILES: CCC(O)c1cc(NCc2cccc(-c3nccn3C)c2)n2nc(C)c(-c3ccc(C)c(C(=O)N(C)CCCO)c3)c2n1]

Prepared in a similar manner to compound 37 using 1-(3-bromo-2-methyl-7-((3-(1-methyl-1H-imidazol-2-yl)benzyl)amino)pyrazolo[1,5-a]pyrimidin-5-yl)propan-1-ol, isomer 1 (intermediate 108) and N-(3-hydroxypropyl)-N,2-dimethyl-5-(4,4,5,5-tetramethyl-1,3,2-dioxaborolan-2-yl)benzamide (Intermediate 36) to give the title compound. LCMS (method J): rt=0.65, [M+H]⁺=582.

Compound 70

N-(3-Hydroxypropyl)-5-(5-(1-hydroxypropyl)-2-methyl-7-((3-(1-methyl-1H-imidazol-2-yl)benzyl)amino)pyrazolo[1,5-a]pyrimidin-3-yl)-N,2-dimethyl-benzamide, Isomer 2

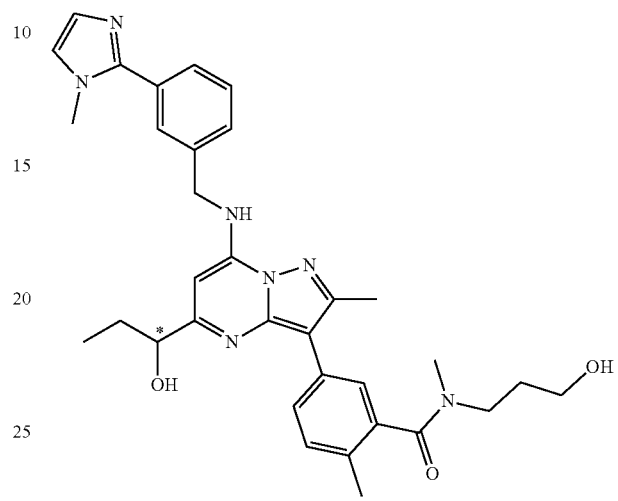

Prepared in a similar manner to compound 37 using 1-(3-bromo-2-methyl-7-((3-(1-methyl-1H-imidazol-2-yl)benzyl)amino)pyrazolo[1,5-a]pyrimidin-5-yl)propan-1-ol, isomer 2 (Intermediate 109) and N-(3-hydroxypropyl)-N,2-dimethyl-5-(4,4,5,5-tetramethyl-1,3,2-dioxaborolan-2-yl)benzamide (Intermediate 36) to give the title compound. LCMS (method J): rt=0.61, [M+H]⁺=582.

Compound 71

2-((5-(5-(1-Hydroxyethyl)-2-methyl-7-((3-(1-methyl-1H-imidazol-2-yl)benzyl)amino)pyrazolo[1,5-a]pyrimidin-3-yl)-2-methoxyphenyl)sulfonyl)ethan-1-ol, Isomer 1

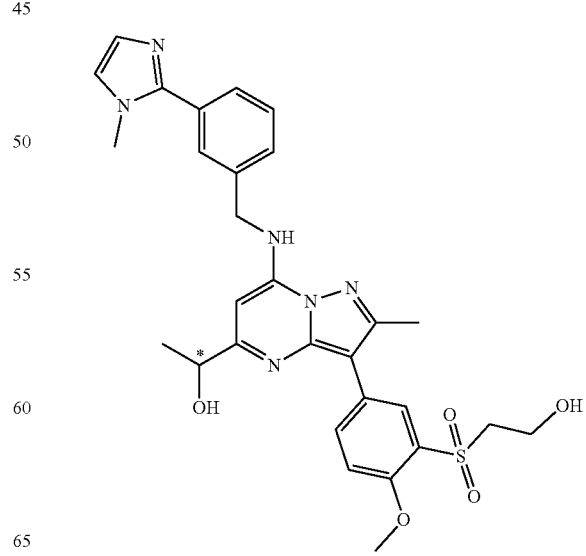

Prepared in a similar manner to compound 37 using 1-(3-bromo-2-methyl-7-((3-(1-methyl-1H-imidazol-2-yl)benzyl)amino)pyrazolo[1,5-a]pyrimidin-5-yl)ethan-1-ol, isomer 1 (Intermediate 111) and 2-((2-methoxy-5-(4,4,5,5-tetramethyl-1,3,2-dioxaborolan-2-yl)phenyl)sulfonyl)ethanol (Intermediate 19) to give the title compound. LCMS (method F): rt=0.87, [M+H]$^+$=577.

Compound 72

2-((5-(5-(1-Hydroxyethyl)-2-methyl-7-((3-(1-methyl-1H-imidazol-2-yl)benzyl)amino)pyrazolo[1,5-a]pyrimidin-3-yl)-2-methoxyphenyl)sulfonyl)ethan-1-ol, Isomer 2

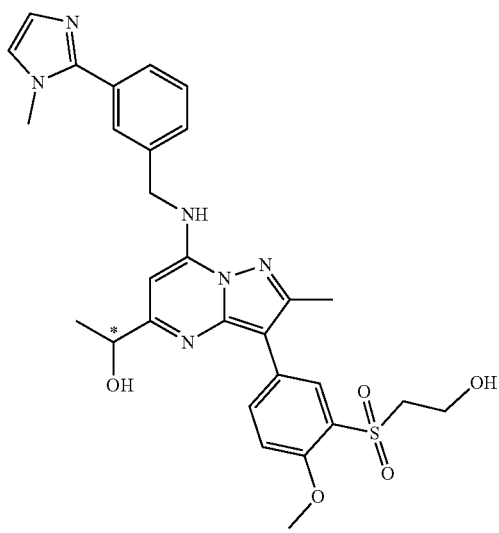 [SMILES: COc1ccc(-c2c(C)nn3c(NCc4cccc(-c5nccn5C)c4)cc(C(C)O)nc23)cc1S(=O)(=O)CCO]

Prepared in a similar manner to compound 37 using 1-(3-bromo-2-methyl-7-((3-(1-methyl-1H-imidazol-2-yl)benzyl)amino)pyrazolo[1,5-a]pyrimidin-5-yl)ethan-1-ol, isomer 2 (intermediate 112) and 2-((2-methoxy-5-(4,4,5,5-tetramethyl-1,3,2-dioxaborolan-2-yl)phenyl)sulfonyl)ethanol (Intermediate 19) to give the title compound. LCMS (method F): rt=0.86, [M+H]$^+$=577.

Compound 73

2-Chloro-5-(5-(1-hydroxyethyl)-2-methyl-7-((3-(1-methyl-1H-imidazol-2-yl)benzyl)amino)pyrazolo[1,5-a]pyrimidin-3-yl)-N-(3-hydroxypropyl)-N-methyl-benzamide, Isomer 1

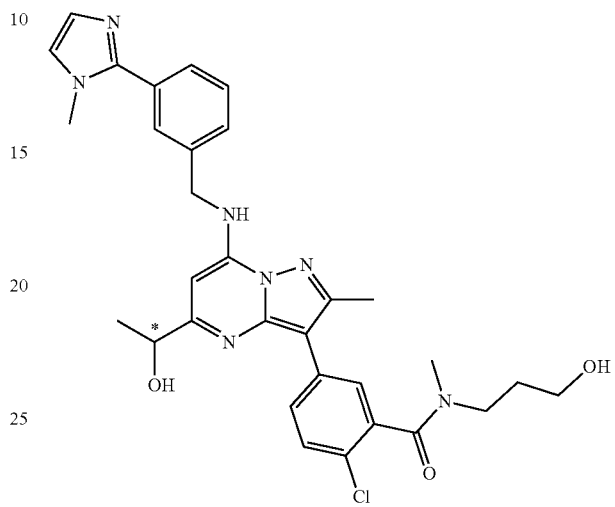

Prepared in a similar manner to compound 37 using 1-(3-bromo-2-methyl-7-((3-(1-methyl-1H-imidazol-2-yl)benzyl)amino)pyrazolo[1,5-a]pyrimidin-5-yl)ethan-1-ol, isomer 1 (intermediate 111) and 2-chloro-N-(3-hydroxypropyl)-N-methyl-5-(4,4,5,5-tetramethyl-1,3,2-dioxaborolan-2-yl)benzamide (Intermediate 23) to give the title compound. LCMS (method F): rt=0.93, [M+H]$^+$=588.

Compound 74

2-Chloro-5-(5-(1-hydroxyethyl)-2-methyl-7-((3-(1-methyl-1H-imidazol-2-yl)benzyl)amino)pyrazolo[1,5-a]pyrimidin-3-yl)-N-(3-hydroxypropyl)-N-methyl-benzamide, Isomer 2

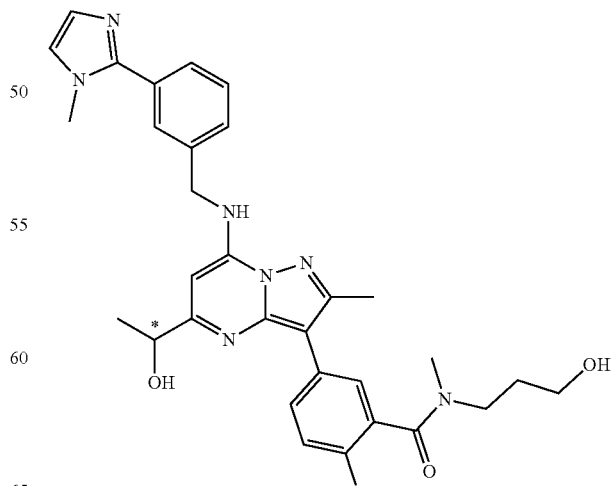

187

Prepared in a similar manner to compound 37 using 1-(3-bromo-2-methyl-7-((3-(1-methyl-1H-imidazol-2-yl)benzyl)amino)pyrazolo[1,5-a]pyrimidin-5-yl)ethan-1-ol, isomer 2 (intermediate 112) and 2-chloro-N-(3-hydroxypropyl)-N-methyl-5-(4,4,5,5-tetramethyl-1,3,2-dioxaborolan-2-yl)benzamide (Intermediate 23) to give the title compound. LCMS (method F): rt=0.93, [M+H]$^+$=588.

Compound 75

1-(3-(3-((2-Hydroxyethyl)sulfonyl)-4-methoxyphenyl)-2-methyl-7-((3-(1-methyl-1H-imidazol-2-yl)benzyl)amino)pyrazolo[1,5-a]pyrimidin-5-yl)propan-1-ol, Isomer 1

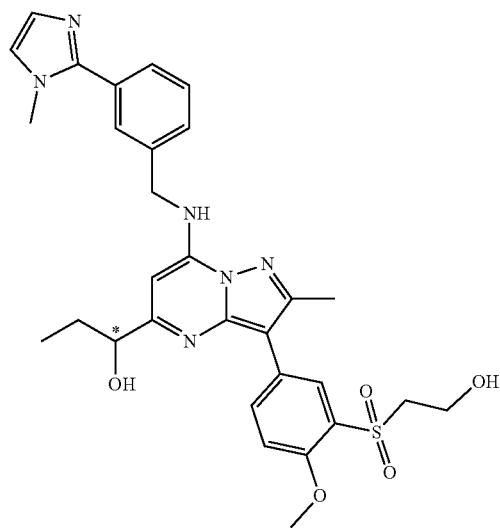 [SMILES: CCC(O)c1cc(NCc2cccc(-c3nccn3C)c2)n2nc(C)c(-c3ccc(OC)c(S(=O)(=O)CCO)c3)c2n1]

Prepared in a similar manner to compound 37 using 1-(3-bromo-2-methyl-7-((3-(1-methyl-1H-imidazol-2-yl)benzyl)amino)pyrazolo[1,5-a]pyrimidin-5-yl)propan-1-ol, isomer 1 (intermediate 108) and 2-((2-methoxy-5-(4,4,5,5-tetramethyl-1,3,2-dioxaborolan-2-yl)phenyl)sulfonyl)ethanol (Intermediate 19) to give the title compound. LCMS (method F): rt=0.91, [M+H]$^+$=591.

188

Compound 76

1-(3-(3-((2-Hydroxyethyl)sulfonyl)-4-methoxyphenyl)-2-methyl-7-((3-(1-methyl-1H-imidazol-2-yl)benzyl)amino)pyrazolo[1,5-a]pyrimidin-5-yl)propan-1-ol, Isomer 2

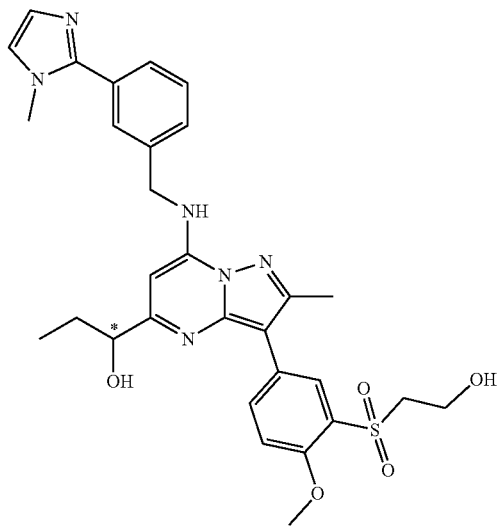 [SMILES: CCC(O)c1cc(NCc2cccc(-c3nccn3C)c2)n2nc(C)c(-c3ccc(OC)c(S(=O)(=O)CCO)c3)c2n1]

Prepared in a similar manner to Compound 37 using 1-(3-bromo-2-methyl-7-((3-(1-methyl-1H-imidazol-2-yl)benzyl)amino)pyrazolo[1,5-a]pyrimidin-5-yl)propan-1-ol, isomer 2 (Intermediate 109) and 2-((2-methoxy-5-(4,4,5,5-tetramethyl-1,3,2-dioxaborolan-2-yl)phenyl)sulfonyl)ethanol (Intermediate 19) to give the title compound. LCMS (method F): rt=0.91, [M+H]$^+$=591.

Compound 77

5-(5-(1-Hydroxypropyl)-2-methyl-7-((3-(1-methyl-1H-imidazol-2-yl)benzyl)amino)pyrazolo[1,5-a]pyrimidin-3-yl)-2-methoxy-N-methyl-N-(tetrahydro-2H-pyran-4-yl)benzamide, Isomer 1

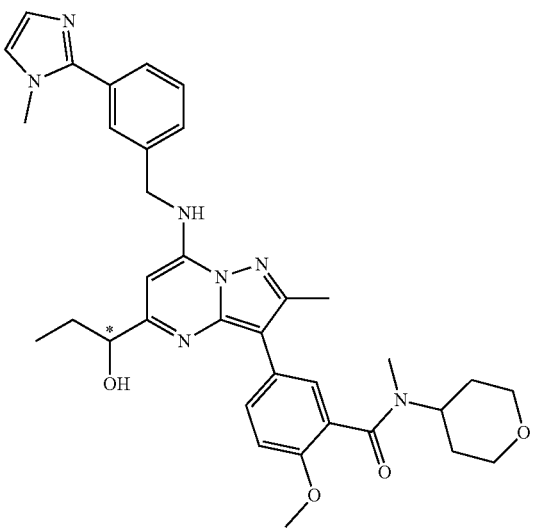 [SMILES: CCC(O)c1cc(NCc2cccc(-c3nccn3C)c2)n2nc(C)c(-c3ccc(OC)c(C(=O)N(C)C4CCOCC4)c3)c2n1]

Prepared in a similar manner to compound 37 using 1-(3-bromo-2-methyl-7-((3-(1-methyl-1H-imidazol-2-yl)benzyl)amino)pyrazolo[1,5-a]pyrimidin-5-yl)propan-1-ol, isomer 1 (intermediate 108) and 2-methoxy-N-methyl-N-(tetrahydro-2H-pyran-4-yl)-5-(4,4,5,5-tetramethyl-1,3,2-dioxaborolan-2-yl)benzamide (Intermediate 34) to give the title compound. LCMS (method J): rt=0.63, [M+H]$^+$=624.

Compound 78

5-(5-(1-Hydroxypropyl)-2-methyl-7-((3-(1-methyl-1H-imidazol-2-yl)benzyl)amino)pyrazolo[1,5-a]pyrimidin-3-yl)-2-methoxy-N-methyl-N-(tetrahydro-2H-pyran-4-yl)benzamide, Isomer 2

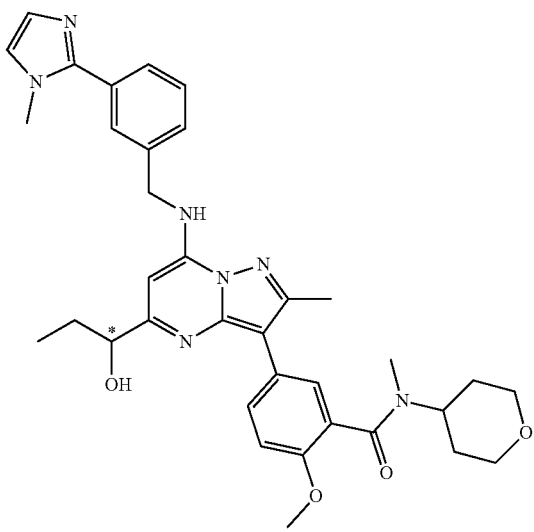 [SMILES: CCC(O)c1cc(NCc2cccc(-c3nccn3C)c2)n2nc(C)c(-c3ccc(OC)c(C(=O)N(C)C4CCOCC4)c3)c2n1]

Prepared in a similar manner to compound 37 using 1-(3-bromo-2-methyl-7-((3-(1-methyl-1H-imidazol-2-yl)benzyl)amino)pyrazolo[1,5-a]pyrimidin-5-yl)propan-1-ol, isomer 2 (Intermediate 109) and 2-methoxy-N-methyl-N-(tetrahydro-2H-pyran-4-yl)-5-(4,4,5,5-tetramethyl-1,3,2-dioxaborolan-2-yl)benzamide (Intermediate 34) to give the title compound. LCMS (method J): rt=0.64, [M+H]$^+$=624.

Compound 79

5-(5-(1-Hydroxycyclopropyl)-2-methyl-7-((3-(1-methyl-1H-imidazol-2-yl)benzyl)amino)pyrazolo[1,5-a]pyrimidin-3-yl)-N-(3-hydroxypropyl)-N,2-dimethylbenzamide

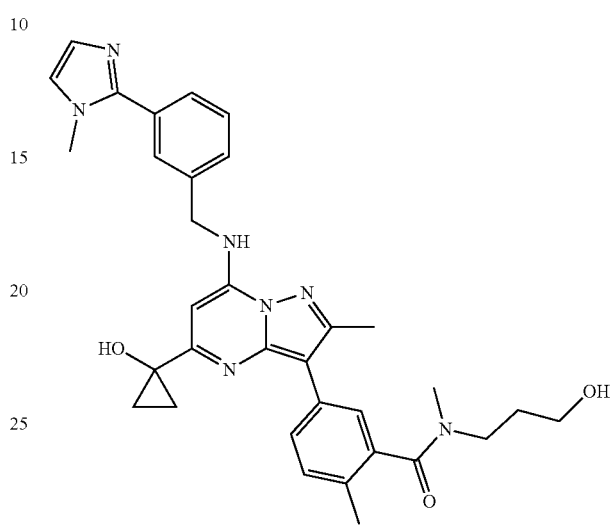

tert-Butyl (3-bromo-5-(1-((tert-butyldimethylsilyl)oxy)cyclopropyl)-2-methylpyrazolo[1,5-a]pyrimidin-7-yl)(3-(1-methyl-1H-imidazol-2-yl)benzyl)carbamate (Intermediate 115, 26 mg, 0.039 mmol), potassium phosphate (24 mg, 0.113 mmol), XPhos (2 mg, 4.20 μmol), XPhos Pd G2 (3 mg, 3.81 μmol) and N-(3-hydroxypropyl)-N,2-dimethyl-5-(4,4,5,5-tetramethyl-1,3,2-dioxaborolan-2-yl)benzamide (Intermediate 36, 25 mg, 0.053 mmol) were combined in 1,4-dioxane (0.4 mL) and water (0.133 mL). The mixture was heated to 60° C. in a sealed vial for 1 h 45 min. XPhos Pd G2 (3 mg, 3.81 μmol) and N-(3-hydroxypropyl)-N,2-dimethyl-5-(4,4,5,5-tetramethyl-1,3,2-dioxaborolan-2-yl)benzamide (Intermediate 36, 25 mg, 0.053 mmol) were added. After 1 h, the reaction temperature was increased to 80° C. After 2 h XPhos Pd G2 (3 mg, 3.81 μmol) and N-(3-hydroxypropyl)-N,2-dimethyl-5-(4,4,5,5-tetramethyl-1,3,2-dioxaborolan-2-yl)benzamide (Intermediate 36, 25 mg, 0.053 mmol) were added and the mixture heated to 100° C. for 1 h. The mixture was partitioned between water (10 mL) and ethyl acetate (10 mL). The separated aqueous phase was washed with ethyl acetate (2×10 mL) and the combined organics passed through a hydrophobic frit and concentrated under reduced pressure. The residue was dissolved in 1,4-dioxane (1.0 mL) and then HCl (4 M in 1,4-dioxane) (0.1 mL) was added. The mixture was stirred at room temperature for 4 days. Saturated aqueous sodium bicarbonate (3 mL) was added and the mixture stirred for 10 min. Water (10 mL) and DCM (10 mL) were added and the phases partitioned. The separated aqueous phase was washed with DCM (2×5 mL) and the combined organic layers passed through a hydrophobic frit and concentrated under reduced pressure. The residue was purified by MDAP (method A). The fractions containing desired product were combined and concentrated under reduced pressure to give the title compound. LCMS (method F): rt=0.97, [M+H]$^+$=580.

Compound 80

N—((S)-1-Hydroxypropan-2-yl)-5-(5-(1-hydroxy-propyl)-2-methyl-7-((3-(1-methyl-1H-imidazol-2-yl)benzyl)amino)pyrazolo[1,5-a]pyrimidin3-yl)-N,2-dimethylbenzamide, Isomer 1

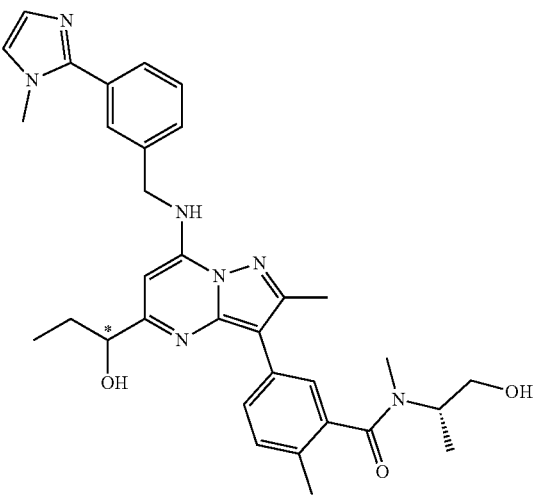 [SMILES: CCC(O)c1cc(NCc2cccc(-c3nccn3C)c2)n2nc(C)c(-c3ccc(C)c(C(=O)N(C)[C@@H](C)CO)c3)c2n1]

Prepared in a similar manner to compound 37 using 1-(3-bromo-2-methyl-7-((3-(1-methyl-1H-imidazol-2-yl)benzyl)amino)pyrazolo[1,5-a]pyrimidin-5-yl)propan-1-ol, isomer 1 (intermediate 108) and (S)—N-(1-hydroxypropan-2-yl)-N,2-dimethyl-5-(4,4,5,5-tetramethyl-1,3,2-dioxaborolan-2-yl)benzamide (Intermediate 45) to give the title compound. LCMS (method J): rt=0.62, [M+H]$^+$=582.

Compound 81

N—((S)-1-Hydroxypropan-2-yl)-5-(5-(1-hydroxy-propyl)-2-methyl-7-((3-(1-methyl-1H-imidazol-2-yl)benzyl)amino)pyrazolo[1,5-a]pyrimidin3-yl)-N,2-dimethylbenzamide, Isomer 2

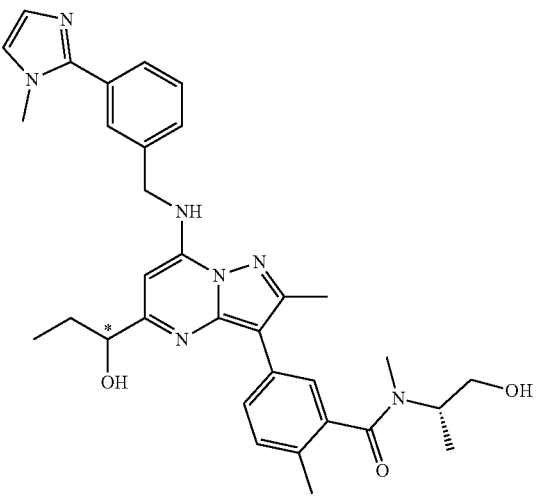 [SMILES: CCC(O)c1cc(NCc2cccc(-c3nccn3C)c2)n2nc(C)c(-c3ccc(C)c(C(=O)N(C)[C@@H](C)CO)c3)c2n1]

Prepared in a similar manner to compound 37 using 1-(3-bromo-2-methyl-7-((3-(1-methyl-1H-imidazol-2-yl)benzyl)amino)pyrazolo[1,5-a]pyrimidin-5-yl)propan-1-ol, isomer 2 (Intermediate 109) and (S)—N-(1-hydroxypropan-2-yl)-N,2-dimethyl-5-(4,4,5,5-tetramethyl-1,3,2-dioxaborolan-2-yl)benzamide (intermediate 45) to give the title compound. LCMS (method J): rt=0.61, [M+H]$^+$=582.

Compound 82

5-(5-(2-Hydroxypropan-2-yl)-2-methyl-7-((3-(1-methyl-1H-imidazol-2-yl)benzyl)amino)pyrazolo[1,5-a]pyrimidin-3-yl)-N-(2-hydroxypropyl)-2-methoxy-N-methylbenzamide

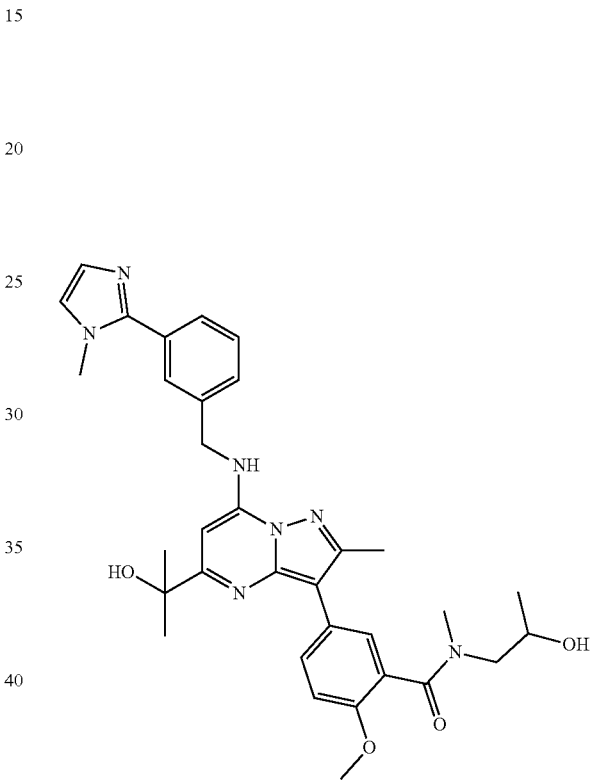

5-(5-(2-Hydroxypropan-2-yl)-2-methyl-7-((3-(1-methyl-1H-imidazol-2-yl)benzyl)amino)pyrazolo[1,5-a]pyrimidin-3-yl)-2-methoxybenzoic acid (intermediate 120, 65 mg, 0.101 mmol), HATU (47 mg, 0.124 mmol) and DIPEA (0.055 mL, 0.315 mmol) were stirred in THF (1 mL) at room temperature for 5 min after which 1-(methylamino)propan-2-ol (13 mg, 0.146 mmol) was added. After 2 h, additional HATU (12 mg, 0.032 mmol) and DIPEA (0.018 mL, 0.101 mmol) were added. After 1.5 hours the reaction mixture was purified by MDAP (method A). Product fractions were combined and dried under a stream of inert gas to give the title compound. LCMS (method F): rt=0.96, [M+H]$^+$=598.

Compounds 83 and 84

5-(5-(2-Hydroxypropan-2-yl)-2-methyl-7-((3-(1-methyl-1H-imidazol-2-yl)benzyl)amino)pyrazolo[1,5-a]pyrimidin-3-yl)-N-(2-hydroxypropyl)-2-methoxy-N-methylbenzamide, isomer 1 (Compound 83) and isomer 2 (Compound 84)

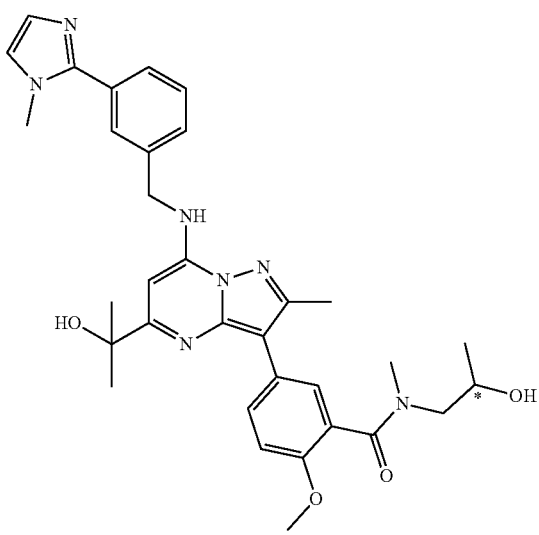 [SMILES: COc1ccc(-c2c(C)nn3c(NCc4cccc(-c5nccn5C)c4)cc(C(C)(C)O)nc23)cc1C(=O)N(C)CC(C)O]

Compound 82 was purified on a Chiralpak IC column (30 mm×250 mm, 5 μm), eluting with 30% ethanol (containing 0.2% isporopylamine) in heptane (containing 0.2% isporopylamine) to give the title compounds. Isomer 1: LCMS (method F): rt=0.94, [M+H]$^+$=598. Chiral HPLC: rt 28.8, 100%. Isomer 2: LCMS (method F): rt=0.94, [M+H]$^+$=598. Chiral HPLC: rt 33.68, 96.6%.

Compound 85

2-((2-Methoxy-5-(2-methyl-7-((3-(1-methyl-1H-imidazol-2-yl)benzyl)amino)-5-((tetrahydro-2H-pyran-4-yl)methyl)pyrazolo[1,5-a]pyrimidin-3-yl)phenyl)sulfonyl)ethan-1-ol

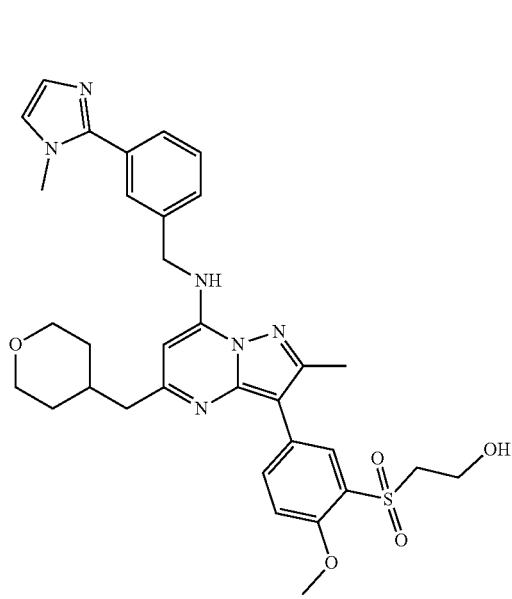 [SMILES: COc1ccc(-c2c(C)nn3c(NCc4cccc(-c5nccn5C)c4)cc(CC4CCOCC4)nc23)cc1S(=O)(=O)CCO]

Prepared in a similar manner to compound 9 using 3-iodo-2-methyl-N-(3-(1-methyl-1H-imidazol-2-yl)benzyl)-5-((tetrahydro-2H-pyran-4-yl)methyl)pyrazolo[1,5-a]pyrimidin-7-amine (Intermediate 122) and 2-((2-methoxy-5-(4,4,5,5-tetramethyl-1,3,2-dioxaborolan-2-yl)phenyl)sulfonyl)ethanol (Intermediate 19) to give the title compound. LCMS (method F): rt=0.94, [M+H]$^+$=631.

Compound 86

2-(3-(3-((2-Hydroxyethyl)sulfonyl)-4-methoxyphenyl)-2-methyl-7-((3-(1-methyl-1H-imidazol-2-yl)benzyl)amino)pyrazolo[1,5-a]pyrimidin-5-yl)butan-1-ol

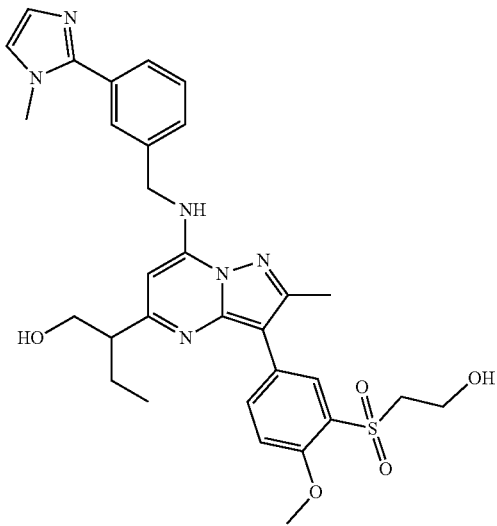 [SMILES: CCC(CO)c1cc(NCc2cccc(-c3nccn3C)c2)n2nc(C)c(-c3ccc(OC)c(S(=O)(=O)CCO)c3)c2n1]

Prepared in a similar manner to compound 37 using 2-(3-iodo-2-methyl-7-((3-(1-methyl-1H-imidazol-2-yl)benzyl)amino)pyrazolo[1,5-a]pyrimidin-5-yl)butan-1-ol (Intermediate 104) and 2-((2-methoxy-5-(4,4,5,5-tetramethyl-1,3,2-dioxaborolan-2-yl)phenyl)sulfonyl)ethanol (Intermediate 19) to give the title compound. LCMS (method F): rt=0.92, [M+H]$^+$=605.

Compound 87

3-(5-(2-Hydroxypropan-2-yl)-2-methyl-7-((3-(1-methyl-1H-imidazol-2-yl)benzyl)amino)pyrazolo[1,5-a]pyrimidin-3-yl)-N-(3-hydroxypropyl)-N-methylbenzamide

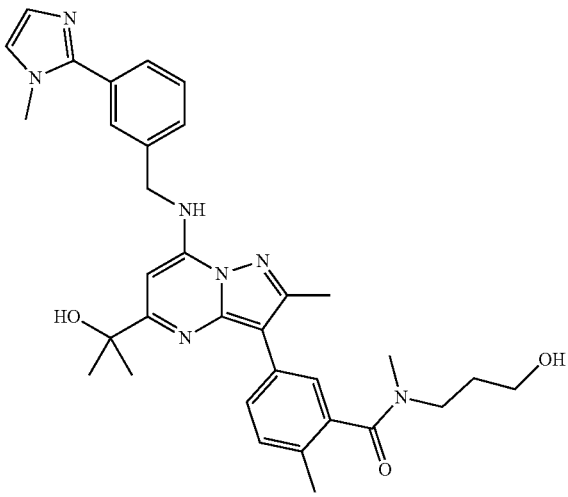 [SMILES: Cc1ccc(-c2c(C)nn3c(NCc4cccc(-c5nccn5C)c4)cc(C(C)(C)O)nc23)cc1C(=O)N(C)CCCO]

2-(3-Bromo-2-methyl-7-((3-(1-methyl-1H-imidazol-2-yl)benzyl)amino)pyrazolo[1,5-a]pyrimidin-5-yl)propan-2-ol (Intermediate 43, 150 mg, 0.313 mmol), potassium phosphate (165 mg, 0.777 mmol), dicyclohexyl(2',4',6'-triisopropyl-[1,1'-biphenyl]-2-yl)phosphane (12 mg, 0.025 mmol), XPhos Pd G2 (22 mg, 0.028 mmol) and N-(3-hydroxypropyl)-N-methyl-3-(4,4,5,5-tetramethyl-1,3,2-dioxaborolan-2-yl)benzamide (Intermediate 123, 219 mg, 0.412 mmol) were combined in a microwave vial. 1,4-Dioxane (1.8 mL) and water (0.6 mL) were added, the vial sealed and the mixture heated to 100° C. in a microwave reactor for 1 h. After cooling, the organic layer of the biphasic reaction mixture was filtered through cotton wool and purified directly by MDAP (method A). The residue obtained was partitioned between aqueous saturated sodium bicarbonate (10 mL) and DCM (5 mL). The separated aqueous phase was washed with further DCM (2×5 mL). The organics were combined, passed through a hydrophobic frit, concentrated under a stream of inert gas and dried under high vacuum at 40° C. for 1 day to give the title compound. LCMS (method F): rt=0.94, [M+H]$^+$=568.

BIOLOGICAL ASSAYS a) PI4 KB Activity Assay

The in vitro inhibition of human PI4KIII-beta 13-828 (D316-330) activity was determined by using the ADP-GLO Kinase assay kit from Promega. Inhibitors were dissolved in 100% DMSO at a concentration of 1 mM. Dilutions were prepared in 100% DMSO using a 1 in 3 serial step dilution. A 60 nL stamp from an 11-point titration was transferred to a white low volume 384 well Greiner assay plate ensuring a final DMSO concentration of 1% across the plate and a top final concentration of inhibitor of 10 µM. The PI4KIII-beta assay contained 25 mM Hepes pH 7.5 (NaOH), 10 mM MgCl2, 0.5 mM EGTA, 0.1% Triton X-100, 2 mM TCEP, and 0.1 mg/ml BSA, 1 mM ATP, 60 µM phosphatidylinositol, and 1.5 nM human PI4K-beta 13-828 (D316-330) in a total volume of 6 µL. The assay was initiated with the addition of enzyme, covered, and incubated at room temperature for 3 hours. The assays were stopped with the addition of 6 µl ADP-GLO Reagent containing 0.1% CHAPS to deplete the unconsumed ATP. The plates were incubated at room temperature for 60 min and then 12 µl of the Kinase Detection Reagent containing 0.1% CHAPS was added to convert ADP to ATP and introduce luciferase and luciferin. After 40 min incubation at room temperature the luminescent signal was read on a BMG Labtech PHERAstar FS with the following settings; Gain 3600, Focal height 13.7 mm, measurement interval time 1 s, Settling time 0.2 s. The inhibitory effect of the PI4K-beta activity of the compounds was evaluated by the IC50 of the response relative to the high, no compound, and low, no enzyme, controls by fitting to the four parameter dose response question.

When tested in this assay: all Compounds gave a mean pIC50 of greater than or equal to 8.1; compounds 1-7, 9-11, 14, 15, 17-20, 22-29 and 31-87 gave a mean pIC50 of greater than or equal to 8.4; Compounds 17 and 19 gave a mean pIC50 of 8.6; Compound 21 gave a mean pIC50 of 8.2; and Compound 22 gave a mean pIC50 of 8.5.

b) Residence Time Assay
Caliper Conditioning Assay

Compound dilutions were prepared in 100% DMSO using a 1 in 3 serial step dilution and a top concentration of 1 mM. A 200 nL stamp from a 12-point titration was transferred to a black 384-well Greiner assay plate ensuring a final DMSO concentration of 1% across the plate and a top final concentration of inhibitor of 10 μM in 20 μL final assay volume. To a well of a 384-well assay plate 10 μL of 2× Enzyme buffer was pre-incubated with compound for 1 h. Buffer without enzyme was used as 100%-inh control. 10 μL of 2× substrate solution was added to initiate the assay such that the final concentrations were 2 mM ATP and 1 μM Bodipy-PI and the plate was incubated at 25° C. for 3 hours. The enzymatic reaction was terminated by adding 40 μL of stop buffer and Substrate (PI) and product (PIP) present in each sample were separated electrophoretically using a LabChip 3000 capillary electrophoresis instrument CALIPER LABCHIP 3000 Drug Discovery System and detected using blue laser (480 nm) for excitation and green CCD (520 nm) for detection (CCD2). Negative control samples (0%-inhibition in the absence of inhibitor) and positive control samples (100%-inhibition, in the absence of enzyme) were assembled in replicates of 48 (4 replicates per caliper sipper) and were used to calculate %-inhibition values in each test well. Percent inhibition (Pinh) was determined using following equation:

$$Pinh = (PSRO\% - PSRinh)/(PSRO\% - PSR100\%) \times 100$$

Where PSRinh is the product sum ratio in the presence of inhibitor, PSRO % is the average product sum ratio in the absence of inhibitor and PSR100% is the average product sum ratio in 100%-inhibition control samples; the IC50 values of inhibitors are determined by fitting the inhibition curves (Pinh versus inhibitor concentration) to the 4 parameter sigmoid dose-response model using XLfit 4 software (IBDS).

Jump Dilution

In a small Eppendorf tube, 5 μL of 2× enzyme solution (0.4 μM-0.8 μM) was mixed with 5 μL 2× compound solution containing 40 to 120-fold the IC50 value determined at 2 mM ATP as described above, and incubated for 1 h at room temperature. The assay was initiated by rapidly mixing 2 μL of the enzyme preincubation mixture with 800 μL substrate mix containing 2 mM ATP and 1 μM Bodipy-PI. 60 μL of each sample was transferred into low volume Greiner 384-well plate, and the Substrate (PI) and product (PIP) present in each sample were separated electrophoretically using a LabChip 3000 capillary electrophoresis instrument CALIPER LABCHIP 3000 Drug Discovery System and detected using blue laser (480 nm) for excitation and green CCD (520 nm) for detection (CCD2) for approximately 8 h (200 measurements from each well). The progress curves, in % conversion against time, in the presence of compound are compared to that in control samples without compound. The curves were fit to the progress curve equation using XLfit software:

$$[P] = Vs \times t + ((Vi - Vs)/Kobs) \times (1 - \exp(-Kobs \times t))$$

Where Vi is the initial velocity of the enzyme, Vs is the steady state velocity in the presence of diluted inhibitor, and t is the time after dilution.

The observed Vi, Vs and Kobs values will depend on the nature of inhibitor (i.e. rapid equilibrium versus tight binding). Depending on the initial assay conditions (relative concentration of compound versus enzyme), Vi and Vs parameters can be pre-fitted and/or locked. For slow dissociating compounds >[E], the initial enzyme velocity (after rapid dilution) is generally not locked; Steady state velocity can be locked to that in the presence of residual compound (derived from the IC50 curve). For some rapid equilibrium compounds (½ residence<assay resolution) tested>[E], the initial velocity could be locked to the theoretical %-activity derived from the IC50 curves at the corresponding compound concentrations and the steady state velocity could be pre-fitted to control but not locked. For the remainder of rapid equilibrium or slow dissociation compounds, an alternative approach of preestimating but unlocking Vi and Vs to the theoretical velocities derived from the IC50 curves at the corresponding compound concentrations can be taken, for example, in cases such as when the above strategies fail to produce appropriate fits.

In this assay, Compound 17 showed a mean residence time of 542 minutes; Compound 19 showed a mean residence time of 997 minutes; Compound 21 showed a mean residence time of 528 minutes; and Compound 22 showed a mean residence time of 1666 minutes.

c) Cytopathic Effect (CPE) Assay Protocol

The in vitro inhibition of PI4 KB activity was determined by analysis of the inhibition of ATP-depletion in HeLa Ohio cells in response to infection with human rhinovirus Type A Strain 16 (HRVA16). ATP levels were determined using CellTiter-GLO reagent from Promega. Compounds that inhibit PI4 KB are also potent inhibitors of human rhinoviruses and are able to protect HeLa Ohio cells from CPE induced by viral infection and replication. Protected cells remain viable following viral infection and therefore have greater ATP levels.

Compounds were dissolved in 100% DMSO to a concentration of 3 mM and subsequent dilutions were prepared in 100% DMSO using a 1:3 serial step dilution. A 0.5 μL stamp from an 10-point titration was transferred to a white 96 well Greiner tissue culture flat bottom plate (655083). A 0.5 μL stamp of 100% DMSO was stamped into columns 11 and 12 of the plate, ensuring a final assay DMSO concentration of 0.33% across the plate and a compound top final assay concentration of 10 μM.

HeLa Ohio cells were cultured at 37° C., 5% CO2 in media (DMEM supplemented with 10% Australian origin foetal bovine serum and 2 mM glutamax). Cells were passaged when confluency reached >80%. For the assay, cells were grown to 80-90% confluency before detachment.

Cells were detached for the assay by washing with PBS and detached using 3 mL TrypLE Express for 5 mL at 37° C. Detached cells were mixed with 7 mL of media and centrifuged at 300 g for 5 min. The cell pellet was resuspended in 50 mL media and counted on a Beckman Coulter ViCell. Cells were diluted to $6.6 \times 10^4$ cells/mL and some of the cell volume was removed into a new tube to be used as a column 12 control. HRVA16 stock was added to the remaining cell suspension at the appropriate dilution for the virus stock to achieve an MOI of 1.

150 μL of the cell+virus suspension was added per well to columns 1-11 using a Multidrop Combi. 150 μL of the separate cell suspension was added per well to columns 12 using a multichannel pipette. Assay plates were sealed and incubated at 33° C., 5% CO2 for 2 days. After 2 days, assay plates were removed from the incubator and allowed to equilibrate to room temperature. 60 μL of CellTiter-Glo reagent was added to all wells using a Thermo Scientific Multidrop Combi. Plates were incubated at room temperature for 20 min before reading on an a Perkin Elmer Envision (Settings: Gripper height 2.5, Fixed measurement height (mm) 6.5, Distance between plate and detector 0, Measurement time (s) 0.1, Glow (ct2) correction factor (0%)).

The inhibitory effect of the compounds on the PI4 KB activity was evaluated by the IC50 of the response relative to the high (no virus, column 12) and low (virus+no inhibitor, column 11) controls by fitting to a four parameter dose response equation.

When tested in this assay: all compounds gave a mean pIC50 equal to or greater than 7.2; compounds 1-8, 10-15 and 17-87 gave a mean pIC50 of greater or equal to 7.6; compounds 1, 3, 5, 6, 7, 10-12, 14, 15, 17-25, 29, 31, 33-37, 39-53, 55-59, 61-68, 70, 76, 80-82, 84 and 86 gave a mean pIC50 of greater than or equal to 8.4; Compounds 17 and 19 gave a mean pIC50 of 8.9; Compound 21 gave a mean pIC50 of 8.8; and Compound 22 gave a mean pIC50 of at least 9.1.

d) Human Microsomal Metabolic Stability Assay

Protocol Summary

Test compound (0.5 µM) was incubated with pooled liver microsomes. Test compound was incubated over the course of a 45 min experiment and the test compound was analysed by LC-MS/MS.

Experimental Procedure

Pooled human liver microsomes were purchased from a reputable commercial supplier, for example Corning Life Sciences. Microsomes (final protein concentration 0.5 mg/mL), 50 mM phosphate buffer pH7.4 and NADPH (final concentration=1 mM) were pre-incubated at 37° C. prior to the addition of test compound (final substrate concentration=0.5 µM; final DMSO concentration=0.25%) to initiate the reaction. The final incubation volume was 500 µL. A control incubation was included for each compound tested where 50 mM phosphate buffer pH7.4 was added instead of NADPH (minus NADPH). Two control compounds were included with each species. All incubations are performed singularly for each test compound.

Each compound was incubated for 45 minutes and samples (50 µL) of incubate were taken at 0, 5, 15, 30 and 45 min. The control (minus NADPH) was sampled at 45 min only. The reactions were stopped by the addition of 100 µL acetonitrile containing internal standard to the sample. The terminated samples were centrifuged at 2,500 rpm for 20 min at 4° C. to precipitate the protein.

Quantitative Analysis

Following protein precipitation, the samples were analysed using generic LC-MS/MS conditions.

Data Analysis

From a plot of ln peak area ratio (compound peak area/internal standard peak area) against time, the gradient of the line was determined. Subsequently, intrinsic clearance was calculated using the equations below, then converted to mL/min/g:

Elimination rate constant $(k)=(-\text{gradient})$

Half life $(t\frac{1}{2})$ (min)=$0.693 \div k$

Intrinsic Clearance (CLint) (µL/min/mg protein)=$(V \times 0.693) \div t_{1/2}$ where V=Incubation volume µL/mg microsomal protein.

When tested in this assay, the intrinsic clearance of Compound 17 was 28.9 mL/min/g; the intrinsic clearance of Compound 19 was 11.6 mL/min/g; the intrinsic clearance of Compound 21 was 34.0 mL/min/g; and the intrinsic clearance of Compound 22 was 33.7 mL/min/g.

e) Spleen Concentration Assay

Compounds 17, 18, 19, 22 and 23 were tested in this spleen accumulation assay. Compounds were administered intravenously to rats to determine what the level of the compound in the spleen would be if all of the inhaled dose was absorbed (either orally or through the lungs) and systemic circulation was exposed to the full dose.

Compounds 17, 19, 22 and 23 were formulated in 2% DMSO in Kleptose (aq, 10% w/v). Compound 18 was formulated in a 5:45:50 ratio of DMSO:PEG200:water.

Formulations were administered as intravenous infusions (1 mg/kg over 1 h) to a single male, Wistar Han rat. 12 hours after the start of dosing, rats were euthanised and spleens were collected.

Approximately 0.5 g samples of spleen were taken and homogenised in 4 mL water. 100 µL of the resulting homogenates were prepared by protein precipitation with 300 µL of acetonitrile containing an internal standard and assayed (along with calibration standards prepared in the same manner) by reversed-phase liquid chromatography-mass spectrometry, using a heated electrospray source and operated in the positive ion multiple reaction monitoring mode. The liquid chromatography column used was a Waters Cortecs C18 2.7 µm particle size, 50×2.1 mm column at 60° C., and the mobile phase, operated as a gradient, utilised (A) 0.1% formic acid (aq) and (B) 0.1% formic acid in acetonitrile, operated at a flow rate of 1 mL/min.

All compounds had a concentration in the spleen of less than 30 ng/g. Compounds 17, 19, 22 and 23 had a concentration in the spleen of less than 7 ng/g. In particular, compound 17 had a concentration in the spleen of 1.76 ng/g and compound 22 had a concentration in the spleen of 5.54 ng/g.

What is claimed is:

1. A compound of formula (I):

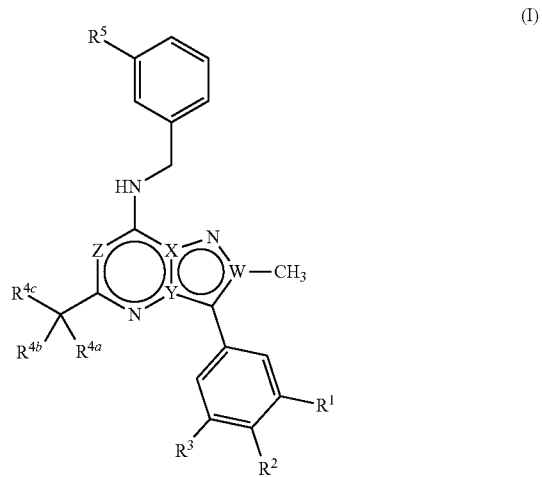

a stereoisomer thereof, or a pharmaceutically acceptable salt thereof, wherein:

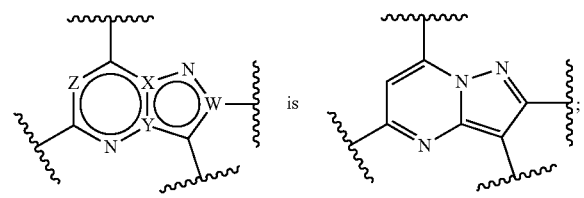

$R^1$ is $C(O)NR^{1a}R^{1b}$, $OC_{1-4}$ alkyl, $S(O)R^{1c}$, $S(O)_2NR^{1a}R^{1b}$, or $S(O)_2R^{1c}$;

$R^{1a}$ is $C_{1-3}$ alkyl, $C_{1-3}$ haloalkyl, $C_{1-3}$ hydroxyalkyl, $C_{1-3}$ alkyl-$OC_{1-3}$ alkyl, tetrahydrofuranyl, or tetrahydropyranyl;

$R^{1b}$ is H or $C_{1-3}$ alkyl; or

R$^{1a}$ and R$^{1b}$, together with the nitrogen heteroatom to which they are attached, form a 4- to 7-membered heterocyclic ring;
  wherein the 4- to 7-membered heterocyclic ring contains ring carbon atoms and optionally 1 ring oxygen heteroatom, wherein the total number of ring atoms including the nitrogen heteroatom attached to R$^{1a}$ and R$^{1b}$, the ring carbon atoms, and the ring oxygen heteroatom is from 4 to 7; and
  a) wherein the 4- to 7-membered heterocyclic ring is optionally substituted by 1 or 2 substituents independently selected from the group consisting of halo, C$_{1-3}$ alkyl, C$_{1-3}$ hydroxyalkyl, OH, OC$_{1-3}$ alkyl, and =O; or
  b) wherein the 4- to 7-membered heterocyclic ring is ortho-fused or spiro-fused to an unsubstituted 4- to 6-membered cycloalkyl ring or an unsubstituted, saturated 4- to 6-membered heterocyclic ring;
R$^{1c}$ is C$_{1-3}$ alkyl, C$_{1-3}$ hydroxyalkyl, C$_{1-3}$ alkyl-OC$_{1-3}$ alkyl, OH, or OC$_{1-3}$ alkyl;
R$^2$ is H, halo, C$_{1-3}$ alkyl, or OR$^{2a}$;
R$^{2a}$ is H, CH$_3$, CH$_2$CH$_3$, or CH$_2$CH$_2$CH$_3$;
R$^3$ is H or halo;
(i) R$^{4a}$ is H, halo, or C$_{1-3}$ alkyl;
  R$^{4b}$ is C$_{1-3}$ alkyl, C$_{1-2}$ hydroxyalkyl, or cyclopropyl; or
  R$^{4a}$ and R$^{4b}$, together with the carbon atom to which they are attached, form a saturated 3- to 6-membered ring;
    wherein the 3- to 6-membered ring contains ring carbon atoms and optionally 1 ring oxygen heteroatom, wherein the total number of the ring carbon atoms and the ring oxygen heteroatom is from 3 to 6; and
    wherein the 3- to 6-membered ring is optionally substituted by 1 substituent selected from the group consisting of C$_{1-3}$ alkyl and C$_{1-2}$ hydroxyalkyl; and
  R$^{4c}$ is CH$_2$OH, CH(OH)CH$_3$, CH$_2$CH$_2$OH, or OH; or
(ii) R$^{4a}$ is H, halo, C$_{1-3}$ alkyl, or OH;
  R$^{4b}$ is H, halo, or C$_{1-3}$ alkyl; and
  R$^{4c}$ is unsubstituted oxetanyl, unsubstituted tetrahydrofuranyl, or unsubstituted tetrahydropyranyl; or
(iii) R$^{4a}$ is H; and
  R$^{4b}$ and R$^{4c}$, together with the carbon atom to which they are attached, form an unsubstituted oxetanyl, unsubstituted tetrahydrofuranyl, or unsubstituted tetrahydropyranyl; and
R$^5$ is pyrazol-1-yl or imidazol-2-yl;
  wherein the pyrazol-1-yl is optionally substituted at the 4-position by 1 CH$_3$ substituent and optionally substituted at the 5-position by 1 C$_{1-3}$ alkyl substituent; and
  wherein the imidazol-2-yl is optionally substituted at the 1-position by 1 C$_{1-3}$ alkyl substituent and optionally substituted at the 5-position by 1 CH$_3$ substituent.

2. The compound according to claim 1, a stereoisomer thereof, or a pharmaceutically acceptable salt thereof, wherein R$^1$ is C(O)NR$^{1a}$R$^{1b}$ or S(O)$_2$R$^{1c}$.

3. The compound according to claim 2, a stereoisomer thereof, or a pharmaceutically acceptable salt thereof, wherein R$^1$ is C(O)NR$^{1a}$R$^{1b}$.

4. The compound according to claim 3, a stereoisomer thereof, or a pharmaceutically acceptable salt thereof, wherein R$^{1a}$ is C$_{1-3}$ hydroxyalkyl or tetrahydropyranyl.

5. The compound according to claim 4, a stereoisomer thereof, or a pharmaceutically acceptable salt thereof, wherein R$^{1a}$ is C$_{1-3}$ hydroxyalkyl.

6. The compound according to claim 3, a stereoisomer thereof, or a pharmaceutically acceptable salt thereof, wherein R$^{1a}$ is CH$_2$CH$_2$OH, CH$_2$CH$_2$CH$_2$OH, or CH(CH$_3$)CH$_2$OH.

7. The compound according to claim 3, a stereoisomer thereof, or a pharmaceutically acceptable salt thereof, wherein R$^{1b}$ is C$_{1-3}$ alkyl.

8. The compound according to claim 7, a stereoisomer thereof, or a pharmaceutically acceptable salt thereof, wherein R$^{1b}$ is CH$_3$ or CH$_2$CH$_3$.

9. The compound according to claim 1, a stereoisomer thereof, or a pharmaceutically acceptable salt thereof, wherein R$^2$ is Cl, C$_{1-3}$ alkyl, or OR$^{2a}$.

10. The compound according to claim 9, a stereoisomer thereof, or a pharmaceutically acceptable salt thereof, wherein R$^2$ is C$_{1-3}$ alkyl.

11. The compound according to claim 1, a stereoisomer thereof, or a pharmaceutically acceptable salt thereof, wherein R$^3$ is H.

12. The compound according to claim 1, a stereoisomer thereof, or a pharmaceutically acceptable salt thereof, wherein:
  R$^2$ is H, Cl, C$_{1-3}$ alkyl, or OR$^{2a}$;
  R$^{2a}$ is H, CH$_3$, CH$_2$CH$_3$, or CH$_2$CH$_2$CH$_3$; and
  R$^3$ is H or F.

13. The compound according to claim 1, a stereoisomer thereof, or a pharmaceutically acceptable salt thereof, wherein R$^{4a}$ is CH$_3$.

14. The compound according to claim 1, a stereoisomer thereof, or a pharmaceutically acceptable salt thereof, wherein R$^{4b}$ is C$_{1-3}$ alkyl.

15. The compound according to claim 1, a stereoisomer thereof, or a pharmaceutically acceptable salt thereof, wherein:
  R$^{4a}$ is CH$_3$; and
  R$^{4b}$ is CH$_3$.

16. The compound according to claim 1, a stereoisomer thereof, or a pharmaceutically acceptable salt thereof, wherein:
(i) R$^{4a}$ is H, F, or C$_{1-3}$ alkyl;
  R$^{4b}$ is C$_{1-3}$ alkyl, C$_{1-2}$ hydroxyalkyl, or cyclopropyl; or
  R$^{4a}$ and R$^{4b}$, together with the carbon atom to which they are attached, form an saturated 3- to 6-membered ring;
    wherein the 3- to 6-membered ring contains ring carbon atoms and optionally 1 ring oxygen heteroatom, wherein a total number of the ring carbon atoms and the ring oxygen heteroatom is from 3 to 6; and; and
    wherein the 3- to 6-membered ring is optionally substituted by 1 substituent selected from the group consisting of C$_{1-3}$ alkyl and C$_{1-2}$ hydroxyalkyl; and
  R$^{4c}$ is CH$_2$OH, CH(OH)CH$_3$, CH$_2$CH$_2$OH, or OH; or
(ii) R$^{4a}$ is H, F, C$_{1-3}$ alkyl, or OH;
  R$^{4b}$ is H, F, or C$_{1-3}$ alkyl; and
  R$^{4c}$ is unsubstituted oxetanyl, unsubstituted tetrahydrofuranyl, or unsubstituted tetrahydropyranyl; or
(iii) R$^{4a}$ is H; and
  R$^{4b}$ and R$^{4c}$, together with the carbon atom to which they are attached, form an unsubstituted oxetanyl, unsubstituted tetrahydrofuranyl, or unsubstituted tetrahydropyranyl.

17. The compound according to claim 1, a stereoisomer thereof, or a pharmaceutically acceptable salt thereof, wherein $R^5$ is imidazol-2-yl, wherein the imidazol-2-yl is optionally substituted at the 1-position by 1 $C_{1-3}$ alkyl substituent and optionally substituted at the 5-position by 1 $CH_3$ substituent.

18. The compound according to claim 1, a stereoisomer thereof, or a pharmaceutically acceptable salt thereof, wherein $R^5$ is 1-methyl-1H-imidazol-2-yl.

19. The compound according to claim 1, wherein the compound is of the following formula:

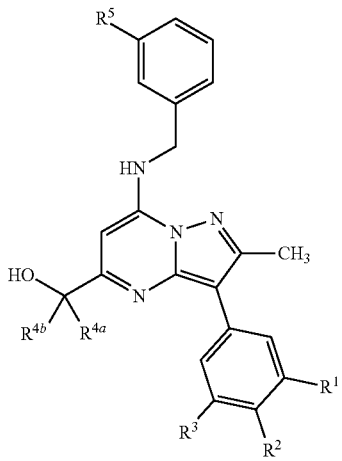

a stereoisomer thereof, or a pharmaceutically acceptable salt thereof,
wherein:
- $R^1$ is $C(O)NR^{1a}R^{1b}$, $OC_{1-4}$ alkyl, $S(O)R^{1c}$, $S(O)_2NR^{1a}R^{1b}$, or $S(O)_2R^{1c}$;
- $R^{1a}$ is $C_{1-3}$ alkyl, $C_{1-3}$ haloalkyl, $C_{1-3}$ hydroxyalkyl, or $C_{1-3}$ alkyl-$OC_{1-3}$ alkyl;
- $R^{1b}$ is H or $C_{1-3}$ alkyl; or
- $R^{1a}$ and $R^{1b}$, together with the nitrogen heteroatom to which they are attached, form a 4- to 7-membered heterocyclic ring;
    wherein the 4- to 7-membered heterocyclic ring contains ring carbon atoms and optionally 1 ring oxygen heteroatom, wherein the total number of ring atoms including the nitrogen heteroatom attached to $R^{1a}$ and $R^{1b}$, the ring carbon atoms, and the ring oxygen heteroatom is from 4 to 7; and
    a) wherein the 4- to 7-membered heterocyclic ring is optionally substituted by 1 or 2 substituents independently selected from the group consisting of halo, $C_{1-3}$ alkyl, OH, $OC_{1-3}$ alkyl, and =O; or
    b) wherein the 4- to 7-membered heterocyclic ring is ortho-fused or spiro-fused to an unsubstituted 4- to 6-membered cycloalkyl ring or an unsubstituted, saturated 4- to 6-membered heterocyclic ring;
- $R^{1c}$ is $C_{1-3}$ alkyl, $C_{1-3}$ hydroxyalkyl, $C_{1-3}$ alkyl-$OC_{1-3}$ alkyl, OH, or $OC_{1-3}$ alkyl;
- $R^2$ is H, Cl, $C_{1-3}$ alkyl, or $OR^{2a}$;
- $R^{2a}$ is H, $CH_3$, $CH_2CH_3$, or $CH_2CH_2CH_3$;
- $R^3$ is H or F;
- $R^{4a}$ is H or $CH_3$;
- $R^{4b}$ is $C_{1-3}$ alkyl or $C_{1-2}$ hydroxyalkyl; and
- $R^5$ is pyrazol-1-yl or imidazol-2-yl;
    wherein the pyrazol-1-yl is optionally substituted at the 4-position by 1 $CH_3$ substituent and optionally substituted at the 5-position by 1 $C_{1-3}$ alkyl substituent; and wherein the imidazol-2-yl is optionally substituted at the 1-position by 1 $C_{1-3}$ alkyl substituent and optionally substituted at the 5-position by 1 $CH_3$ substituent.

20. The compound according to claim 1, wherein the compound is of formula (Ic):

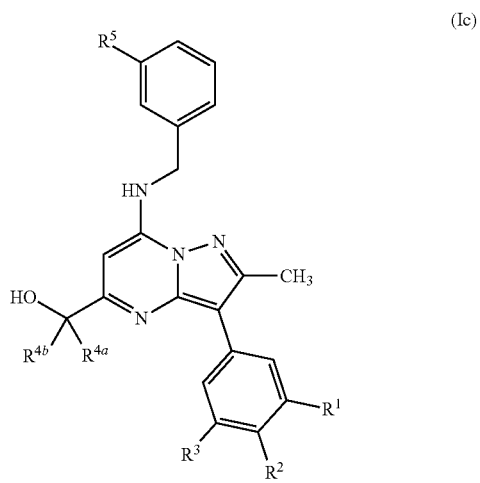

(Ic)

a stereoisomer thereof, or a pharmaceutically acceptable salt thereof,
wherein:
- $R^1$ is $C(O)NR^{1a}R^{1b}$ or $S(O)_2R^{1c}$;
- $R^{1a}$ is $C_{1-3}$ hydroxyalkyl or tetrahydropyranyl;
- $R^{1b}$ is $C_{1-3}$ alkyl; or
- $R^{1a}$ and $R^{1b}$, together with the nitrogen heteroatom to which they are attached, form a 4- to 7-membered heterocyclic ring;
    wherein the 4- to 7-membered heterocyclic ring contains ring carbon atoms and optionally 1 ring oxygen heteroatom, wherein the total number of ring atoms including the nitrogen heteroatom attached to $R^{1a}$ and $R^{1b}$, the ring carbon atoms, and the ring oxygen heteroatom is from 4 to 7; and
    a) wherein the 4- to 7-membered heterocyclic ring is optionally substituted by 1 or 2 substituents independently selected from the group consisting of halo, $C_{1-3}$ alkyl, $C_{1-3}$ hydroxyalkyl, OH, $OC_{1-3}$ alkyl, and =O; or
    b) wherein the 4- to 7-membered heterocyclic ring is ortho-fused or spiro-fused to an unsubstituted 4- to 6-membered cycloalkyl ring or an unsubstituted, saturated 4- to 6-membered heterocyclic ring;
- $R^{1c}$ is $C_{1-3}$ hydroxyalkyl;
- $R^2$ is H, Cl, $C_{1-3}$ alkyl, or $OCH_3$;
- $R^3$ is H or F;
- $R^{4a}$ is $CH_3$;
- $R^{4b}$ is $C_{1-3}$ alkyl; and
- $R^5$ is imidazol-2-yl, wherein the imidazol-2-yl is optionally substituted at the 1-position by 1 $C_{1-3}$ alkyl substituent and optionally substituted at the 5-position by 1 $CH_3$ substituent.

21. The compound according to claim 20, a stereoisomer thereof, or a pharmaceutically acceptable salt thereof, wherein:
- $R^{1a}$ is $C_{1-3}$ hydroxyalkyl or tetrahydropyranyl; and
- $R^{1b}$ is $C_{1-3}$ alkyl.

22. The compound according to claim 1, wherein the compound is:

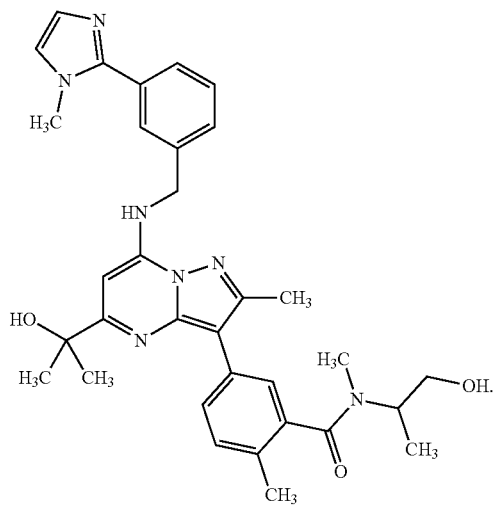 [SMILES: Cc1ccc(-c2c(C)nn3c(NCc4cccc(-c5nccn5C)c4)cc(C(C)(C)O)nc23)cc1C(=O)N(C)C(C)CO]

or a pharmaceutically acceptable salt thereof.

23. The compound according to claim 1, wherein the compound is:

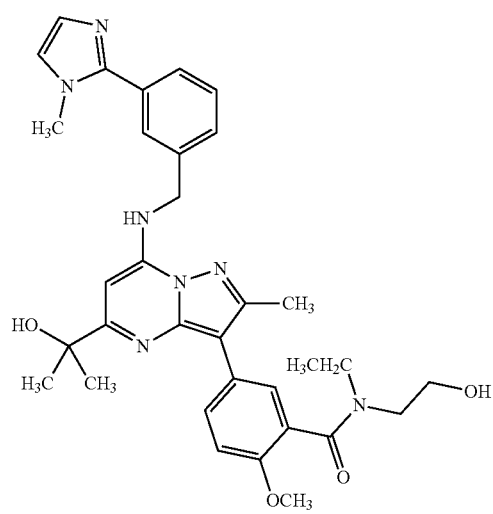

or a pharmaceutically acceptable salt thereof.

24. The compound according to claim 1, wherein the compound is:

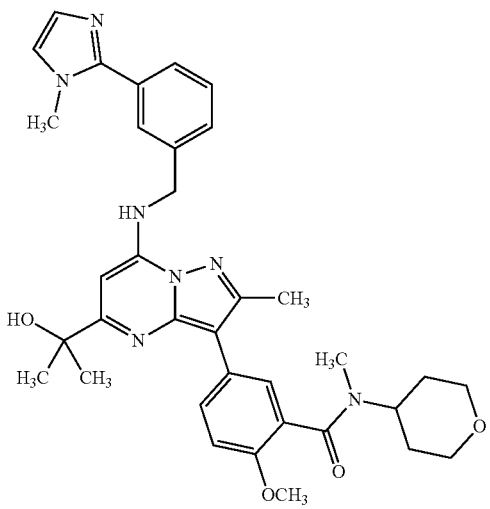 [SMILES: COc1ccc(-c2c(C)nn3c(NCc4cccc(-c5nccn5C)c4)cc(C(C)(C)O)nc23)cc1C(=O)N(C)C1CCOCC1]

or a pharmaceutically acceptable salt thereof.

25. The compound according to claim 1, or a stereoisomer thereof, wherein the stereoisomer of the compound is:

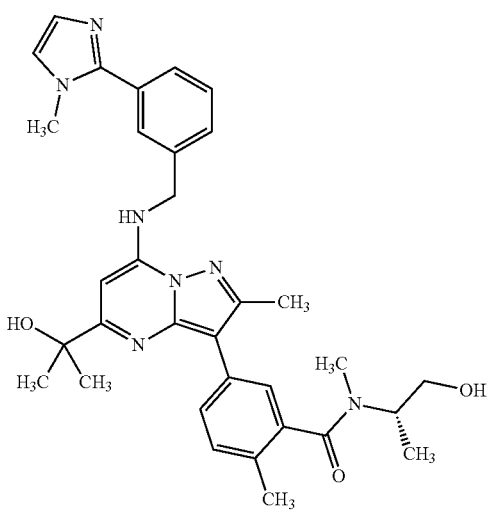 [SMILES: Cc1ccc(-c2c(C)nn3c(NCc4cccc(-c5nccn5C)c4)cc(C(C)(C)O)nc23)cc1C(=O)N(C)[C@@H](C)CO]

or a pharmaceutically acceptable salt thereof.

26. The compound according to claim 1, or a stereoisomer thereof, wherein the stereoisomer of the compound is:
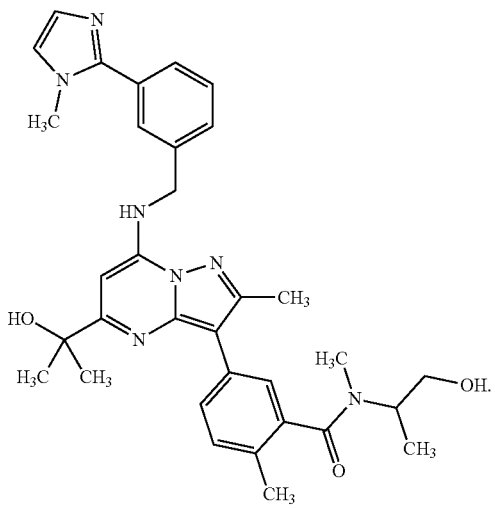 [SMILES: Cc1ccc(-c2c(C)nn3c(NCc4cccc(-c5nccn5C)c4)cc(C(C)(C)O)nc23)cc1C(=O)N(C)C(C)CO]
27. The compound according to claim 1, wherein the compound is:
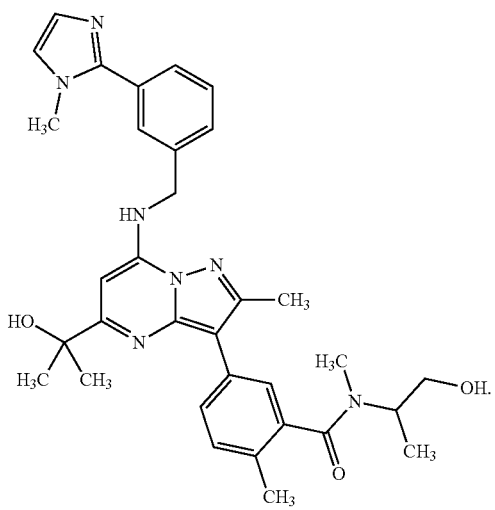 [SMILES: Cc1ccc(-c2c(C)nn3c(NCc4cccc(-c5nccn5C)c4)cc(C(C)(C)O)nc23)cc1C(=O)N(C)C(C)CO]
28. The compound according to claim 1, or a stereoisomer thereof, wherein the compound, or a stereoisomer thereof, is selected from the group consisting of:
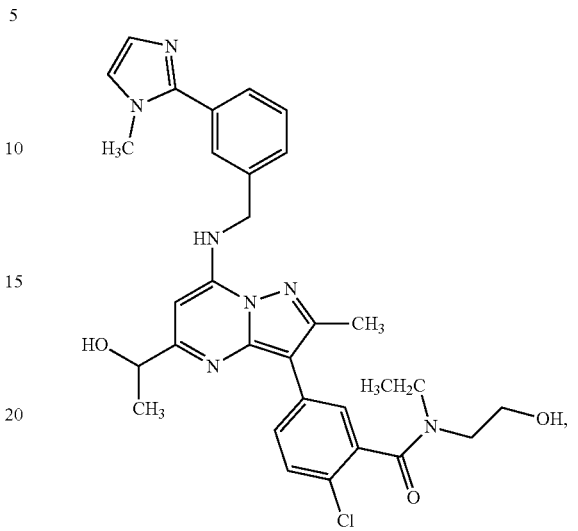
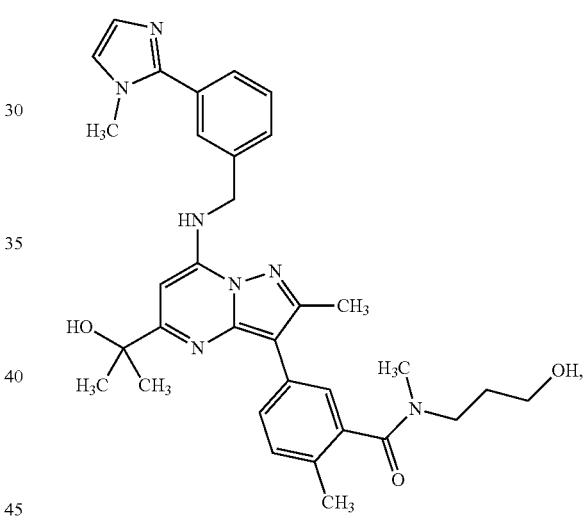
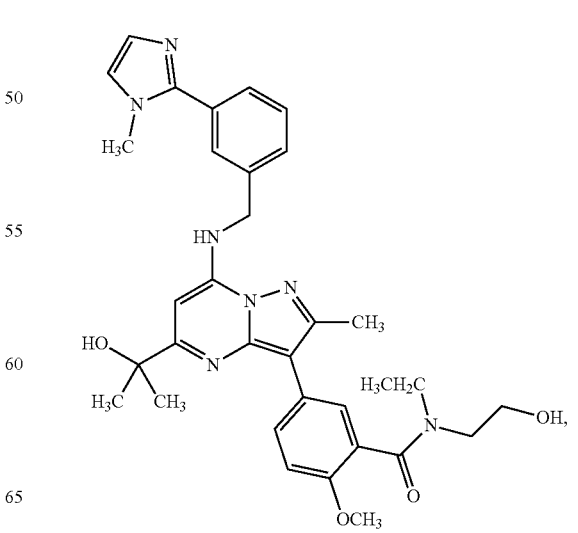

209
-continued
210
-continued
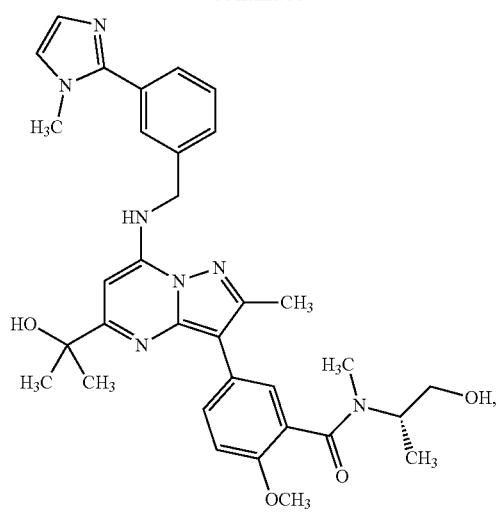
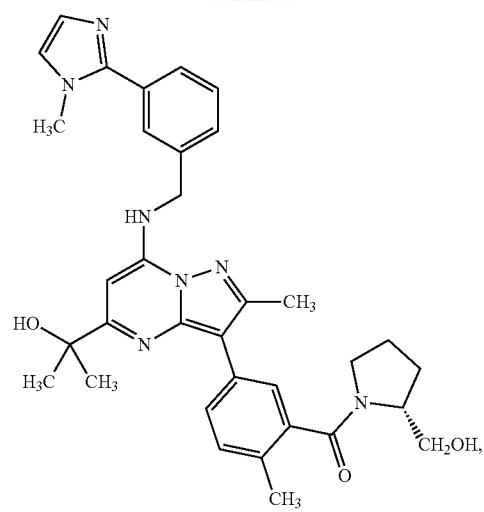
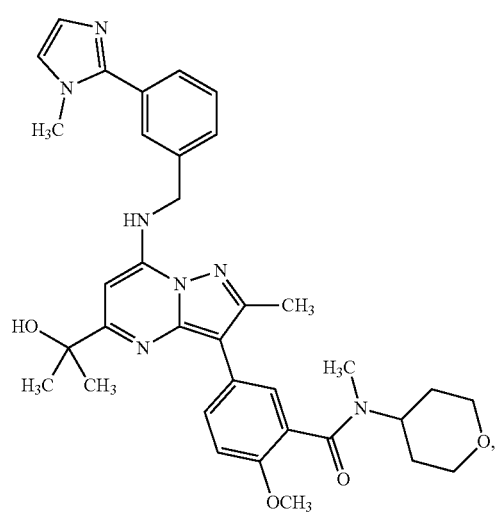
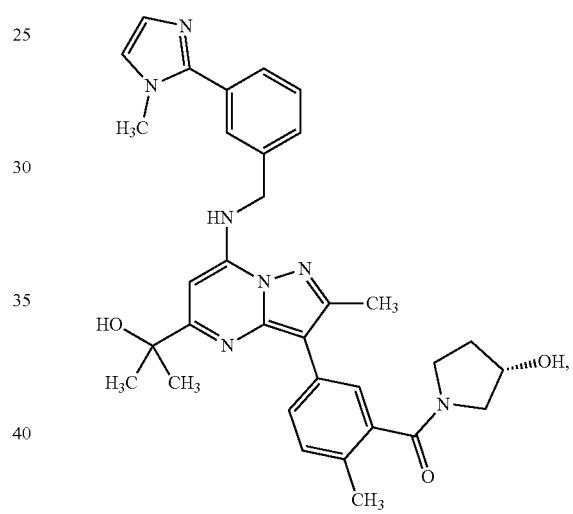
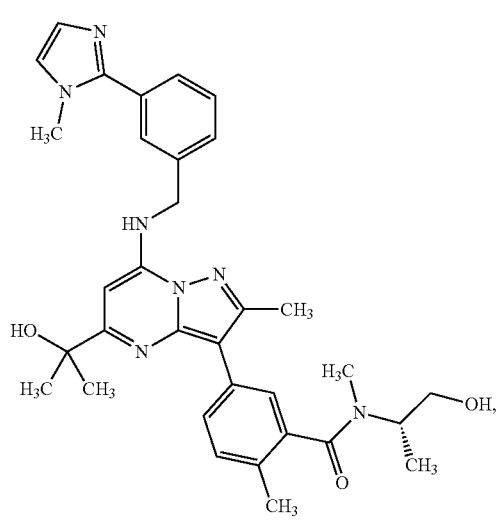
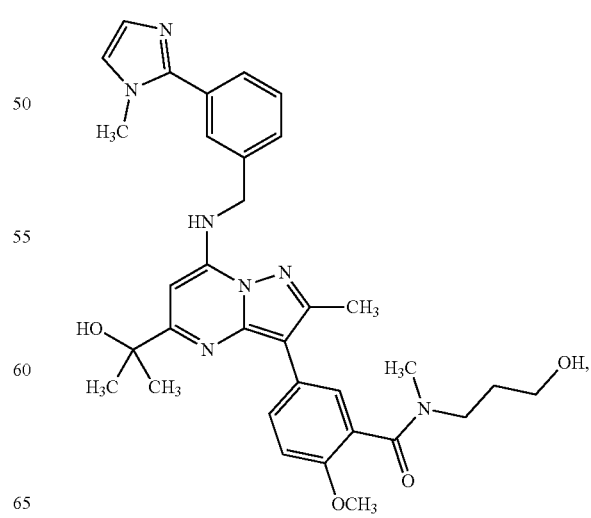

211
-continued
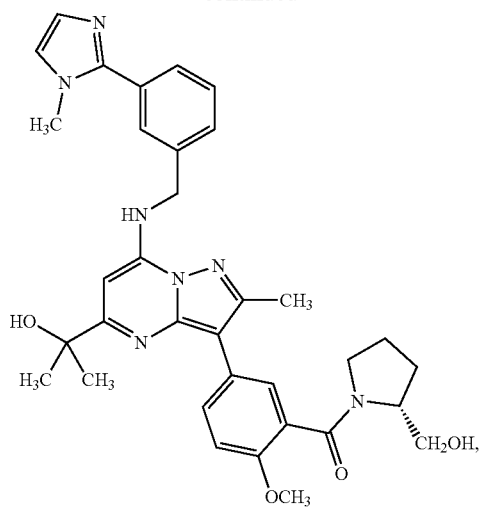
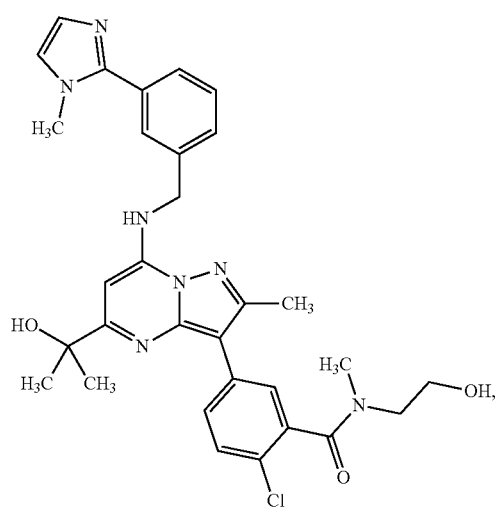
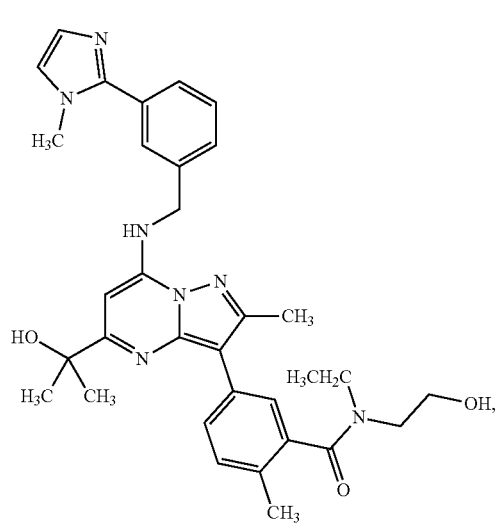
212
-continued
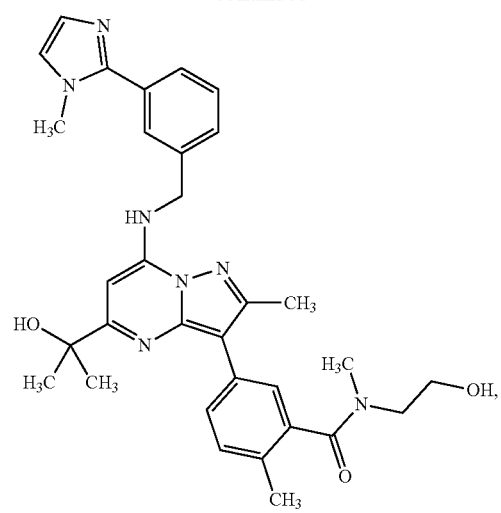
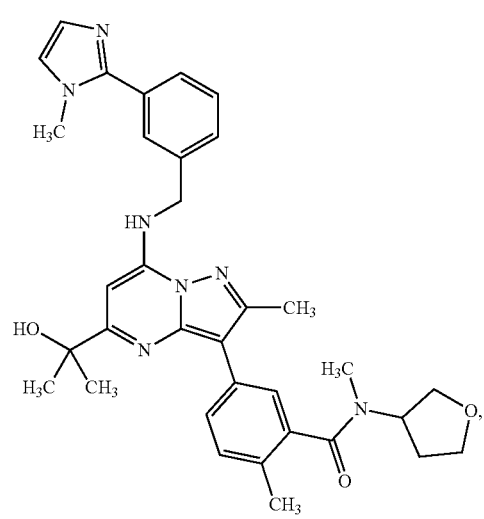
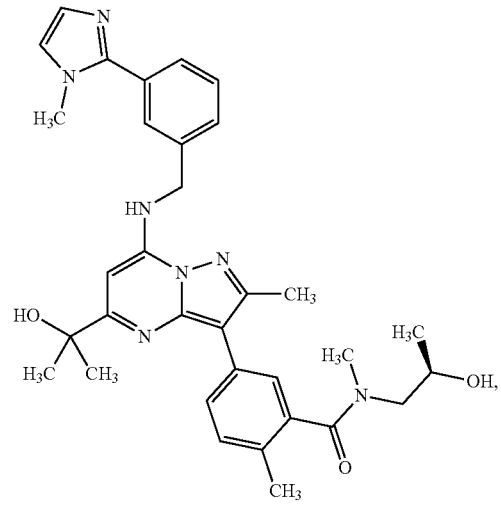

213
-continued

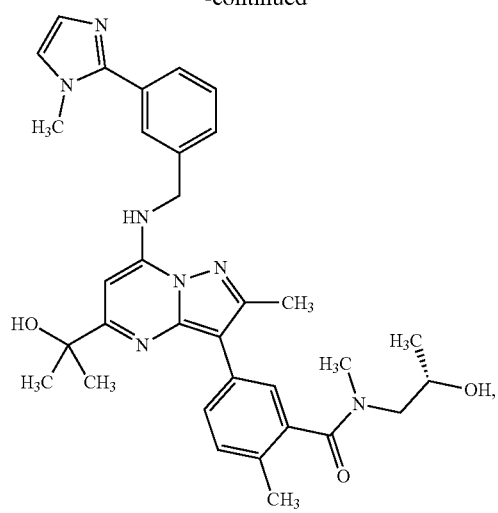

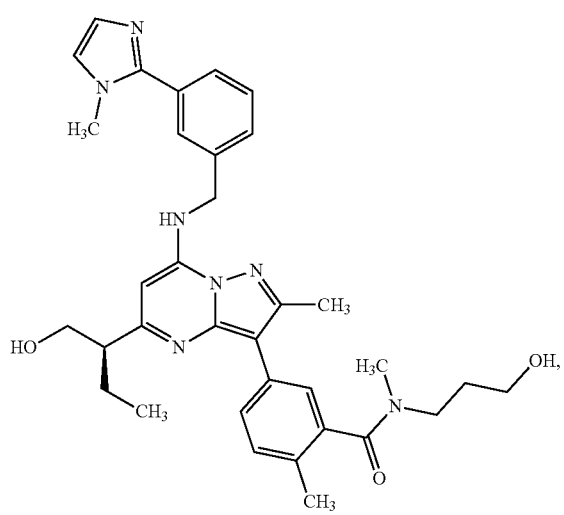

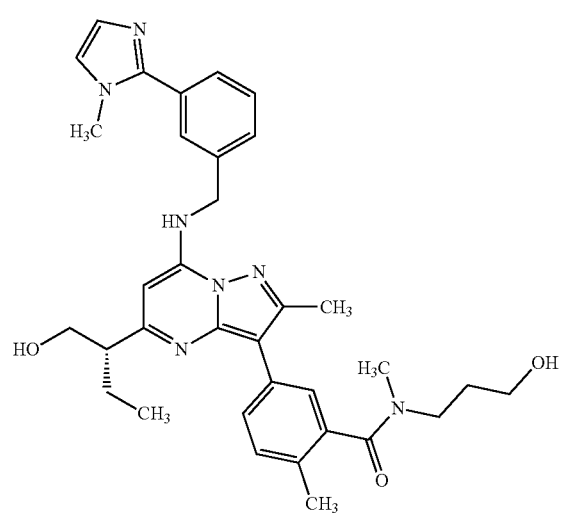

214
-continued

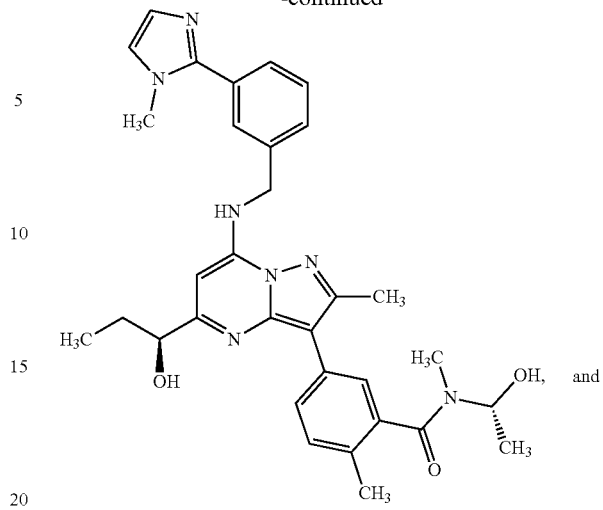

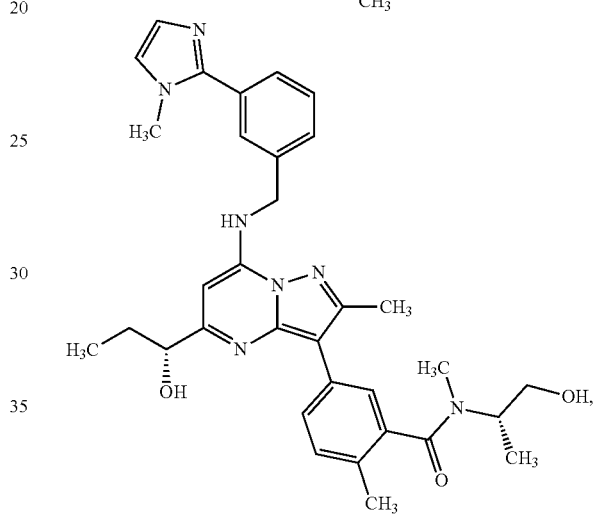

and

29. A pharmaceutical formulation comprising a pharmaceutically acceptable excipient and a compound according to claim 1, a stereoisomer thereof, or a pharmaceutically acceptable salt thereof.

30. A pharmaceutical formulation comprising a pharmaceutically acceptable excipient and the stereoisomer according to claim 25, or a pharmaceutically acceptable salt thereof.

31. A pharmaceutical formulation comprising a pharmaceutically acceptable excipient and the stereoisomer according to claim 26.

32. A method for inhibiting phosphatidylinositol 4-kinase III beta activity in a patient, wherein the method comprises administering to the patient in need thereof a therapeutically effective amount of a compound according to claim 1, a stereoisomer thereof, or a pharmaceutically acceptable salt thereof.

33. The method according to claim 32, wherein the patient has a viral infection.

34. The method according to claim 32, wherein the patient has a disorder caused by or exacerbated by a viral infection, and wherein the disorder caused by or exacerbated by a viral infection is selected from the group consisting of acute bronchitis, asthma, bronchiectasis, bronchiolitis, chronic obstructive pulmonary disease, congestive heart failure, cystic fibrosis, otitis media, pneumonia, a secondary bacterial infection, and sinusitis.

35. The method according to claim 34, wherein the disorder cause by or exacerbated by a viral infection is asthma.

36. The method according to claim 34, wherein the disorder caused by or exacerbated by a viral infection is chronic obstructive pulmonary disease.

37. A method for inhibiting phosphatidylinositol 4-kinase III beta activity in a patient, wherein the method comprises administering to the patient in need thereof a therapeutically effective amount of the stereoisomer according to claim 25, or a pharmaceutically acceptable salt thereof.

38. The method according to claim 37, wherein the patient has a viral infection.

39. The method according to claim 37, wherein the patient has a disorder caused by or exacerbated by a viral infection, and wherein the disorder caused by or exacerbated by a viral infection is selected from the group consisting of acute bronchitis, asthma, bronchiectasis, bronchiolitis, chronic obstructive pulmonary disease, congestive heart failure, cystic fibrosis, otitis media, pneumonia, a secondary bacterial infection, and sinusitis.

40. The method according to claim 39, wherein the disorder caused by or exacerbated by a viral infection is asthma.

41. The method according to claim 39, wherein the disorder caused by or exacerbated by a viral infection is chronic obstructive pulmonary disease.

42. A method for inhibiting phosphatidylinositol 4-kinase III beta activity in a patient wherein the method comprises administering to the patient in need thereof a therapeutically effective amount of the stereoisomer according to claim 26.

43. The method according to claim 42, wherein the patient has a viral infection.

44. The method according to claim 42, wherein the patient has a disorder caused by or exacerbated by a viral infection, and wherein the disorder caused by or exacerbated by a viral infection is selected from the group consisting of acute bronchitis, asthma, bronchiectasis, bronchiolitis, chronic obstructive pulmonary disease, congestive heart failure, cystic fibrosis, otitis media, pneumonia, a secondary bacterial infection, and sinusitis.

45. The method according to claim 44, wherein the disorder caused by or exacerbated by a viral infection is asthma.

46. The method according to claim 44, wherein the disorder caused by or exacerbated by a viral infection is chronic obstructive pulmonary disease.

\* \* \* \* \*